US009969716B2

(12) United States Patent
Albrecht et al.

(10) Patent No.: US 9,969,716 B2
(45) Date of Patent: May 15, 2018

(54) INDOLE DERIVATIVES AS MODULATORS OF METHYL MODIFYING ENZYMES, COMPOSITIONS AND USES THEREOF

(71) Applicant: Constellation Pharmaceuticals, Inc., Cambridge, MA (US)

(72) Inventors: Brian K. Albrecht, Cambridge, MA (US); James Edmund Audia, Cambridge, MA (US); Les A. Dakin, Natick, MA (US); Martin Duplessis, Somerville, MA (US); Victor S. Gehling, Somerville, MA (US); Jean-Christophe Harmange, Andover, MA (US); Christopher G. Nasveschuk, Stoneham, MA (US); Rishi G. Vaswani, Lexington, MA (US)

(73) Assignee: Constellation Pharmaceuticals, Inc., Cambridge, MA (US)

(*) Notice: Subject to any disclaimer, the term of this patent is extended or adjusted under 35 U.S.C. 154(b) by 0 days. days.

(21) Appl. No.: 14/911,343

(22) PCT Filed: Aug. 15, 2014

(86) PCT No.: PCT/US2014/051201
§ 371 (c)(1),
(2) Date: Feb. 10, 2016

(87) PCT Pub. No.: WO2015/023915
PCT Pub. Date: Feb. 19, 2015

(65) Prior Publication Data
US 2016/0185757 A1 Jun. 30, 2016

Related U.S. Application Data

(60) Provisional application No. 61/866,224, filed on Aug. 15, 2013.

(51) Int. Cl.
| | | |
|---|---|---|
| *C07D 401/14* | (2006.01) | |
| *C07D 401/12* | (2006.01) | |
| *C07D 405/14* | (2006.01) | |
| *C07D 413/14* | (2006.01) | |

(52) U.S. Cl.
CPC ......... *C07D 401/14* (2013.01); *C07D 401/12* (2013.01); *C07D 405/14* (2013.01); *C07D 413/14* (2013.01)

(58) Field of Classification Search
None
See application file for complete search history.

(56) References Cited

U.S. PATENT DOCUMENTS

| | | | |
|---|---|---|---|
| 4,738,971 A | 4/1988 | Eriksoo et al. | |
| 5,308,854 A | 5/1994 | Hoffman, Jr. et al. | |
| 7,838,520 B2 | 11/2010 | Delorme et al. | |
| 8,410,088 B2 | 4/2013 | Kuntz et al. | |
| 8,536,179 B2 | 9/2013 | Miller et al. | |
| 8,846,935 B2 | 9/2014 | Duquenne et al. | |
| 9,051,269 B2 | 6/2015 | Albrecht et al. | |
| 9,085,583 B2 * | 7/2015 | Albrecht ............... | C07D 401/14 |
| 9,206,128 B2 | 12/2015 | Albrecht et al. | |
| 9,371,331 B2 | 6/2016 | Albrecht et al. | |
| 9,374,093 B2 | 6/2016 | Pelley et al. | |
| 9,409,865 B2 | 8/2016 | Albrecht et al. | |
| 9,469,646 B2 | 10/2016 | Albrecht et al. | |
| 2003/0207875 A1 | 11/2003 | Gymer et al. | |
| 2003/0229081 A1 | 12/2003 | Maduskuie | |
| 2004/0186138 A1 | 9/2004 | Annoura et al. | |
| 2005/0266473 A1 | 12/2005 | Zhang et al. | |
| 2006/0035938 A1 | 2/2006 | Bladh et al. | |
| 2007/0155744 A1 | 7/2007 | Jones et al. | |
| 2008/0027050 A1 | 1/2008 | Terauchi et al. | |
| 2008/0227826 A1 | 9/2008 | Frechette et al. | |
| 2008/0280917 A1 | 11/2008 | Albrecht et al. | |
| 2009/0029991 A1 | 1/2009 | Stokes et al. | |
| 2009/0075833 A1 | 3/2009 | Chinnaiyan et al. | |
| 2009/0270361 A1 | 10/2009 | Ito et al. | |
| 2010/0069630 A1 | 3/2010 | Lee et al. | |
| 2010/0222420 A1 | 9/2010 | Chinnaiyan et al. | |
| 2010/0261743 A1 | 10/2010 | Londregan et al. | |
| 2010/0298270 A1 | 11/2010 | Keana et al. | |
| 2011/0105509 A1 | 5/2011 | Kaila et al. | |
| 2011/0212946 A1 | 9/2011 | Barrow et al. | |
| 2012/0071418 A1 | 3/2012 | Copeland et al. | |
| 2012/0264734 A1 | 10/2012 | Kuntz et al. | |
| 2013/0040906 A1 | 2/2013 | Kuntz et al. | |
| 2013/0230511 A1 | 9/2013 | Heymach et al. | |
| 2013/0310379 A1 | 11/2013 | Albrecht et al. | |

(Continued)

FOREIGN PATENT DOCUMENTS

| | | |
|---|---|---|
| WO | 2003/020722 A1 | 3/2003 |
| WO | 2003/079986 A2 | 10/2003 |

(Continued)

OTHER PUBLICATIONS

Williams et al. Foye's Principles of Medicinal Chemistry, 5th edition, pp. 50 and 59-61, 2002.*
Woo, et al., "Biological Evaluation of Tanshindiols as EZH2 Histone Methyltransferase Inhibitors," Bioorganic & Medicinal Chemistry Letters, 24(11), 2014, 2486-2492.
Knutson et al., "Selective Inhibition of EZH2 by EPZ-6438 Leads to Potent Antitumor Activity in EZH2-Mutant Non-Hodgkin Lymphoma," Molecular Cancer Therapeutics, 13(4), 2014, 842-854.
Amatangelo et al., "Three-Dimensional Culture Sensitizes Epithelial Ovarian Cancer Cells to EZH2 Methyltransferase Inhibition," Cell Cycle, 12(13), 2013, 2113-2119.
Van Aller, et al., "Long Residence Time Inhibition of EZH2 in Activated Polycomb Repressive Complex 2," ACS Chem. Biol., 9(3), 2014, 622-629.
Knutson, et al., "Durable Tumor Regression in Genetically Altered Malignant Rhabdoid Tumors by Inhibition of Methyltransferase EZH2," Proceedings of the National Academy of Sciences of the United States of America, 110(19), 2013, 7922-7927.

(Continued)

*Primary Examiner* — Anna Pagonakis
(74) *Attorney, Agent, or Firm* — McCarter & English, LLP; Steven G. Davis; Michael J. DeGrazia

(57) ABSTRACT

Agents for modulating methyl modifying enzymes, compositions and uses thereof are provided herein.

21 Claims, No Drawings

(56) References Cited

U.S. PATENT DOCUMENTS

| | | |
|---|---|---|
| 2014/0107122 A1 | 4/2014 | Kuntz et al. |
| 2014/0142083 A1 | 5/2014 | Kuntz et al. |
| 2015/0368229 A1 | 12/2015 | Albrecht et al. |
| 2015/0376190 A1 | 12/2015 | Albrecht et al. |
| 2016/0009718 A1 | 1/2016 | Albrecht et al. |
| 2016/0333016 A1 | 11/2016 | Albrecht et al. |

FOREIGN PATENT DOCUMENTS

| | | | |
|---|---|---|---|
| WO | 2007/011626 | A2 | 1/2007 |
| WO | 2007/014838 | A1 | 2/2007 |
| WO | 2007/067968 | A2 | 6/2007 |
| WO | 2009/006577 | A2 | 1/2009 |
| WO | 2009/087285 | A1 | 7/2009 |
| WO | 2009/153721 | A1 | 12/2009 |
| WO | 2011/131741 | A1 | 10/2011 |
| WO | 2011/140324 | A1 | 11/2011 |
| WO | 2011/140325 | A1 | 11/2011 |
| WO | 2012/005805 | A1 | 1/2012 |
| WO | 2012/024543 | A1 | 2/2012 |
| WO | 2012/051492 | A2 | 4/2012 |
| WO | 2012/068589 | A2 | 5/2012 |
| WO | 2012/075080 | A1 | 6/2012 |
| WO | 2012/115885 | A1 | 8/2012 |
| WO | 2012/118812 | A2 | 9/2012 |
| WO | 2013/039988 | A1 | 3/2013 |
| WO | 2013/049770 | A2 | 4/2013 |
| WO | 2013/067296 | A1 | 5/2013 |
| WO | 2013/067300 | A1 | 5/2013 |
| WO | 2013/067302 | A1 | 5/2013 |
| WO | 2013/075083 | A1 | 5/2013 |
| WO | 2013/075084 | A1 | 5/2013 |
| WO | 2013/078320 | A1 | 5/2013 |
| WO | 2013/120104 | A2 | 8/2013 |
| WO | 2013/138361 | A1 | 9/2013 |
| WO | 2013/155317 | A1 | 10/2013 |
| WO | 2013/155464 | A1 | 10/2013 |
| WO | 2013/173441 | A2 | 11/2013 |
| WO | 2014/049488 | A1 | 4/2014 |
| WO | 2014/062720 | A2 | 4/2014 |
| WO | 2014/062733 | A2 | 4/2014 |
| WO | 2014/071109 | A1 | 5/2014 |
| WO | 2014/077784 | A1 | 5/2014 |
| WO | 2014/085666 | A1 | 6/2014 |
| WO | 2014/092905 | A1 | 6/2014 |
| WO | 2014/097041 | A1 | 6/2014 |
| WO | 2014/100080 | A1 | 6/2014 |
| WO | 2014/124418 | A1 | 8/2014 |
| WO | 2014/151142 | A1 | 9/2014 |
| WO | 2015/023915 | A1 | 2/2015 |
| WO | 2015/200650 | A1 | 12/2015 |

OTHER PUBLICATIONS

Qi, et al., "Selective Inhibition of Ezh2 by a Small Molecule Inhibitor Blocks Tumor Cells Proliferation," Proceedings of the National Academy of Sciences of the United States of America, 109(52), 2012, 21360-21365.

Verma, et al., "Identification of Potent, Selective, Cell-Active Inhibitors of the Histone Lysine Methyltransferase EZH2," ACS Medicinal Chemistry Letters, 3(12), 2012, 1091-1096.

McCabe, et al., "EZH2 Inhibition as a Therapeutic Strategy for Lymphoma with EZH2-Activating Mutations," Nature, 492(7427), 2012, 108-112.

Knutson, et al., "A Selective Inhibitor of EZH2 Blocks H3K27 Methylation and Kills Mutant Lymphoma Cells," Nature Chemical Biology, 8(11), 2012, 890-896.

Alexei Vazquez, "Optimization of Personalized Therapies for Anticancer Treatment," BMC Systems Biology, 2013, 7:31, 11 pages, http://www.biomedcentral.com/1752-0509/7/31.

Konze, et al., "An Orally Bioavailable Chemical Probe of the Lysine Methyltransferases EZH2 and EZH1," ACS Chemical Biology, (2013), 8(6), 1324-1334, CAPLUS, DOI: 10.1021/cb400133j.

Fiskus, et al., "Combined Epigenetic Therapy with the Histone Methyltransferase EZH2 Inhibitor 3-Deazaneplanocin A and the Histone Deacetylase Inhibitor Panobinostat Against Human AML Cells," Blood, Sep. 24, 2009, 114:13, pp. 2733-2743.

Fiskus, et al., "Histone Deacetylase Inhibitors Deplete Enhancer of Zeste 2 and Associated Polycomb Repressive Complex 2 Proteins in Human Acute Leukemia Cells," Molecular Cancer Therapeutics, 2006;5:3096-3104.

International Search Report, International Application No. PCT/US2013/025639, International Filing Date Feb. 11, 2013, dated May 8, 2013, 9 pages.

PubChem Compound Summary for CID 6918837, Jul. 28, 2006, 2 pages.

Yap, et al., "Somatic mutations at EZH2 Y641 act dominantly through a mechanism of selectively altered PRC2 catalytic activity, to increase H3K27 trimethylation," Blood, vol. 117, No. 8, Feb. 24, 2011, pp. 2451-2459.

PubChem Compound Summary for CID 40170690, May 30, 2009, 2 pages.

PubChem Compound Summary for CID 50961558, Mar. 29, 2011, 2 pages.

PubChem Compound Summary for CID 73087, Aug. 1, 2005, 2 pages.

Spannhoff, et al., "The Emerging Therapeutic Potential of Histone Methyltransferase and Demethylase Inhibitors," Chem Med Chem, 2009, 4:1568-1582.

Extended European Search Report issued in European Application No. 13746186.9, dated Aug. 5, 2015. 6 pages.

Ito et al., "A Medium-term Rat Liver Bioassay for Rapid in Vivo Detection of Carcinogenic Potential of Chemicals" Cancer Science 94(1), 3-8 (2003).

Registry, May 25, 2011, RN: 1300453-83-1.
Registry, Sep. 1, 2011, RN: 1326727-17-6.
Registry, Sep. 2, 2011, RN: 1327055-57-1.
Registry, Sep. 4, 2011, RN: 1328132-30-4.
Registry, Sep. 5, 2011, RN: 1328462-28-7.
Registry, Sep. 29, 2011, RN: 1333889-30-7.
Registry, Sep. 6, 2011, RN 1328976-87-9.
Registry, Sep. 7, 2011, RN 1329352-49-9.
Registry, Sep. 7, 2011, RN: 1329234-68-5.

STN registry database compound 1002886-67-0 from the Zinc (Soichet Laboratory) (entered STN on Feb. 12, 2008).

STN registry database compound 950111-40-7 from Chemical Library Supplier Enamine (entered STN on Oct. 10, 2007).

Venkatesh et al., "Role of the Development Scientist in Compound Lead Selection and Optimization" J. Pharm. Sci. vol. 89, No. 2, 145-154 (2000).

U.S. Appl. No. 13/988,180, filed Aug. 5, 2013, (National Stage of PCT/US2011/061740).

U.S. Appl. No. 14/358,558, filed May 15, 2014, U.S. Pat. No. 9,206,128 (National Stage of PCT/US2012/065796).

U.S. Appl. No. 14/358,455, filed May 15, 2014, (National Stage of PCT/US2012/065797).

U.S. Appl. No. 14/707,874, filed May 8, 2015, U.S. Pat. No. 9,409,865 (continuation of U.S. Appl. No. 14/358,455).

U.S. Appl. No. 14/839,273, filed Aug. 28, 2015, U.S. Pat. No. 9,469,646.

U.S. Appl. No. 15/257,275, filed Sep. 6, 2016, (continuation of U.S. Appl. No. 14/839,273).

U.S. Appl. No. 14/377,214, filed Aug. 7, 2014, U.S. Pat. No. 9,085,583 (National Stage of PCT/US2013/025639).

U.S. Appl. No. 14/661,797, filed Mar. 18, 2015, U.S. Pat. No. 9,371,331 (continuation of U.S. Appl. No. 14/377,214).

U.S. Appl. No. 15/155,749, filed May 16, 2016, (continuation of U.S. Appl. No. 14/661,797).

U.S. Appl. No. 14/769,471, filed Aug. 21, 2015, (National Stage of PCT/US2014/025081).

CAS Registry No. 1061629-12-6 (Jul. 15, 2014).
CAS Registry No. 1100242-53-2 (Jul. 15, 2014).
CAS Registry No. 1118826-71-3 (Jul. 15, 2014).
CAS Registry No. 1269034-31-2 (Jul. 15, 2014).
CAS Registry No. 1269039-62-4 (Jul. 15, 2014).
CAS Registry No. 1278089-62-5 (Jul. 15, 2014).

(56) References Cited

OTHER PUBLICATIONS

CAS Registry No. 1290560-58-5 (Jul. 15, 2014).
Shared, K. Verma et al, "Identification of Potent, Selective, Cell-Active Inhibitors of the Histone Lysine Methyltransferase EZH2", ACS Medicinal Chemistry Letters, vol. 2, No. 12, Dec. 13, 2012, pp. 1091-1096.
STN registry database compound 322425-80-9 (entered STN on Feb. 20, 2001).
Copending U.S. Appl. No. 15/257,275, filed Sep. 6, 2016, Modulators of Methyl Modifying Enzymes, Compositions and Uses Thereof.

\* cited by examiner

INDOLE DERIVATIVES AS MODULATORS OF METHYL MODIFYING ENZYMES, COMPOSITIONS AND USES THEREOF

CROSS-REFERENCE TO RELATED APPLICATIONS

This application is a 35 U.S.C. § 371 national stage filing of PCT?US2014/051201, filed Aug. 15, 2014, which claims priority to U.S. Provisional Application No. 61/866,224, filed Aug. 15, 2013. The entire contents of each of the foregoing applications are incorporated herein by reference.

BACKGROUND OF THE INVENTION

Eukaryotic chromatin is composed of macromolecular complexes called nucleosomes. A nucleosome has 147 base pairs of DNA wrapped around a protein octamer having two subunits of each of histone protein H2A, H2B, H3, and H4. Histone proteins are subject to post-translational modifications which in turn affect chromatin structure and gene expression. One type of post-translational modification found on histones is methylation of lysine and arginine residues. Histone methylation plays a critical role in the regulation of gene expression in eukaryotes. Methylation affects chromatin structure and has been linked to both activation and repression of transcription (Zhang and Reinberg, Genes Dev. 15:2343-2360, 2001). Enzymes that catalyze attachment and removal of methyl groups from histones are implicated in gene silencing, embryonic development, cell proliferation, and other processes.

One class of histone methylases is characterized by the presence of a SET domain, comprising about 130 amino acids. EZH2 is an example of a human SET-domain containing methylase. EZH2 associates with EED (Embryonic Ectoderm Development) and SUZ12 (suppressor of zeste 12 homolog) to form a complex known as PRC2 (Polycomb Group Repressive Complex 2) having the ability to trimethylate histone H3 at lysine 27 (Cao and Zhang, Mol. Cell 15:57-67, 2004). PRC2 complexes can also include RBAP46 and RBAP48 subunits. Another example is the related methylase EZH1.

The oncogenic activities of EZH2 have been shown by a number of studies. In cell line experiments, over-expression of EZH2 induces cell invasion, growth in soft agar, and motility while knockdown of EZH2 inhibits cell proliferation and cell invasion (Kleer et al., 2003, Proc. Nat. Acad. Sci. USA 100:11606-11611; Varambally et al., (2002), "The polycomb group protein EZH2 is involved in progression of prostate cancer," Nature 419, 624-629). It has been shown that EZH2 represses the expression of several tumor suppressors, including E-cadherin, DAB2IP and RUNX3 among others. In xenograft models, EZH2 knockdown inhibits tumor growth and metastasis. Recently, it has been shown that down modulation of EZH2 in murine models blocks prostate cancer metastasis (Min et al., "An oncogene-tumor suppressor cascade drives metastatic prostate cancer by coordinately activating Ras and nuclear factor—kappaB," Nat Med. 2010 March; 16(3):286-94). EZH2 overexpression is associated with aggressiveness of certain cancers such as breast cancer (Kleer et al., Proc. Nat. Acad. Sci. USA 100:11606-11611, 2003). Recent studies also suggest that prostate cancer specific oncogenic fusion gene TMPRSS2-ERG induces repressive epigenetic programs via direct activation of EZH2 (Yu et al., "An Integrated Network of Androgen Receptor, Polycomb, and TMPRSS2-ERG Gene Fusions in Prostate Cancer Progression," Cancer Cell. 2010 May 18; 17(5):443-454).

SUMMARY OF THE INVENTION

The present disclosure encompasses the recognition that methyl modifying enzymes, in particular EZH2 and mutant forms thereof, are an attractive target for modulation, given their role in the regulation of diverse biological processes. It has now been found that compounds of this invention, and pharmaceutically acceptable compositions thereof, are effective as agents that modulate the activity of EZH2 and, in some cases, EZH1. In some embodiments, the present invention provides a compound having structural formula I:

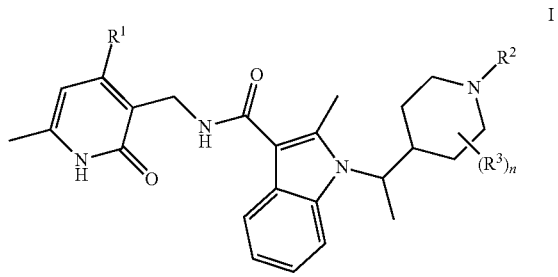

or a substantially pure enantiomer thereof, or a pharmaceutically acceptable salt of either of the foregoing, wherein each variable is independently as defined above and described herein.

In some embodiments, the present invention provides a compound having structural formula II:

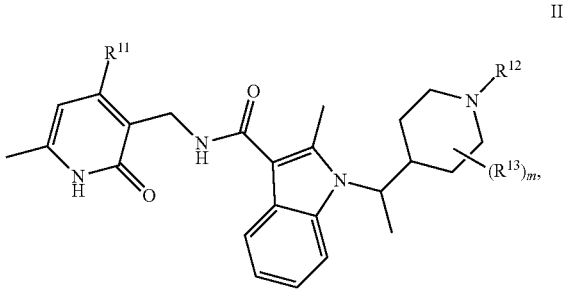

or a substantially pure enantiomer thereof, or a pharmaceutically acceptable salt of either of the foregoing, wherein each variable is independently as defined above and described herein.

In some embodiments, the present invention provides a compound having structural formula III:

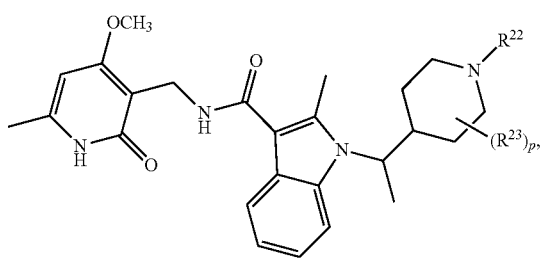

or a substantially pure enantiomer thereof, or a pharmaceutically acceptable salt of either of the foregoing, wherein each variable is independently as defined above and described herein.

In some embodiments, a provided compound is set forth in Table 1 or Table 2, infra,
or a pharmaceutically acceptable salt thereof.

Compounds of the present invention, and pharmaceutically acceptable compositions thereof, are useful for treating a variety of diseases, disorders or conditions, associated with a methyl modifying enzyme. Such diseases, disorders, or conditions include those described herein.

Compounds provided by this invention are also useful for the study of methyl modifying enzymes in biological and pathological phenomena; the study of intracellular signal transduction pathways mediated by methyl modifying enzymes and the comparative evaluation of new methyl modifying enzyme modulators.

DETAILED DESCRIPTION OF CERTAIN EMBODIMENTS

1. General Description of Compounds of the Invention

In certain embodiments, the present invention provides a compound of formula I:

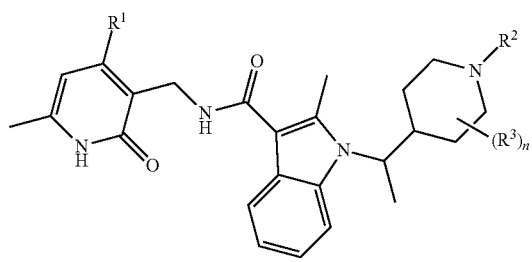

or a substantially pure enantiomer thereof, or a pharmaceutically acceptable salt of either of the foregoing, wherein:
$R^1$ is selected from —Cl, —$CH_3$, —$CH_2CH_3$, —$CH_2CH_2CH_3$, —$NH(CH_3)$, —$OCH_3$, —$OCHF_2$, —$OCF_3$, and —$OCH_2CF_3$;
$R^2$ is selected from -aryl, -cycloalkyl, —$CH_2$-aryl, —$CH_2$-heteroaryl, —$CH_2$-cycloalkyl, —$CH_2CH_2$-heterocyclyl, —$S(O)_2$-aryl, —$S(O)_2$-heteroaryl, —$S(O)_2$-cycloalkyl, —$S(O)_2$-heterocyclyl, —$S(O)_2$—$CH_2CH_2$-heterocyclyl, —$C(O)$-cycloalkyl, —$C(O)$-aryl, —$C(O)$-heterocyclyl, —$C(O)$—$CH_2$-aryl, —$C(O)$—$CH_2$-heteroaryl, —$C(O)$—$N(CH_3)_2$, —$C(O)$—$[OCH_2CH_2]_{2\text{-}6}$-$OCH_3$, —$C(O)CH_2CN$, —$C(O)CH_2CH_2CH_3$, —$C(O)CH_2CH(CH_3)_2$, —$CH_2CH_2CN$, —$CH_2CH_2S(O)_2CH_3$, —$CH_2S(O)_2CH_3$, —$CH_2CH_2NHC(O)CH_3$, —$CH_2CH(OCH_3)CF_3$, —$CH_2CH_2CH_2CF_3$, —$CH_2CH(OH)CF_3$, —$CH(CH_2F)CH_2F$, and —$R^4$—$C(R^5)(R^6)$—$R^7$, wherein:
$R^4$ is selected from —$CH_2$—, —$CH(CH_3)$—, —$C(CH_3)_2$—, —$C(O)$— and —$S(O)_2$—;
each of $R^5$ and $R^6$ is independently selected from fluoro, —$CH_3$, and —$CH_2CH_3$, or $R^5$ and $R^6$ are taken together to form =O;
$R^7$ is selected from hydrogen, fluoro, —CN, —$CH_3$, —$CH_2OH$, —$CH_2OCH_3$, —$CF_2H$, —$CFH_2$, —$CF_3$, —$CF_2CH_3$, —$CH_2CH_3$, —$OCH_3$, and —$N(C_1\text{-}C_3$ alkyl$)_2$, and
any aryl, heteroaryl, heterocyclyl or cycloalkyl portion of $R^2$ is optionally substituted with up to two substituents independently selected from bromo, chloro, fluoro, —CN, —$CH_3$, —$CF_3$, —$C(O)CH_3$, and morpholin-4-ylmethyl;
each $R^3$, when present, is independently selected from =O and fluoro;
n is 0, 1, 2, 3, or 4; and wherein:
when n is 0, $R^1$ is —$CH_3$, —$CH_2CH_3$, —$OCH_3$, or —$OCHF_2$, $R^5$ is fluoro, and $R^6$ is fluoro, then $R^7$ is other than fluoro;
when n is 0, $R^1$ is —$CH_3$, —$CH_2CH_3$, —$OCH_3$, or —$OCHF_2$, $R^5$ is —$CH_3$, and $R^6$ is —$CH_3$, then $R^7$ is other than hydrogen; and
the compound is other than:

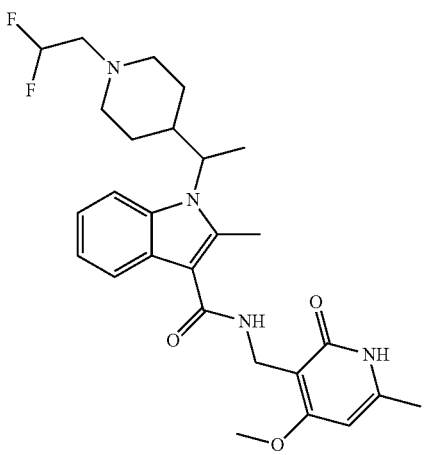

or a substantially pure enantiomer thereof or a pharmaceutically acceptable salt thereof.

In some embodiments, the present invention provides a compound having structural formula II:

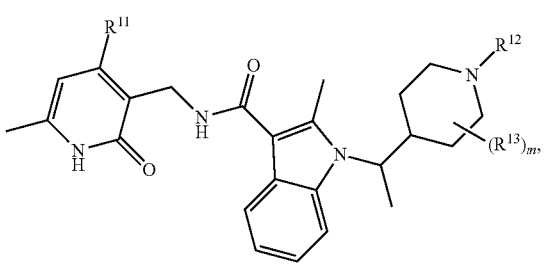

or a substantially pure enantiomer thereof, or a pharmaceutically acceptable salt of either of the foregoing, wherein:

$R^{11}$ is selected from Cl, —CH$_3$, —CH$_2$CH$_3$, —CH$_2$CH$_2$CH$_3$, —NH(CH$_3$), —OCH$_3$, —OCHF$_2$, —OCF$_3$, and —OCH$_2$CF$_3$;

$R^{12}$ is selected from optionally substituted pyridin-3-yl; optionally substituted pyrimidin-4-yl; optionally substituted pyrazin-2-yl; pyridin-2-yl substituted with one or more substituents independently selected from halo, methyl and morpholin-4-ylmethyl; pyrimidin-2-yl substituted with one or more substituents independently selected from halo, methyl and morpholin-4-ylmethyl; oxetan-3-yl substituted with one or more fluoro; and azetidin-3-yl substituted with acetyl;

each $R^{13}$, when present, is independently selected from =O and fluoro; and m is 0, 1, 2, 3, or 4.

In some embodiments, the present invention provides a compound having structural formula III:

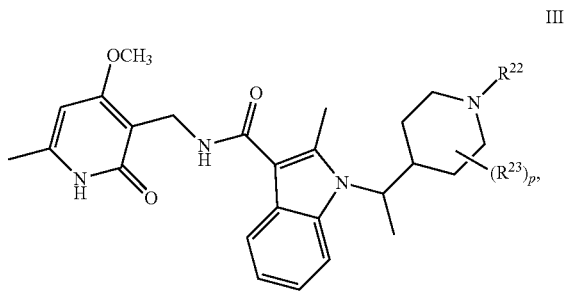

III or a substantially pure enantiomer thereof, or a pharmaceutically acceptable salt of either of the foregoing, wherein:

$R^{22}$ is selected from hydrogen and methyl; and each $R^{23}$ is selected from halo or C$_1$-C$_4$ alkyl, or $R^{22}$ and one $R^{23}$ bound to an adjacent carbon atom are taken together to form a heterocyclyl or heteroaryl fused to the piperidine ring, wherein the fused ring is optionally substituted with methyl or =O; and p is 1, 2, 3 or 4.

2. Compounds and Definitions

Definitions of specific functional groups and chemical terms are described in more detail below. For purposes of this invention, the chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; Carruthers, *Some Modern Methods of Organic Synthesis*, 3$^{rd}$ Edition, Cambridge University Press, Cambridge, 1987; the entire contents of each of which are incorporated herein by reference.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}$C- or $^{14}$C-enriched carbon are within the scope of this invention. Such compounds are useful, for example, as analytical tools, as probes in biological assays, or as therapeutic agents in accordance with the present invention.

Where a particular enantiomer is preferred, it may, in some embodiments be provided substantially free of the corresponding enantiomer, and may also be referred to as "optically enriched." "Optically-enriched," as used herein, means that the compound is made up of a significantly greater proportion of one enantiomer. In certain embodiments the compound is made up of at least about 90% by weight of a preferred enantiomer. In other embodiments the compound is made up of at least about 95%, 98%, or 99% by weight of a preferred enantiomer. Preferred enantiomers may be isolated from racemic mixtures by any method known to those skilled in the art, including chiral high pressure liquid chromatography (HPLC) and the formation and crystallization of chiral salts or prepared by asymmetric syntheses. See, for example, Jacques et al., *Enantiomers, Racemates and Resolutions* (Wiley Interscience, New York, 1981); Wilen, et al., *Tetrahedron* 33:2725 (1977); Eliel, E. L. *Stereochemistry of Carbon Compounds* (McGraw-Hill, N Y, 1962); Wilen, S. H. *Tables of Resolving Agents and Optical Resolutions* p. 268 (E. L. Eliel, Ed., Univ. of Notre Dame Press, Notre Dame, Ind. 1972).

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR$^+$ (as in N-substituted pyrrolidinyl)).

As used herein a "direct bond" or "covalent bond" refers to a single, double or triple bond. In certain embodiments, a "direct bond" or "covalent bond" refers to a single bond.

The terms "halo" and "halogen" as used herein refer to an atom selected from fluorine (fluoro, —F), chlorine (chloro, —Cl), bromine (bromo, —Br), and iodine (iodo, —I).

The term "aliphatic" or "aliphatic group", as used herein, denotes a hydrocarbon moiety that may be straight-chain (i.e., unbranched), branched, or cyclic (including fused, bridging, and spiro-fused polycyclic) and may be completely saturated or may contain one or more units of unsaturation, but which is not aromatic. Unless otherwise specified, aliphatic groups contain 1-6 carbon atoms. In some embodiments, aliphatic groups contain 1-4 carbon atoms, and in yet other embodiments aliphatic groups contain 1-3 carbon atoms. Suitable aliphatic groups include, but are not limited to, linear or branched, alkyl, alkenyl, and alkynyl groups, and hybrids thereof such as (cycloalkyl) alkyl, (cycloalkenyl)alkyl or (cycloalkyl)alkenyl.

The term "unsaturated", as used herein, means that a moiety has one or more units of unsaturation.

As used herein, the term "bivalent $C_{1-8}$ (or $C_{1-6}$) saturated or unsaturated, straight or branched, hydrocarbon chain", refers to bivalent alkylene, alkenylene, and alkynylene chains that are straight or branched as defined herein.

The term "alkylene" refers to a bivalent alkyl group. An "alkylene chain" is a polymethylene group, i.e., —$(CH_2)_n$—, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

The term "alkenylene" refers to a bivalent alkenyl group. A substituted alkenylene chain is a polymethylene group containing at least one double bond in which one or more hydrogen atoms are replaced with a substituent. Suitable substituents include those described below for a substituted aliphatic group.

The term "alkynylene" refers to a bivalent alkynyl group.

The term "methylene unit" refers to a divalent —$CH_2$— group present in an alkyl, alkenyl, alkynyl, alkylene, alkenylene, or alkynylene moiety.

The term "$C_0$ alkylene" as used herein means a bond. Thus, a moiety defined herein as "—($C_0$-$C_6$ alkylene)-aryl" includes both -aryl (i.e., $C_0$ alkylene-aryl) and —($C_1$-$C_6$ alkylene)-aryl.

The term "alkyl," as used herein, refers to a monovalent saturated, straight- or branched-chain hydrocarbon radical derived from an aliphatic moiety containing between one and six carbon atoms by removal of a single hydrogen atom. In some embodiments, alkyl contains 1-5 carbon atoms. In another embodiment, alkyl contains 1-4 carbon atoms. In still other embodiments, alkyl contains 1-3 carbon atoms. In yet another embodiment, alkyl contains 1-2 carbons. Examples of alkyl radicals include, but are not limited to, methyl, ethyl, n-propyl, isopropyl, n-butyl, iso-butyl, sec-butyl, sec-pentyl, iso-pentyl, tert-butyl, n-pentyl, neopentyl, n-hexyl, sec-hexyl, and the like.

The term "alkenyl," as used herein, denotes a monovalent group derived from a straight- or branched-chain aliphatic moiety having at least one carbon-carbon double bond by the removal of a single hydrogen atom. In certain embodiments, alkenyl contains 2-6 carbon atoms. In certain embodiments, alkenyl contains 2-5 carbon atoms. In some embodiments, alkenyl contains 2-4 carbon atoms. In another embodiment, alkenyl contains 2-3 carbon atoms. Alkenyl groups include, for example, ethenyl ("vinyl"), propenyl ("allyl"), butenyl, 1-methyl-2-buten-1-yl, and the like.

The term "alkynyl," as used herein, refers to a monovalent group derived from a straight- or branched-chain aliphatic moiety having at least one carbon-carbon triple bond by the removal of a single hydrogen atom. In certain embodiments, alkynyl contains 2-6 carbon atoms. In certain embodiments, alkynyl contains 2-5 carbon atoms. In some embodiments, alkynyl contains 2-4 carbon atoms. In another embodiment, alkynyl contains 2-3 carbon atoms. Representative alkynyl groups include, but are not limited to, ethynyl, 2-propynyl ("propargyl"), 1-propynyl, and the like.

The term "carbocyclyl" (also referred to herein as "carbocycle" "cycloaliphatic" or "cycloalkyl"), as used herein, means a monocyclic hydrocarbon or bicyclic hydrocarbon that is completely saturated or that contains one or more units of unsaturation, but where there is no ring is aromatic.

The term "aryl" used alone or as part of a larger moiety as in "aralkyl", "aralkoxy", or "aryloxyalkyl", refers to monocyclic and bicyclic carbon ring systems having a total of five to 10 ring members, wherein at least one ring in the system is aromatic and wherein each ring in the system contains three to seven ring members. The term "aryl" may be used interchangeably with the term "aryl ring". In certain embodiments of the present invention, "aryl" refers to an aromatic ring system which includes, but not limited to, phenyl, biphenyl, naphthyl, anthracyl and the like, which may bear one or more substituents. Also included within the scope of the term "aryl", as it is used herein, is a group in which an aromatic ring is fused to one or more carbocyclyl rings regardless of whether the aromatic carbon ring or the carbocyclic ring is the pendant ring, or a group in which an aromatic carbon ring is fused to one or more heteroaryl or heterocyclyl, rings, such as indanyl, phthalimidyl, naphthimidyl, phenantriidinyl, or tetrahydronaphthyl, and the like, wherein the pendant ring of the fused ring system is the aromatic carbon ring.

The terms "heteroaryl" and "heteroar-", used alone or as part of a larger moiety, e.g., "heteroaralkyl", or "heteroaralkoxy", refer to groups having 5 to 10 ring atoms, preferably 5, 6, or 9 ring atoms; having 6, 10, or 14 π electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, wherein the pendant ring of the fused ring system is heteroaromatic. Non-limiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, 5,6,7,8-tetrahydroquinolinyl, 5,6,7,8-tetrahydroisoquinolinyl, and pyrido[2,3-b]-1,4-oxazin-3(4H)-one. A heteroaryl group may be mono- or bicyclic. The term "heteroaryl" may be used interchangeably with the terms "heteroaryl ring", "heteroaryl group", or "heteroaromatic", any of which terms include rings that are optionally substituted. The term "heteroaralkyl" refers to an alkyl group substituted by a heteroaryl, wherein the alkyl and heteroaryl portions independently are optionally substituted. The term "heteroarylene" refers to a bivalent mono- or bicyclic heteroaryl ring.

As used herein, the terms "heterocycle", "heterocyclyl", "heterocyclic radical", and "heterocyclic ring" are used interchangeably and refer to a stable 4- to 7-membered monocyclic or 7-10-membered bicyclic heterocyclic moiety that is either saturated or partially unsaturated, and having, in addition to carbon atoms, one or more, preferably one to four, heteroatoms, as defined above. In certain embodiments, a "heterocycle", group is a 1,1'-heterocyclylene group (i.e., a spiro-fused ring). When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $^+$NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothienyl, pyrrolidinyl, pyrrolidonyl, piperidinyl, pyrrolinyl, 1,2,3,4-tetrahydroquinolinyl, 1,2,3,4-tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle", "heterocyclyl", "heterocyclyl ring", "heterocyclic group", "heterocyclic moiety", and "heterocyclic radical", are used interchangeably herein, and also include groups in which a heterocyclyl ring is fused to one or more aryl, heteroaryl, or cycloaliphatic rings, such as indolinyl, 3H-indolyl, chromanyl, phenanthridinyl, 2-azabicyclo [2.2.1]heptanyl, octahydroindolyl, or tetrahydroquinolinyl, wherein the pendant ring of the fused ring system is heterocyclyl. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond between ring atoms but is not aromatic. The term "partially unsaturated" is intended to encompass rings having multiple sites of unsaturation, but is not intended to include aryl or heteroaryl moieties, as herein defined.

As used herein, the terms "carbocyclylene" or "cycloalkylene" are used interchangeably and refer to a bivalent carbocyclyl or cycloalkyl group. In certain embodiments, a carbocyclylene or cycloalkylene group is a 1,1-cycloalkylene group (i.e., a spiro-fused ring). Exemplary 1,1-cycloalkylene groups include

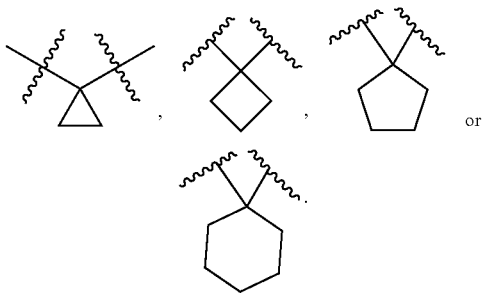

In other embodiments, a cycloalkylene group is a 1,2-cycloalkylene group or a 1,3-cycloalkylene group. Exemplary 1,2-cycloalkylene groups include

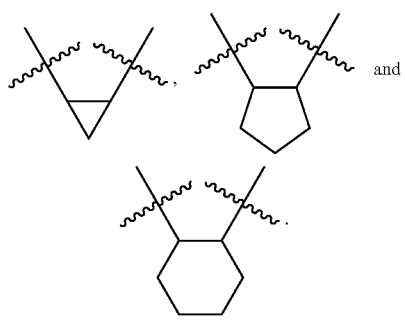

Exemplary 1,3-cycloalkylene groups include

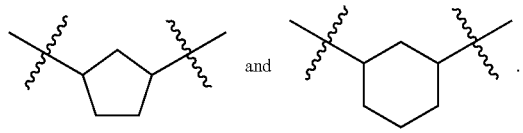

As described herein, compounds of the invention may contain "optionally substituted" moieties. In general, the term "substituted", whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at each position. Combinations of substituents envisioned under this invention are preferably those that result in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; —(CH$_2$)$_{0-4}$R°; —(CH$_2$)$_{0-4}$OR°; —O—(CH$_2$)$_{0-4}$C(O)OR°; —(CH$_2$)$_{0-4}$CH(OR°)$_2$; —(CH$_2$)$_{0-4}$SR°; —(CH$_2$)$_{0-4}$Ph, which may be substituted with R°; —(CH$_2$)$_{0-4}$O(CH$_2$)$_{0-1}$Ph which may be substituted with R°; —CH=CHPh, which may be substituted with R°; —NO$_2$; —CN; —N$_3$; —(CH$_2$)$_{0-4}$N(R°)$_2$; —(CH$_2$)$_{0-4}$N(R°)C(O)R°; —N(R°)C(S)R°; —(CH$_2$)$_{0-4}$N(R°)C(O)NR°$_2$; —N(R°)C(S)NR°$_2$; —(CH$_2$)$_{0-4}$N(R°)C(O)OR°; —N(R°)N(R°)C(O)R°; —N(R°)N(R°)C(O)NR°$_2$; —N(R°)N(R°)C(O)OR°; —(CH$_2$)$_{0-4}$C(O)R°; —C(S)R°; —(CH$_2$)$_{0-4}$C(O)O R°; —(CH$_2$)$_{0-4}$C(O)SR°; —(CH$_2$)$_{0-4}$C(O)OSiR°$_3$; —(CH$_2$)$_{0-4}$OC(O)R°; —OC(O)(CH$_2$)$_{0-4}$SR—; —SC(S)SR°; —(CH$_2$)$_{0-4}$SC(O)R°; —(CH$_2$)$_{0-4}$C(O)NR°$_2$; —C(S)NR°$_2$; —C(S)SR°; —SC(S)SR°; —(CH$_2$)$_{0-4}$OC(O)NR°$_2$; —C(O)N(OR°)R°; —C(O)C(O)R°; —C(O)CH$_2$C(O)R°; —C(NOR°)R°; —(CH$_2$)$_{0-4}$SSR°; —(CH$_2$)$_{0-4}$S(O)$_2$R°; —(CH$_2$)$_{0-4}$S(O)$_2$OR°; —(CH$_2$)$_{0-4}$OS(O)$_2$R°; —S(O)$_2$NR°$_2$; —(CH$_2$)$_{0-4}$S(O)R°; —N(R°)S(O)$_2$NR°$_2$; —N(R°)S(O)$_2$R°; —N(OR°)R°; —C(NH)NR°$_2$; —P(O)$_2$R°; —P(O)R°$_2$; —OP(O)R°$_2$; —OP(O)(OR°)$_2$; —SiR°$_3$; —(C$_{1-4}$ straight or branched)alkylene)O—N(R°)$_2$; or —(C$_{1-4}$ straight or branched)alkylene)C(O)O—N(R°)$_2$, wherein each R° may be substituted as defined below and is independently hydrogen, C$_{1-6}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur, or, notwithstanding the definition above, two independent occurrences of R°, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on R° (or the ring formed by taking two independent occurrences of R° together with their intervening atoms), are independently halogen, —(CH$_2$)$_{0-2}$R$^\bullet$, (haloR$^\bullet$), —(CH$_2$)$_{0-2}$OH, —(CH$_2$)$_{0-2}$OR$^\bullet$, —(CH$_2$)$_{0-2}$CH(OR$^\bullet$)$_2$; —O(haloR$^\bullet$), —CN, —N$_3$, —(CH$_2$)$_{0-2}$C(O)R$^\bullet$, —(CH$_2$)$_{0-2}$C(O)OH, —(CH$_2$)$_{0-2}$C(O)OR$^\bullet$, —(CH$_2$)$_{0-2}$SR$^\bullet$, —(CH$_2$)$_{0-2}$SH, —(CH$_2$)$_{0-2}$NH$_2$, —(CH$_2$)$_{0-2}$NHR$^\bullet$, —(CH$_2$)$_{0-2}$NR$^\bullet{}_2$, —NO$_2$, —OSiR$^\bullet{}_3$, —C(O)SR$^\bullet$, —(C$_{1-4}$ straight or branched alkylene)C(O)OR$^\bullet$, or —SSR$^\bullet$ wherein each R$^\bullet$ is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of R$^\circ$ include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet{}_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R$^\dagger$, NR$^\dagger{}_2$, —C(O)R$^\dagger$, —C(O)OR$^\dagger$, —C(O)C(O)R$^\dagger$, —C(O)CH$_2$C(O)R$^\dagger$, —S(O)$_2$R$^\dagger$, —S(O)$_2$NR$^\dagger{}_2$, —C(S)NR$^\dagger{}_2$, —C(NH)NR$^\dagger{}_2$, or —N(R$^\dagger$)S(O)$_2$R$^\dagger$; wherein each R$^\dagger$ is independently hydrogen, C$_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R$^\dagger$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R$^\dagger$ are independently halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet{}_2$, or —NO$_2$, wherein each R$^\bullet$ is unsubstituted or where preceded by "halo" is substituted only with one or more halogens, and is independently C$_{1-4}$aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

As used herein, the term "inhibitor" is defined as a compound that binds to and/or inhibits a target S-adenosylmethionine (SAM) utilizing enzyme with measurable affinity. In certain embodiments, an inhibitor has an IC$_{50}$ and/or binding constant of less about 50 µM, less than about 1 µM, less than about 500 nM, less than about 100 nM, or less than about 10 nM.

The terms "measurable affinity" and "measurably inhibit," as used herein, means a measurable change in activity of at least one SAM utilizing enzyme between a sample comprising a provided compound, or composition thereof, and at least one SAM dependent enzyme, and an equivalent sample comprising at least one SAM dependent enzyme, in the absence of said compound, or composition thereof.

3. Description of Exemplary Compounds

In certain embodiments, the present invention provides a compound of formula I:

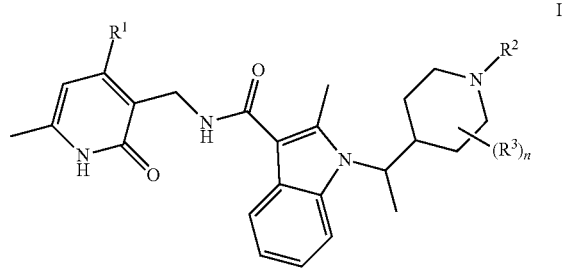

or a substantially pure enantiomer thereof, or a pharmaceutically acceptable salt of either of the foregoing, wherein each variable is independently as defined above and described herein.

As defined generally above and herein, R$^1$ is selected from —Cl, —CH$_3$, —CH$_2$CH$_3$, —CH$_2$CH$_2$CH$_3$, —NH(CH$_3$), —OCH$_3$, —OCHF$_2$, —OCF$_3$, and —OCH$_2$CF$_3$. In some embodiments, R$^1$ is selected from —Cl, —CH$_3$, —CH$_2$CH$_3$, —CH$_2$CH$_2$CH$_3$, —NH(CH$_3$), —OCHF$_2$, —OCF$_3$, and —OCH$_2$CF$_3$. In some embodiments, R$^1$ is selected from —OCH$_3$, chloro, methyl, —OCF$_2$H, —NH(CH$_3$), —CH$_2$CH$_3$, —CH$_2$CH$_2$CH$_3$, and —OCH$_2$CF$_3$. In some embodiments, R$^1$ is selected from —OCH$_3$, chloro, and —OCHF$_2$. In some embodiments, R$^1$ is —Cl. In some embodiments, R$^1$ is —CH$_3$. In some embodiments, R$^1$ is —CH$_2$CH$_3$. In some embodiments, R$^1$ is —CH$_2$CH$_2$CH$_3$. In some embodiments, R$^1$ is —NH(CH$_3$). In some embodiments, R$^1$ is —OCH$_3$. In some embodiments, R$^1$ is —OCHF$_2$. In some embodiments, R$^1$ is —OCF$_3$. In some embodiments, R$^1$ is —OCH$_2$CF$_3$.

As defined generally above and herein, R$^2$ is selected from -aryl, -cycloalkyl, —CH$_2$-aryl, —CH$_2$-heteroaryl, —CH$_2$-cycloalkyl, —CH$_2$CH$_2$-heterocyclyl, —S(O)$_2$-aryl, —S(O)$_2$-heteroaryl, —S(O)$_2$-cycloalkyl, —S(O)$_2$-heterocyclyl, —S(O)$_2$—CH$_2$CH$_2$-heterocyclyl, —C(O)-cycloalkyl, —C(O)-aryl, —C(O)-heterocyclyl, —C(O)—CH$_2$-aryl, —C(O)—CH$_2$-heteroaryl, —C(O)—N(CH$_3$)$_2$, —C(O)—[OCH$_2$CH$_2$]$_{2-6}$-OCH$_3$, —C(O)CH$_2$CN, —C(O)CH$_2$CH$_3$, —C(O)CH$_2$CH(CH$_3$)$_2$, —CH$_2$CH$_2$CN, —CH$_2$CH$_2$S(O)$_2$CH$_3$, —CH$_2$S(O)$_2$CH$_3$, —CH$_2$CH$_2$NHC(O)CH$_3$, —CH$_2$CH(OCH$_3$)CF$_3$, —CH$_2$CH$_2$CH$_2$CF$_3$, —CH$_2$CH(OH)CF$_3$, —CH(CH$_2$F)CH$_2$F, or —R$^4$—C(R$^5$)(R$^6$)—R$^7$, wherein:
R$^4$ is selected from —CH$_2$—, —CH(CH$_3$)—, —C(CH$_3$)$_2$—, —C(O)— and —S(O)$_2$—;

each of $R^5$ and $R^6$ is independently selected from fluoro, —$CH_3$, and —$CH_2CH_3$, or $R^5$ and $R^6$ are taken together to form =O;

$R^7$ is selected from hydrogen, fluoro, —CN, —$CH_3$, —$CH_2OH$, —$CH_2OCH_3$, —$CF_2H$, —$CFH_2$, —$CF_3$, —$CF_2CH_3$, —$CH_2CH_3$, —$OCH_3$, and —$N(C_1$-$C_3$ alkyl$)_2$, and any aryl, heteroaryl, heterocyclyl or cycloalkyl portion of $R^2$ is optionally substituted with up to two substituents independently selected from bromo, chloro, fluoro, —CN, —$CH_3$, —$CF_3$, —$C(O)CH_3$, and morpholin-4-ylmethyl In some embodiments, $R^2$ is selected from -aryl, -cycloalkyl, —$CH_2$-aryl, —$CH_2$-heteroaryl, —$CH_2$-cycloalkyl, —$CH_2CH_2$-heterocyclyl, —$S(O)_2$-aryl, —$S(O)_2$-heteroaryl, —$S(O)_2$-cycloalkyl, —$S(O)_2$-heterocyclyl, —$S(O)_2$—$CH_2CH_2$-heterocyclyl, —$C(O)$-cycloalkyl, —$C(O)$-aryl, —$C(O)$-heterocyclyl, —$C(O)$—$CH_2$-aryl, —$C(O)$—$CH_2$-heteroaryl, —$C(O)$—$N(CH_3)_2$, —$C(O)$—$[OCH_2CH_2]_{2-6}$-$OCH_3$, —$C(O)CH_2CN$, —$C(O)CH_2CH_2CH_3$, —$C(O)CH_2CH(CH_3)_2$, —$CH_2CH_2CN$, —$CH_2CH_2S(O)_2CH_3$, —$CH_2S(O)_2CH_3$, —$CH_2CH_2NHC(O)CH_3$, —$CH_2CH(OCH_3)CF_3$, —$CH_2CH_2CH_2CF_3$, —$CH_2CH(OH)CF_3$, —$CH(CH_2F)CH_2F$. In some embodiments, $R^2$ is selected from -aryl, -cycloalkyl, —$CH_2$-aryl, —$CH_2$-heteroaryl, —$CH_2$-cycloalkyl, —$CH_2CH_2$-heterocyclyl, —$S(O)_2$-aryl, —$S(O)_2$-heteroaryl, —$S(O)_2$-cycloalkyl, —$S(O)_2$-heterocyclyl, —$S(O)_2$—$CH_2CH_2$-heterocyclyl, —$C(O)$-cycloalkyl, —$C(O)$-aryl, —$C(O)$-heterocyclyl, —$C(O)$—$CH_2$-aryl, —$C(O)$—$CH_2$-heteroaryl. In some embodiments, $R^2$ is selected from —$C(O)$—$N(CH_3)_2$, —$C(O)[OCH_2CH_2]_{2-6}$-$OCH_3$, —$C(O)CH_2CN$, —$C(O)CH_2CH_2CH_3$, —$C(O)CH_2CH(CH_3)_2$, —$CH_2CH_2CN$, —$CH_2CH_2S(O)_2CH_3$, —$CH_2S(O)_2CH_3$, —$CH_2CH_2NHC(O)CH_3$, —$CH_2CH(OCH_3)CF_3$, —$CH_2CH_2CH_2CF_3$, —$CH_2CH(OH)CF_3$, —$CH(CH_2F)CH_2F$.

In some embodiments, $R^2$ is -aryl. In some embodiments, $R^2$ is -cycloalkyl. In some embodiments, $R^2$ is —$CH_2$-aryl. In some embodiments, $R^2$ is —$CH_2$-heteroaryl. In some embodiments, $R^2$ is —$CH_2$-cycloalkyl. In some embodiments, $R^2$ is —$CH_2CH_2$-heterocyclyl. In some embodiments, $R^2$ is —$S(O)_2$-aryl. In some embodiments, $R^2$ is —$S(O)_2$-heteroaryl. In some embodiments, $R^2$ is —$S(O)_2$-cycloalkyl. In some embodiments, $R^2$ is —$S(O)_2$-heterocyclyl. In some embodiments, $R^2$ is —$S(O)_2$—$CH_2CH_2$-heterocyclyl. In some embodiments, $R^2$ is —$C(O)$-cycloalkyl. In some embodiments, $R^2$ is —$C(O)$-aryl. In some embodiments, $R^2$ is —$C(O)$-heterocyclyl. In some embodiments, $R^2$ is —$C(O)$—$CH_2$-aryl. In some embodiments, $R^2$ is —$C(O)$—$CH_2$-heteroaryl. In some embodiments, $R^2$ is —$C(O)$—$N(CH_3)_2$. In some embodiments, $R^2$ is —$C(O)$—$[OCH_2CH_2]_{2-6}$-$OCH_3$. In some embodiments, $R^2$ is —$C(O)CH_2CN$. In some embodiments, $R^2$ is —$C(O)CH_2CH_2CH_3$. In some embodiments, $R^2$ is —$C(O)CH_2CH(CH_3)_2$. In some embodiments, $R^2$ is —$CH_2CH_2CN$. In some embodiments, $R^2$ is —$CH_2CH_2S(O)_2CH_3$. In some embodiments, $R^2$ is —$CH_2S(O)_2CH_3$. In some embodiments, $R^2$ is —$CH_2CH_2NHC(O)CH_3$. In some embodiments, $R^2$ is —$CH_2CH(OCH_3)CF_3$. In some embodiments, $R^2$ is —$CH_2CH_2CH_2CF_3$. In some embodiments, $R^2$ is —$CH_2CH(OH)CF_3$. In some embodiments, $R^2$ is —$CH(CH_2F)CH_2F$.

In some embodiments, $R^2$ is —$R^4$—$C(R^5)(R^6)$—$R^7$, wherein each of $R^4$, $R^5$, $R^6$ and $R^7$ is independently as defined above and described herein.

In some embodiments, $R^2$ is selected from —$(CH_2)_3CF_3$, —$CH_2CH(OH)CF_3$, —$CH_2CH(OCH_3)CF_3$, —$CH_2CF_2H$, —$CH_2CF_2CH_3$, —$CH_2CF_2CH_2CH_3$, —$CH_2CF_2CF_3$, —$CH_2CF_2CF_2H$, —$CH_2C(O)N(CH_2CH_3)_2$, —$CH_2C(O)CH_3$, —$CH_2C(CH_3)_2OCH_3$, —$CH_2C(CH_3)_2F$, —$CH_2C(CH_3)_2CF_3$, —$CH(CFH_2)_2$, —$C(O)N(CH_3)_2$, —$C(O)C(CH_3)_3$, —$C(O)C(CH_3)_2CF_3$, —$C(O)[OCH_2CH_2]_6CH_3$, —$C(O)$—$[OCH_2CH_2]_2CH_3$, —$CH_2$-cyclopropyl, —$S(O)_2$-phenyl, —$S(O)_2$-cyclopropyl, —$C(O)$-phenyl, —$C(O)$-cyclopropyl, azetidin-3-ylsulfonyl, morpholin-4-ylethylsulfonyl, morpholin-4-ylcarbonyl, pyrrolidin-1-ylethylsulfonyl, pyridin-2-ylmethyl, piperidin-4-ylsulfonyl, 4-methylpiperazin-1-ylcarbonyl, 4-fluorophenylsulfonyl, 4-fluorophenylmethyl, 4-fluorophenyl, 4-chlorophenyl, 4-(morpholin-1-ylmethyl)phenyl, 3,5-difluorophenylmethyl, 3-(morpholin-4-ylmethyl)phenyl, 2,6-difluorophenylmethyl, 1-trifluoromethylcycloprop-1-ylmethyl, 1-trifluoromethylcycloprop-1-ylcarbonyl, 1-trifluoromethylcyclobut-1-ylmethyl, 1-trifluoromethylcyclobut-1-ylcarbonyl, 1-methylpiperidin-4-ylsulfonyl, 1-methylazetidin-3-ylsulfonyl, 1-fluorocycloprop-1-ylmethyl, and 1-fluorocyclobut-1-ylmethyl. In some embodiments, $R^2$ is —$(CH_2)_3CF_3$. In some embodiments, $R^2$ is —$CH_2CH(OH)CF_3$. In some embodiments, $R^2$ is —$CH_2CH(OCH_3)CF_3$. In some embodiments, $R^2$ is —$CH_2CF_2H$. In some embodiments, $R^2$ is —$CH_2CF_2CH_3$. In some embodiments, $R^2$ is —$CH_2CF_2CH_2CH_3$. In some embodiments, $R^2$ is —$CH_2CF_2CF_3$. In some embodiments, $R^2$ is —$CH_2CF_2CF_2H$. In some embodiments, $R^2$ is —$CH_2C(O)N(CH_2CH_3)_2$. In some embodiments, $R^2$ is —$CH_2C(O)CH_3$. In some embodiments, $R^2$ is —$CH_2C(CH_3)_2OCH_3$. In some embodiments, $R^2$ is —$CH_2C(CH_3)_2F$. In some embodiments, $R^2$ is —$CH_2C(CH_3)_2CF_3$. In some embodiments, $R^2$ is —$CH(CFH_2)_2$. In some embodiments, $R^2$ is —$C(O)N(CH_3)_2$. In some embodiments, $R^2$ is —$C(O)C(CH_3)_3$. In some embodiments, $R^2$ is —$C(O)C(CH_3)_2CF_3$. In some embodiments, $R^2$ is —$C(O)$—$[OCH_2CH_2]_6CH_3$. In some embodiments, $R^2$ is —$C(O)$—$[OCH_2CH_2]_2CH_3$. In some embodiments, $R^2$ is —$CH_2$-cyclopropyl. In some embodiments, $R^2$ is —$S(O)_2$-phenyl. In some embodiments, $R^2$ is —$S(O)_2$-cyclopropyl. In some embodiments, $R^2$ is —$C(O)$-phenyl. In some embodiments, $R^2$ is —$C(O)$-cyclopropyl. In some embodiments, $R^2$ is azetidin-3-ylsulfonyl. In some embodiments, $R^2$ is morpholin-4-ylethylsulfonyl. In some embodiments, $R^2$ is morpholin-4-ylcarbonyl. In some embodiments, $R^2$ is pyrrolidin-1-ylethylsulfonyl. In some embodiments, $R^2$ is pyridin-2-ylmethyl. In some embodiments, $R^2$ is piperidin-4-ylsulfonyl. In some embodiments, $R^2$ is 4-methylpiperazin-1-ylcarbonyl. In some embodiments, $R^2$ is 4-fluorophenylsulfonyl. In some embodiments, $R^2$ is 4-fluorophenylmethyl. In some embodiments, $R^2$ is 4-fluorophenyl. In some embodiments, $R^2$ is 4-chlorophenyl. In some embodiments, $R^2$ is 4-(morpholin-1-ylmethyl)phenyl. In some embodiments, $R^2$ is 3,5-difluorophenylmethyl. In some embodiments, $R^2$ is 3-(morpholin-4-ylmethyl)phenyl. In some embodiments, $R^2$ is 2,6-difluorophenylmethyl. In some embodiments, $R^2$ is 1-trifluoromethylcycloprop-1-ylmethyl. In some embodiments, $R^2$ is 1-trifluoromethylcycloprop-1-ylcarbonyl. In some embodiments, $R^2$ is 1-trifluoromethylcyclobut-1-ylmethyl. In some embodiments, $R^2$ is 1-trifluoromethylcyclobut-1-ylcarbonyl. In some embodiments, $R^2$ is 1-methylpiperidin-4-ylsulfonyl. In some embodiments, $R^2$ is 1-methylazetidin-3-ylsulfonyl. In some embodiments, $R^2$ is 1-fluorocycloprop-1-ylmethyl. In some embodiments, $R^2$ is 1-fluorocyclobut-1-ylmethyl.

In some embodiments, $R^2$ is selected from —$C(CH_3)_2C(O)CH_3$, —$C(O)C(CH_3)_2CH_2CH_3$, —$C(O)C(CH_3)_2OCH_3$, —$C(O)C(O)CH_3$, —$C(O)CF_2CH_2OCH_3$, —$C(O)CH(CH_3)CH_2CH_3$, —$CH(CH_3)CF_2H$, —$CH_2C(CH_3)_2CN$, —$CH_2CF_2CH_2OCH_3$, —$CH_2CF_2CH_2OH$, —$S(O)_2$ C(CH₃)₃, 4-cyanophenylcarbonyl, benzylcarbonyl, 2-methyl-1H-imidazol-1-ylacetyl, 3-methylisoxazol-5-ylacetyl, 1-fluorocyclobutylcarbonyl, 1-methylcyclopentylcarbonyl, 1-methylcyclopropylcarbonyl, 2,2-difluorocyclopropylcarbonyl, 3,3-difluorocyclopentylcarbonyl, 4-methylcyclohexylcarbonyl, cyclobutylcarbonyl, cyclopentylcarbonyl, 1,3-dimehtylazetidin-3-ylcarbonyl, 1-methyl-4-fluoropiperidin-4-ylcarbonyl, 1-methylpiperidin-4-ylcarbonyl, 2,2-difluoropyrrolidin-1-ylcarbonyl, 3-methyloxetan-3-ylcarbonyl, 4,4-difluoropiperidine-1-ylcarbonyl, tetrahydrofuran-3-ylcarbonyl, tetrahydropyran-4-ylcarbonyl, 3-fluorobenzyl, 4-cyanobenzyl, 1-methyl-1H-pyrazol-2-ylmethyl, 1-methyl-1H-pyrazol-3-ylmethyl, 1-methyl-1H-pyrazol-4-ylmethyl, 2,6-dimethylpyridin-4-ylmethyl, 2-cyanopyridin-4-ylmethyl, 2-methylpyridin-4-ylmethyl, 2-trifluoromethylpyridin-4-ylmethyl, 3-fluoropyridin-4-ylmethyl, 4-cyanopyridin-3-ylmethyl, 5-cyanopyridin-2-ylmethyl, 5-fluoropyridin-3-ylmethyl, 6-methylpyridin-2-ylmethyl, 6-methylpyrimidin-4-ylmethyl, pyrazin-2-ylmethyl, pyridin-3-ylmethyl, pyridin-4-ylmethyl, pyridin-3-ylsulfonyl, pyrimidin-2-ylmethyl, pyrimidin-4-ylmethyl, pyrimidin-5-ylmethyl, and cyclopropyl.

In some embodiments, $R^2$ is selected from —CH₂CF₂CF₃, —CH₂CF₂CH₃, —CH₂CF₂CHF₂, —CH₂CHF₂, —CH₂CF₂CH₂CH₃, —CH₂CF(CH₃)₂, 1-trifluoromethylcyclopropylmethyl, 1-trifluoromethylcyclobutylcarbonyl, 3,5-difluorophenylmethyl, 1-fluorocyclobutylmethyl, and 1-fluorocyclopropylmethyl.

In some embodiments, $R^2$ is selected from —C(CH₃)₂C(O)CH₃, —C(O)C(CH₃)₂CH₂CH₃, —C(O)C(CH₃)₂OCH₃, —C(O)CF₂CH₂OCH₃, —C(O)CH₂CH(CH₃)₂, —CH(CH₃)CF₂H, —CH₂C(CH₃)₂OCH₃, —CH₂CF₂CH₂OCH₃, —CH₂CH₂CN, —S(O)₂C(CH₃)₃, 2,6-dimethylpyridin-4-ylmethyl, 1-fluorocyclobutylcarbonyl, 2-cyanopyridin-4-ylmethyl, 2-methylpyridin-4-ylmethyl, 2-trifluoromethylpyridin-4-ylmethyl, 3-fluorobenzyl, 3-fluoropyridin-4-ylmethyl, 4-cyanobenzyl, 4-cyanopyridin-3-ylmethyl, 4-methylcyclohexylcarbonyl, 5-cyanopyridin-2-ylmethyl, 5-fluoropyridin-3-ylmethyl, 6-methylpyridin-2-ylmethyl, 6-methylpyrimidin-4-ylmethyl, benzylcarbonyl, cyclobutylcarbonyl, cyclopropyl, pyrazin-2-ylmethyl, and pyrimidin-4-ylmethyl.

As defined generally above and herein, $R^4$ is selected from —CH₂—, —CH(CH₃)—, —C(CH₃)₂—, —C(O)— and —S(O)₂—. In some embodiments, $R^4$ is —CH₂—. In some embodiments, $R^4$ is —CH(CH₃)—. In some embodiments, $R^4$ is —C(CH₃)₂—. In some embodiments, $R^4$ is —C(O)—. In some embodiments, $R^4$ is —S(O)₂—.

As defined generally above and herein, each of $R^5$ and $R^6$ is independently selected from fluoro, —CH₃, and —CH₂CH₃, or $R^5$ and $R^6$ are taken together to form =O. In some embodiments, each of $R^5$ and $R^6$ is independently selected from fluoro, —CH₃, and —CH₂CH₃. In some embodiments, $R^5$ and $R^6$ are taken together to form =O.

In some embodiments, $R^5$ is selected from fluoro, —CH₃, and —CH₂CH₃. In some embodiments, $R^5$ is fluoro. In some embodiments, $R^5$ is —CH₃. In some embodiments, $R^5$ is —CH₂CH₃.

In some embodiments, $R^6$ is selected from fluoro, —CH₃, and —CH₂CH₃. In some embodiments, $R^6$ is fluoro. In some embodiments, $R^6$ is —CH₃. In some embodiments, $R^6$ is —CH₂CH₃.

As defined generally above and herein, $R^7$ is selected from hydrogen, fluoro, —CN, —CH₃, —CH₂OH, —CH₂OCH₃, —CF₂H, —CFH₂, —CF₃, —CF₂CH₃, —CH₂CH₃, —OCH₃, and —N(C₁-C₃ alkyl)₂. In some embodiments, $R^7$ is hydrogen. In some embodiments, $R^7$ is fluoro. In some embodiments, $R^7$ is —CN. In some embodiments, $R^7$ is —CH₃. In some embodiments, $R^7$ is —CH₂OH. In some embodiments, $R^7$ is —CH₂OCH₃. In some embodiments, $R^7$ is —CF₂H. In some embodiments, $R^7$ is —CFH₂. In some embodiments, $R^7$ is —CF₃. In some embodiments, $R^7$ is —CF₂CH₃. In some embodiments, $R^7$ is —CH₂CH₃. In some embodiments, $R^7$ is —OCH₃. In some embodiments, $R^7$ is —N(C₁-C₃ alkyl)₂.

Any aryl, heteroaryl, heterocyclyl or cycloalkyl portion of $R^2$ is optionally substituted with up to two substituents independently selected from bromo, chloro, fluoro, —CN, —CH₃, —CF₃, —C(O)CH₃, and morpholin-4-ylmethyl. In some embodiments, an aryl, heteroaryl, heterocyclyl or cycloalkyl portion of $R^2$ is substituted with up to two substituents independently selected from bromo, chloro, fluoro, —CN, —CH₃, —CF₃, —C(O)CH₃, and morpholin-4-ylmethyl. In some embodiments, an aryl, heteroaryl, heterocyclyl or cycloalkyl portion of $R^2$ is unsubstituted. In some embodiments, an aryl portion of $R^2$ is substituted with up to two substituents independently selected from bromo, chloro, fluoro, —CN, —CH₃, —CF₃, —C(O)CH₃, and morpholin-4-ylmethyl. In some embodiments, an aryl portion of $R^2$ is unsubstituted. In some embodiments, a heteroaryl portion of $R^2$ is substituted with up to two substituents independently selected from bromo, chloro, fluoro, —CN, —CH₃, —CF₃, —C(O)CH₃, and morpholin-4-ylmethyl. In some embodiments, a heteroaryl portion of $R^2$ is unsubstituted. In some embodiments, a heterocyclyl portion of $R^2$ is substituted with up to two substituents independently selected from bromo, chloro, fluoro, —CN, —CH₃, —CF₃, —C(O)CH₃, and morpholin-4-ylmethyl. In some embodiments, a heterocyclyl portion of $R^2$ is unsubstituted. In some embodiments, a cycloalkyl portion of $R^2$ is substituted with up to two substituents independently selected from bromo, chloro, fluoro, —CN, —CH₃, —CF₃, —C(O)CH₃, and morpholin-4-ylmethyl. In some embodiments, a cycloalkyl portion of $R^2$ is unsubstituted.

In some embodiments, a substituent of an aryl, heteroaryl, heterocyclyl or cycloalkyl portion of $R^2$ is bromo. In some embodiments, a substituent of an aryl, heteroaryl, heterocyclyl or cycloalkyl portion of $R^2$ is chloro. In some embodiments, a substituent of an aryl, heteroaryl, heterocyclyl or cycloalkyl portion of $R^2$ is fluoro. In some embodiments, a substituent of an aryl, heteroaryl, heterocyclyl or cycloalkyl portion of $R^2$ is —CN. In some embodiments, a substituent of an aryl, heteroaryl, heterocyclyl or cycloalkyl portion of $R^2$ is —CH₃. In some embodiments, a substituent of an aryl, heteroaryl, heterocyclyl or cycloalkyl portion of $R^2$ is —CF₃. In some embodiments, a substituent of an aryl, heteroaryl, heterocyclyl or cycloalkyl portion of $R^2$ is —C(O)CH₃. In some embodiments, a substituent of an aryl, heteroaryl, heterocyclyl or cycloalkyl portion of $R^2$ is morpholin-4-ylmethyl.

As defined generally above and herein, each $R^3$, when present, is independently selected from =O and fluoro. In some embodiments, $R^3$ is present. In some embodiments, $R^3$ is absent. In some embodiments, $R^3$ is =O. In some embodiments, $R^3$ is fluoro.

As defined generally above and herein, n is 0, 1, 2, 3, or 4. In some embodiments, n is 0. In some embodiments, n is 1, 2, 3, or 4. In some embodiments, n is 2, 3, or 4. In some embodiments, n is 1 or 2. In some embodiments, n is 2 or 3. In some embodiments, n is 3 or 4. In some embodiments, n is 1. In some embodiments, n is 2. In some embodiments, n is 3. In some embodiments, n is 4.

In some embodiments, $R^2$ is selected from —CH₂-aryl, —CH₂-cycloalkyl, —C(O)-cycloalkyl, and —R⁴—C(R⁵)(R⁶)—R⁷, wherein:

$R^4$ is —CH$_2$—;
each of $R^5$ and $R^6$ is independently selected from fluoro and —CH$_3$;
$R^7$ is selected from hydrogen, fluoro, —CH$_3$, —CF$_2$H, —CF$_3$, and —CF$_2$CH$_3$;
any aryl or cycloalkyl portion of $R^2$ is optionally substituted with up to two substituents independently selected from fluoro and —CF$_3$; and
n is 0.

In some embodiments:
when n is 0, $R^1$ is —CH$_3$, —CH$_2$CH$_3$, —OCH$_3$, or —OCHF$_2$, $R^5$ is fluoro, and $R^6$ is fluoro, then $R^7$ is other than fluoro;
when n is 0, $R^1$ is —CH$_3$, —CH$_2$CH$_3$, —OCH$_3$, or —OCHF$_2$, $R^5$ is —CH$_3$, and $R^6$ is —CH$_3$, then $R^7$ is other than hydrogen; and
the compound is other than:

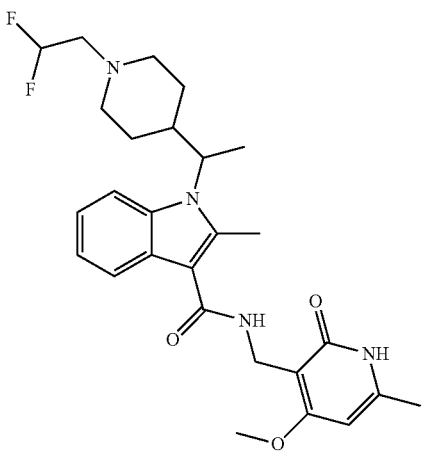 [SMILES: COc1cc(C)[nH]c(=O)c1CNC(=O)c1c(C)n(C(C)C2CCN(CC(F)F)CC2)c2ccccc12]

or a substantially pure enantiomer thereof.

As defined generally above and herein, $R^{11}$ is selected from —Cl, —CH$_3$, —CH$_2$CH$_3$, —CH$_2$CH$_2$CH$_3$, —NH(CH$_3$), —OCH$_3$, —OCHF$_2$, —OCF$_3$, and —OCH$_2$CF$_3$. In some embodiments, $R^{11}$ is selected from —Cl, —CH$_3$, —CH$_2$CH$_3$, —CH$_2$CH$_2$CH$_3$, —NH(CH$_3$), —OCHF$_2$, —OCF$_3$, and —OCH$_2$CF$_3$. In some embodiments, $R^{11}$ is selected from —OCH$_3$, chloro, methyl, —OCF$_2$H, —NH(CH$_3$), —CH$_2$CH$_3$, —CH$_2$CH$_2$CH$_3$, and —OCH$_2$CF$_3$. In some embodiments, $R^{11}$ is selected from chloro, —OCH$_3$, —NH(CH$_3$), and —CH$_3$. In some embodiments, $R^{11}$ is selected from —OCH$_3$, chloro, and —OCHF$_2$. In some embodiments, $R^{11}$ is —Cl. In some embodiments, $R^{11}$ is —CH$_3$. In some embodiments, $R^{11}$ is —CH$_2$CH$_3$. In some embodiments, $R^{11}$ is —CH$_2$CH$_2$CH$_3$. In some embodiments, $R^{11}$ is —NH(CH$_3$). In some embodiments, $R^{11}$ is —OCH$_3$. In some embodiments, $R^{11}$ is —OCHF$_2$. In some embodiments, $R^{11}$ is —OCF$_3$. In some embodiments, $R^{11}$ is —OCH$_2$CF$_3$.

As defined generally above and herein, $R^{12}$ is selected from optionally substituted pyridin-3-yl; optionally substituted pyrimidin-4-yl; optionally substituted pyrazin-2-yl; pyridin-2-yl substituted with one or more substituents independently selected from halo, methyl and morpholin-4-ylmethyl; pyrimidin-2-yl substituted with one or more substituents independently selected from halo, methyl and morpholin-4-ylmethyl; and oxetan-3-yl substituted with one or more fluoro; and azetidin-3-yl substituted with acetyl. In some embodiments, $R^{12}$ is optionally substituted pyridin-3-yl. In some embodiments, $R^{12}$ is substituted pyridin-3-yl. In some embodiments, $R^{12}$ is unsubstituted pyridin-3-yl. In some embodiments, $R^{12}$ is optionally substituted pyrimidin-4-yl. In some embodiments, $R^{12}$ is substituted pyrimidin-4-yl. In some embodiments, $R^{12}$ is unsubstituted pyrimidin-4-yl. In some embodiments, $R^{12}$ is optionally substituted pyrazin-2-yl. In some embodiments, $R^{12}$ is substituted pyrazin-2-yl. In some embodiments, $R^{12}$ is unsubstituted pyrazin-2-yl. In some embodiments, $R^{12}$ is pyridin-2-yl substituted with one or more substituents independently selected from halo, methyl and morpholin-4-ylmethyl. In some embodiments, $R^{12}$ is pyrimidin-2-yl substituted with one of more substituents independently selected from halo, methyl and morpholin-4-ylmethyl. In some embodiments, $R^{12}$ is oxetan-3-yl substituted with one or more fluoro; and azetidin-3-yl substituted with acetyl.

In some embodiments, $R^{12}$ is selected from 5-chloropyrimindin-2-yl, 5-fluoropyrimidin-2-yl, pyridin-3-yl, pyrazin-2-yl, 6-methylpyridin-3-yl, 5-fluoropyridin-2-yl, 5-(morpholin-4-ylmethyl)pyridin-2-yl, pyrimidin-4-yl, and 5-bromopyrimidin-2-yl.

In some embodiments, $R^{12}$ is 1-acetylazetidin-3-yl.

In some embodiments, $R^{12}$ is 5-chloropyrimindin-2-yl. In some embodiments, $R^{12}$ is 5-fluoropyrimidin-2-yl. In some embodiments, $R^{12}$ is pyridin-3-yl. In some embodiments, $R^{12}$ is pyrazin-2-yl. In some embodiments, $R^{12}$ is 6-methylpyridin-3-yl. In some embodiments, $R^{12}$ is 5-fluoropyridin-2-yl. In some embodiments, $R^{12}$ is 5-(morpholin-4-ylmethyl)pyridin-2-yl. In some embodiments, $R^{12}$ is pyrimidin-4-yl. In some embodiments, $R^{12}$ is 5-bromopyrimidin-2-yl.

As defined generally above and herein, each $R^{13}$, when present, is independently selected from =O and fluoro. In some embodiments, $R^{13}$ is present. In some embodiments, $R^{13}$ is absent. In some embodiments, $R^{13}$ is =O. In some embodiments, $R^{13}$ is fluoro.

As defined generally above and herein, m is 0, 1, 2, 3, or 4. In some embodiments, m is 0. In some embodiments, m is 1, 2, 3, or 4. In some embodiments, m is 2, 3, or 4. In some embodiments, m is 1 or 2. In some embodiments, m is 2 or 3. In some embodiments, m is 3 or 4. In some embodiments, m is 1. In some embodiments, m is 2. In some embodiments, m is 3. In some embodiments, m is 4.

In some embodiments, $R^{22}$ is selected from hydrogen and methyl. In some embodiments, $R^{22}$ is hydrogen. In some embodiments, $R^{22}$ is methyl.

In some embodiments, each $R^{23}$ is selected from halo or $C_1$-$C_4$ alkyl. In some embodiments, $R^{23}$ is halo. In some embodiments, $R^{23}$ is —F. In some embodiments, $R^{23}$ is —Cl. In some embodiments, $R^{23}$ is —Br. In some embodiments, $R^{23}$ is —I. In some embodiments, $R^{23}$ is $C_1$-$C_4$ alkyl.

In some embodiments, $R^{22}$ and one $R^{23}$ bound to an adjacent carbon atom are taken together to form a heterocyclyl or heteroaryl fused to the piperidine ring, wherein the fused ring is optionally substituted with methyl or =O. In some embodiments, $^{22}$ and one $R^{23}$ bound to an adjacent carbon atom are taken together to form a heterocyclyl or heteroaryl fused to the piperidine ring, wherein the piperidine ring is unsubstituted. In some embodiments, $R^{22}$ and one $R^{23}$ bound to an adjacent carbon atom are taken together to form a heterocyclyl or heteroaryl fused to the piperidine ring, wherein the fused ring is substituted with methyl or =O. In some embodiments, $R^{22}$ and one $R^{23}$ bound to an adjacent carbon atom are taken together to form a heterocyclyl or heteroaryl fused to the piperidine ring, wherein the fused ring is substituted with methyl. In some embodiments, $R^{22}$ and one $R^{23}$ bound to an adjacent carbon atom are taken together to form a heterocyclyl or heteroaryl fused to the piperidine ring, wherein the fused ring is substituted with =O. In some embodiments, $R^{22}$ and one $R^{23}$ bound to an adjacent carbon atom are taken together to form a heterocyclyl or heteroaryl fused to the piperidine ring, wherein the fused ring is substituted with methyl and =O.

In some embodiments, the moiety represented by

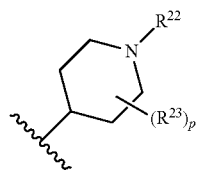

is selected from:

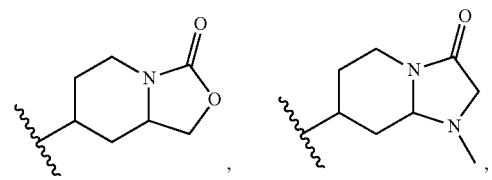

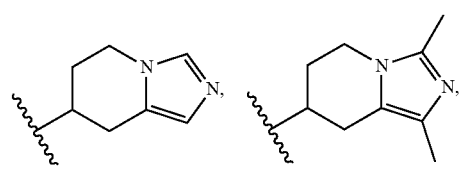

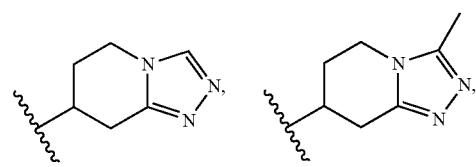

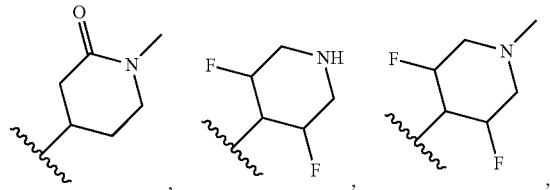

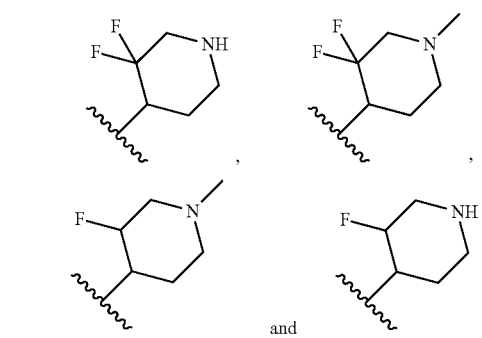

and .

As defined generally above and herein, p is 1, 2, 3, or 4. In some embodiments, p is 2, 3, or 4. In some embodiments, p is 1 or 2. In some embodiments, p is 2 or 3. In some embodiments, p is 3 or 4. In some embodiments, p is 1. In some embodiments, p is 2. In some embodiments, p is 3. In some embodiments, p is 4.

In some embodiments, a compound of formula I has the structure of formula Ia:

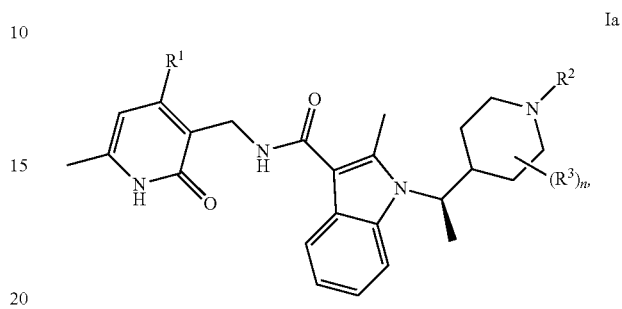

Ia or a pharmaceutically acceptable salt thereof, wherein each variable is independently as defined above and described herein.

In some embodiments, a compound of formula I has the structure of formula Ib:

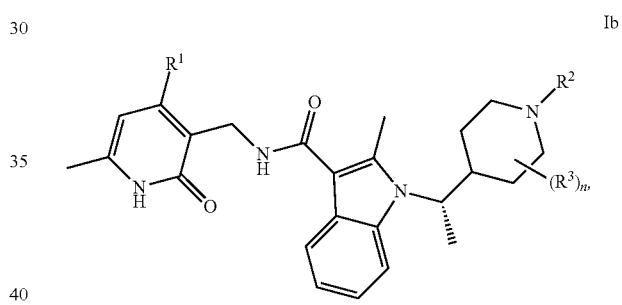

Ib or a pharmaceutically acceptable salt thereof, wherein each variable is independently as defined above and described herein.

In some embodiments, a compound of formula II has the structure of formula IIa:

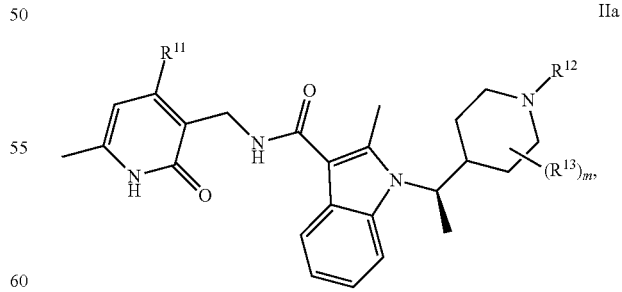

IIa or a pharmaceutically acceptable salt thereof, wherein each variable is independently as defined above and described herein.

In some embodiments, a compound of formula II has the structure of formula IIb:

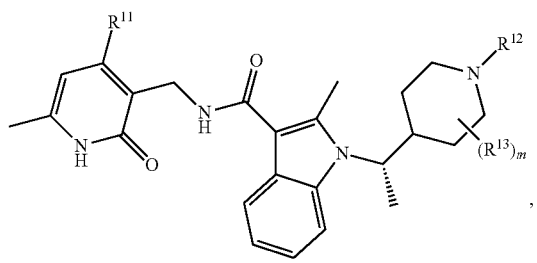

or a pharmaceutically acceptable salt thereof, wherein each variable is independently as defined above and described herein.

In some embodiments, a compound of formula III has the structure of formula IIIa:

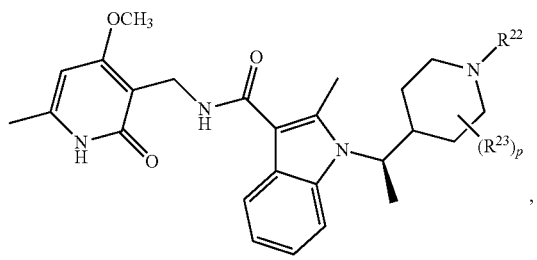

or a pharmaceutically acceptable salt thereof, wherein each variable is independently as defined above and described herein.

In some embodiments, a compound of formula III has the structure of formula IIIb:

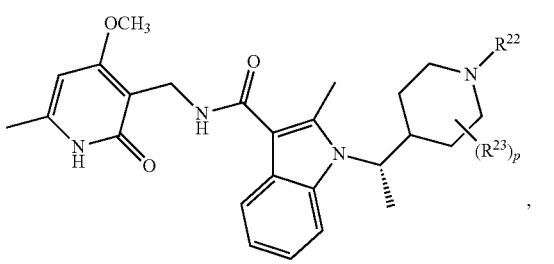

or a pharmaceutically acceptable salt thereof, wherein each variable is independently as defined above and described herein.

Certain exemplary provided compounds, e.g., having structural formula I, II or III, are set forth in Table 1, below. In some embodiments, a provided compound is a compound selected from Table 1, or a pharmaceutically acceptable salt thereof.

TABLE 1

| Certain exemplary provided compounds. | |
|---|---|
| Compound # | Structure |
| 101 | |

US 9,969,716 B2
23                                                                                                              24
TABLE 1-continued
Certain exemplary provided compounds.
| Compound # | Structure |
|---|---|
| 102 | 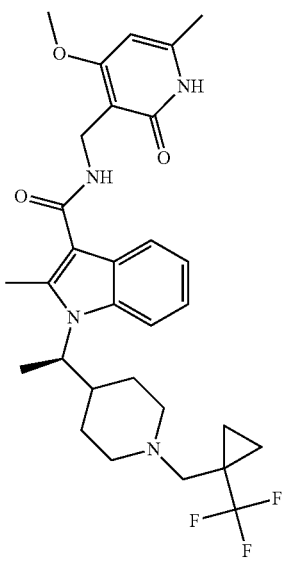 [SMILES: COc1cc(C)[nH]c(=O)c1CNC(=O)c1c(C)n([C@H](C)C2CCN(CC3(C(F)(F)F)CC3)CC2)c2ccccc12] |
| 103 | 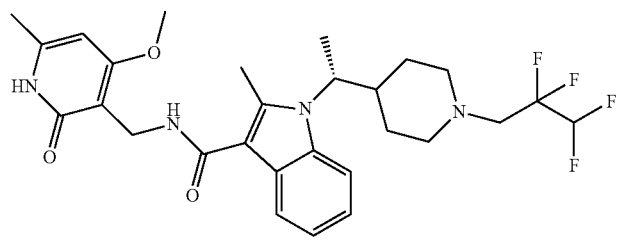 [SMILES: COc1cc(C)[nH]c(=O)c1CNC(=O)c1c(C)n([C@H](C)C2CCN(CC(F)(F)C(F)F)CC2)c2ccccc12] |
| 104 | 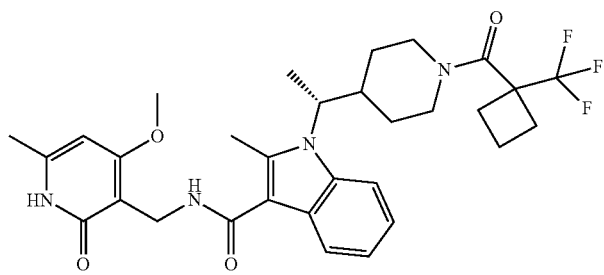 [SMILES: COc1cc(C)[nH]c(=O)c1CNC(=O)c1c(C)n([C@H](C)C2CCN(C(=O)C3(C(F)(F)F)CCC3)CC2)c2ccccc12] |
| 105 | 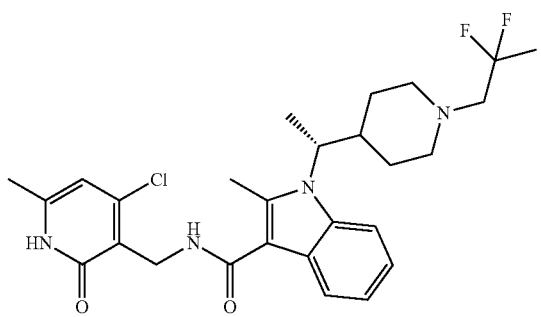 [SMILES: Cc1cc(Cl)c(CNC(=O)c2c(C)n([C@H](C)C3CCN(CC(C)(F)F)CC3)c3ccccc23)c(=O)[nH]1] |

TABLE 1-continued
Certain exemplary provided compounds.
| Compound # | Structure |
|---|---|
| 106 | 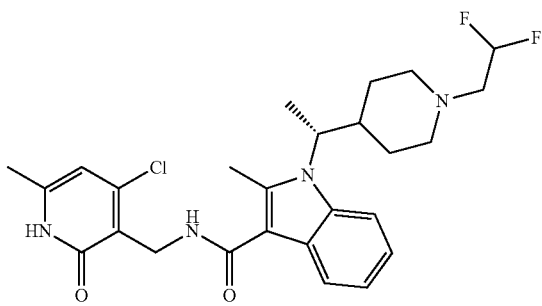 [SMILES: Cc1cc(Cl)c(CNC(=O)c2c(C)n([C@H](C)C3CCN(CC(F)F)CC3)c3ccccc23)c(=O)[nH]1] |
| 107 | 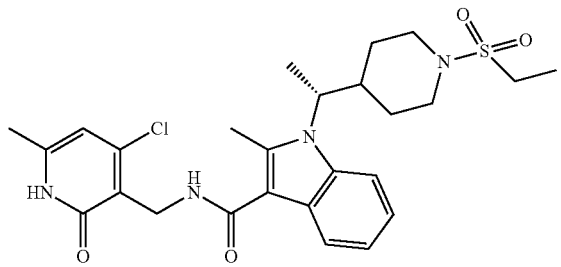 [SMILES: CCS(=O)(=O)N1CCC([C@@H](C)n2c(C)c(C(=O)NCc3c(Cl)cc(C)[nH]c3=O)c3ccccc32)CC1] |
| 108 | 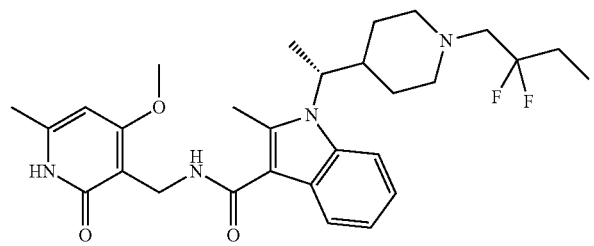 [SMILES: CCC(F)(F)CN1CCC([C@@H](C)n2c(C)c(C(=O)NCc3c(OC)cc(C)[nH]c3=O)c3ccccc32)CC1] |
| 109 | 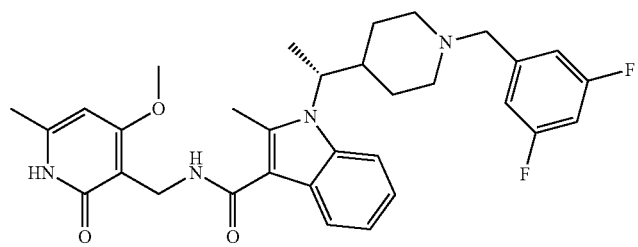 [SMILES: COc1cc(C)[nH]c(=O)c1CNC(=O)c1c(C)n([C@H](C)C2CCN(Cc3cc(F)cc(F)c3)CC2)c2ccccc12] |
| 110 | 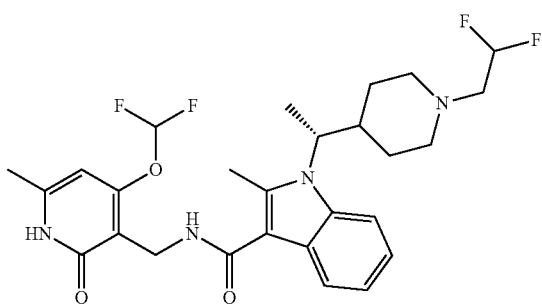 [SMILES: Cc1cc(OC(F)F)c(CNC(=O)c2c(C)n([C@H](C)C3CCN(CC(F)F)CC3)c3ccccc23)c(=O)[nH]1] |

TABLE 1-continued

Certain exemplary provided compounds.

| Compound # | Structure |
|---|---|
| 111 | 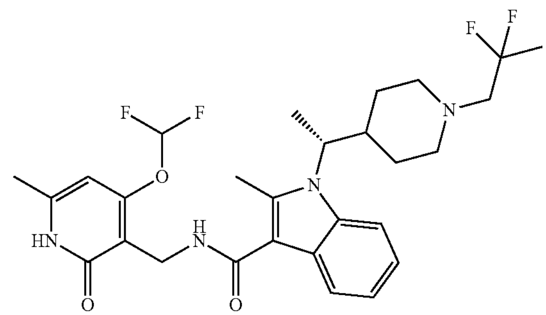 [SMILES: Cc1cc(OC(F)F)c(CNC(=O)c2c(C)n([C@H](C)C3CCN(CC(C)(F)F)CC3)c3ccccc23)c(=O)[nH]1] |
| 112 | 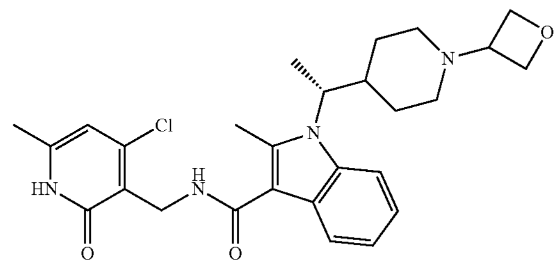 [SMILES: Cc1cc(Cl)c(CNC(=O)c2c(C)n([C@H](C)C3CCN(C4COC4)CC3)c3ccccc23)c(=O)[nH]1] |
| 113 | 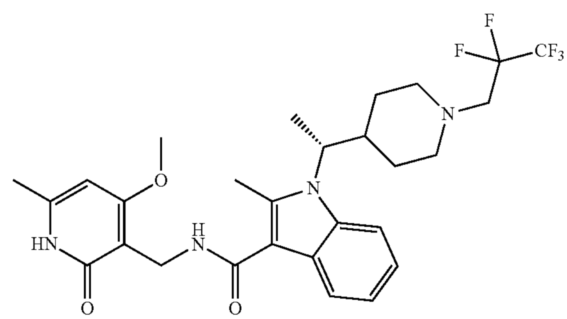 [SMILES: COc1cc(C)[nH]c(=O)c1CNC(=O)c1c(C)n([C@H](C)C2CCN(CC(F)(F)C(F)(F)F)CC2)c2ccccc12] |
| 114 | 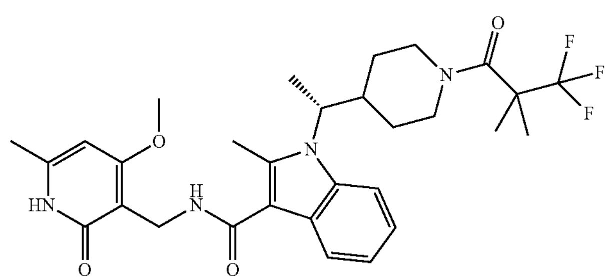 [SMILES: COc1cc(C)[nH]c(=O)c1CNC(=O)c1c(C)n([C@H](C)C2CCN(C(=O)C(C)(C)C(F)(F)F)CC2)c2ccccc12] |
| 115 | 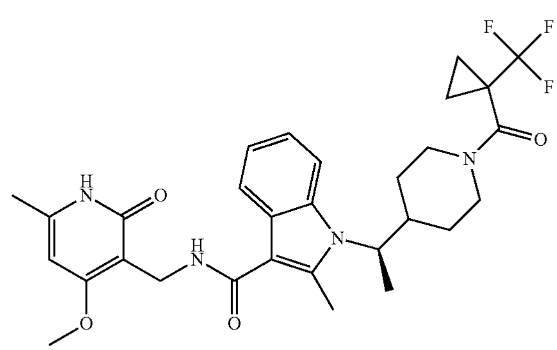 [SMILES: COc1cc(C)[nH]c(=O)c1CNC(=O)c1c(C)n([C@H](C)C2CCN(C(=O)C3(C(F)(F)F)CC3)CC2)c2ccccc12] |

TABLE 1-continued
Certain exemplary provided compounds.
| Compound # | Structure |
|---|---|
| 116 | 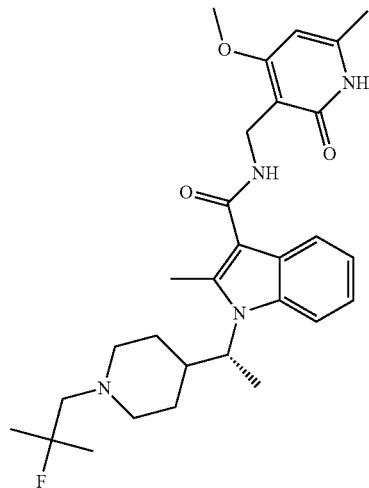 [SMILES: COc1cc(C)[nH]c(=O)c1CNC(=O)c1c(C)n([C@H](C)C2CCN(CC(C)(C)F)CC2)c2ccccc12] |
| 117 | 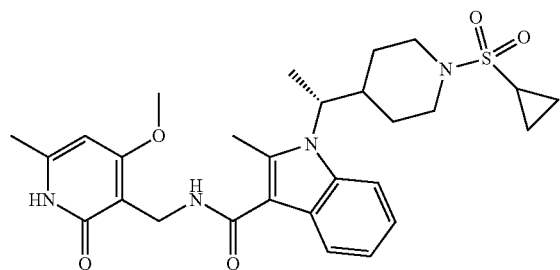 [SMILES: COc1cc(C)[nH]c(=O)c1CNC(=O)c1c(C)n([C@H](C)C2CCN(S(=O)(=O)C3CC3)CC2)c2ccccc12] |
| 118 | 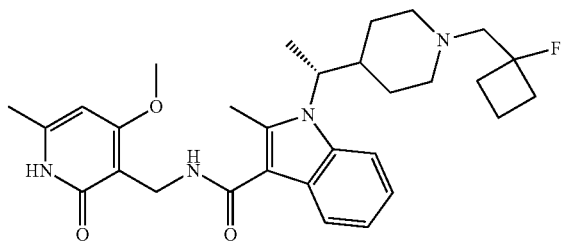 [SMILES: COc1cc(C)[nH]c(=O)c1CNC(=O)c1c(C)n([C@H](C)C2CCN(CC3(F)CCC3)CC2)c2ccccc12] |
| 119 | 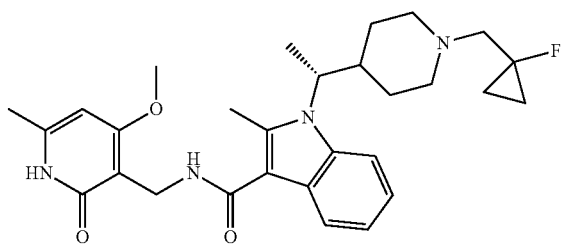 [SMILES: COc1cc(C)[nH]c(=O)c1CNC(=O)c1c(C)n([C@H](C)C2CCN(CC3(F)CC3)CC2)c2ccccc12] |
| 120 | 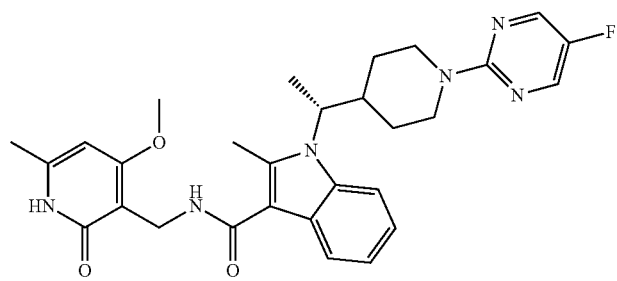 |

US 9,969,716 B2
31            32
TABLE 1-continued
Certain exemplary provided compounds.
| Compound # | Structure |
|---|---|
| 121 | 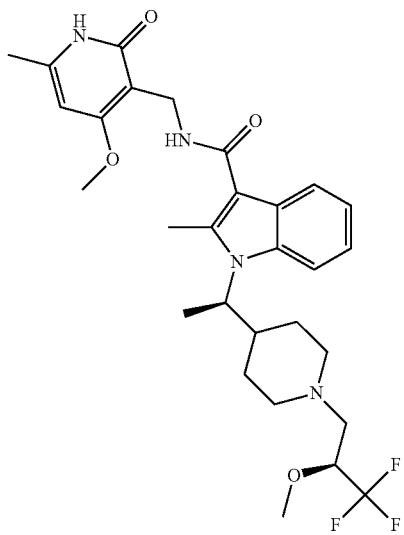 [SMILES: COc1cc(C)[nH]c(=O)c1CNC(=O)c1c(C)n([C@H](C)C2CCN(C[C@H](OC)C(F)(F)F)CC2)c2ccccc12] |
| 122 | 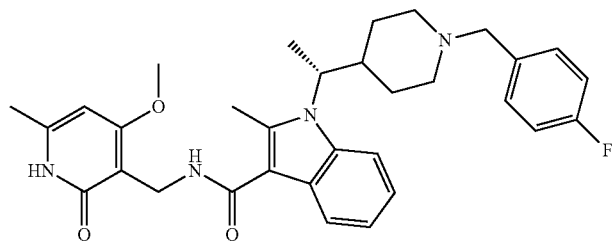 [SMILES: COc1cc(C)[nH]c(=O)c1CNC(=O)c1c(C)n([C@H](C)C2CCN(Cc3ccc(F)cc3)CC2)c2ccccc12] |
| 123 | 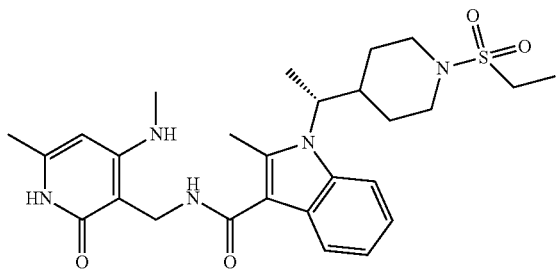 [SMILES: CCS(=O)(=O)N1CCC([C@@H](C)n2c(C)c(C(=O)NCc3c(NC)cc(C)[nH]c3=O)c3ccccc32)CC1] |
| 124 | 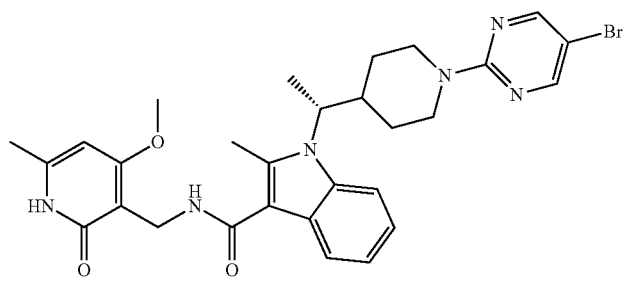 [SMILES: COc1cc(C)[nH]c(=O)c1CNC(=O)c1c(C)n([C@H](C)C2CCN(c3ncc(Br)cn3)CC2)c2ccccc12] |

TABLE 1-continued
Certain exemplary provided compounds.
| Compound # | Structure |
|---|---|
| 125 | 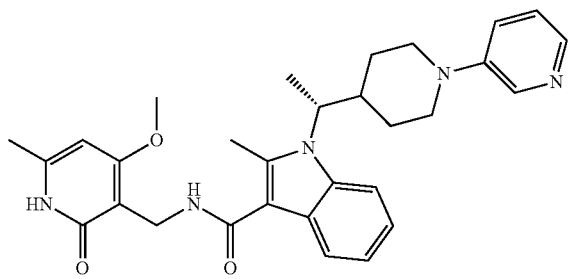 [SMILES: COc1cc(C)[nH]c(=O)c1CNC(=O)c1c(C)n([C@H](C)C2CCN(c3cccnc3)CC2)c2ccccc12] |
| 126 | 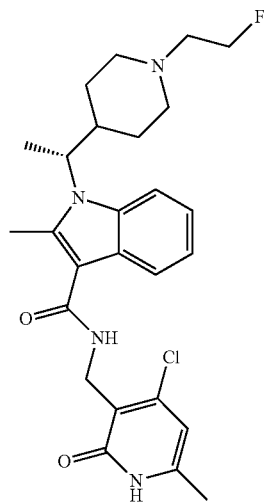 [SMILES: Cc1cc(Cl)c(CNC(=O)c2c(C)n([C@H](C)C3CCN(CCF)CC3)c3ccccc23)c(=O)[nH]1] |
| 127 | 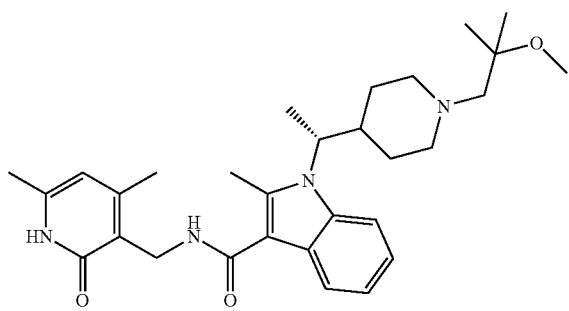 |
| 128 | 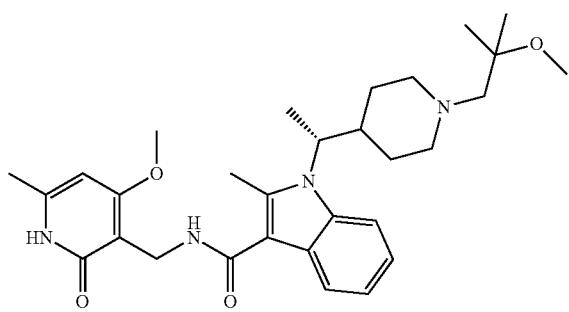 |

TABLE 1-continued
Certain exemplary provided compounds.
| Compound # | Structure |
|---|---|
| 129 | 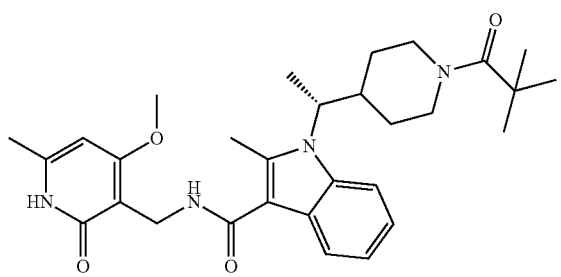 [SMILES: COc1cc(C)[nH]c(=O)c1CNC(=O)c1c(C)n([C@H](C)C2CCN(C(=O)C(C)(C)C)CC2)c2ccccc12] |
| 130 | 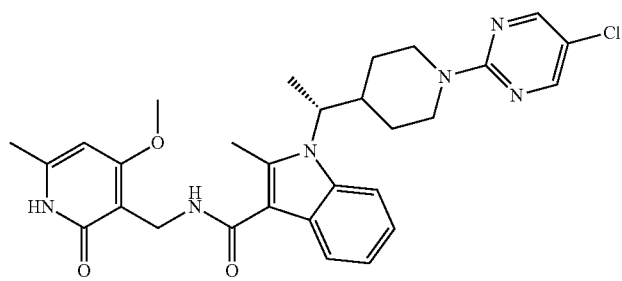 |
| 131 | 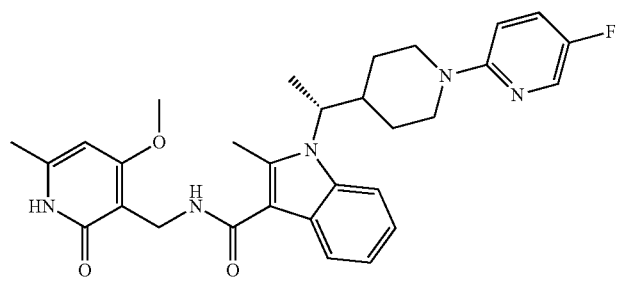 [SMILES: COc1cc(C)[nH]c(=O)c1CNC(=O)c1c(C)n([C@H](C)C2CCN(c3ccc(F)cn3)CC2)c2ccccc12] |
| 132 | 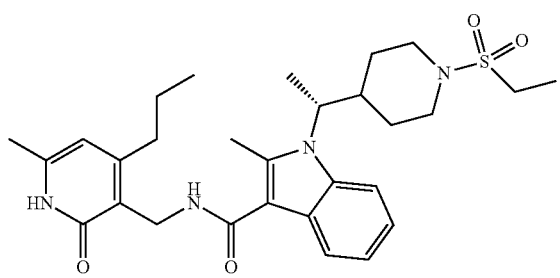 [SMILES: CCCc1cc(C)[nH]c(=O)c1CNC(=O)c1c(C)n([C@H](C)C2CCN(S(=O)(=O)CC)CC2)c2ccccc12] |
| 133 | 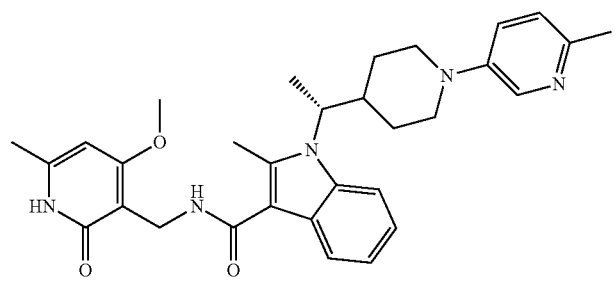 |

US 9,969,716 B2
37 38
TABLE 1-continued
Certain exemplary provided compounds.
| Compound # | Structure |
|---|---|
| 134 | 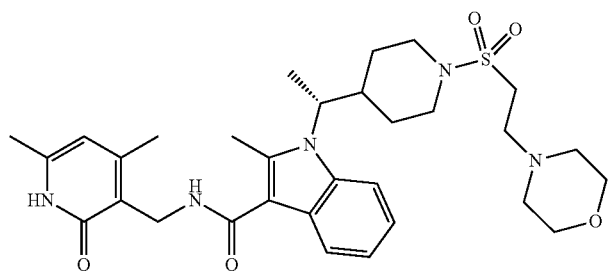 [SMILES: Cc1cc(C)c(CNC(=O)c2c(C)n([C@H](C)C3CCN(S(=O)(=O)CCN4CCOCC4)CC3)c3ccccc23)c(=O)[nH]1] |
| 135 | 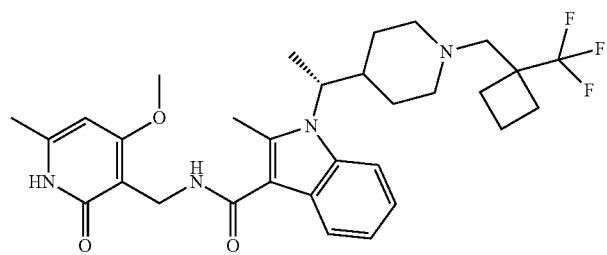 [SMILES: COc1cc(C)[nH]c(=O)c1CNC(=O)c1c(C)n([C@H](C)C2CCN(CC3(C(F)(F)F)CCC3)CC2)c2ccccc12] |
| 136 | 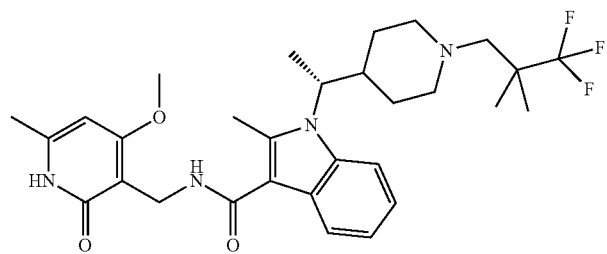 [SMILES: COc1cc(C)[nH]c(=O)c1CNC(=O)c1c(C)n([C@H](C)C2CCN(CC(C)(C)C(F)(F)F)CC2)c2ccccc12] |
| 137 | 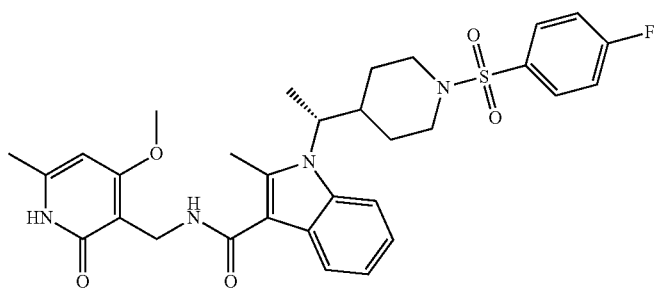 [SMILES: COc1cc(C)[nH]c(=O)c1CNC(=O)c1c(C)n([C@H](C)C2CCN(S(=O)(=O)c3ccc(F)cc3)CC2)c2ccccc12] |
| 138 | 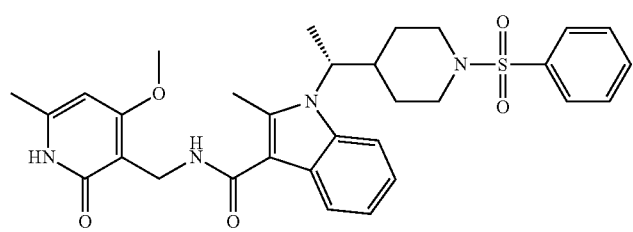 [SMILES: COc1cc(C)[nH]c(=O)c1CNC(=O)c1c(C)n([C@H](C)C2CCN(S(=O)(=O)c3ccccc3)CC2)c2ccccc12] |

TABLE 1-continued
Certain exemplary provided compounds.
| Compound # | Structure |
|---|---|
| 139 | 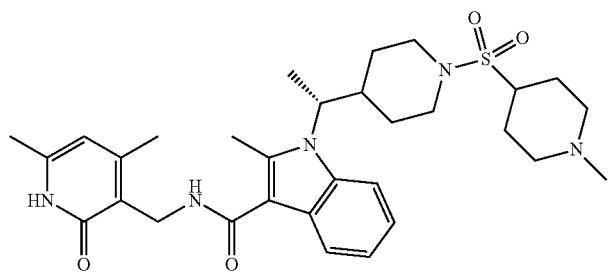 |
| 140 | 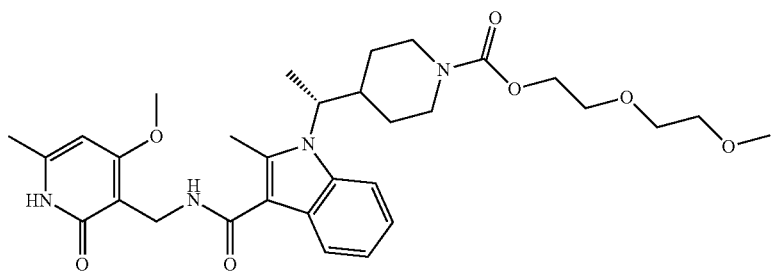 |
| 141 | 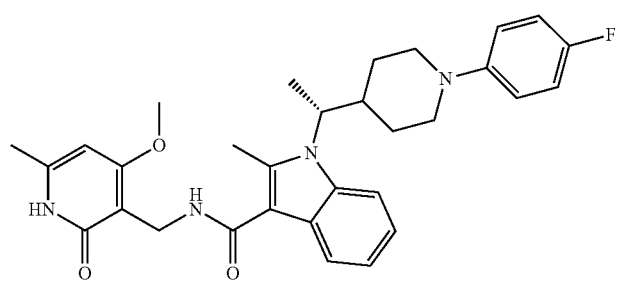 |
| 142 | 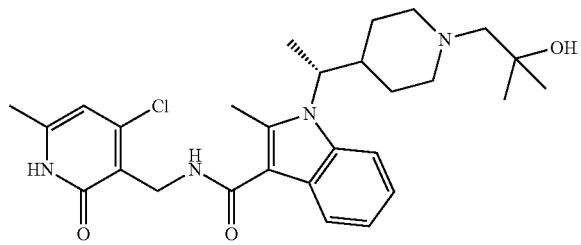 [SMILES: Cc1cc(Cl)c(CNC(=O)c2c(C)n([C@H](C)C3CCN(CC(C)(C)O)CC3)c3ccccc23)c(=O)[nH]1] |
| 143 | 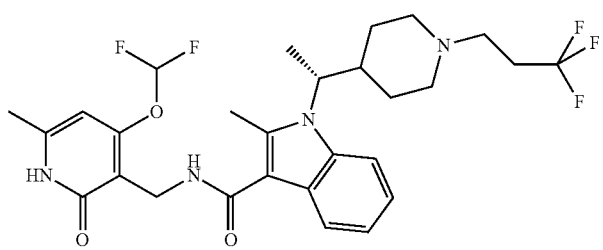 [SMILES: Cc1cc(OC(F)F)c(CNC(=O)c2c(C)n([C@H](C)C3CCN(CCC(F)(F)F)CC3)c3ccccc23)c(=O)[nH]1] |

TABLE 1-continued

Certain exemplary provided compounds.

| Compound # | Structure |
|---|---|
| 144 | (structure) |
| 145 | (structure) |
| 146 | (structure) |
| 147 | (structure) |
| 148 | (structure) |

US 9,969,716 B2
43                                                                                             44
TABLE 1-continued
Certain exemplary provided compounds.
| Compound # | Structure |
|---|---|
| 149 | 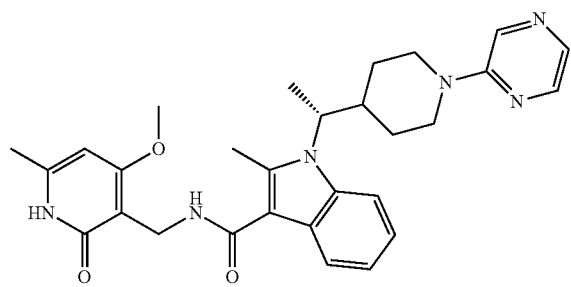 [SMILES: COc1cc(C)[nH]c(=O)c1CNC(=O)c1c(C)n([C@H](C)C2CCN(c3cnccn3)CC2)c2ccccc12] |
| 150 | 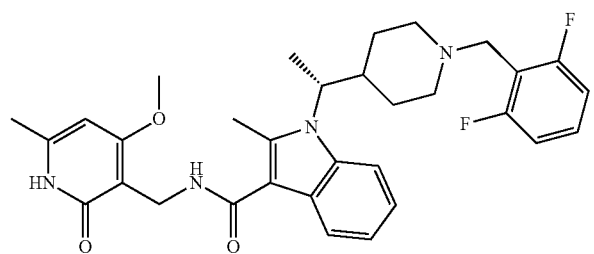 [SMILES: COc1cc(C)[nH]c(=O)c1CNC(=O)c1c(C)n([C@H](C)C2CCN(Cc3c(F)cccc3F)CC2)c2ccccc12] |
| 151 | 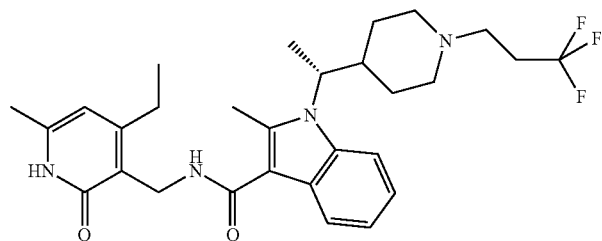 [SMILES: CCc1cc(C)[nH]c(=O)c1CNC(=O)c1c(C)n([C@H](C)C2CCN(CCC(F)(F)F)CC2)c2ccccc12] |
| 152 | 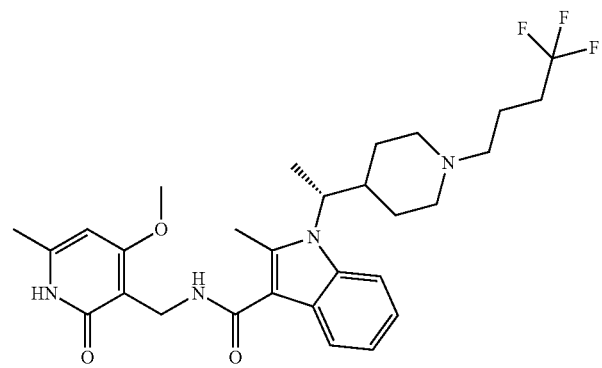 [SMILES: COc1cc(C)[nH]c(=O)c1CNC(=O)c1c(C)n([C@H](C)C2CCN(CCCC(F)(F)F)CC2)c2ccccc12] |
| 153 | 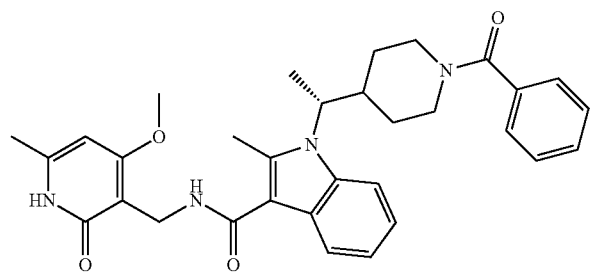 [SMILES: COc1cc(C)[nH]c(=O)c1CNC(=O)c1c(C)n([C@H](C)C2CCN(C(=O)c3ccccc3)CC2)c2ccccc12] |

TABLE 1-continued
Certain exemplary provided compounds.
| Compound # | Structure |
|---|---|
| 154 | 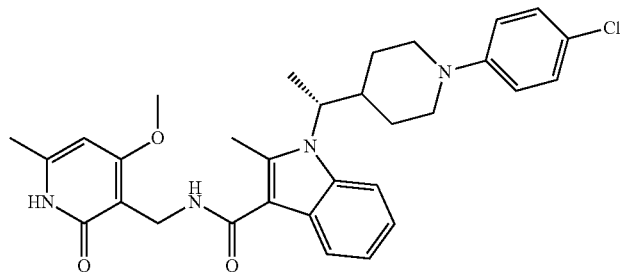 [SMILES: COc1cc(C)[nH]c(=O)c1CNC(=O)c1c(C)n([C@H](C)C2CCN(c3ccc(Cl)cc3)CC2)c2ccccc12] |
| 155 | 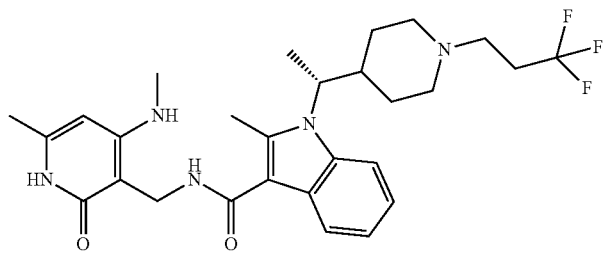 [SMILES: CNc1cc(C)[nH]c(=O)c1CNC(=O)c1c(C)n([C@H](C)C2CCN(CCC(F)(F)F)CC2)c2ccccc12] |
| 156 | 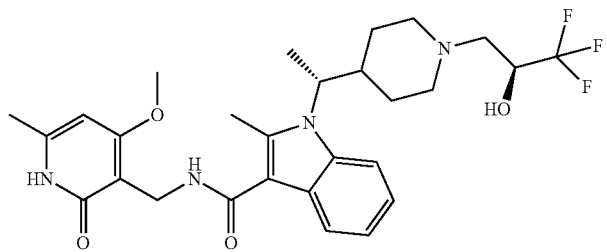 [SMILES: COc1cc(C)[nH]c(=O)c1CNC(=O)c1c(C)n([C@H](C)C2CCN(C[C@H](O)C(F)(F)F)CC2)c2ccccc12] |
| 157 | 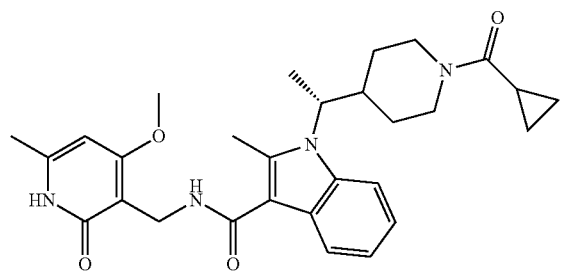 [SMILES: COc1cc(C)[nH]c(=O)c1CNC(=O)c1c(C)n([C@H](C)C2CCN(C(=O)C3CC3)CC2)c2ccccc12] |
| 158 | 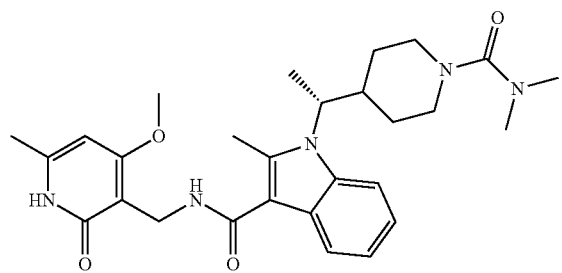 |

TABLE 1-continued

Certain exemplary provided compounds.

| Compound # | Structure |
|---|---|
| 159 | 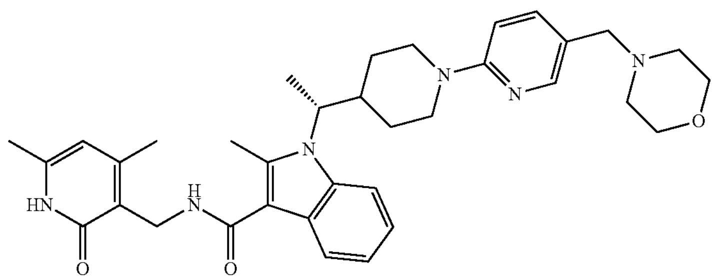 [SMILES: Cc1cc(C)c(CNC(=O)c2c(C)n([C@H](C)C3CCN(c4ccc(CN5CCOCC5)cn4)CC3)c3ccccc23)c(=O)[nH]1] |
| 160 | 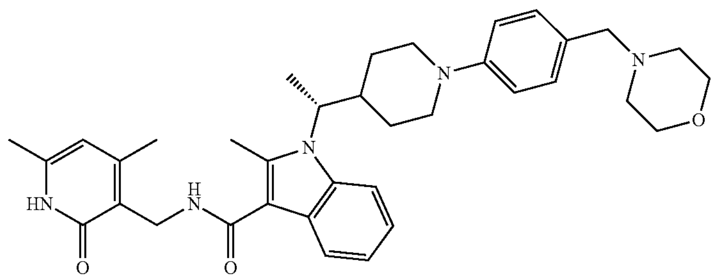 [SMILES: Cc1cc(C)c(CNC(=O)c2c(C)n([C@H](C)C3CCN(c4ccc(CN5CCOCC5)cc4)CC3)c3ccccc23)c(=O)[nH]1] |
| 161 | 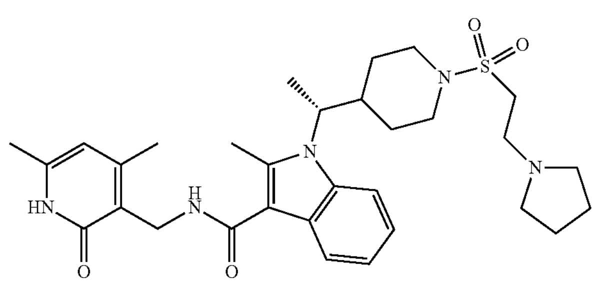 [SMILES: Cc1cc(C)c(CNC(=O)c2c(C)n([C@H](C)C3CCN(S(=O)(=O)CCN4CCCC4)CC3)c3ccccc23)c(=O)[nH]1] |
| 162 | 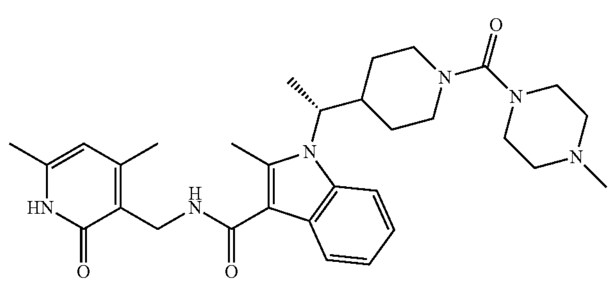 |
| 163 | 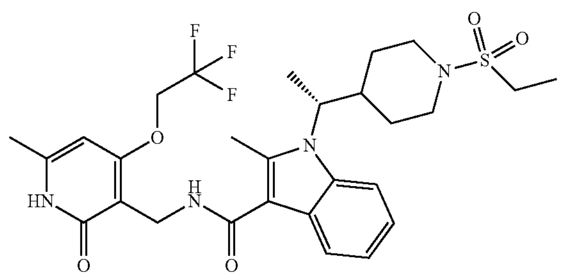 [SMILES: CCS(=O)(=O)N1CCC([C@@H](C)n2c(C)c(C(=O)NCc3c(OCC(F)(F)F)cc(C)[nH]c3=O)c3ccccc32)CC1] |

TABLE 1-continued

Certain exemplary provided compounds.

| Compound # | Structure |
|---|---|
| 164 | 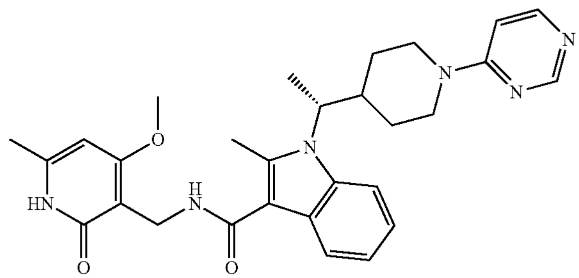 [SMILES: COc1cc(C)[nH]c(=O)c1CNC(=O)c1c(C)n([C@H](C)C2CCN(c3ccncn3)CC2)c2ccccc12] |
| 165 | 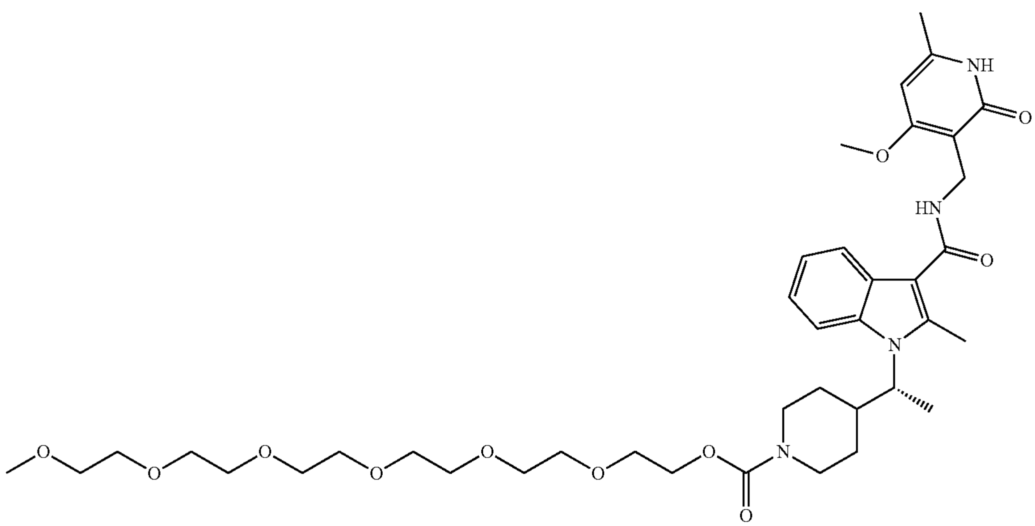 [SMILES: COCCOCCOCCOCCOCCOCCOC(=O)N1CCC([C@@H](C)n2c(C)c(C(=O)NCc3c(OC)cc(C)[nH]c3=O)c3ccccc32)CC1] |
| 166 | 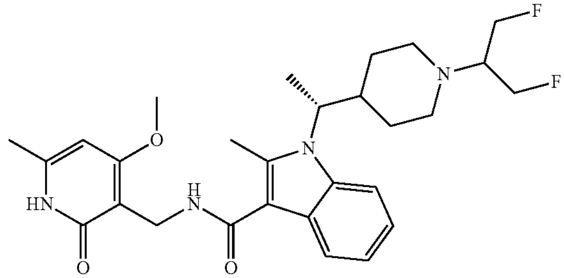 [SMILES: COc1cc(C)[nH]c(=O)c1CNC(=O)c1c(C)n([C@H](C)C2CCN(C(CF)CF)CC2)c2ccccc12] |

TABLE 1-continued
Certain exemplary provided compounds.
| Compound # | Structure |
|---|---|
| 167 | 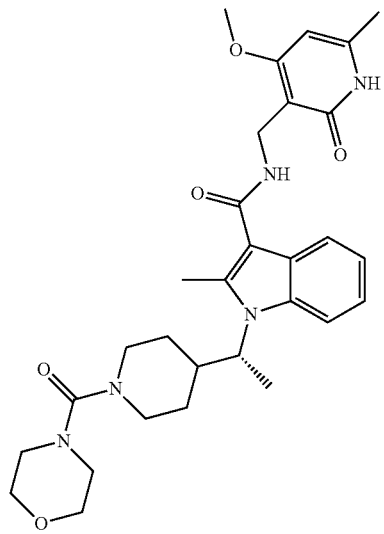 [SMILES: COc1cc(C)[nH]c(=O)c1CNC(=O)c1c(C)n([C@H](C)C2CCN(C(=O)N3CCOCC3)CC2)c2ccccc12] |
| 168 | 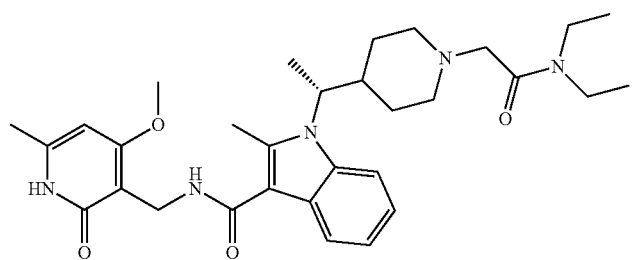 [SMILES: CCN(CC)C(=O)CN1CCC([C@@H](C)n2c(C)c(C(=O)NCc3c(OC)cc(C)[nH]c3=O)c3ccccc32)CC1] |
| 169 | 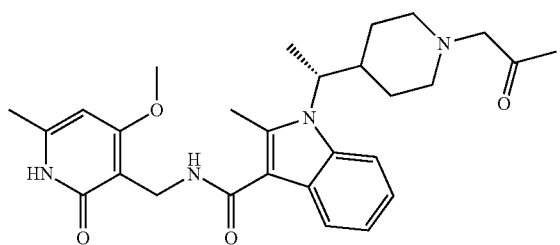 [SMILES: COc1cc(C)[nH]c(=O)c1CNC(=O)c1c(C)n([C@H](C)C2CCN(CC(C)=O)CC2)c2ccccc12] |
| 170 | 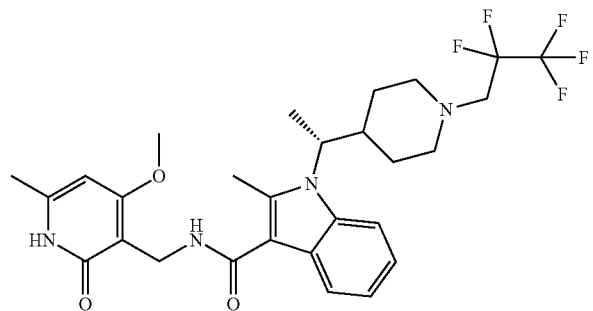 [SMILES: COc1cc(C)[nH]c(=O)c1CNC(=O)c1c(C)n([C@H](C)C2CCN(CC(F)(F)C(F)(F)F)CC2)c2ccccc12] |

TABLE 1-continued
Certain exemplary provided compounds.
| Compound # | Structure |
|---|---|
| 171 | 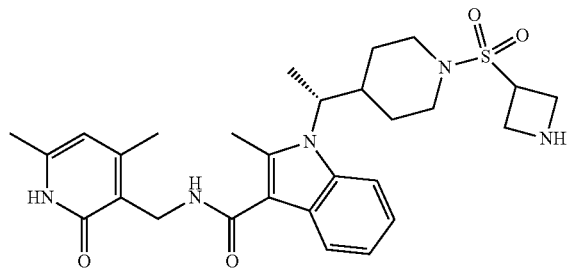 [SMILES: Cc1cc(C)c(CNC(=O)c2c(C)n([C@H](C)C3CCN(S(=O)(=O)C4CNC4)CC3)c3ccccc23)c(=O)[nH]1] |
| 172 | 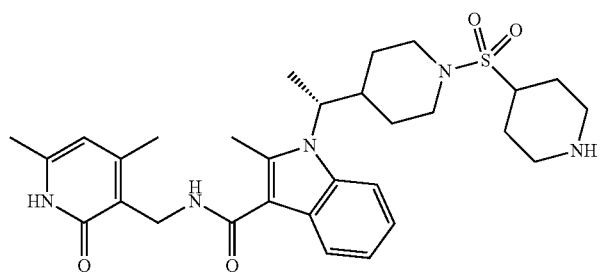 [SMILES: Cc1cc(C)c(CNC(=O)c2c(C)n([C@H](C)C3CCN(S(=O)(=O)C4CCNCC4)CC3)c3ccccc23)c(=O)[nH]1] |
| 173 | 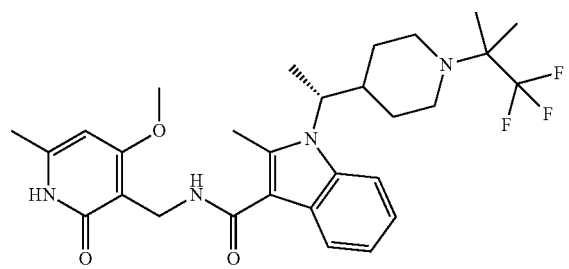 [SMILES: COc1cc(C)[nH]c(=O)c1CNC(=O)c1c(C)n([C@H](C)C2CCN(C(C)(C)C(F)(F)F)CC2)c2ccccc12] |
| 174 | 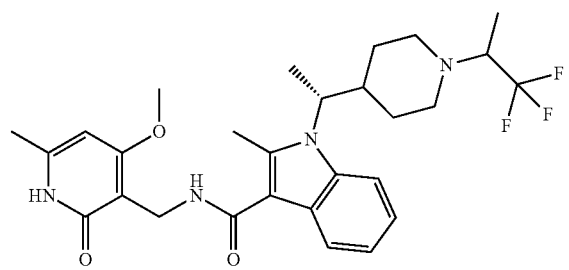 [SMILES: COc1cc(C)[nH]c(=O)c1CNC(=O)c1c(C)n([C@H](C)C2CCN(C(C)C(F)(F)F)CC2)c2ccccc12] |
| 175 | 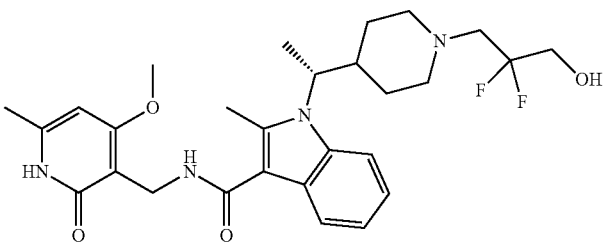 [SMILES: COc1cc(C)[nH]c(=O)c1CNC(=O)c1c(C)n([C@H](C)C2CCN(CC(F)(F)CO)CC2)c2ccccc12] |

TABLE 1-continued

Certain exemplary provided compounds.

| Compound # | Structure |
|---|---|
| 176 | 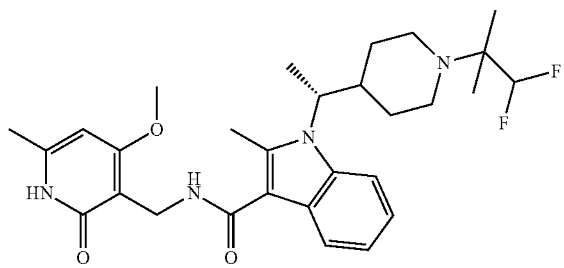 [SMILES: COc1cc(C)[nH]c(=O)c1CNC(=O)c1c(C)n([C@H](C)C2CCN(C(C)(C)C(F)F)CC2)c2ccccc12] |
| 177 | 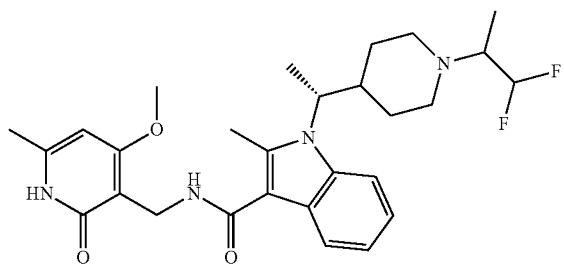 [SMILES: COc1cc(C)[nH]c(=O)c1CNC(=O)c1c(C)n([C@H](C)C2CCN(C(C)C(F)F)CC2)c2ccccc12] |
| 178 | 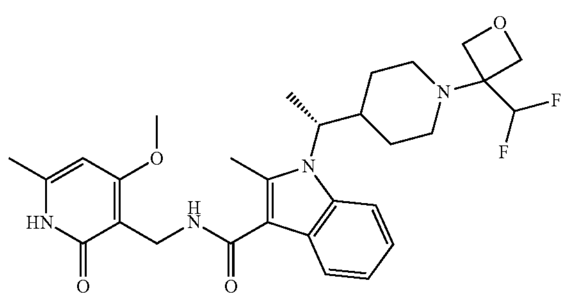 [SMILES: COc1cc(C)[nH]c(=O)c1CNC(=O)c1c(C)n([C@H](C)C2CCN(C3(C(F)F)COC3)CC2)c2ccccc12] |
| 179 | 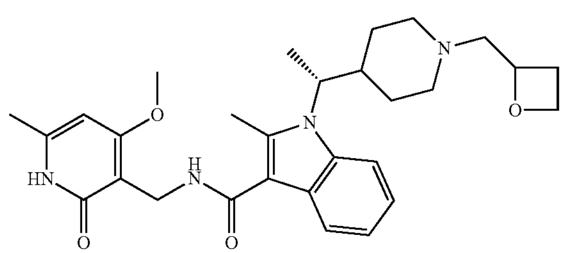 [SMILES: COc1cc(C)[nH]c(=O)c1CNC(=O)c1c(C)n([C@H](C)C2CCN(CC3CCO3)CC2)c2ccccc12] |
| 180 | 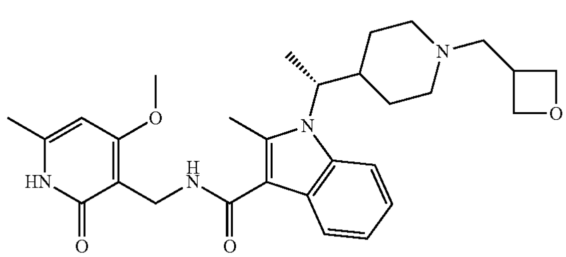 [SMILES: COc1cc(C)[nH]c(=O)c1CNC(=O)c1c(C)n([C@H](C)C2CCN(CC3COC3)CC2)c2ccccc12] |

US 9,969,716 B2
TABLE 1-continued
Certain exemplary provided compounds.
| Compound # | Structure |
|---|---|
| 181 | 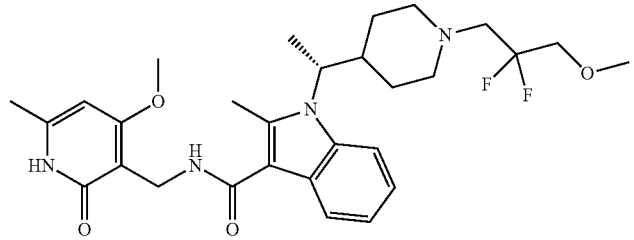 |
| 182 | 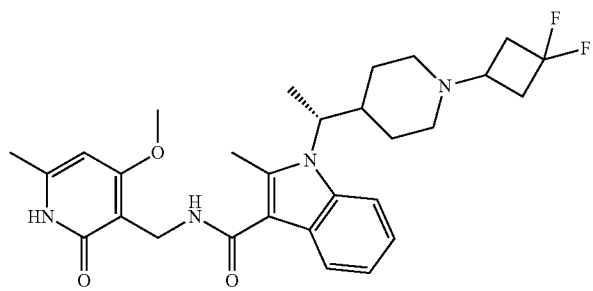 [SMILES: COc1cc(C)[nH]c(=O)c1CNC(=O)c1c(C)n([C@H](C)C2CCN(C3CC(F)(F)C3)CC2)c2ccccc12] |
| 183 | 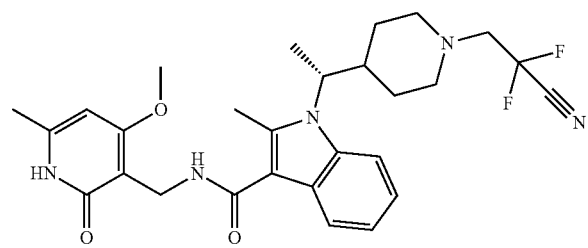 [SMILES: COc1cc(C)[nH]c(=O)c1CNC(=O)c1c(C)n([C@H](C)C2CCN(CC(F)(F)C#N)CC2)c2ccccc12] |
| 184 | 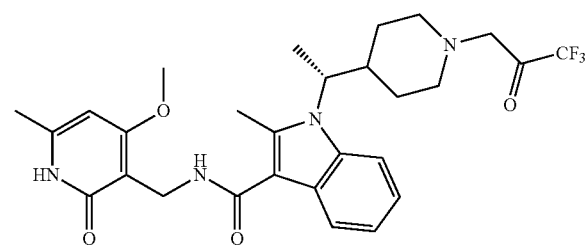 [SMILES: COc1cc(C)[nH]c(=O)c1CNC(=O)c1c(C)n([C@H](C)C2CCN(CC(=O)C(F)(F)F)CC2)c2ccccc12] |
| 185 | 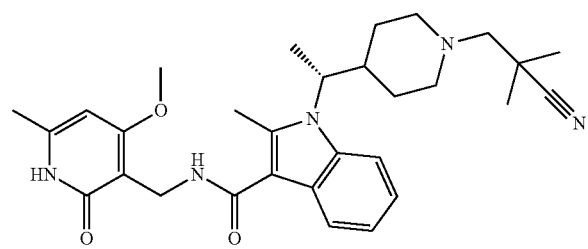 [SMILES: COc1cc(C)[nH]c(=O)c1CNC(=O)c1c(C)n([C@H](C)C2CCN(CC(C)(C)C#N)CC2)c2ccccc12] |
| 186 | 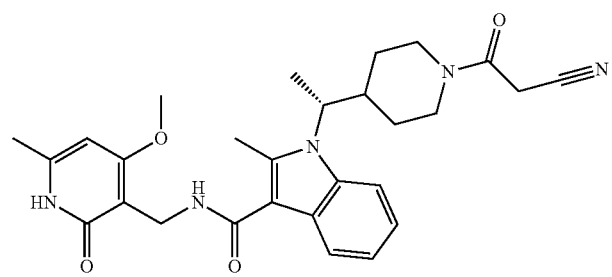 [SMILES: COc1cc(C)[nH]c(=O)c1CNC(=O)c1c(C)n([C@H](C)C2CCN(C(=O)CC#N)CC2)c2ccccc12] |

TABLE 1-continued

Certain exemplary provided compounds.

| Compound # | Structure |
|---|---|
| 187 | 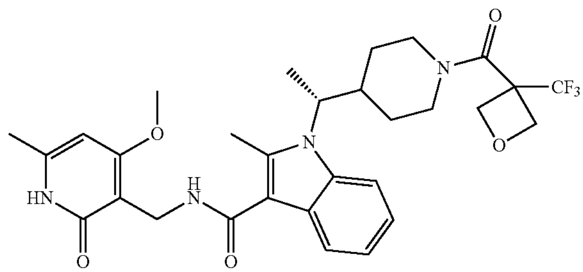 [SMILES: COc1cc(C)[nH]c(=O)c1CNC(=O)c1c(C)n([C@H](C)C2CCN(C(=O)C3(C(F)(F)F)COC3)CC2)c2ccccc12] |
| 188 | 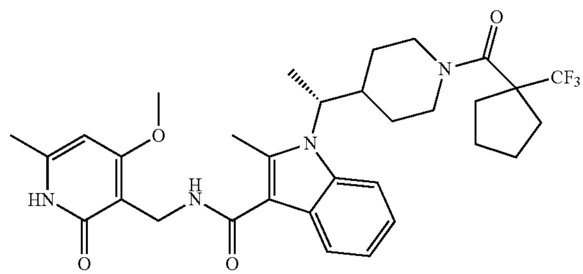 [SMILES: COc1cc(C)[nH]c(=O)c1CNC(=O)c1c(C)n([C@H](C)C2CCN(C(=O)C3(C(F)(F)F)CCCC3)CC2)c2ccccc12] |
| 189 | 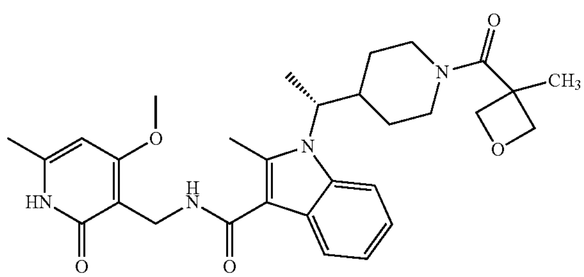 |
| 190 | 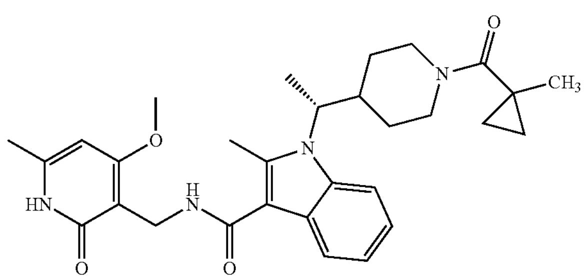 |
| 191 | 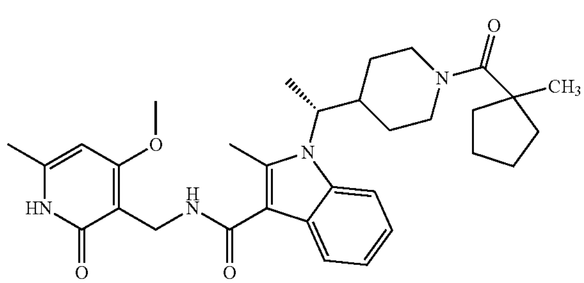 |

US 9,969,716 B2
TABLE 1-continued
Certain exemplary provided compounds.
| Compound # | Structure |
|---|---|
| 192 | 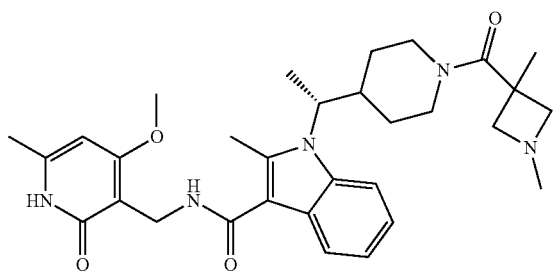 [SMILES: COc1cc(C)[nH]c(=O)c1CNC(=O)c1c(C)n([C@H](C)C2CCN(C(=O)C3(C)CN(C)C3)CC2)c2ccccc12] |
| 193 | 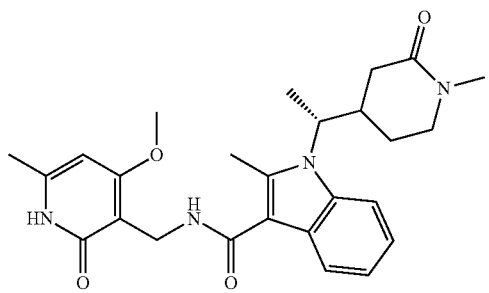 |
| 194 | 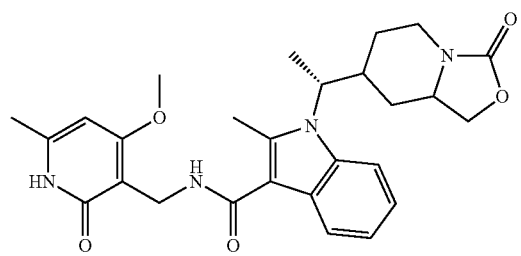 [SMILES: COc1cc(C)[nH]c(=O)c1CNC(=O)c1c(C)n([C@H](C)C2CCN3C(=O)OCC3C2)c2ccccc12] |
| 195 | 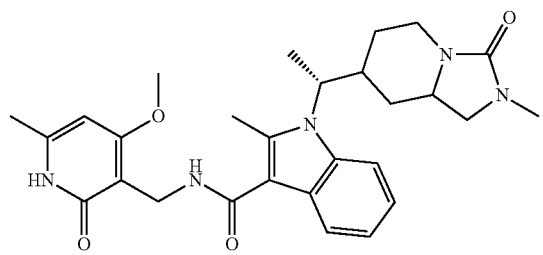 |
| 196 | 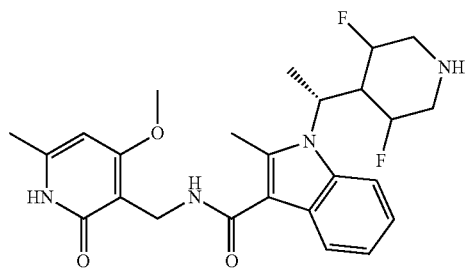 [SMILES: COc1cc(C)[nH]c(=O)c1CNC(=O)c1c(C)n([C@H](C)C2C(F)CNCC2F)c2ccccc12] |

TABLE 1-continued
Certain exemplary provided compounds.
| Compound # | Structure |
|---|---|
| 197 | 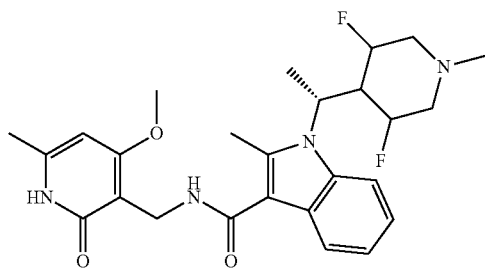 |
| 198 | 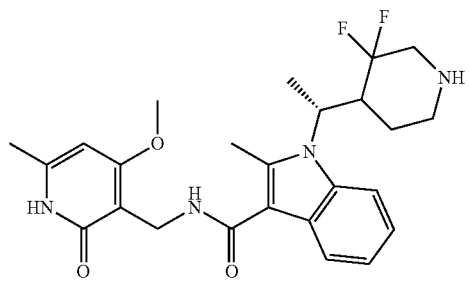 [SMILES: COc1cc(C)[nH]c(=O)c1CNC(=O)c1c(C)n([C@H](C)C2CCNCC2(F)F)c2ccccc12] |
| 199 | 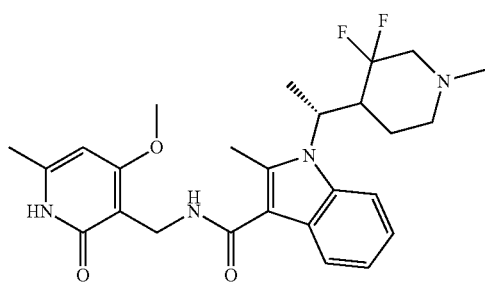 |
| 200 | 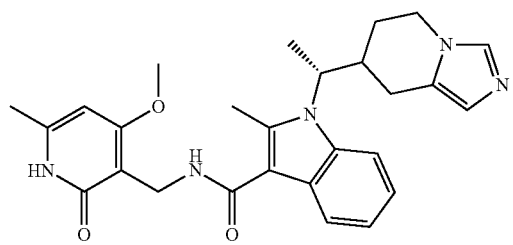 |
| 201 | 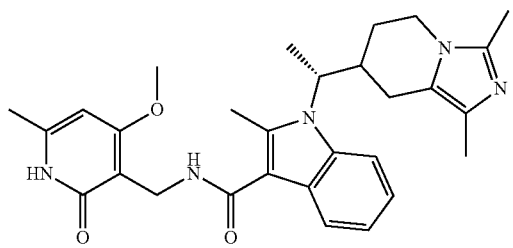 |

TABLE 1-continued

Certain exemplary provided compounds.

| Compound # | Structure |
|---|---|
| 202 | 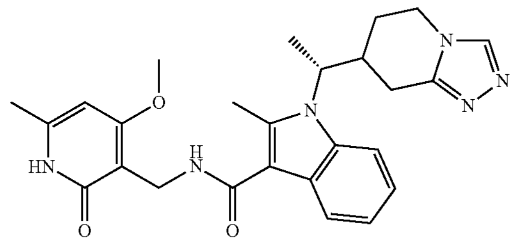 [SMILES: COc1cc(C)[nH]c(=O)c1CNC(=O)c1c(C)n([C@H](C)C2CCn3cnnc3C2)c2ccccc12] |
| 203 | 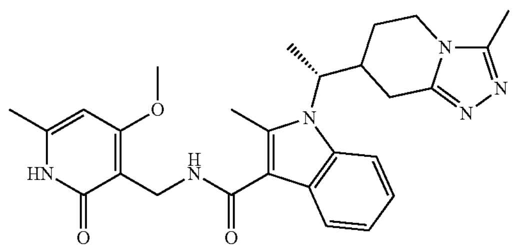 |
| 204 | 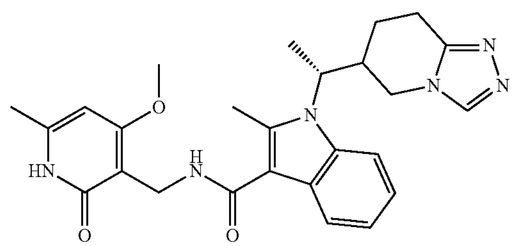 [SMILES: COc1cc(C)[nH]c(=O)c1CNC(=O)c1c(C)n([C@H](C)C2CCc3nncn3C2)c2ccccc12] |
| 205 | 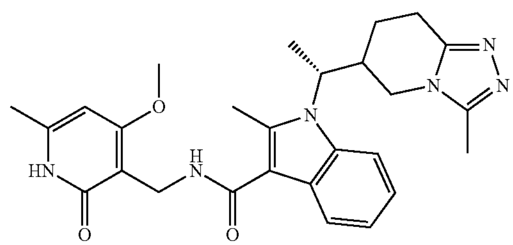 |
| 206 | 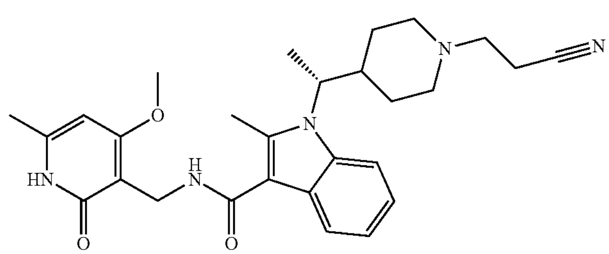 [SMILES: COc1cc(C)[nH]c(=O)c1CNC(=O)c1c(C)n([C@H](C)C2CCN(CCC#N)CC2)c2ccccc12] |
| 207 | 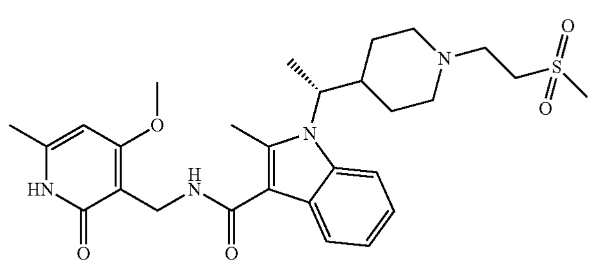 |

TABLE 1-continued
Certain exemplary provided compounds.
| Compound # | Structure |
|---|---|
| 208 | 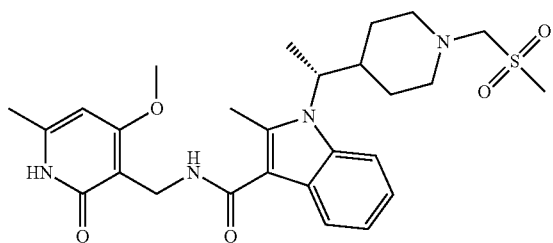 [SMILES: COc1cc(C)[nH]c(=O)c1CNC(=O)c1c(C)n([C@H](C)C2CCN(CS(C)(=O)=O)CC2)c2ccccc12] |
| 209 | 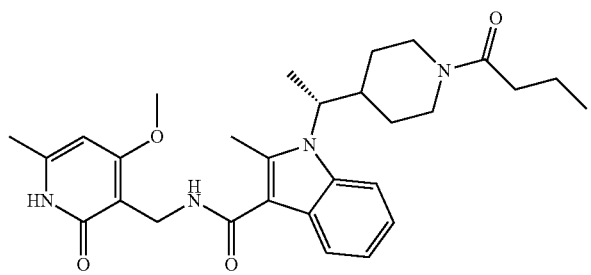 [SMILES: CCCC(=O)N1CCC([C@@H](C)n2c(C)c(C(=O)NCc3c(OC)cc(C)[nH]c3=O)c3ccccc32)CC1] |
| 210 | 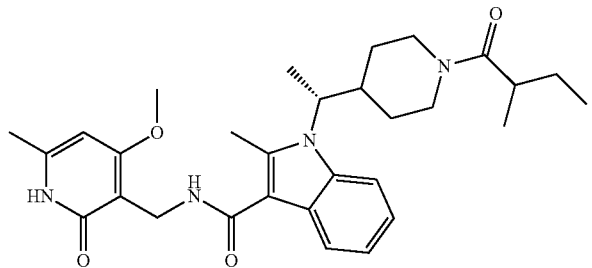 [SMILES: CCC(C)C(=O)N1CCC([C@@H](C)n2c(C)c(C(=O)NCc3c(OC)cc(C)[nH]c3=O)c3ccccc32)CC1] |
| 211 | 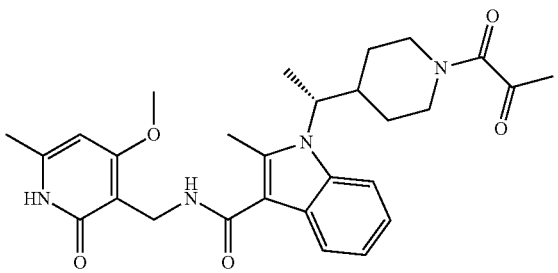 [SMILES: COc1cc(C)[nH]c(=O)c1CNC(=O)c1c(C)n([C@H](C)C2CCN(C(=O)C(C)=O)CC2)c2ccccc12] |
| 212 | 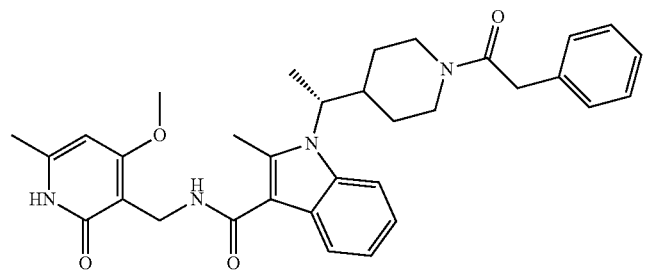 [SMILES: COc1cc(C)[nH]c(=O)c1CNC(=O)c1c(C)n([C@H](C)C2CCN(C(=O)Cc3ccccc3)CC2)c2ccccc12] |

TABLE 1-continued
Certain exemplary provided compounds.
| Compound # | Structure |
|---|---|
| 213 | 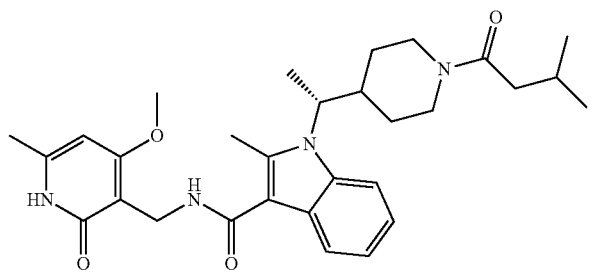 [SMILES: COc1cc(C)[nH]c(=O)c1CNC(=O)c1c(C)n([C@H](C)C2CCN(C(=O)CC(C)C)CC2)c2ccccc12] |
| 214 | 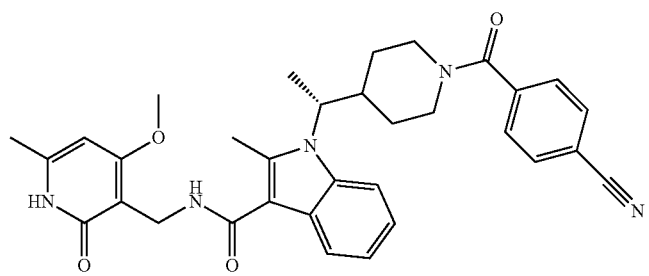 [SMILES: COc1cc(C)[nH]c(=O)c1CNC(=O)c1c(C)n([C@H](C)C2CCN(C(=O)c3ccc(C#N)cc3)CC2)c2ccccc12] |
| 215 | 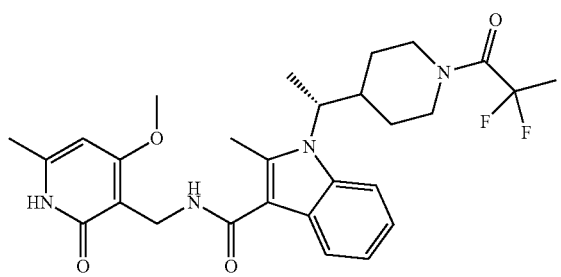 [SMILES: COc1cc(C)[nH]c(=O)c1CNC(=O)c1c(C)n([C@H](C)C2CCN(C(=O)C(C)(F)F)CC2)c2ccccc12] |
| 216 | 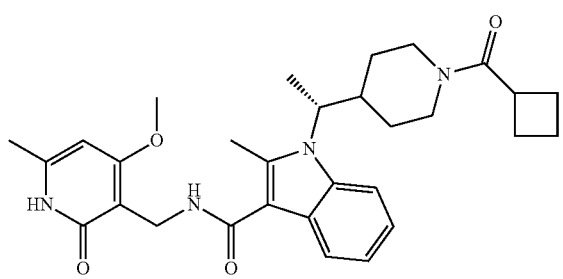 [SMILES: COc1cc(C)[nH]c(=O)c1CNC(=O)c1c(C)n([C@H](C)C2CCN(C(=O)C3CCC3)CC2)c2ccccc12] |
| 217 | 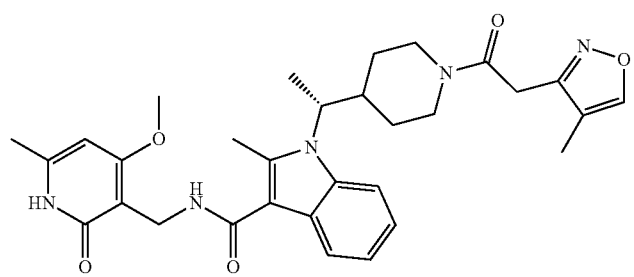 [SMILES: COc1cc(C)[nH]c(=O)c1CNC(=O)c1c(C)n([C@H](C)C2CCN(C(=O)Cc3nocc3C)CC2)c2ccccc12] |

US 9,969,716 B2
71                                                                                                       72
TABLE 1-continued
Certain exemplary provided compounds.
| Compound # | Structure |
|---|---|
| 218 | 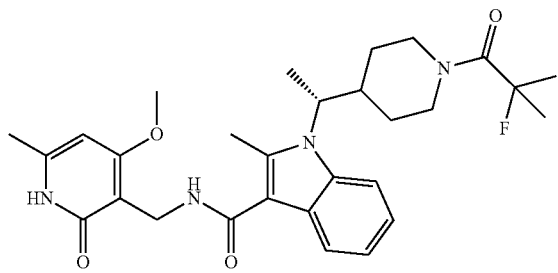 [SMILES: COc1cc(C)[nH]c(=O)c1CNC(=O)c1c(C)n([C@H](C)C2CCN(C(=O)C(C)(C)F)CC2)c2ccccc12] |
| 219 | 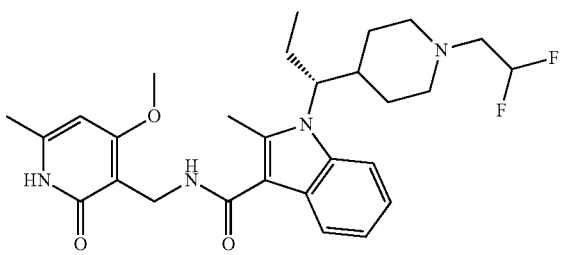 [SMILES: CC[C@H](C1CCN(CC(F)F)CC1)n1c(C)c(C(=O)NCc2c(OC)cc(C)[nH]c2=O)c2ccccc21] |
| 220 | 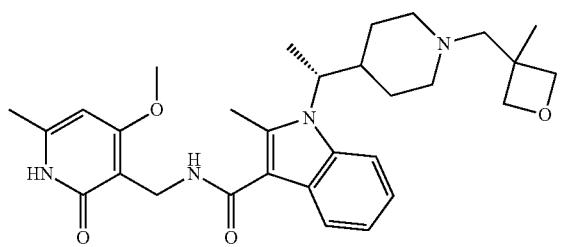 [SMILES: COc1cc(C)[nH]c(=O)c1CNC(=O)c1c(C)n([C@H](C)C2CCN(CC3(C)COC3)CC2)c2ccccc12] |
| 221 | 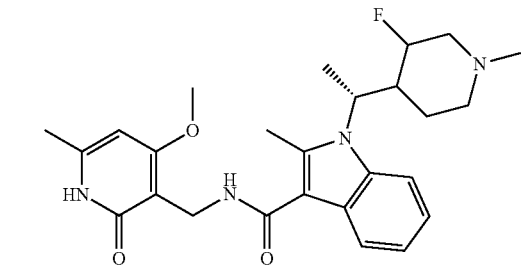 |
| 222 | 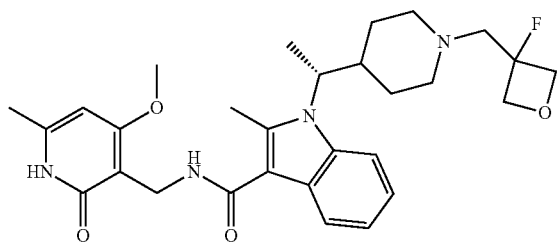 [SMILES: COc1cc(C)[nH]c(=O)c1CNC(=O)c1c(C)n([C@H](C)C2CCN(CC3(F)COC3)CC2)c2ccccc12] |

TABLE 1-continued
Certain exemplary provided compounds.
| Compound # | Structure |
|---|---|
| 223 | 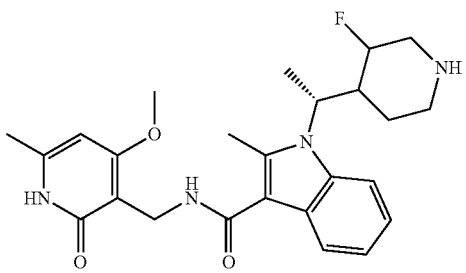 [SMILES: COc1cc(C)[nH]c(=O)c1CNC(=O)c1c(C)n([C@H](C)C2CCNCC2F)c2ccccc12] |
| 224 | 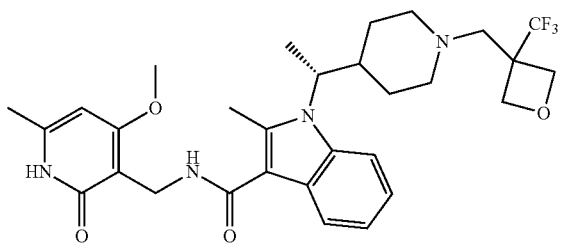 [SMILES: COc1cc(C)[nH]c(=O)c1CNC(=O)c1c(C)n([C@H](C)C2CCN(CC3(C(F)(F)F)COC3)CC2)c2ccccc12] |
| 225 | 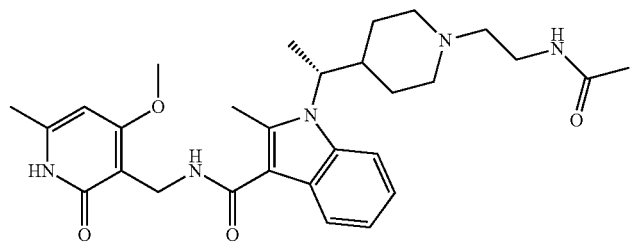 [SMILES: COc1cc(C)[nH]c(=O)c1CNC(=O)c1c(C)n([C@H](C)C2CCN(CCNC(C)=O)CC2)c2ccccc12] |
| 226 | 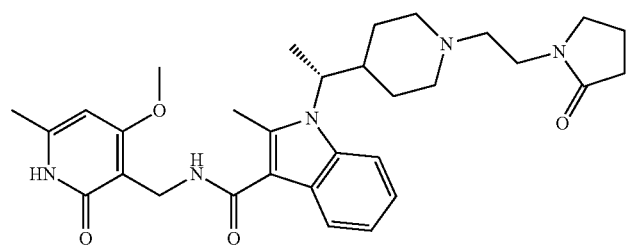 [SMILES: COc1cc(C)[nH]c(=O)c1CNC(=O)c1c(C)n([C@H](C)C2CCN(CCN3CCCC3=O)CC2)c2ccccc12] |
| 227 | 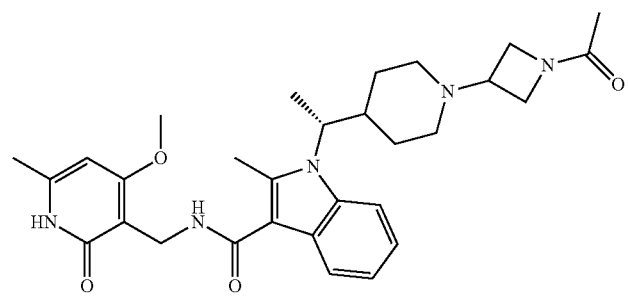 [SMILES: COc1cc(C)[nH]c(=O)c1CNC(=O)c1c(C)n([C@H](C)C2CCN(C3CN(C(C)=O)C3)CC2)c2ccccc12] |

TABLE 1-continued
Certain exemplary provided compounds.
| Compound # | Structure |
|---|---|
| 228 | 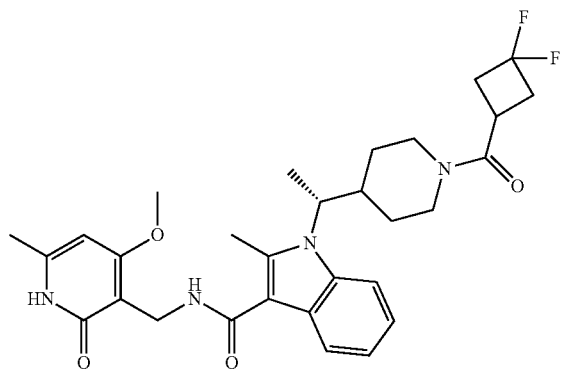 [SMILES: COc1cc(C)[nH]c(=O)c1CNC(=O)c1c(C)n([C@H](C)C2CCN(C(=O)C3CC(F)(F)C3)CC2)c2ccccc12] |
| 229 | 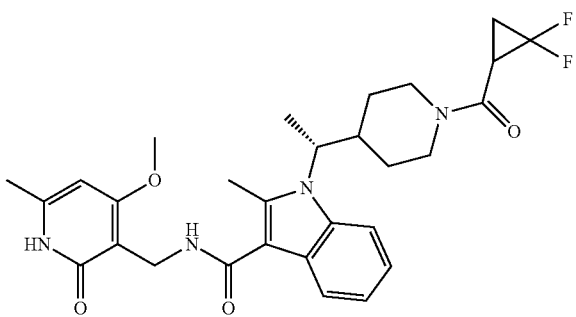 [SMILES: COc1cc(C)[nH]c(=O)c1CNC(=O)c1c(C)n([C@H](C)C2CCN(C(=O)C3CC3(F)F)CC2)c2ccccc12] |
| 230 | 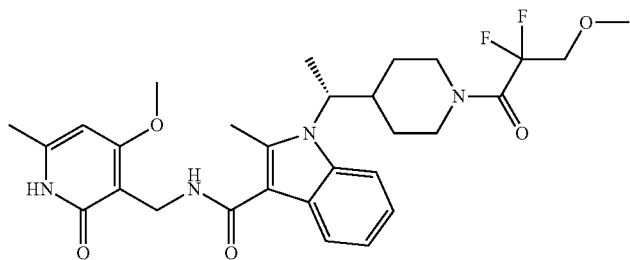 |
| 231 | 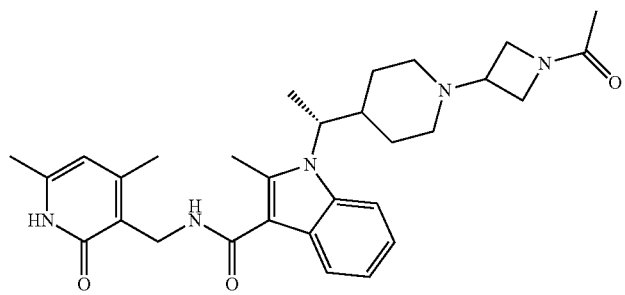 [SMILES: CC(=O)N1CC(N2CCC([C@@H](C)n3c(C)c(C(=O)NCc4c(C)cc(C)[nH]c4=O)c4ccccc43)CC2)C1] |
| 232 | 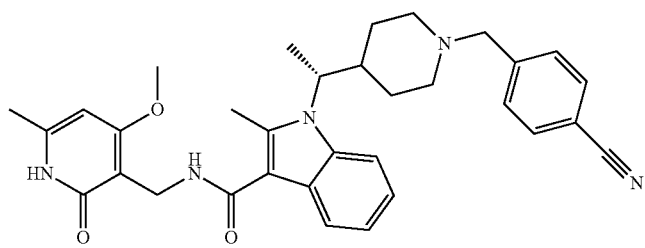 [SMILES: COc1cc(C)[nH]c(=O)c1CNC(=O)c1c(C)n([C@H](C)C2CCN(Cc3ccc(C#N)cc3)CC2)c2ccccc12] |

TABLE 1-continued

Certain exemplary provided compounds.

| Compound # | Structure |
|---|---|
| 233 | 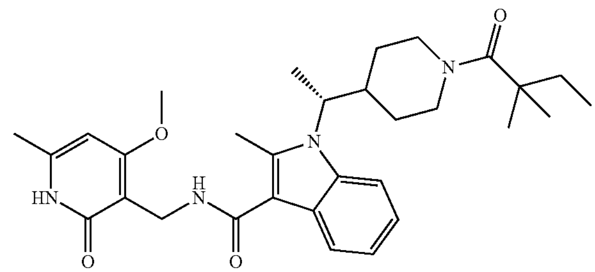 [SMILES: CCC(C)(C)C(=O)N1CCC([C@@H](C)n2c(C)c(C(=O)NCc3c(OC)cc(C)[nH]c3=O)c3ccccc32)CC1] |
| 234 | 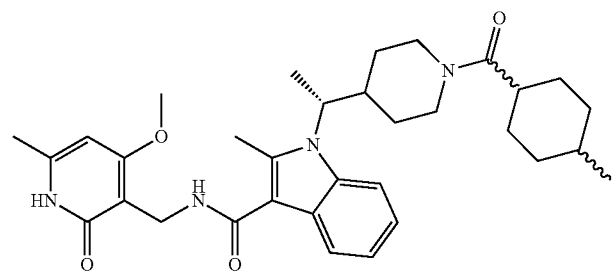 |
| 235 | 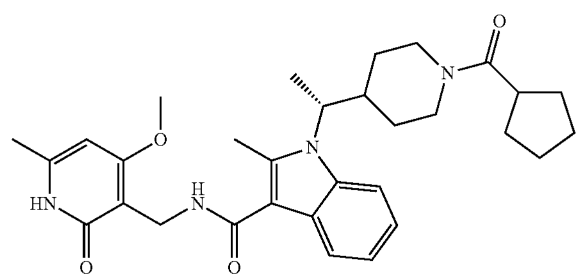 |
| 236 | 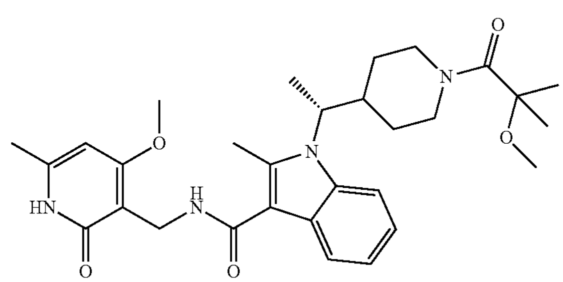 [SMILES: COc1cc(C)[nH]c(=O)c1CNC(=O)c1c(C)n([C@H](C)C2CCN(C(=O)C(C)(C)OC)CC2)c2ccccc12] |
| 237 | 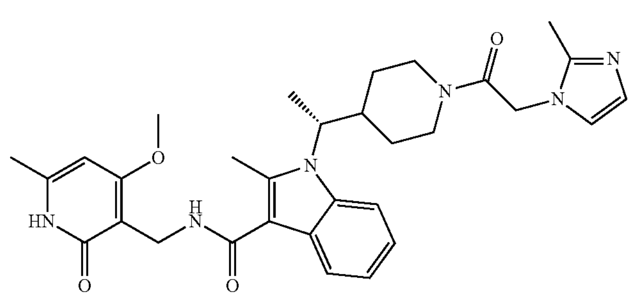 [SMILES: COc1cc(C)[nH]c(=O)c1CNC(=O)c1c(C)n([C@H](C)C2CCN(C(=O)Cn3ccnc3C)CC2)c2ccccc12] |

TABLE 1-continued

Certain exemplary provided compounds.

| Compound # | Structure |
|---|---|
| 238 | 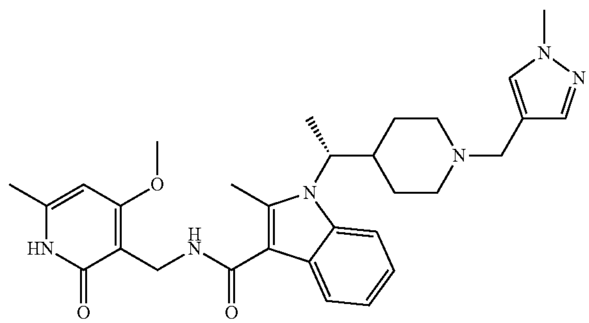 [SMILES: COc1cc(C)[nH]c(=O)c1CNC(=O)c1c(C)n([C@H](C)C2CCN(Cc3cnn(C)c3)CC2)c2ccccc12] |
| 239 | 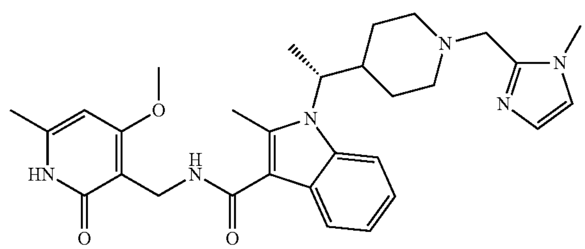 |
| 240 | 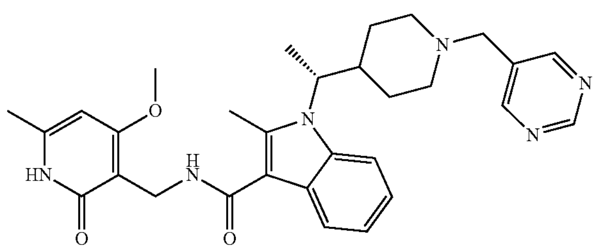 [SMILES: COc1cc(C)[nH]c(=O)c1CNC(=O)c1c(C)n([C@H](C)C2CCN(Cc3cncnc3)CC2)c2ccccc12] |
| 241 | 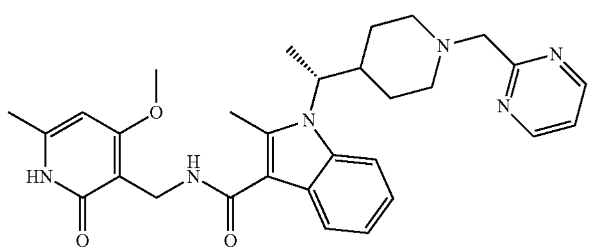 [SMILES: COc1cc(C)[nH]c(=O)c1CNC(=O)c1c(C)n([C@H](C)C2CCN(Cc3ncccn3)CC2)c2ccccc12] |
| 242 | 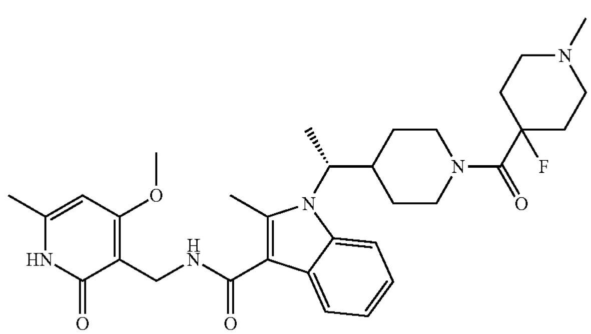 |

| Compound # | Structure |
|---|---|
| 243 | 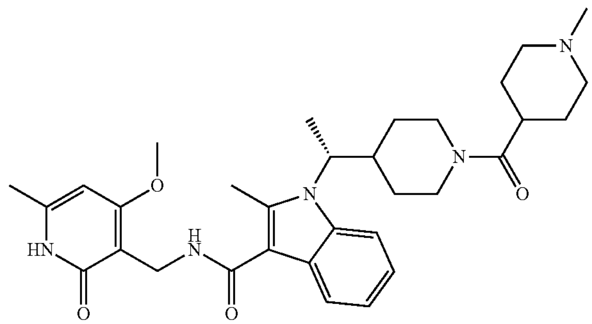 |
| 244 | 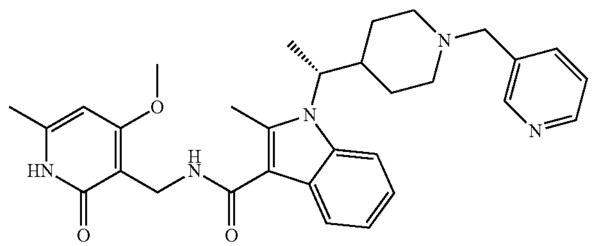 [SMILES: COc1cc(C)[nH]c(=O)c1CNC(=O)c1c(C)n([C@H](C)C2CCN(Cc3cccnc3)CC2)c2ccccc12] |
| 245 | 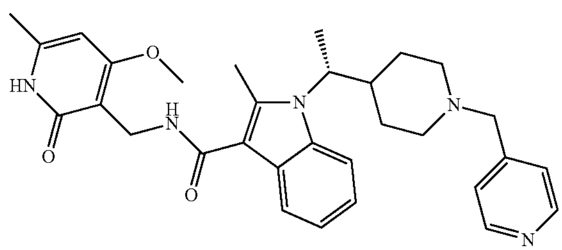 [SMILES: COc1cc(C)[nH]c(=O)c1CNC(=O)c1c(C)n([C@H](C)C2CCN(Cc3ccncc3)CC2)c2ccccc12] |
| 246 | 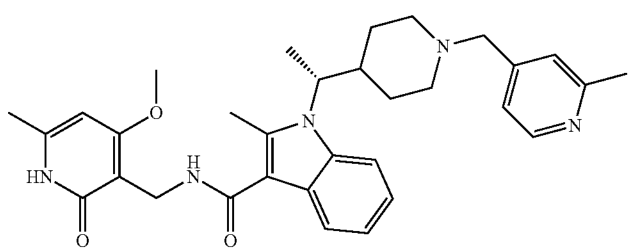 |
| 247 | 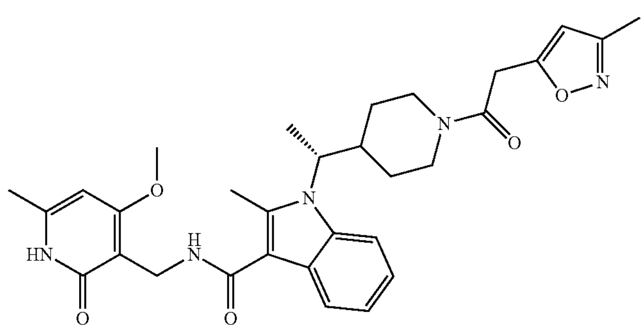 |

TABLE 1-continued

Certain exemplary provided compounds.

| Compound # | Structure |
|---|---|
| 248 | 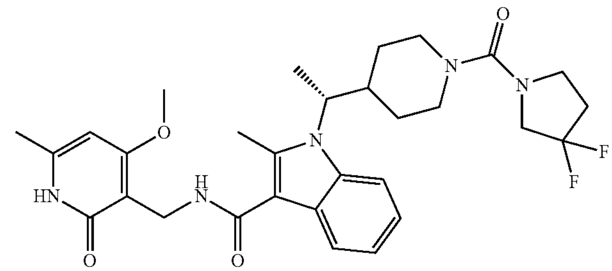 [SMILES: COc1cc(C)[nH]c(=O)c1CNC(=O)c1c(C)n([C@H](C)C2CCN(C(=O)N3CCC(F)(F)C3)CC2)c2ccccc12] |
| 249 | 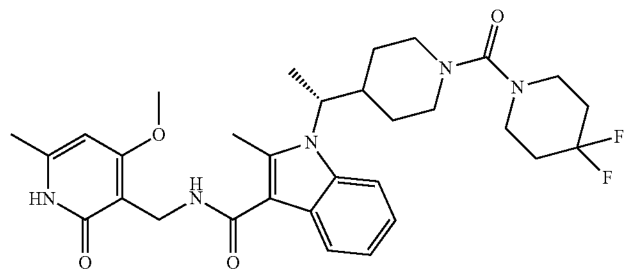 [SMILES: COc1cc(C)[nH]c(=O)c1CNC(=O)c1c(C)n([C@H](C)C2CCN(C(=O)N3CCC(F)(F)CC3)CC2)c2ccccc12] |
| 250 | 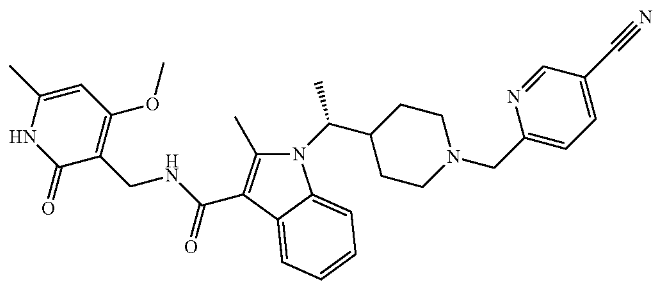 [SMILES: COc1cc(C)[nH]c(=O)c1CNC(=O)c1c(C)n([C@H](C)C2CCN(Cc3ccc(C#N)cn3)CC2)c2ccccc12] |
| 251 | 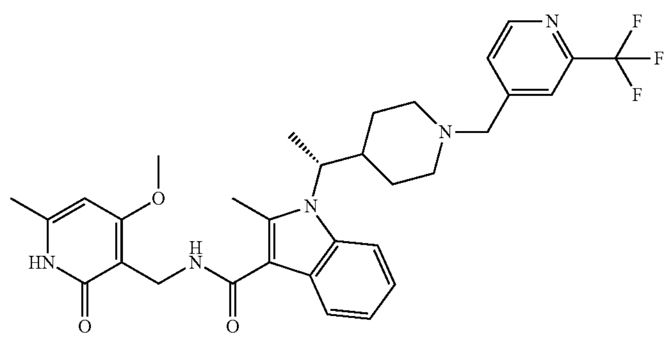 [SMILES: COc1cc(C)[nH]c(=O)c1CNC(=O)c1c(C)n([C@H](C)C2CCN(Cc3ccnc(C(F)(F)F)c3)CC2)c2ccccc12] |
| 252 | 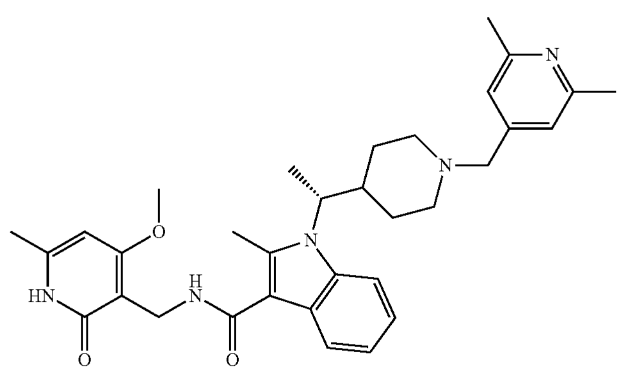 |

TABLE 1-continued
Certain exemplary provided compounds.
| Compound # | Structure |
|---|---|
| 253 | 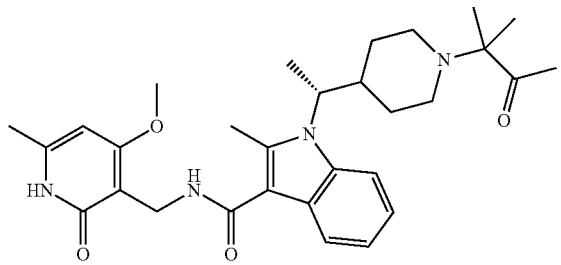 [SMILES: COc1cc(C)[nH]c(=O)c1CNC(=O)c1c(C)n([C@H](C)C2CCN(C(C)(C)C(C)=O)CC2)c2ccccc12] |
| 254 | 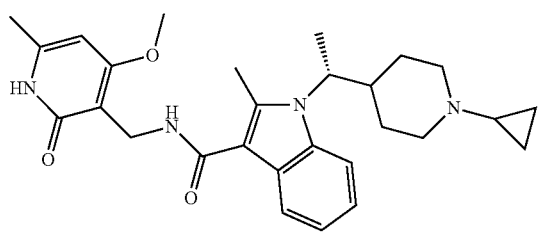 [SMILES: COc1cc(C)[nH]c(=O)c1CNC(=O)c1c(C)n([C@H](C)C2CCN(C3CC3)CC2)c2ccccc12] |
| 255 | 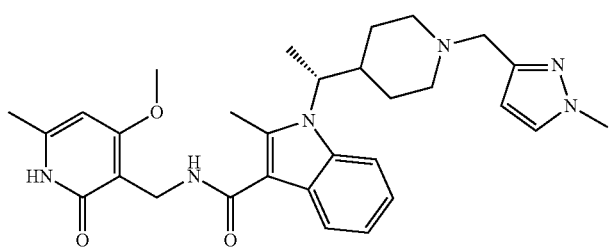 |
| 256 | 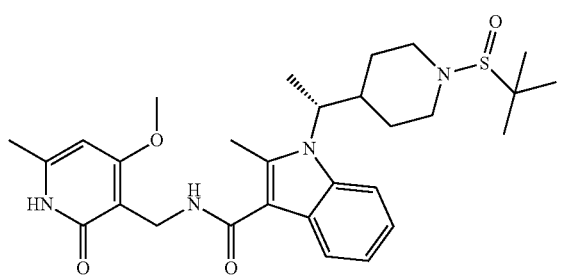 [SMILES: COc1cc(C)[nH]c(=O)c1CNC(=O)c1c(C)n([C@H](C)C2CCN(S(=O)C(C)(C)C)CC2)c2ccccc12] |
| 257 | 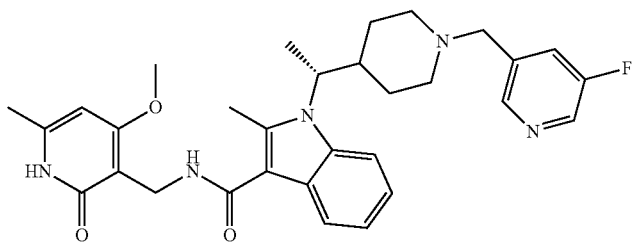 [SMILES: COc1cc(C)[nH]c(=O)c1CNC(=O)c1c(C)n([C@H](C)C2CCN(Cc3cncc(F)c3)CC2)c2ccccc12] |
| 258 | 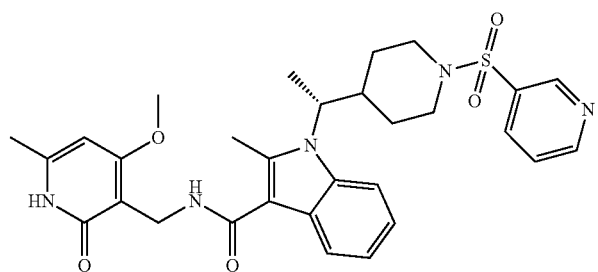 [SMILES: COc1cc(C)[nH]c(=O)c1CNC(=O)c1c(C)n([C@H](C)C2CCN(S(=O)(=O)c3cccnc3)CC2)c2ccccc12] |

TABLE 1-continued
Certain exemplary provided compounds.
| Compound # | Structure |
|---|---|
| 259 | 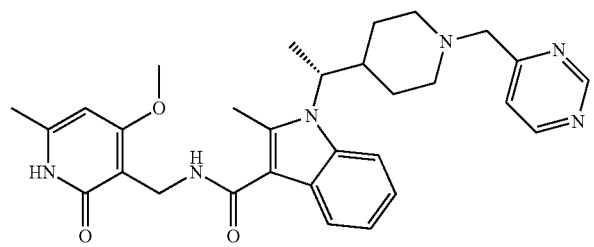 [SMILES: COc1cc(C)[nH]c(=O)c1CNC(=O)c1c(C)n([C@H](C)C2CCN(Cc3ccncn3)CC2)c2ccccc12] |
| 260 | 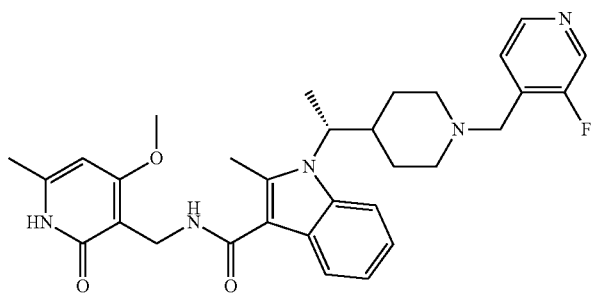 [SMILES: COc1cc(C)[nH]c(=O)c1CNC(=O)c1c(C)n([C@H](C)C2CCN(Cc3ccncc3F)CC2)c2ccccc12] |
| 261 | 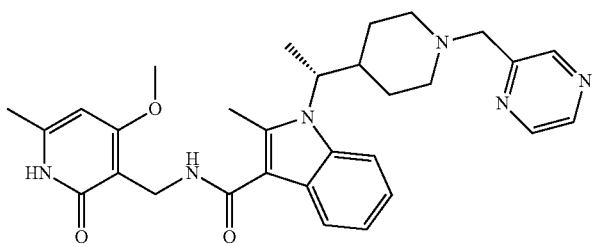 [SMILES: COc1cc(C)[nH]c(=O)c1CNC(=O)c1c(C)n([C@H](C)C2CCN(Cc3cnccn3)CC2)c2ccccc12] |
| 262 | 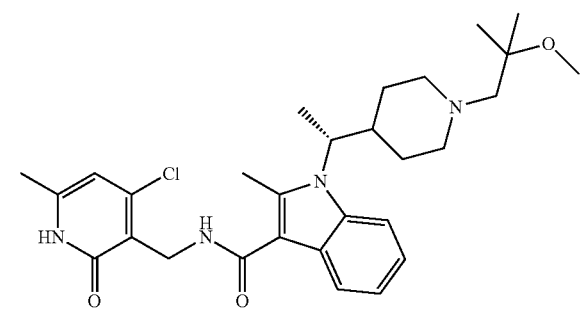 |
| 263 | 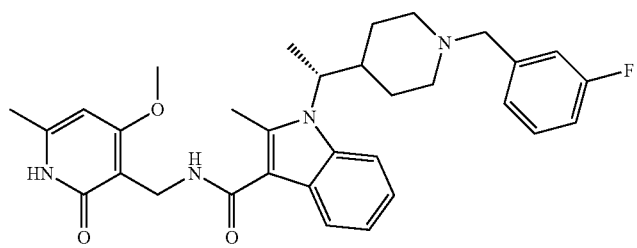 [SMILES: COc1cc(C)[nH]c(=O)c1CNC(=O)c1c(C)n([C@H](C)C2CCN(Cc3cccc(F)c3)CC2)c2ccccc12] |

TABLE 1-continued

Certain exemplary provided compounds.

| Compound # | Structure |
|---|---|
| 264 | 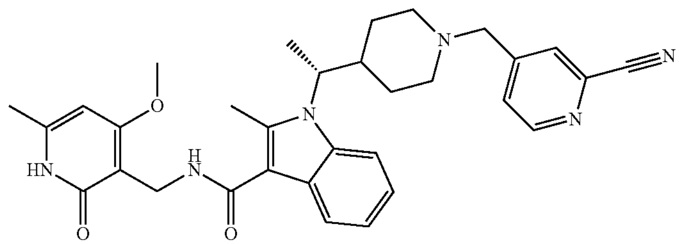 [SMILES: COc1cc(C)[nH]c(=O)c1CNC(=O)c1c(C)n([C@H](C)C2CCN(Cc3ccnc(C#N)c3)CC2)c2ccccc12] |
| 265 | 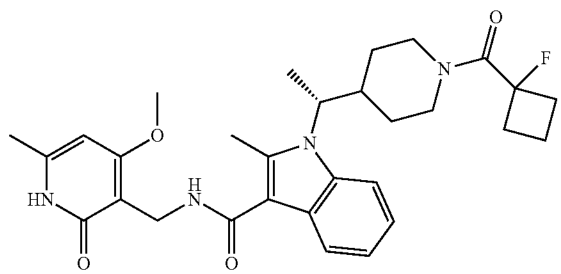 [SMILES: COc1cc(C)[nH]c(=O)c1CNC(=O)c1c(C)n([C@H](C)C2CCN(C(=O)C3(F)CCC3)CC2)c2ccccc12] |
| 266 | 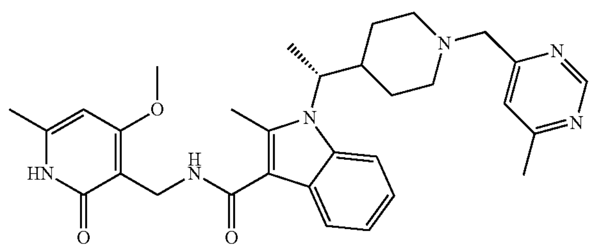 [SMILES: COc1cc(C)[nH]c(=O)c1CNC(=O)c1c(C)n([C@H](C)C2CCN(Cc3cc(C)ncn3)CC2)c2ccccc12] |
| 267 | 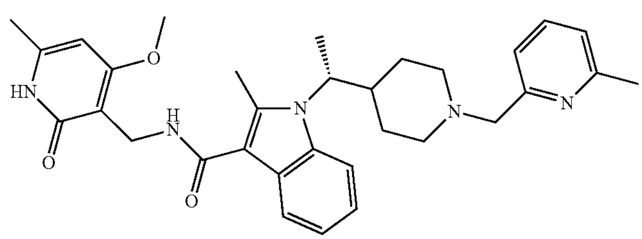 |
| 268 | 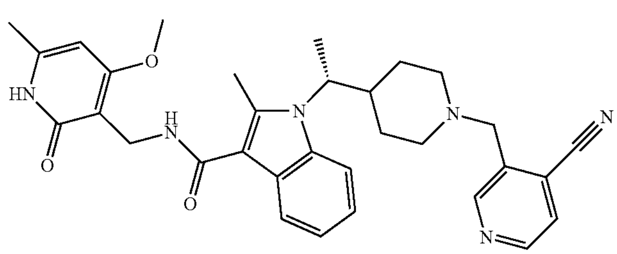 [SMILES: COc1cc(C)[nH]c(=O)c1CNC(=O)c1c(C)n([C@H](C)C2CCN(Cc3cnccc3C#N)CC2)c2ccccc12] |
| 269 | 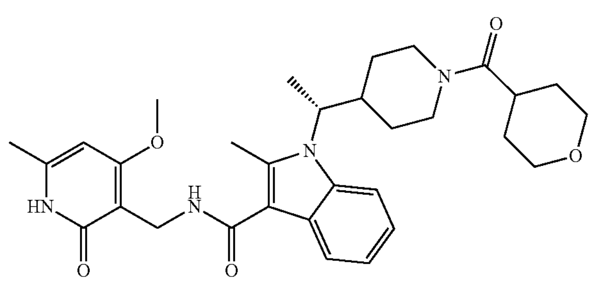 [SMILES: COc1cc(C)[nH]c(=O)c1CNC(=O)c1c(C)n([C@H](C)C2CCN(C(=O)C3CCOCC3)CC2)c2ccccc12] |

TABLE 1-continued

Certain exemplary provided compounds.

| Compound # | Structure |
|---|---|
| 270 | 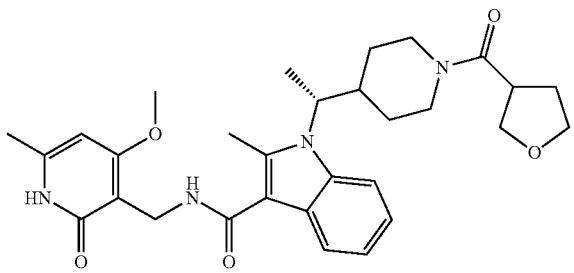 [SMILES: COc1cc(C)[nH]c(=O)c1CNC(=O)c1c(C)n([C@H](C)C2CCN(C(=O)C3CCOC3)CC2)c2ccccc12] |

*Compound 234 is a mixture of two different trans diastereomers about the cyclohexyl ring as indicated by the wavy bond in the depicted structure In some embodiments, a provided compound is a compound selected from Table 2, or a pharmaceutically acceptable salt thereof.

TABLE 2

Exemplary provided compounds.

| | |
|---|---|
| 142 | 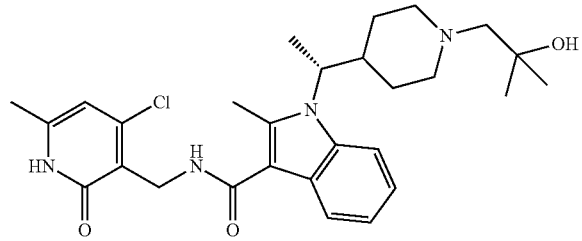 [SMILES: Cc1cc(Cl)c(CNC(=O)c2c(C)n([C@H](C)C3CCN(CC(C)(C)O)CC3)c3ccccc23)c(=O)[nH]1] |
| 155 | 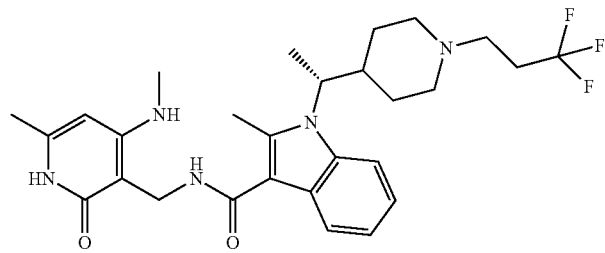 [SMILES: CNc1cc(C)[nH]c(=O)c1CNC(=O)c1c(C)n([C@H](C)C2CCN(CCC(F)(F)F)CC2)c2ccccc12] |
| 151 | 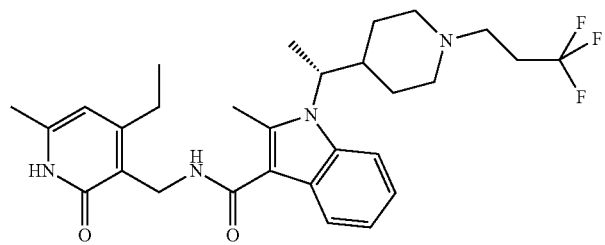 [SMILES: CCc1cc(C)[nH]c(=O)c1CNC(=O)c1c(C)n([C@H](C)C2CCN(CCC(F)(F)F)CC2)c2ccccc12] |
| 143 | 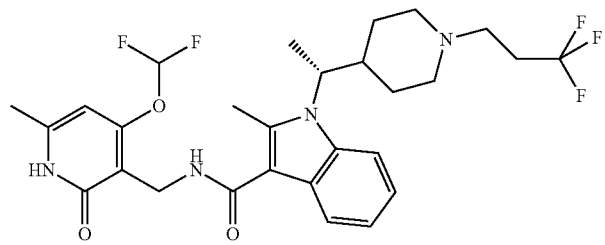 [SMILES: Cc1cc(OC(F)F)c(CNC(=O)c2c(C)n([C@H](C)C3CCN(CCC(F)(F)F)CC3)c3ccccc23)c(=O)[nH]1] |

TABLE 2-continued
Exemplary provided compounds.
126
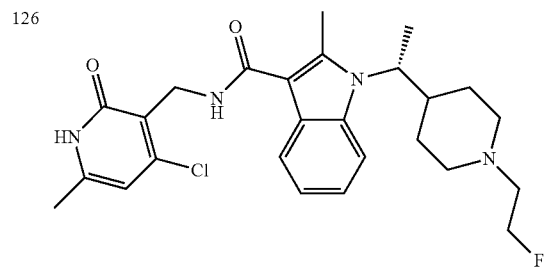
219
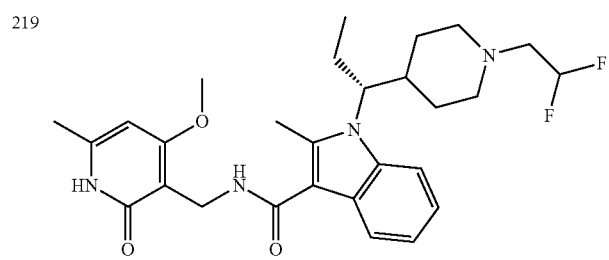
112
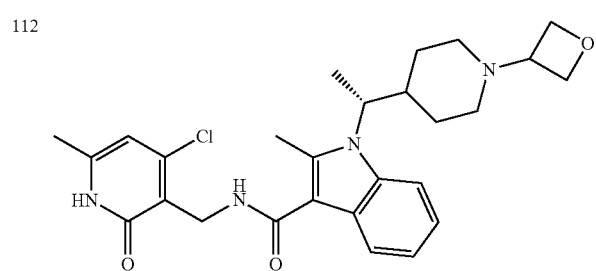
204
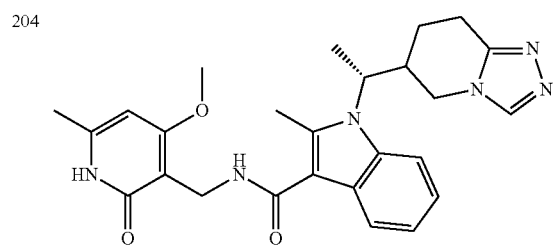
205
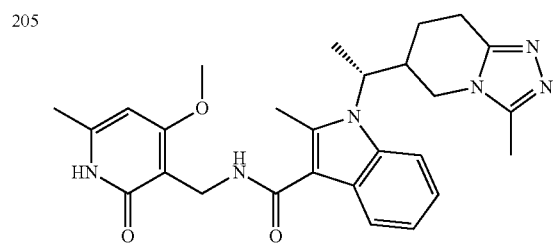
123
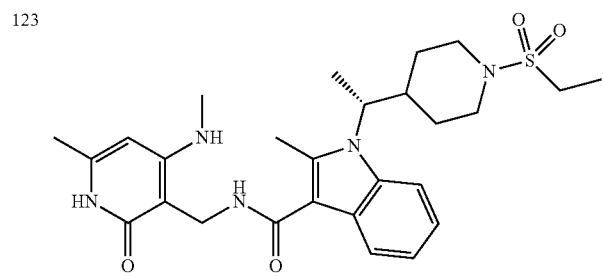

TABLE 2-continued

Exemplary provided compounds.

132

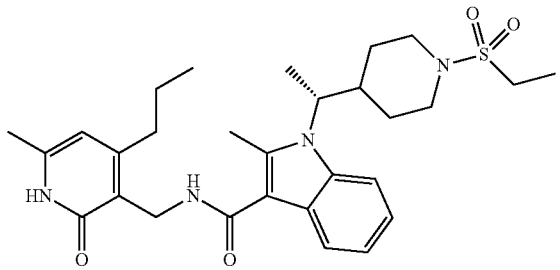 [SMILES: CCCc1cc(C)[nH]c(=O)c1CNC(=O)c1c(C)n([C@H](C)C2CCN(S(=O)(=O)CC)CC2)c2ccccc12]

163

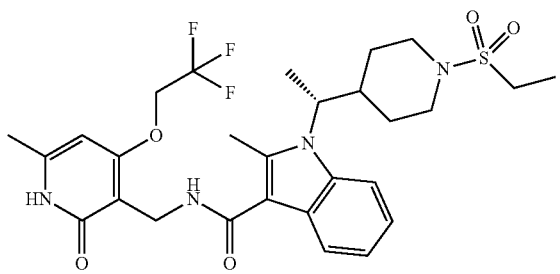 [SMILES: CCS(=O)(=O)N1CCC([C@@H](C)n2c(C)c(C(=O)NCc3c(OCC(F)(F)F)cc(C)[nH]c3=O)c3ccccc32)CC1]

107

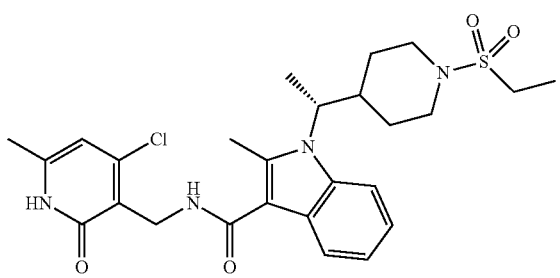 [SMILES: CCS(=O)(=O)N1CCC([C@@H](C)n2c(C)c(C(=O)NCc3c(Cl)cc(C)[nH]c3=O)c3ccccc32)CC1]

4. Uses, Formulation and Administration

Pharmaceutically Acceptable Compositions

According to another embodiment, the invention provides a composition comprising a compound of this invention or a pharmaceutically acceptable derivative thereof and a pharmaceutically acceptable carrier, adjuvant, or vehicle. The amount of compound in compositions of this invention is such that is effective to measurably modulate a histone methyl modifying enzyme, or a mutant thereof, in a biological sample or in a patient. In certain embodiments, the amount of compound in compositions of this invention is such that is effective to measurably modulate a histone methyl modifying enzyme, or a mutant thereof, in a biological sample or in a patient.

In certain embodiments, a composition of this invention is formulated for administration to a patient in need of such composition. In some embodiments, a composition of this invention is formulated for oral administration to a patient.

The term "patient," as used herein, means an animal, preferably a mammal, and most preferably a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

A "pharmaceutically acceptable derivative" means any non-toxic salt, ester, salt of an ester or other derivative of a compound of this invention that, upon administration to a recipient, is capable of providing, either directly or indirectly, a compound of this invention or an inhibitorily active metabolite or residue thereof.

Compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, provided pharmaceutically acceptable compositions may be formulated in a suitable ointment containing the active component suspended or dissolved in one or more carriers. Carriers for topical administration of compounds of this invention include, but are not limited to, mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, provided pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

Pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, pharmaceutically acceptable compositions of this invention are formulated for oral administration. Such formulations may be administered with or without food. In some embodiments, pharmaceutically acceptable compositions of this invention are administered without food. In other embodiments, pharmaceutically acceptable compositions of this invention are administered with food.

The amount of compounds of the present invention that may be combined with the carrier materials to produce a composition in a single dosage form will vary depending upon the host treated and the particular mode of administration. Preferably, provided compositions should be formulated so that a dosage of between 0.01-100 mg/kg body weight/day of the inhibitor can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Uses of Compounds and Pharmaceutically Acceptable Compositions

Compounds and compositions described herein are generally useful for the modulating of activity of one or more enzymes involved in epigenetic regulation and in particular EZH1 and EZH2 and, even more specifically EZH2 and mutant forms thereof. In some embodiments, compounds of the present invention down-regulate or suppress the activity of EZH2. In some embodiments, compounds of the present invention are antagonists of EZH2 activity. In some embodiments, compounds of the present invention down-regulate or suppress the activity of EZH1. In some embodiments, compounds of the present invention are antagonists of EZH1 activity.

In some embodiments, compounds and compositions of the present invention are useful in treating diseases and/or disorders associated with overexpression of EZH1 or EZH2 and/or expression of a mutant form of EZH2, particularly those mutant forms that alter EZH2 substrate activity. The study of EZH2 deletions, missense and frameshift mutations suggest that EZH2 functions as a tumor suppressor in blood disorders such as myelodysplastic syndromes (MDS) and myeloid malignancies (Ernst et al., Nat Genet. 2010 August;

42(8):722-6; Nikoloski et al., Nat Genet. 2010 August; 42(8):665-7). In some embodiments, compounds and compositions of the present invention are useful in treating diseases and/or disorders associated with the presence of EZH2 having a Y641N, Y641C, Y641F, Y641H, Y641S, A677G, or A687 mutation. In a particular aspect of this embodiment, the EZH2 has a Y641N mutation.

In some embodiments, the present invention provides a method of treating a subject suffering from a disease and/or disorder associated with overexpression of EZH1 or EZH2 and/or expression of a mutant form of EZH2 comprising the step of administering a compound of Formula I, II, or III (e.g., a compound from Table 1), a compound from Table 2 or a composition comprising any of the foregoing. In some embodiments, the above method additionally comprises the preliminary step of determining if the subject is overexpressing EZH2 or expressing a mutant form of EZH2.

In some embodiment, the present invention the disease or disorder associated with the presence of a mutant form of EZH2 is a human B cell lymphoma. In some embodiments, the disease and/or disorder associated with the presence of Y641N EZH2 is follicular lymphoma or diffuse large-B-cell lymphoma. In some embodiments, compounds or compositions of the present invention are useful in treating blood disorders, such as myelodysplastic syndromes, leukemia, anemia and cytopenia. Sneeringer et al., "Coordinated activities of wild-type plus mutant EZH2 drive tumor-associated hypertrimethylation of lysine 27 on histone H3 (H3K27) in human B-cell lymphomas," Proceedings of the National Academy of Sciences, PNAS Early Edition published ahead of print on Nov. 15, 2010.

In some embodiments, compounds and compositions of the present invention are useful in treating diseases and/or disorders associated with cellular proliferation. In some embodiments, compounds and compositions of the present invention are useful in treating diseases and/or disorders associated with misregulation of cell cycle or DNA repair. In some embodiments, compounds and compositions of the present invention are useful in treating cancer. Exemplary types of cancer include breast cancer, prostate cancer, colon cancer, renal cell carcinoma, glioblastoma multiforme cancer, bladder cancer, melanoma, bronchial cancer, lymphoma and liver cancer.

In some embodiments, the present invention provides a method of reducing the activity of EZH2 in a subject comprising the step of administering a compound of Formula I, II, or III (e.g., a compound from Table 1), a compound from Table 2 or a composition comprising any of the foregoing. In some embodiments, the present invention provides a method of reducing the activity of wide-type EZH2 in a subject comprising the step of administering a compound of Formula I, II, or III (e.g., a compound from Table 1), a compound from Table 2 or a composition comprising any of the foregoing. In some embodiments, the present invention provides a method of reducing the activity of wild-type EZH1 in a subject comprising the step of administering a compound of Formula I, II, or III (e.g., a compound from Table 1), a compound from Table 2 or a composition comprising any of the foregoing. In some embodiments, the present invention provides a method of reducing the activity of a mutant form of EZH2 in a subject comprising the step of administering a compound of Formula I, II, or III (e.g., a compound from Table 1), a compound from Table 2 or a composition comprising any of the foregoing. In some embodiments, the present invention provides a method of reducing the activity of a mutant form of EZH2 in a subject comprising the step of administering a compound of Formula I, II, III, a compound from Table 2 or a composition comprising any of the foregoing, wherein the mutant form of EZH2 is selected from Y641N, Y641C, Y641F, Y641H, Y641S, A677G, or A687V EZH2. Each of these mutations alter the EZH2 substrate activity, and thus facilitate the conversion from a di- to a tri-methylated K27 state. In a more specific aspect, the present invention provides a method of reducing the activity of a mutant form of EZH2 in a subject comprising the step of administering a compound of Formula I, II, or III (e.g., a compound from Table 1), a compound from Table 2 or a composition comprising any of the foregoing, wherein the mutant form of EZH2 is Y641N EZH2.

In some embodiments, the present invention provides a method of treating a subject suffering from a disease and/or disorder associated with EZH2, wherein the method additionally comprises the preliminary step of determining if the subject is expressing a mutant form of EZH2, such as Y641N, Y641C, Y641F, Y641H, Y641S, A677G, or A687V EZH2. In some embodiments, the present invention provides a method of reducing the activity of a mutant form of EZH2, such as Y641N, Y641C, Y641F, Y641H, Y641S, A677G, or A687V EZH2, in a subject in need thereof comprising the step of administering a compound of Formula I, II, or III (e.g., a compound from Table 1), a compound from Table 2 or a composition comprising any of the foregoing. In some embodiments, the present invention provides a method of treating a subject suffering from a disease and/or disorder associated with EZH2, wherein the method additionally comprises the preliminary step of determining if the subject has increased levels of histone H3 Lys-27-specific trimethylation (H3K27me3), as compared to a subject known not to express a mutant form of EZH2.

EQUIVALENTS

The representative examples that follow are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples that follow and the references to the scientific and patent literature cited herein. It should further be appreciated that the contents of those cited references are incorporated herein by reference to help illustrate the state of the art.

It will be appreciated that for compound preparations described herein, when reverse phase HPLC is used to purify a compound, a compound may exist as an acid addition salt. In some embodiments, a compound may exist as a formic acid or mono-, di-, or tri-trifluoroacetic acid salt.

It will further be appreciated that the present invention contemplates individual compounds described herein. Where individual compounds exemplified are isolated and/or characterized as a salt, for example, as a trifluoroacetic acid salt, the present invention contemplates a free base of the salt, as well as other pharmaceutically acceptable salts of the free base.

The following examples contain important additional information, exemplification and guidance that can be adapted to the practice of this invention in its various embodiments and the equivalents thereof

EXAMPLES

As depicted in the Examples below, in certain exemplary embodiments, compounds are prepared according to the following general procedures. It will be appreciated that, although the synthetic methods and Schemes depict the synthesis of certain compounds of the present invention, the following methods and other methods known to one of ordinary skill in the art can be applied to all compounds and subclasses and species of each of these compounds, as described herein.

Unless otherwise noted, all solvents, chemicals, and reagents were obtained commercially and used without purification. The $^1$H NMR spectra were obtained in CDCl$_3$, d$_6$-DMSO, CD$_3$OD, or d$_6$-acetone at 25° C. at 300 MHz on an OXFORD (Varian) with chemical shift (δ, ppm) reported relative to TMS as an internal standard. HPLC-MS chromatograms and spectra were obtained with Shimadzu LC-MS-2020 system. Chiral analysis and purification were obtained with Yilite P270.

General Synthetic Scheme:

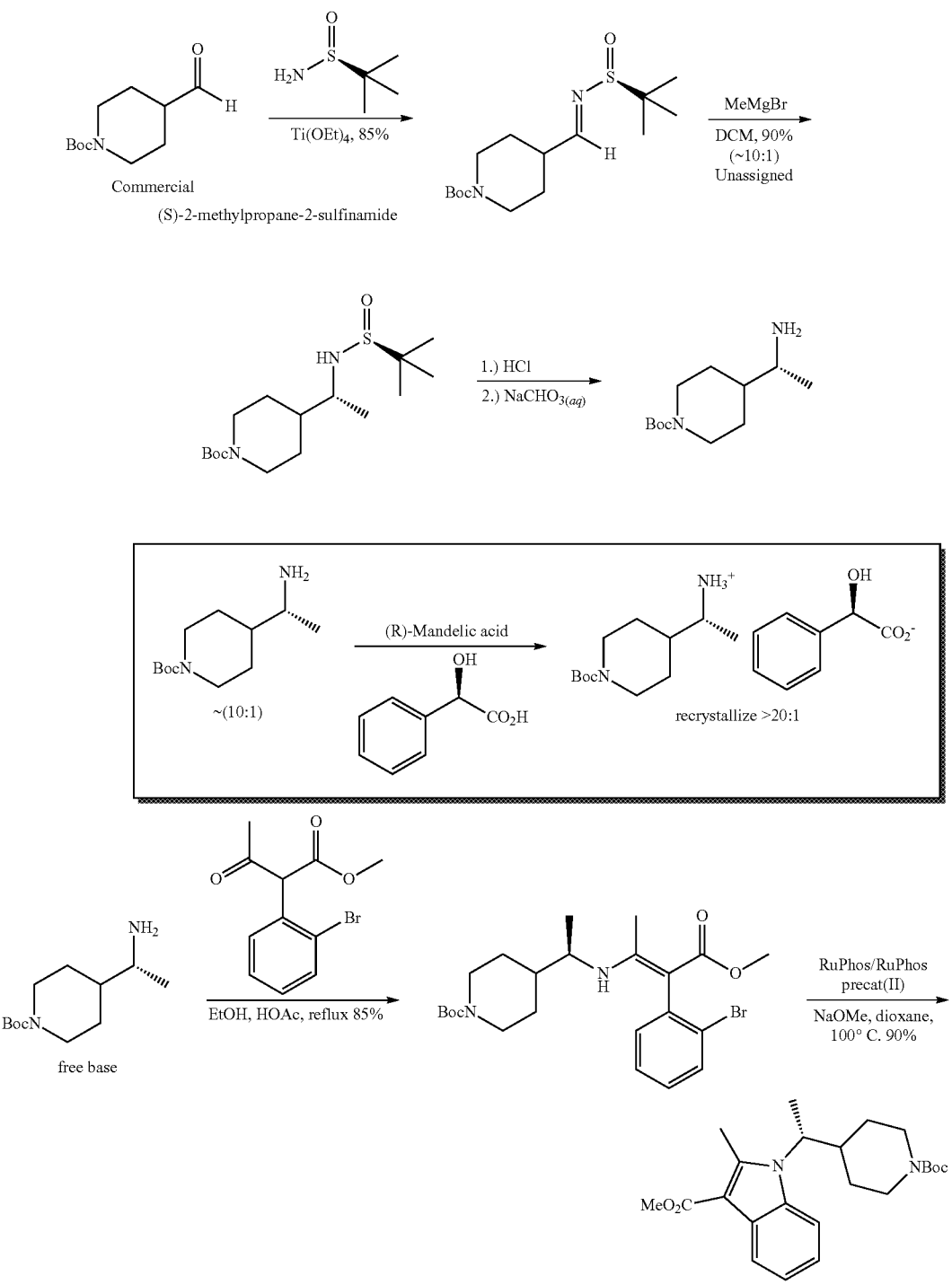

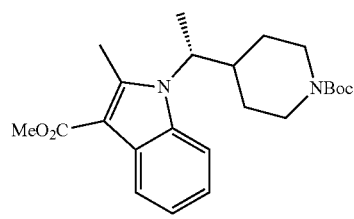 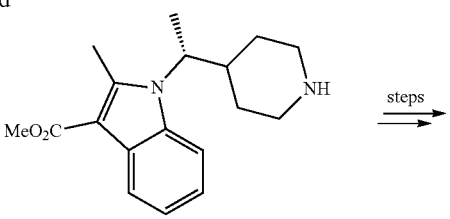

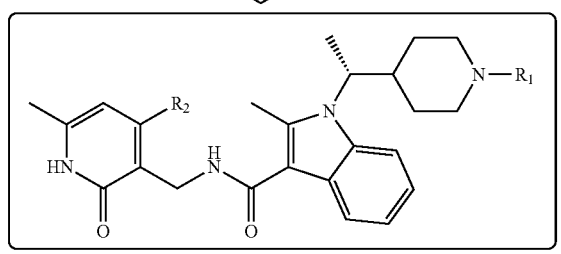

(S)-2-methylpropane-2-sulfinamide

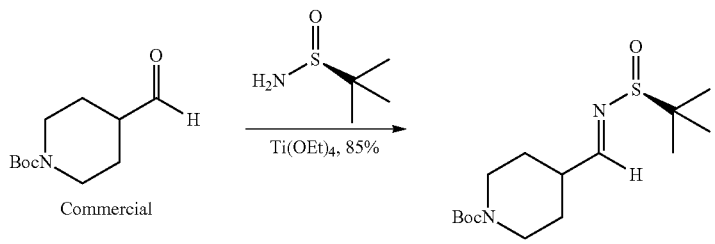

Commercial (S,E)-tert-butyl 4-(((tert-butylsulfinyl)imino)methyl)piperidine-1-carboxylate A 1 L round bottom flask was charged with a magnetic stir bar, tert-butyl 4-formylpiperidine-1-carboxylate (25 g, 117.22 mmol), (S)-2-methylpropane-2-sulfinamide (16.34 g, 134.8 mmol), DCM (200 mL) and tetraethoxytitanium (46.7 mL, 222.7 mmol). The reaction was then allowed to stir overnight at ambient temperature. The reaction was quenched with 50 mL of brine and 10 mL of 10% HCl. A solid formed which was removed via vacuum filtration using a Buchner funnel. The resulting filter cake was washed with additional DCM (~500 mL) and the filtrate was dried with MgSO₄, filtered, and concentrated in vacuo to afford the title compound as a free flowing off-white solid (30.74 grams, 83%).

tert-butyl 4-((R)-1-((S)-1,1-dimethylethylsulfinamido)ethyl)piperidine-1-carboxylate To a round bottomed flask charged with a magnetic stir bar was added (S,E)-tert-butyl 4-((tert-butylsulfinylimino)methyl)piperidine-1-carboxylate (36.4 g, 115 mmol) and DCM (400 mL). The solution was cooled to 0° C. in an ice bath with stirring. To this solution was added MeMgBr (77 ml, 3M in diethyl ether, 230 mmol) and the reaction allowed to stir for 4 h while warming to room temperature. The reaction was carefully quenched via the addition of saturated aqueous NH₄Cl. The resulting solids were broken up by the addition of 1N HCl (~20 mL). The layers were separated and the aqueous phase was extracted with DCM. The combined organic phase was dried over Na₂SO₄, filtered, and concentrated in vacuo to afford the title compound (29 g, >10:1 dr) which is used without further purification in the next step.

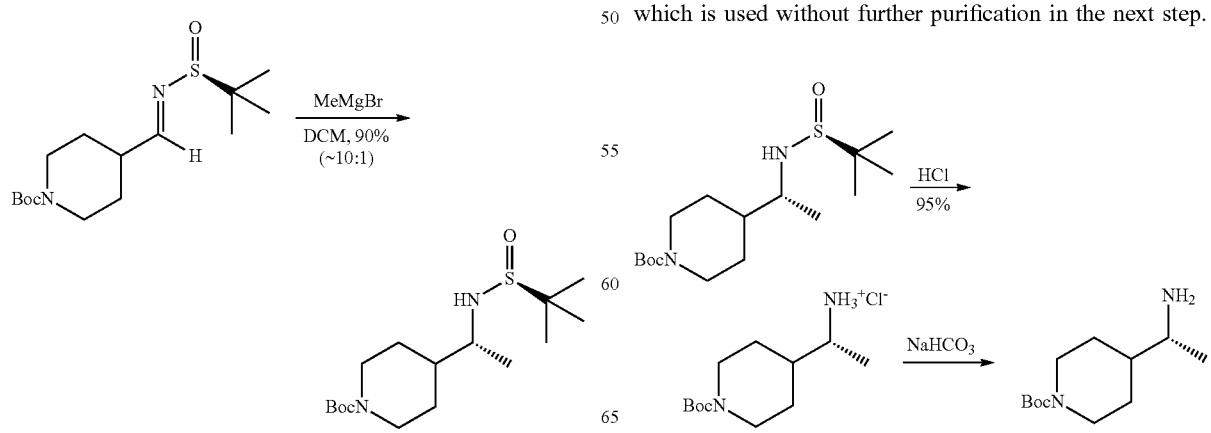

(R)-tert-butyl 4-(1-aminoethyl)piperidine-1-carboxylate

To a 1 L round bottomed flask charged with a magnetic stir bar was added crude tert-butyl 4-((R)-1-((S)-1,1-dimethylethylsulfinamido)ethyl)piperidine-1-carboxylate (29 g) and MeOH (200 mL). A solution of 4 N HCl in 1,4-dioxane (24.06 ml, 96 mmol) was then added. The resulting mixture was then stirred at room temperature for 1 h. The organics were then removed in vacuo to afford a sticky solid which was suspended in ethyl acetate/hexanes (1:1, ~150 mL) which was agitated for 1 h. White solids were obtained which were collected via vacuum filtration using a Buchner funnel. The filter cake was washed with additional hexanes and was collected to afford the pure HCl salt as a free flowing solid. This material was then treated with sat'd aqueous NaHCO₃ (~500 mL) and extracted with DCM (2×500 mL). The combined organic phase was dried with MgSO₄, filtered, and the filtrate was conc. in vacuo affording the title compound (22 g) which was used without further purification.

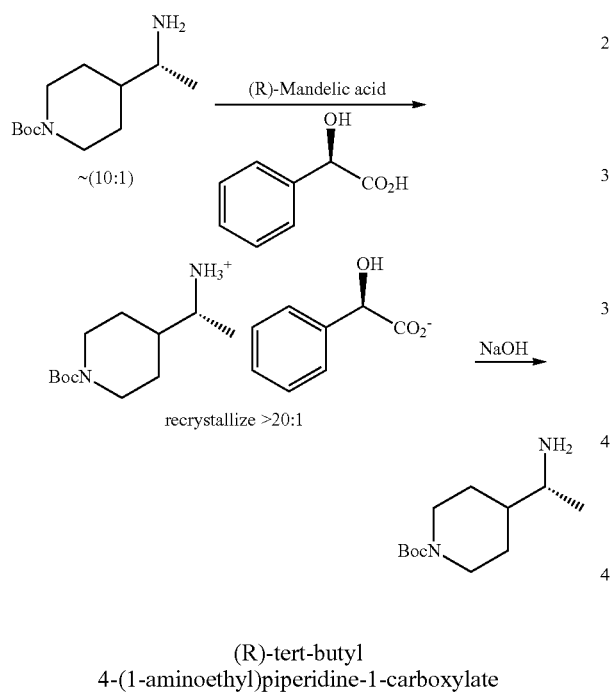

(R)-tert-butyl 4-(1-aminoethyl)piperidine-1-carboxylate

To a solution of tert-butyl 4-(1-aminoethyl)piperidine-1-carboxylate (92 g, 403.5 mmol) in acetone (150 mL) was added (R)-(+)-mandelic acid (61.5 g, 405 mmol). The mixture was stirred at room temperature until a precipitate formed. Additional acetone (250 mL) was added and the mixture was heated to reflux for 4 h. The formed solids were collected via vacuum filtration and the filtrate was allowed to cool to room temperature for 15 h. Additional solids formed from the filtrate which were collected via vacuum filtration and rinsed with acetone. The combined solids were recrystallized from acetone/ethanol (12/1, ~14 mL/g), collected and dried. The resulting material was free based with 1N aq. NaOH (~600 mL) and the mixture was extracted with DCM (1.2 L). The organic layer was washed dried over sodium sulfate, filtered, and concentrated to the title compound as a white solid (40.5 g). MS (M+H⁺) m/z: calc'd. 229.33; found 228.73. ¹H NMR (CDCl₃, 400 MHz) δ 4.13 (s, 2H), 2.63-2.71 (m, 3H), 1.73-1.70 (m, 2H), 1.43 (s, 9H), 1.15-1.26 (m, 5H), 1.03 (d, J=6.4 Hz, 3H).

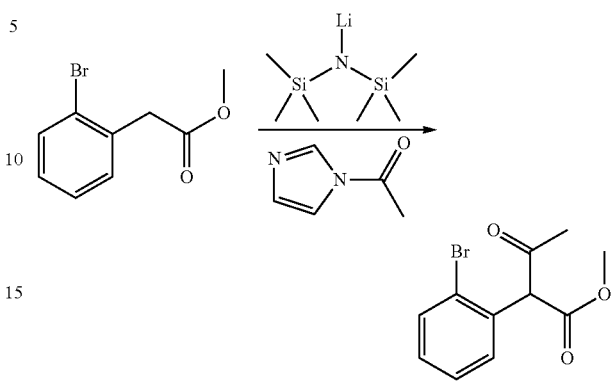

Methyl 2-(2-bromophenyl)-3-oxobutanoate

A round bottom flask was charged with a magnetic stir bar and methyl 2-(2-bromophenyl)acetate (25 g, 109 mmol) and THF (50 mL). This solution was cooled to −78° C. before drop wise addition of a 1M solution of LiHMDS in THF (218 ml, 218 mmol). The reaction was stirred for 30 min at −78° C. before addition of 1-(1H-imidazol-1-yl)ethanone (14.42 g, 131 mmol) as a solution in a mixture of THF:DMF (112 mL THF, 24 mL DMF). The solution was stirred for 1 h before quenching with sat'd aqueous NH₄Cl (~250 mL) and diluting with EtOAc. The layers were separated and the aqueous phase was extracted with additional EtOAc (~2× 250 mL). The combined organic extract was washed with brine, dried over Na₂SO₄, filtered, and concentrated in vacuo. The crude residue was purified via silica gel chromatography using an eluent of ethyl acetate/hexanes (10:1) to afford methyl 2-(2-bromophenyl)-3-oxobutanoate (32.5 g, 102 mmol, 93% yield).

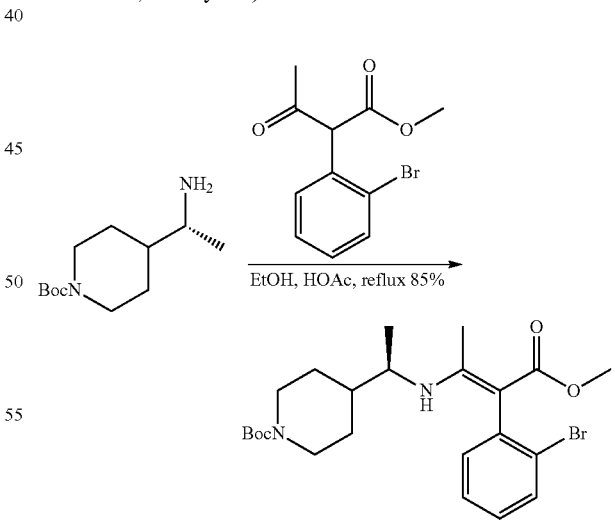

(R,E)-tert-butyl 4-(1-((3-(2-bromophenyl)-4-methoxy-4-oxobut-2-en-2-yl)amino)ethyl)piperidine-1-carboxylate A 500 mL round bottom flask was charged with a magnetic stir bar, (R)-tert-butyl 4-(1-aminoethyl)piperidine-1- carboxylate (17.56 g, 76.91 mmol), ethanol (200 mL), methyl 2-(2-bromophenyl)-3-oxobutanoate (17.38 g, 64.09 mmol), and acetic acid (4.4 mL, 76.91 mmol). The reaction vessel was fitted with a reflux condenser and the reaction was heated to reflux for 18 h before being allowed to cool to rt. The ethanol was removed in vacuo and the resulting material was washed with sat'd aqueous NaHCO₃, extracted with ethyl acetate, dried with MgSO₄, filtered, and concentrated in vacuo to afford the crude material. This material was purified via silica gel chromatography (330 grams) using ethyl acetate/hexanes (1:4) as eluent to afford the title compound as a white sticky solid (22.8 g, 47.36 mmol).

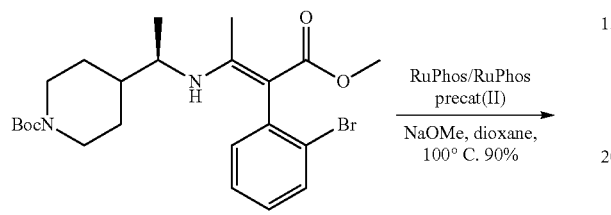

allowed to cool to room temperature, was filtered through a bed of Celite, and the filtrate was concentrated in vacuo to afford the crude product. This material was purified via silica gel chromatography (330 g) using hexanes/ethyl acetate (4:1) as eluent to afford the title compound (17.3 g, 43.19 mmol).

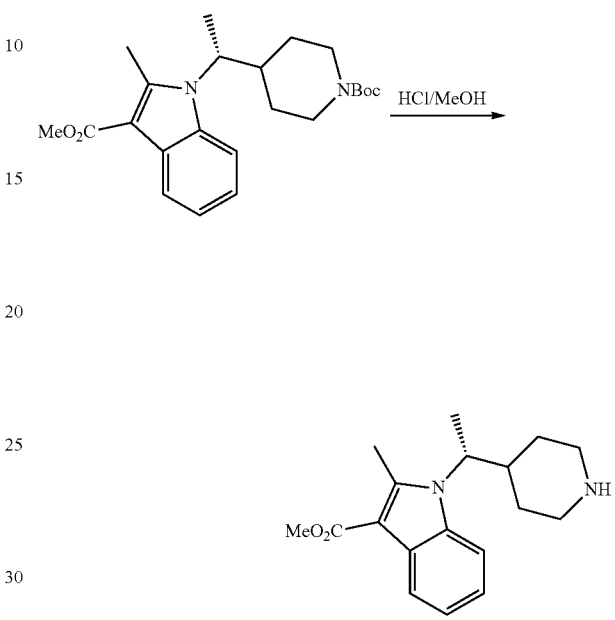

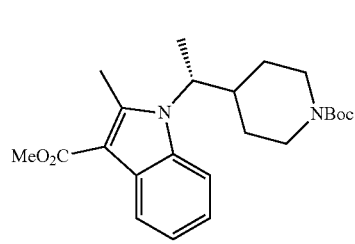

(R)-methyl 1-(1-(1-(tert-butoxycarbonyl)piperidin-4-yl)ethyl)-2-methyl-1H-indole-3-carboxylate A 500 mL round bottom flask was charged with a magnetic stir bar, (R,E)-tert-butyl 4-(1-((3-(2-bromophenyl)-4-methoxy-4-oxobut-2-en-2-yl)amino)ethyl)piperidine-1-carboxylate (23 g, 47.78 mmol), 1,4-dioxane (200 mL), chloro-(2-dicyclohexylphosphino-2',6'-diisopropoxy-1,1'-biphenyl)[2-(2-aminoethyl phenyl]palladium(II)-methyl-t-butyl ether adduct (0.78 g, 0.96 mmol), RuPhos (0.45 g, 0.96 mmol), and sodium methoxide (3.66 g, 67.72 mmol). The reaction was purged and placed under an atmosphere of nitrogen and heated to 110° C. with stirring for 12 h. The reaction was (R)-methyl 2-methyl-1-(1-(piperidin-4-yl)ethyl)-1H-indole-3-carboxylate A 250 mL round bottom flask was charged with a magnetic stir bar, (R)-methyl 1-(1-(1-(tert-butoxycarbonyl)piperidin-4-yl)ethyl)-2-methyl-1H-indole-3-carboxylate (4.00 g, 9.99 mmol), MeOH (30 mL) and 4N HCl in dioxane (10 mL). The reaction was allowed to stir at ambient temperature for 6 h before being concentrated in vacuo. The resulting solids were treated with sat'd aqueous NaHCO₃ and extracted with ethyl acetate. The organic extract was dried with MgSO₄, filtered, and conc in vacuo to afford the title compound (3.5 grams) as a white solid which was used directly without further purification.

The compounds in the following table were prepared according to the above procedure using the appropriate starting materials and modifications:

| Name | Structure | m/z |
|---|---|---|
| (R)-N-((4-methoxy-6-methyl-2-oxo-1,2-dihydropyridin-3-yl)methyl)-2-methyl-1-(1-(piperidin-4-yl)ethyl)-1H-indole-3-carboxamide | 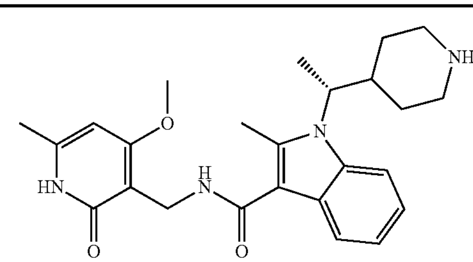 | 437 |

Procedure A: Generic Acylation/Reduction

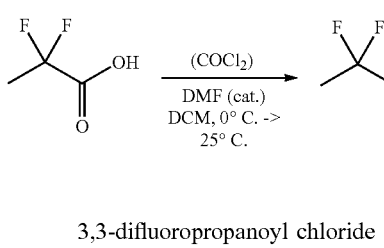

3,3-difluoropropanoyl chloride

To a 500 mL round bottom flask charged with a magnetic stir bar was added 2,2-difluoropropanoic acid (7.5 g, 68.14 mmol) and DCM (250 mL). The mixture was cooled to 0° C., and oxalyl dichloride (5.48 ml, 8.22 g, 64.73 mmol) is added over 1 minute. To this solution was added DMF (500 µl, 6.43 mmol) and the solution was warmed to room temperature with stirring until bubbling has ceased (about one hour). The solution is used as is in the subsequent step (assume quantitative yield).

(R)-Methyl 1-(1-(1-(2,2-difluoropropanoyl)piperidin-4-yl)ethyl)-2-methyl-1H-indole-3-carboxylate To a 1 L round bottom flask equipped with a magnetic stirrer was added (R)-methyl 2-methyl-1-(1-(piperidin-4-yl)ethyl)-1H-indole-3-carboxylate (7.5 g, 24.97 mmol), DCM (200 mL), and N-ethyl-N-isopropylpropan-2-amine (8.07 g, 62.43 mmol). The mixture was cooled to 0° C. in an ice bath and purged with nitrogen. To this stirred mixture of 2,2-difluoropropanoyl chloride (7.79 g, 60.62 mmol) in DCM through via an addition funnel over 15 minutes. The reaction was allowed to stir for an additional 30 minutes while warming to room temperature. The mixture was carefully quenched with saturated aqueous NaHCO$_3$, the organic phase separated, washed with brine, dried with Na$_2$SO$_4$, filtered, and evaporated under reduced pressure. The resulting material was purified by column chromatography (120 g silica column, 10% to 30% EtOAc in hexanes), to afford the title compound (9.1 g, 23.19 mmol) 92% yield.

(R)-Methyl 1-(1-(1-(2,2-difluoropropyl)piperidin-4-yl)ethyl)-2-methyl-1H-indole-3-carboxylate A 1 L 3-necked flask was equipped with magnetic stirrer and was fitted with a reflux condenser and an oil-filled bubbler outlet. The vessel was purged and placed under an atmosphere of nitrogen. (R)-methyl 2-methyl-1-(1-(1-(trifluoromethyl)cyclobutanecarbonyl)piperidin-4-yl)ethyl)-1H-indole-3-carboxylate (9.1 g, 23.19 mmol) was dissolved in THF (150 mL) and cannulated in the reaction flask. The reaction was cooled to 0° C. in an ice bath and borane (1.0 M THF solution, 55 ml, 55 mmol) was added over 10 minutes via syringe. When intense bubbling subsided, the reaction mixture was heated to reflux for 2 hours. The reaction was then cooled to 0° C. followed by the careful addition of MeOH (80 ml) (caution: violent H$_2$ gas evolution). The reaction was then stirred at 0° C. for 5 minutes, and then allowed to warm to room temperature, and then heated to 65° C. for 45 minutes and was then transferred to a 1 L-round bottom flask. The volatiles were evaporated under reduced pressure. The material was purified by column chromatography (120 g silica column, 10% to 40% EtOAc in hexanes) to afford the title compound (7.96 g, 21.03 mmol) 90% yield.

Procedure B: Ester Saponification

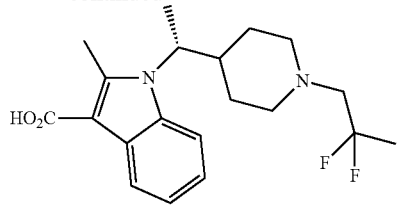

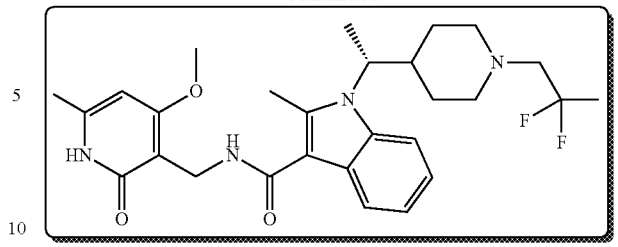

(R)-1-(1-(1-(2,2-difluoropropyl)piperidin-4-yl)ethyl)-2-methyl-1H-indole-3-carboxylic acid In a 1 L round bottom flask equipped with a magnetic stirrer, (R)-methyl 1-(1-(1-(2,2-difluoropropyl)piperidin-4-yl)ethyl)-2-methyl-1H-indole-3-carboxylate (7.96 g, 21.03 mmol) was dissolved in ethanol (80 mL), and a sodium hydroxide solution (6 M aqueous, 16 mL, 96 mmol) was added. The reaction was then heated to reflux (85° C.) for 16 hours and was then cooled to 0° C. A hydrochloric acid solution (2 M aqueous) was added until a pH of 6 was obtained. A precipitate formed which was collected via vacuum filtration using a Buchner funnel. The cake was washed with additional water (~100 mL) and dried in vacuo to afford the title compound (7.65 g, 21 mmol) as an off-white solid (quant. yield).

The compounds in the following table were prepared according to the above procedure using the appropriate starting materials and modifications:

| Name | Structure | m/z |
|---|---|---|
| (R)-1-(1-(1-(tert-butoxycarbonyl)piperidin-4-yl)ethyl)-2-methyl-1H-indole-3-carboxylic acid | 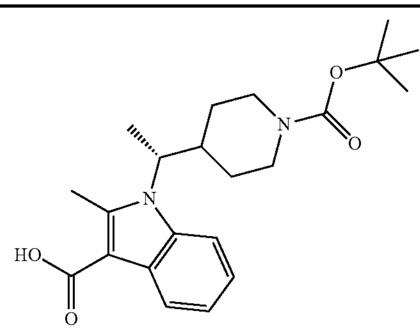 | 387 |

Procedure C: Amide Bond Formation Methods

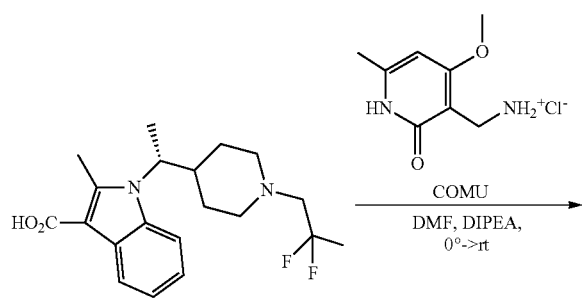

(R)-1-(1-(1-(2,2-difluoropropyl)piperidin-4-yl)ethyl)-N-((4-methoxy-6-methyl-2-oxo-1,2-dihydropyridin-3-yl)methyl)-2-methyl-1H-indole-3-carboxamide (Compound 101)

A 500 mL round bottom flask was charged with a magnetic stir bar, (4-methoxy-6-methyl-2-oxo-1,2-dihydropyridin-3-yl)methanaminium chloride (7.3 g, 35.7 mmol), DMF (60 mL), (R)-1-(1-(1-(2,2-difluoropropyl)piperidin-4-yl)ethyl)-2-methyl-1H-indole-3-carboxylic acid (7.65 g, 21 mmol), and Hunig's base (15 ml, 84 mmol). The mixture was sonicated for 5 minutes before being cooled to 0° C. To the stirred reaction mixture was added COMU (13.5 g, 31.5 mmol). The solution was stirred at 0° C. for 15 min before the ice bath was removed. The reaction was allowed to warm to room temperature with stirring overnight. The reaction mixture was then diluted with saturated aqueous $NaHCO_3$ (300 mL) and extracted with EtOAc (2×200 mL). The combined organic layer was washed with water, brine, dried over $Na_2SO_4$, filtered, and concentrated. The crude material was purified via silica gel chromatography (330 grams) with DCM/MeOH (10:1) with 1% $NH_4OH$ to afford the title compound as an off white solid. (6.1 g, 11.85 mmol, 56% yield). LCMS 537 (M+1)$^+$ 515 $^1$H NMR (400 MHz, DMSO-d6) δ=11.60 (s, 1H), 7.79-7.65 (m, 2H), 7.60 (d, J=8.0 Hz, 1H), 7.16-6.99 (m, 2H), 6.15 (s, 1H), 4.38-4.25 (m, 2H), 4.21-4.10 (m, 1H), 3.84 (s, 3H), 3.03-2.90 (m, 1H), 2.75-2.54 (m, 6H), 2.25-2.11 (m, 5H), 1.88 (br. s., 2H), 1.66-1.45 (m, 6H), 1.43-1.26 (m, 1H), 1.12-0.97 (m, 1H), 0.70-0.61 (m, 1H).

The compounds in the following table were prepared according to the above procedure using the appropriate starting materials and modifications:

| Name | Structure | m/z |
|---|---|---|
| (R)-tert-butyl 4-(1-(3-(((4-methoxy-6-methyl-2-oxo-1,2-dihydropyridin-3-yl)methyl)carbamoyl)-2-methyl-1H-indol-1-yl)ethyl)piperidine-1-carboxylate | 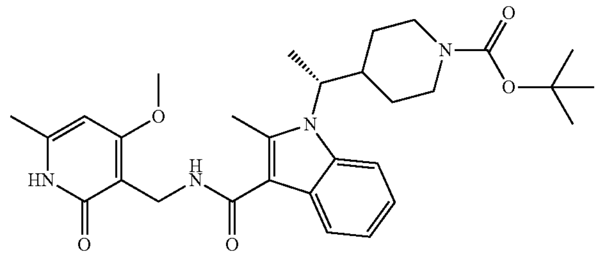 [SMILES: COc1cc(C)[nH]c(=O)c1CNC(=O)c1c(C)n([C@H](C)C2CCN(C(=O)OC(C)(C)C)CC2)c2ccccc12] | 537 |

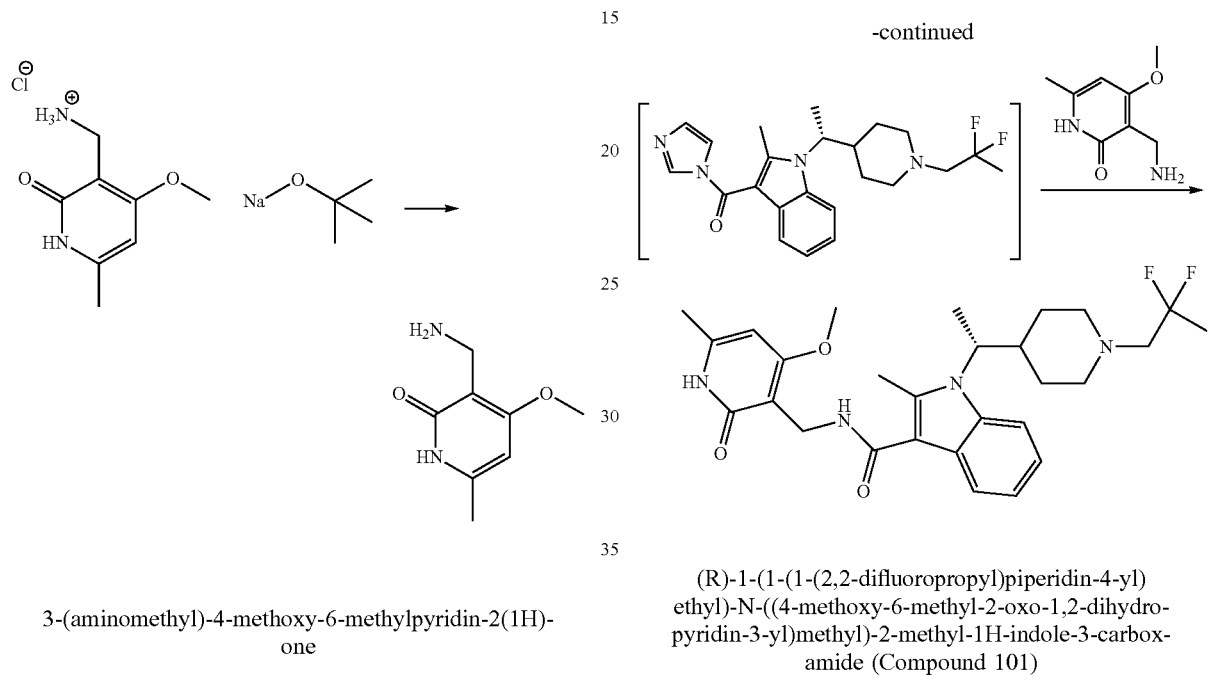

3-(aminomethyl)-4-methoxy-6-methylpyridin-2(1H)-one (R)-1-(1-(1-(2,2-difluoropropyl)piperidin-4-yl)ethyl)-N-((4-methoxy-6-methyl-2-oxo-1,2-dihydropyridin-3-yl)methyl)-2-methyl-1H-indole-3-carboxamide (Compound 101)

To a 500 mL round bottom flask containing (4-methoxy-6-methyl-2-oxo-1,2-dihydropyridin-3-yl)methanaminium chloride (10.99 g, 53.7 mmol) was added DCM (100 mL). To the resultant heterogeneous mixture was added MeOH (100 mL) to solubilize the ammonium salt. After stirring for 15 min, sodium 2-methylpropan-2-olate (5.05 g, 52.5 mmol) was added in one portion. The yellow homogeneous mixture was stirred for 15 min, at which point the solution turned heterogeneous and milky. The mixture was concentrated in vacuo to give a light yellow solid. The solids were suspended in DCM (15 mL) and stirred for 5 min. The resultant mixture was filtered through a pad of Celite and the filter cake was washed with DCM (3λ). The filtrate was concentrated to give the title compound (8.87 g, 52.73 mmol) as a white flaky solid.

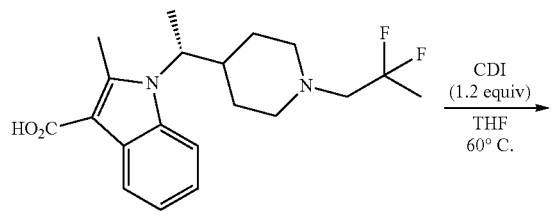

To a solution of (R)-1-(1-(1-(2,2-difluoropropyl)piperidin-4-yl)ethyl)-2-methyl-1H-indole-3-carboxylic acid (5.01 g, 13.74 mmol) in THF (50.0 mL) was added di(1H-imidazol-1-yl)methanone (2.56 g, 15.83 mmol) in one-portion. The reaction was then heated to 65° C. for 2 h with stirring. The reaction mixture was cooled to room temperature and 3-(aminomethyl)-4-methoxy-6-methylpyridin-2(1H)-one (3.85 g, 22.89 mmol) was added. The heterogeneous mixture was heated to 65° C. with stirring for 24 h. The reaction mixture was then cooled to room temperature and partitioned between EtOAc and water. The pH of the mixture was neutralized with 1N HCl to pH ~7. The resulting biphasic heterogeneous mixture was filtered over a pad of Celite and the filter cake was washed with EtOAc (1×). The biphasic filtrate was transferred to a separatory funnel and the organic layer was removed. The aqueous layer was extracted with EtOAc (2×) and the combined organic extracts were washed with water (2×), brine, dried over Na₂SO₄ and concentrated in vacuo to give the crude material which was dissolved in hot EtOH (25 mL, ~3.8 volumes) and allowed to cool gradually to room temperature while stirring. A slurry formed to which hexanes were added (total 60 mL, 9 volumes). The mixture was allowed to stir for 1.5 h and the solids were collected via vacuum filtration using a Buchner funnel. The solids were washed with additional hexanes (3λ). The filter cake was collected and dried in vacuo to afford the title compound as a white solid (6.15 g, 11.95 mmol). LCMS 537 (M+1)⁺ 515 ¹H NMR (400 MHz, DMSO-d6) d=11.60 (s, 1H), 7.79-7.65 (m, 2H), 7.60 (d, J=8.0 Hz, 1H), 7.16-6.99 (m, 2H), 6.15 (s, 1H), 4.38-4.25 (m, 2H), 4.21-4.10 (m, 1H), 3.84 (s, 3H), 3.03-2.90 (m, 1H), 2.75-2.54 (m, 6H), 2.25-2.11 (m, 5H), 1.88 (br. s., 2H), 1.66-1.45 (m, 6H), 1.43-1.26 (m, 1H), 1.12-0.97 (m, 1H), 0.70-0.61 (m, 1H).

Procedure D: Sulfonamide/Acylation Method

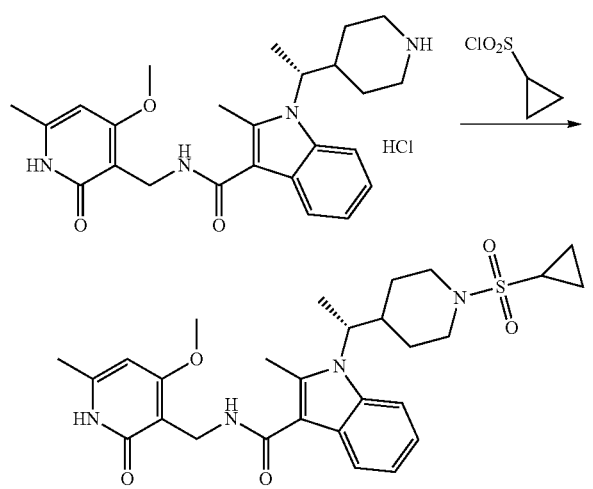

(R)-1-(1-(1-(cyclopropylsulfonyl)piperidin-4-yl)ethyl)-N-((4-methoxy-6-methyl-2-oxo-1,2-dihydropyridin-3-yl)methyl)-2-methyl-1H-indole-3-carboxamide (Compound 117)

A pyrex vial was charged with (R)—N-((4-methoxy-6-methyl-2-oxo-1,2-dihydropyridin-3-yl)methyl)-2-methyl-1-(1-(piperidin-4-yl)ethyl)-1H-indole-3-carboxamide hydrochloride (0.103 g, 0.218 mmol), DCM (5 mL) and Hunig's Base (0.152 ml, 0.872 mmol) was added. This solution was cooled (0° C.) and cyclopropanesulfonyl chloride (23 uL, 0.229 mmol) was added and the reaction was stirred for 0.5 h at that temperature. The cold bath was removed and the reaction was stirred at ambient temperature for 2 h. The reaction was concentrated then deposited onto silica gel with aid of DCM and purified by column chromatography using 10% MeOH in EtOAc as eluent to provide the title compound (66 mg, 56%) as a white solid. LCMS 541 (M+1)⁺.

Procedure E: Reductive Amination Method

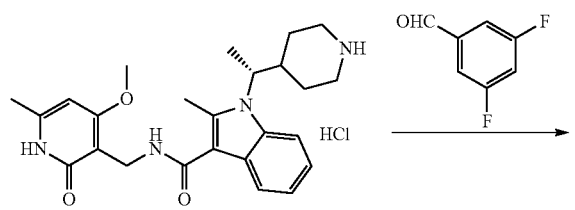

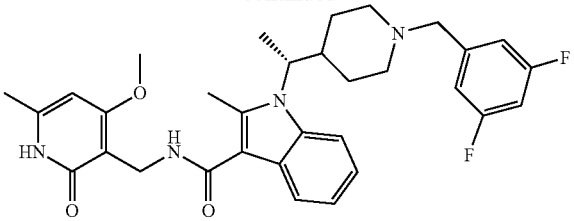

(R)-1-(1-(1-(3,5-difluorobenzyl)piperidin-4-yl)ethyl)-N-((4-methoxy-6-methyl-2-oxo-1,2-dihydropyridin-3-yl)methyl)-2-methyl-1H-indole-3-carboxamide (Compound 109)

To a resealable vial was added (R)—N-((4-methoxy-6-methyl-2-oxo-1,2-dihydropyridin-3-yl)methyl)-2-methyl-1-(1-(piperidin-4-yl)ethyl)-1H-indole-3-carboxamide hydrochloride (50 mg, 0.11 mmol) and MeOH:DCM (1:1). To this solution was added 3,5-difluorobenzaldehyde (0.08 g, 0.55 mmol) and the solution stirred at room temperature for 10 min before addition of sodium triacetoxyborohydride (0.07 g, 0.33 mmol). The solution was stirred at room temperature overnight. The reaction was quenched with sat'd aqueous sodium bicarbonate and extracted with ethyl acetate. The organic extract was concentrated in vacuo and purified via silica gel chromatography (25 g) using 10% MeOH in EtOAc as eluent to provide the title compound (30 mg) as a white solid. LCMS 563 (M+1)⁺ 1H NMR (400 MHz, DMSO-d6) δ=11.61 (s, 1H), 7.77-7.66 (m, 2H), 7.64-7.56 (m, 1H), 7.12-7.01 (m, 3H), 7.00-6.93 (m, 2H), 6.15 (s, 1H), 4.38-4.26 (m, 2H), 4.17 (br. s., 1H), 3.84 (s, 3H), 3.43 (s, 2H), 2.91-2.81 (m, 1H), 2.72-2.56 (m, 4H), 2.19 (s, 3H), 2.03-1.86 (m, 2H), 1.67 (br. s., 1H), 1.56-1.46 (m, 4H), 1.43-1.33 (m, 1H), 1.14-1.05 (m, 1H), 0.70 (br. s., 1H).

Procedure F: Nucleophilic Aromatic Substitution Method

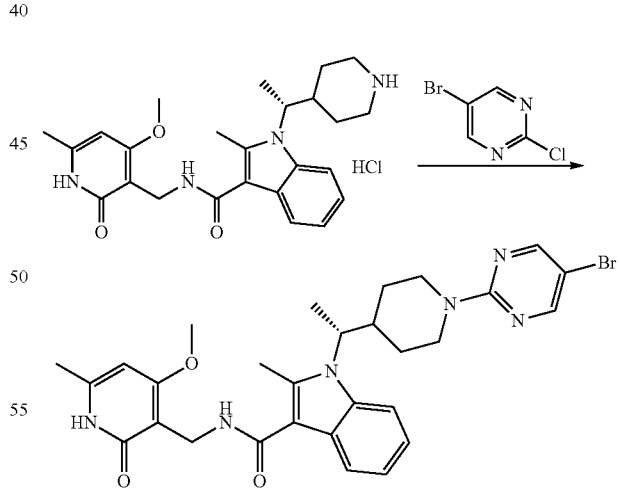

Method 19: (R)-1-(1-(1-(5-bromopyrimidin-2-yl)piperidin-4-yl)ethyl)-N-((4-methoxy-6-methyl-2-oxo-1,2-dihydropyridin-3-yl)methyl)-2-methyl-1H-indole-3-carboxamide (Compound 124)

To (R)—N-((4-methoxy-6-methyl-2-oxo-1,2-dihydropyridin-3-yl)methyl)-2-methyl-1-(1-(piperidin-4-yl)ethyl)-

1H-indole-3-carboxamide hydrochloride (109 mg, 0.23 mmol) dissolved in i-PrOH (2.5 mL) was added successively DIEA (200 ul, 1.15 mol) and the 2,5-dichloropyrimidine (41 mg, 0.28 mmol). The reaction was heated to 80° C. with stirring for 4 h before being allowed to cool to rt. The reaction mixture was concentrated in vacuo and the resulting material was purified via silica gel chromatography (25 g) using a gradient of 0% to 10% MeOH in EtOAc to afford the title compound. LCMS 549 (M+1)⁺.

Procedure G: Epoxide Alkylation Method

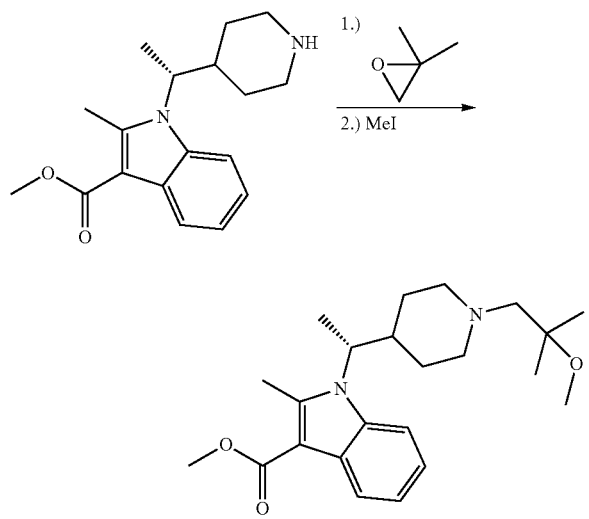

(R)-methyl 1-(1-(1-(2-methoxy-2-methylpropyl) piperidin-4-yl)ethyl)-2-methyl-1H-indole-3-carboxylate In a pyrex vial (R)-methyl 2-methyl-1-(1-(piperidin-4-yl) ethyl)-1H-indole-3-carboxylate (306 mg, 1.02 mmol) was dissolved in EtOH (3 mL) then 2,2-dimethyloxirane (110 uL, 1.24 mmol) was added and the reaction was heated at 80° C. for 24 h. The reaction was concentrated in vacuo to afford the title compound which was used directly in the next step. In a pyrex vial (R)-methyl 1-(1-(1-(2-hydroxy-2-methylpropyl)piperidin-4-yl)ethyl)-2-methyl-1H-indole-3-carboxylate (383 mg, 1.03 mmol) and sodium hydride (82 mg, 2.06 mmol) were diluted in DMF (4 mL). The solution was heated at 50° C. for 1 h then cooled to 0° C. and iodomethane (71 uL, 1.13 mmol) was added. The reaction was mixed at ambient temperature overnight. The reaction was judged to be complete after 24 h. The reaction was poured into water and extracted with EtOAc, the combined organic layers were washed 2x with water, 1x with brine, filtered, concentrated and purified by silica gel chromatography using 5% MeOH in EtOAc as eluent to provide the title compound as a (294 mg, 74%) as a clear oil.

Procedure H: Piperidine Alkylation Method

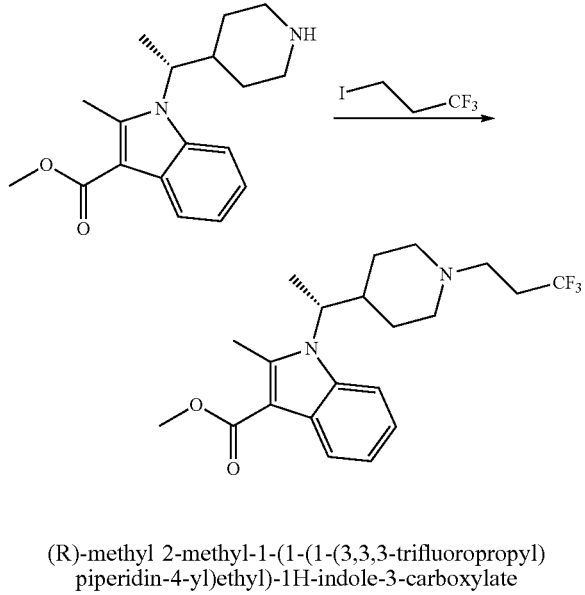

(R)-methyl 2-methyl-1-(1-(1-(3,3,3-trifluoropropyl) piperidin-4-yl)ethyl)-1H-indole-3-carboxylate A sealed tube was charged with a magnetic stir bar, (R)-methyl 2-methyl-1-(1-(piperidin-4-yl)ethyl)-1H-indole-3-carboxylate (2.45 g, 8.16 mmol) (free base), DMF (20 mL), 1,1,1-trifluoro-3-iodopropane (1.92 mL, 16.32 mmol), and potassium carbonate (7 grams, 50 mmol). The vessel was sealed and heated to 70° C. with stirring for 4 h before being allowed to cool to rt. The reaction was filtered through a bed of Celite which was rinsed with ethyl acetate (2×100 mL). The filtrate was washed with water, dried with MgSO4, filtered, and concentrated in vacuo to afford the crude product which was purified via silica gel chromatography (50 g) using ethyl acetate/hexanes (1:1) as eluent to afford the title compound (2.98 g, 7.52 mmol).

Procedure I: Piperidine Arylation Cross-Coupling Method

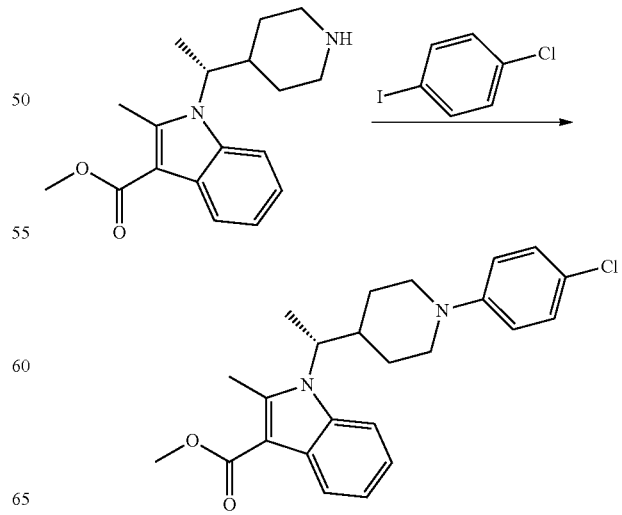

(R)-methyl 1-(1-(1-(4-chlorophenyl)piperidin-4-yl)ethyl)-2-methyl-1H-indole-3-carboxylate A sealed tube was charged with a magnetic stir bar, 1-chloro-4-iodobenzene (113 mg, 0.474 mmol), (R)-methyl 2-methyl-1-(1-(piperidin-4-yl)ethyl)-1H-indole-3-carboxylate (95 mg, 0.316 mmol), sodium methoxide (26 mg, 0.474 mmol), and RuPhos Precatalyst, generation II (20 mg) (catalog #707589, ALDRICH). To the solids was added 1,4-dioxane (1 mL) and the reaction was purged and placed under nitrogen. The vessel was then heated to 100° C. with stirring for 24 h before being allowed to cool to rt. This material was purified via silica gel chromatography using 20% ethyl acetate in hexanes to afford the title compound (47 mg, 36%).

Procedure J: Urea Formation Method

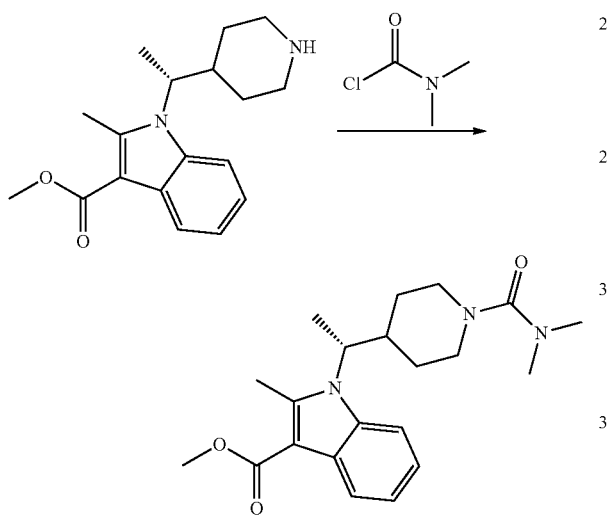

(R)-methyl 1-(1-(1-(dimethylcarbamoyl)piperidin-4-yl)ethyl)-2-methyl-1H-indole-3-carboxylate (R)-methyl 2-methyl-1-(1-(piperidin-4-yl)ethyl)-1H-indole-3-carboxylate (200 mg, 0.666 mmol) is dissolved in pyridine (2 ml) and Hunig's base (355 uL, 2.0 mmol), dimethylcarbamic chloride (0.179 g, 1.665 mmol) is added and the mixture is heated to 60° C. for 4 hours. The reaction was extracted with EtOAc and washed with 1 M HCl The organic phase was washed with brine, dried with Na$_2$SO$_4$, filtered, evaporated to afford the title compound which was used directly without further purification.

Synthesis of 3-(aminomethyl)-4-methoxy-6-methylpyridin-2-ol

The title intermediate was synthesized according to the following Scheme:

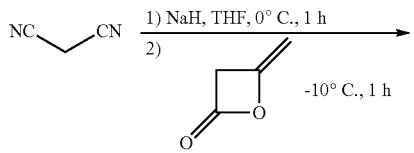

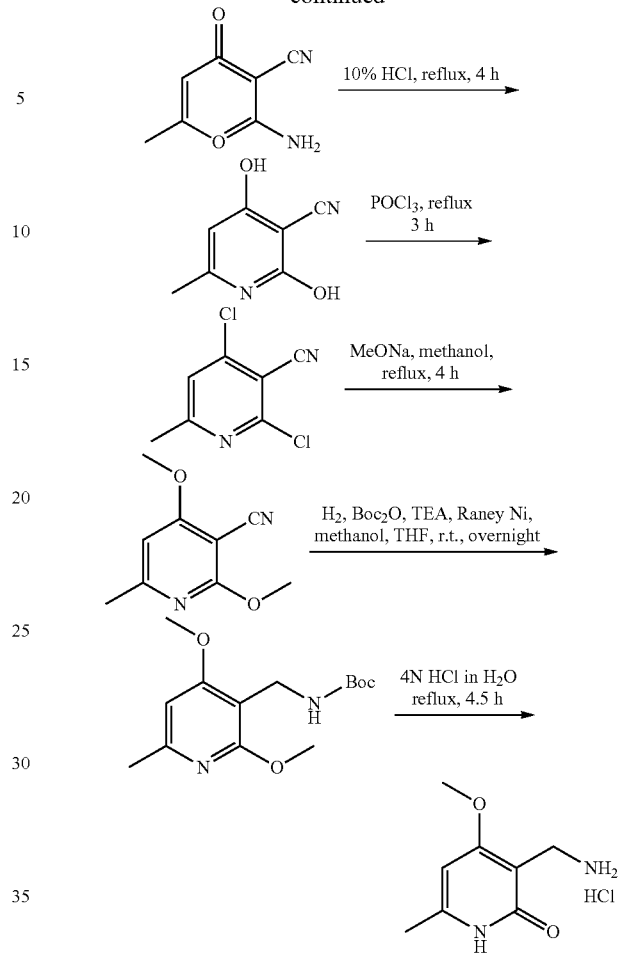

Step 1: 2-amino-6-methyl-4-oxo-4H-pyran-3-carbonitrile

Malononitrile (110 g, 1.67 mol) was dissolved in dry THF (1000 ml) and cooled in an ice-water bath. NaH (60% in mineral oil, 67 g, 1.67 mol) was added portion wise below 10° C. very carefully while the reaction flask was evacuated with N$_2$ gas. After the addition was completed, the mixture was stirred at 0° C. for 30 minutes. Then 4-methyleneoxetan-2-one (140 g, 1.67 mol) was added drop wise at 0° C. After the addition was completed, the mixture was stirred at −10° C. for 1 h. The reaction mixture was neutralized with 4N HCl and concentrated under vacuum to afford compound 2-amino-6-methyl-4-oxo-4H-pyran-3-carbonitrile as an orange oil. The crude product was used to next step without further purification.

Step 2: 2,4-dihydroxy-6-methylnicotinonitrile 2-amino-6-methyl-4-oxo-4H-pyran-3-carbonitrile from above was dissolved in 4N HCl/H$_2$O (2.5 L) and the reaction was heated to reflux for 5 h with stirring. The reaction was then allowed to cool to rt and a precipitate formed. The precipitate was collected via vacuum filtration, washed with H$_2$O (500 mL), ethanol (500 mL) and MTBE (200 mL) and dried under high vacuum. 2,4-dihydroxy-6-methylnicotinonitrile was obtained as a yellow powder. (165 g, yield 66%).

Step 3: 2,4-dichloro-6-methylnicotinonitrile 2,4-dihydroxy-6-methylnicotinonitrile (40 g, 266.4 mmol) was dissolved in POCl₃ (120 ml) and DMF was added (4 drops). The mixture was heated to reflux for 3 h and was then concentrated under vacuum. The residue was dissolved in EtOAc (2 L) and carefully neutralized by treatment with sat'd aqueous NaHCO₃. The mixture was then filtered through Celite and the organic layer was separated, dried over Na₂SO₄ and concentrated under vacuum to give 2,4-dichloro-6-methylnicotinonitrile as an off-white solid. (45 g, yield 90%).

Step 4: 2,4-dimethoxy-6-methylnicotinonitrile 2,4-dichloro-6-methylnicotinonitrile (45 g, 240 mmol) was dissolved in MeOH (300 ml). NaOMe (30% in MeOH, 100 ml, 1680 mmol) was added and the mixture was heated to reflux for 4 h. The reaction was then allowed to cool to rt and the reaction mixture was neutralized with acetic acid. The solvent was removed under vacuum and the residue was treated with H₂O (300 ml) and MTBE (100 ml). The resulting solids were co-evaporated with THF (300 ml) to give 2,4-dimethoxy-6-methylnicotinonitrile as a dark-yellow solid. (40 g, yield 95%).

Step 5: tert-butyl ((2,4-dimethoxy-6-methylpyridin-3-yl)methyl)carbamate 2,4-dimethoxy-6-methylnicotinonitrile (10.0 g, 56 mmol) was dissolved in the mixture of THF (260 ml) and methanol (260 ml). Raney Nickel (wet, 10.0 g), TEA (29.0 g, 280 mmol) and Boc₂O (36.8 g, 168 mmol) were added. Then the mixture was hydrogenated (1 atom) at rt overnight. The reaction mixture was then filtered through a bed of Celite to afford ((2,4-dimethoxy-6-methylpyridin-3-yl)methyl)carbamate as a yellow solid. (88%).

Step 6: 3-(aminomethyl)-4-methoxy-6-methylpyridin-2-ol tert-butyl ((2,4-dimethoxy-6-methylpyridin-3-yl)methyl) carbamate (83 g, 294 mmol) was dissolved in 4 N HCl/H₂O (830 ml). Then the mixture was then heated to reflux with stirring for 4.5 h. After the mixture was concentrated under vacuum to afford a brown oil which was suspended in EtOH (300 ml) for 15 min to give a yellow precipitate. The precipitate was filtered, washed with ethanol (100 ml) and MTBE (100 ml) and dried under high vacuum to give 38 g of fraction 1 3-(aminomethyl)-4-methoxy-6-methylpyridin-2-ol (Purity 98% by LCMS, yield 63%) as a yellow powder. In the meantime, the filtration from fraction 1 was concentrated under vacuum and the residue was solidified by ethanol (100 ml). The precipitate was filtered, washed with ethanol (100 ml) and MTBE (100 ml) and dried under high vacuum to give 20 g of fraction 2 3-(aminomethyl)-4-methoxy-6-methylpyridin-2-ol (Purity 94% by LCMS, yield 33%) as a yellow powder.

Synthesis of 3-(aminomethyl)-4-ethyl-6-methylpyridin-2(1H)-one

The title intermediate was synthesized according to the following Scheme:

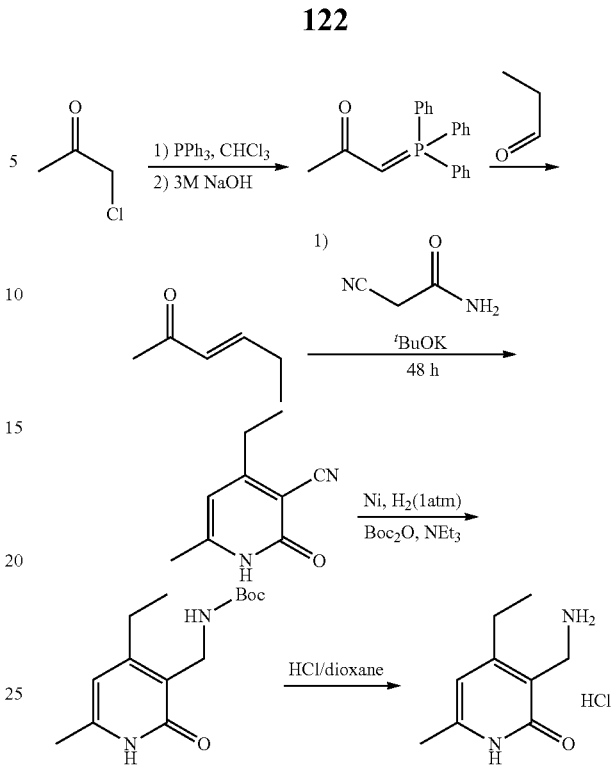

Step 1: 1-(triphenylphosphoranylidene)propan-2-one

A solution of 1-chloropropan-2-one (50 g, 540.4 mmol) in chloroform (150 mL) was added drop wise to a solution of triphenylphosphine (141.72 g, 540.4 mmol) in chloroform (150 mL) under nitrogen. The mixture was stirred at 70° C. for 12 h, and the resulting phosphonium salt was filtered. The precipitate was washed with ethyl acetate and dried under vacuum. The dried phosphonium salt was suspended in a mixture of water (250 mL) and methanol (250 mL), and the mixture was stirred for 1 h. Aqueous sodium hydroxide (2.00 M) was added to the mixture until a pH between 7 and 8 was reached. The mixture was then stirred vigorously for 1 h. The phosphorane precipitate was filtered and washed with water. After drying in vacuum, the phosphorane was recrystallized from ethyl acetate and dried under vacuum to afford 1-(triphenylphosphoranylidene)propan-2-one (40.00 g, 23.3%) as a white solid.

Step 2: hex-3-en-2-one

To a solution of 1-(triphenylphosphoranylidene)propan-2-one (40 g, 125.65 mmol) in dichloromethane (150 mL) was added propionaldehyde (45.83 g, 789.07 mmol) at rt. The reaction mixture was then stirred at rt for 12 h. After concentration, the residue was then distilled under vacuum to give hex-3-en-2-one (5.36 g, 43.5%).

Step 3: 4-ethyl-6-methyl-2-oxo-1,2-dihydropyridine-3-carbonitrile

To a stirred solution of potassium 2-methylpropan-2-olate (4.92 g, 43.81 mmol) and 2-cyanoacetamide (4.05 g, 48.19 mmol) in (methylsulfinyl)methane (60 mL) was added hex-3-en-2-one (4.30 g, 43.81 mmol) under nitrogen atmosphere at 25° C. The reaction mixture was then stirred at 25° C. for 30 min, and then additional potassium 2-methylpropan-2- olate (14.75 g, 131.44 mmol) was added. Nitrogen gas was displaced by oxygen gas and the mixture was stirred at 25° C. for 48 h. The mixture was diluted with 4 volumes water (240 mL), and then 5 volumes of 4 N HCl (300 mL), which were added slowly. The reaction mixture was filtered, washed with water, and dried to give 4-ethyl-6-methyl-2-oxo-1,2-dihydropyridine-3-carbonitrile (1.30 g, 18.3%) as a gray solid.

Step 4: tert-butyl ((4-ethyl-6-methyl-2-oxo-1,2-dihydropyridin-3-yl)methyl)carbamate To a solution of Raney Ni (0.8 g) in methanol/tetrahydrofuran (72 mL, 1/1) was added 4-ethyl-6-methyl-2-oxo-1,2-dihydropyridine-3-carbonitrile (1.20 g, 7.40 mmol), triethylamine (1.50 g, 14.80 mmol) and di-tert-butyl dicarbonate (1.94 g, 8.88 mmol). The reaction mixture was stirred at rt under hydrogen pressure (1 atm) for 20 h. The reaction mixture was filtered through a bed of Celite and the filtrate was diluted with ethyl acetate, washed with brine and dried over anhydrous sodium sulfate. The solvent was then removed under vacuum to afford crude tert-butyl ((4-ethyl-6-methyl-2-oxo-1,2-dihydropyridin-3-yl)methyl)carbamate (1.46 g, 71.2%) as a white solid for the next step.

Step 5: 3-(aminomethyl)-4-ethyl-6-methylpyridin-2(1H)-one tert-butyl ((4-ethyl-6-methyl-2-oxo-1,2-dihydropyridin-3-yl)methyl)carbamate (1.00 g, 3.75 mmol) was dissolved in a solution of hydrogen chloride 4N in 1,4-dioxane (20 mL). The mixture was stirred for 2 h. The reaction mixture was filtered and the residue was washed with dichloromethane, dried to afford 3-(aminomethyl)-4-ethyl-6-methylpyridin-2(1H)-one hydrochloride (593 mg, 77.9%) as a light yellow solid. LRMS (M+H$^+$) m/z: calcd 166.11; found 167.1. $^1$H NMR (400 MHz, D$_2$O): δ ppm 6.31 (s, 1H), 4.06 (s, 2H), 2.57 (q, J=7.86 Hz, 2H), 2.25 (s, 3H), 1.10 (t, J=7.53 Hz, 3H).

Synthesis of 3-(aminomethyl)-4-(difluoromethoxy)-6-methylpyridin-2(1H)-one

The title intermediate was synthesized according to the following Scheme:

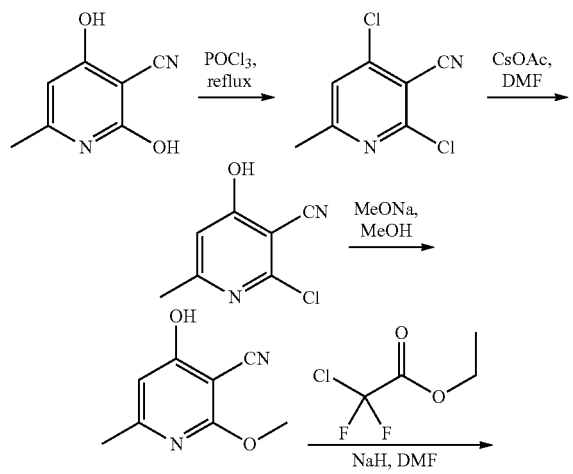

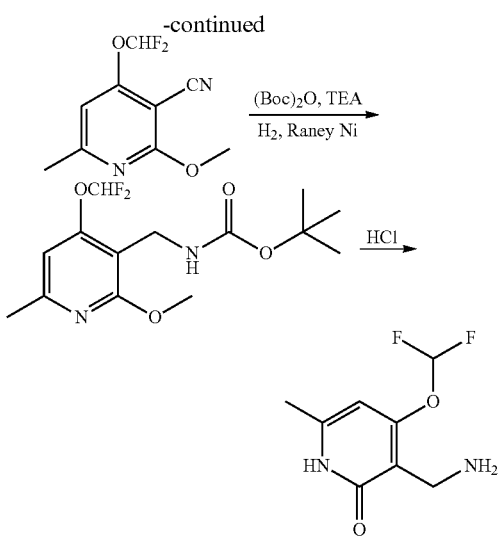

Step 1: 2,4-dichloro-6-methylnicotinonitrile

To a solution of 2,4-dihydroxy-6-methylnicotinonitrile (20.0 g, 133.0 mmol) in POCl$_3$ (150 mL) was stirred at 120° C. for 2 hours under N$_2$. It was partitioned between water (500 mL) and ethyl acetate (500 mL), the organic layer was dried and concentrated to afford 2,4-dichloro-6-methylnicotinonitrile (15.3 g brown solid, 61.4% yield).

Step 2: 2-chloro-4-hydroxy-6-methylnicotinonitrile

A mixture of 2,4-dichloro-6-methylnicotinonitrile (12.0 g, 64.2 mmol), CsOAc (37.0 g, 193.0 mmol) in N,N-dimethylformamide (50 mL) was stirred at 80° C. overnight under N$_2$. The mixture was partitioned between water (800 mL) and ethyl acetate (800 mL), the organic layer was dried and concentrated to afford 2-chloro-4-hydroxy-6-methylnicotinonitrile (9.0 g brown solid, 84.1% yield).

Step 3: 4-hydroxy-2-methoxy-6-methylnicotinonitrile

A mixture of 2-chloro-4-hydroxy-6-methylnicotinonitrile (2.0 g, 11.9 mmol), sodium methanolate (3.2 g, 59.5 mmol) in methanol (20 mL) was stirred at 60° C. overnight under N$_2$. The mixture was quenched with HCl (1M) to pH=2. It was partitioned between water (500 mL) and ethyl acetate (500 mL), the organic layer was dried and concentrated to afford 4-hydroxy-2-methoxy-6-methylnicotinonitrile (2.0 g brown solid, 100% yield).

Step 4: 4-(difluoromethoxy)-2-methoxy-6-methylnicotinonitrile

To a solution of 4-hydroxy-2-methoxy-6-methylnicotinonitrile (2.0 g, 12.2 mmol) in N,N-dimethylformamide (10 mL) was added sodium hydride (880 mg, 36.6 mmol) at 0° C. and the mixture was stirred for 0.5 hour, Ethyl 2-chloro-2,2-difluoroacetate (5.4 g, 39.0 mmol) was added with vigorous stirring, over the course of 20 min. The suspension was warmed to 80° C. overnight under N$_2$. The mixture was quenched into Na$_2$CO$_3$ (200 mL). It was partitioned between water (500 mL) and ethyl acetate (500 mL), the organic layer was dried and concentrated to afford the crude, which was purified by flash column (PE:EA=20:1) to afford 4-(difluoromethoxy)-2-methoxy-6-methylnicotinonitrile (550 mg yellow solid, 22.0% yield).

Step 5: tert-butyl ((4-(difluoromethoxy)-2-methoxy-6-methylpyridin-3-yl)methyl)carbamate To a solution of 4-(difluoromethoxy)-2-methoxy-6-methylnicotinonitrile (550 mg, 2.58 mmol), di-tert-butyl dicarbonate (844 mg, 3.87 mmol), triethylamine (391 mg, 3.87 mmol) and Raney Ni (2 g) in Tetrahydrofuran (10 mL) was stirred at room temperature overnight under H$_2$. It was filtered and the filtrate was concentrated to afford tert-butyl ((4-(difluoromethoxy)-2-methoxy-6-methylpyridin-3-yl)methyl)carbamate. (830 mg yellow solid, 100% yield).

Step 6: 3-(aminomethyl)-4-(difluoromethoxy)-6-methylpyridin-2(1H)-one

To a solution of tert-butyl((4-(difluoromethoxy)-2-methoxy-6-methylpyridin-3-yl)methyl)carbamate (830 mg, 2.61 mmol) in HCl (10 mL) was stirred at 100° C. for 1.5 hours under N$_2$. The mixture was concentrated to afford 3-(aminomethyl)-4-(difluoromethoxy)-6-methylpyridin-2(1H)-one (430 mg, yellow solid, 80.8% yield). LCMS (M+H+) m/z: calcd 204.07; found 205.0. $^1$H NMR (400 MHz, DMSO): δ 7.62-7.26 (t, 1H), 6.26 (s, 1H), 3.84-3.82 (d, J=6.0 Hz, 2H).

Synthesis of 3-(aminomethyl)-4,6-dimethylpyridin-2(1H)-one

The title intermediate was synthesized according to the following scheme:

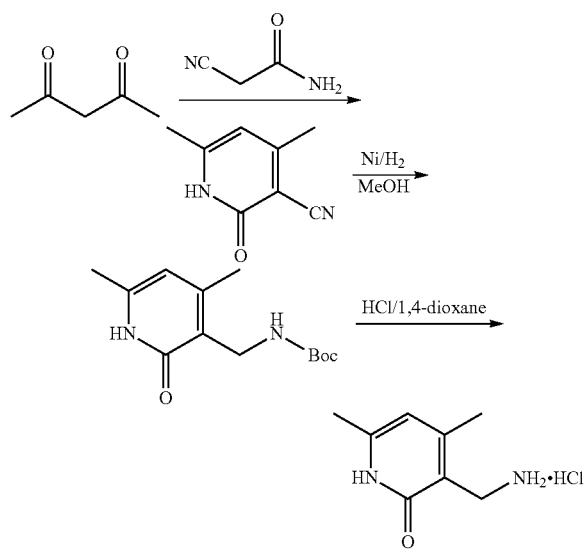

Step 1: 4,6-dimethyl-2-oxo-1,2-dihydropyridine-3-carbonitrile

To a solution of pentane-2,4-dione (100 g, 1.0 mol) in H$_2$O (2 L) were added 2-cyanoacetamide (84 g, 1.0 mol) and K$_2$CO$_3$ (13.8 g, 0.1 mol). Then the mixture was stirred at room temperature for 16 h. The reaction solution was filtrated to give crude product. The crude was washed with water and concentrated to give 4,6-dimethyl-2-oxo-1,2-dihydropyridine-3-carbonitrile (138 g, 93%).

Step 2: tert-butyl ((4,6-dimethyl-2-oxo-1,2-dihydropyridin-3-yl)methyl)carbamate To a solution of 4,6-dimethyl-2-oxo-1,2-dihydropyridine-3-carbonitrile (40 g, 0.27 mol) in THF/CH$_3$OH (1:1, 2 L) were added Ni (40 g), Boc$_2$O (110 g, 0.5 mol) and Et$_3$N (50 g, 0.5 mol). Then the mixture was stirred in H$_2$ atmosphere at room temperature for 48 h. The reaction solution was filtrated and concentrated to give crude product. The crude was added H$_2$O (200 mL) and extracted by DCM (600 mL*3). The organic layer was concentrated to give tert-butyl ((4,6-dimethyl-2-oxo-1,2-dihydropyridin-3-yl)methyl)carbamate (40 g, 56%) for next step.

Step 3: 3-(aminomethyl)-4,6-dimethylpyridin-2(1H)-one tert-butyl ((4,6-dimethyl-2-oxo-1,2-dihydropyridin-3-yl)methyl)carbamate (40 g, 0.27 mol) was added into dioxane/HCl (1 L) and the mixture was stirred at room temperature for 4 h. The reaction solution was filtrated and concentrated to give crude product. The crude was washed with ethyl acetate (100 mL*2) and EtOH (50 mL*1) and concentrated to give 3-(aminomethyl)-4,6-dimethylpyridin-2(1H)-one hydrochloride (15 g, 40%). LCMS (M+H+) m/z: calcd. 152.19; found 153.1. (DMSO, 400 MHz) δ 11.84 (s, 1H), 8.07 (s, 3H), 5.96 (s, 1H), 3.76-7.75 (d, J=5.6 Hz, 2H), 2.21 (s, 3H), 2.15 (s, 3H).

Method 18. Synthesis of 3-(aminomethyl)-4-chloro-6-methylpyridin-2(1H)-one

The title intermediate was synthesized according to the following scheme:

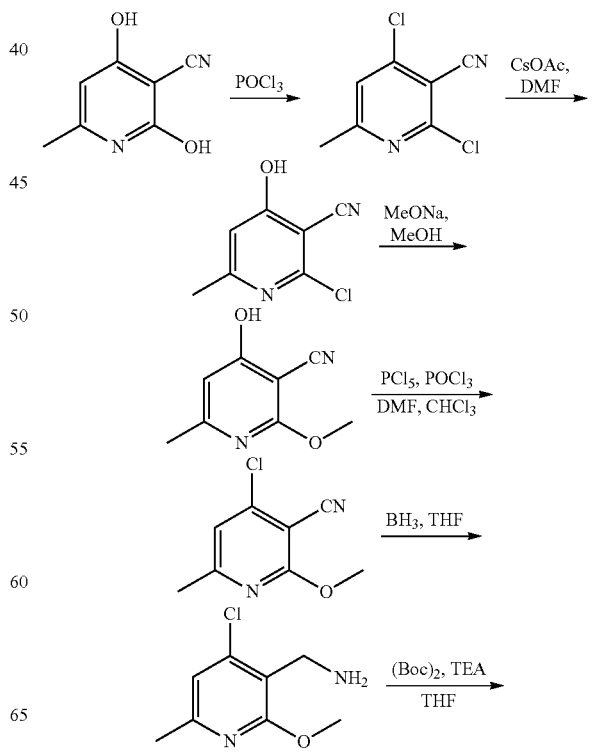

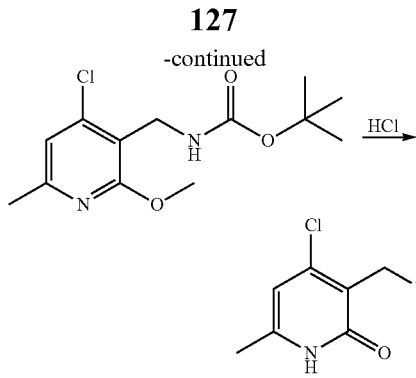

Step 1: 2,4-dichloro-6-methylnicotinonitrile

A mixture of 2,4-dihydroxy-6-methylnicotinonitrile (80.0 g, 533.3 mmol) in phosphorus oxychloride (150 mL) was stirred at reflux for 2 hours under nitrogen. The mixture was quenched with sat'd aqueous sodium bicarbonate to pH=8. It was partitioned between water (2000 mL) and ethyl acetate (1000 mL), the organic layer was dried by sodium sulfate and concentrated to afford 2,4-dichloro-6-methylnicotinonitrile (85.0 g brown solid, 86.10% yield). LCMS (M+H+) m/z: calc'd 186.98; found 186.6.

Step 2: 2-chloro-4-hydroxy-6-methylnicotinonitrile

A mixture of 2,4-dichloro-6-methylnicotinonitrile (10.0 g, 53.47 mmol) and cesium acetate (30.79 g, 160.41 mmol) in N,N-dimethylformamide (50 mL) was stirred at 80° C. overnight under nitrogen. The mixture was partitioned between water (800 mL) and ethyl acetate (800 mL), the organic layer was dried by sodium sulfate and concentrated to afford 2-chloro-4-hydroxy-6-methylnicotinonitrile as a brown solid (8.8 g, 98% yield). LCMS (M+H+) m/z: calc'd 169.01; found 168.8.

Step 3: 4-hydroxy-2-methoxy-6-methylnicotinonitrile

A mixture of 2-chloro-4-hydroxy-6-methylnicotinonitrile (8.8 g, 52.20 mmol) and sodium methanolate (14.1 g, 261.0 mmol) in methanol (50 mL) was stirred at 60° C. overnight under nitrogen. The mixture was quenched with aqueous hydrochloric acid (1M) to pH=5. It was partitioned between water (500 mL) and ethyl acetate (500 mL), the organic layer was dried by sodium sulfate and concentrated to afford 4-hydroxy-2-methoxy-6-methylnicotinonitrile as a brown solid (8.0 g, 93% yield). LCMS (M+H+) m/z: calcd 165.06; found 164.8.

Step 4: 4-chloro-2-methoxy-6-methylnicotinonitrile

A mixture of 4-hydroxy-2-methoxy-6-methylnicotinonitrile (8.0 g, 48.73 mmol), pentachlorophosphorane (20.3 g, 97.47 mmol) and phosphorus oxychloride (14.9 g, 97.47 mmol) and N,N-dimethylformamide (5 mL) in chloroform (100 mL) was stirred at 60° C. for 0.5 hours under nitrogen. The mixture was quenched with saturated aqueous sodium bicarbonate to pH=8. It was partitioned between water (1000 mL) and ethyl acetate (1000 mL), the organic layer was dried by sodium sulfate and concentrated to afford the crude product 4-chloro-2-methoxy-6-methylnicotinonitrile as a brown solid (8.0 g, 89% yield) which was used next step directly without further purification.

Step 5: (4-chloro-2-methoxy-6-methylpyridin-3-yl)methanamine

To a solution of 4-chloro-2-methoxy-6-methylnicotinonitrile (8.0 g, 43.81 mmol) in tetrahydrofuran (50 mL) was added borane (5.3 mL). The mixture was stirred at 60° C. for 2 hours under nitrogen. The mixture was quenched by methanol (10 mL) at 0° C. The mixture was concentrated to afford the crude product (4-chloro-2-methoxy-6-methylpyridin-3-yl)methanamine as a brown solid (7.0 g, 92% yield which was used in the next step directly without purification.

Step 6: tert-butyl((4-chloro-2-methoxy-6-methyl-pyridin-3-yl)methyl)carbamate A mixture of (4-chloro-2-methoxy-6-methylpyridin-3-yl)methanamine (7.0 g, 37.51 mmol), di-tert-butyl oxalate (15.17 g, 75.01 mmol) and triethylamine (11.39 g, 112.52 mmol) in tetrahydrofuran (50 mL) was stirred at 20° C. for 16 hours under nitrogen. The reaction was partitioned between water (500 mL) and ethyl acetate (500 mL), the organic layer was dried with sodium sulfate and concentrated to afford the crude product, which was purified by flash column (petroleum ether: ethyl acetate=40:1) to afford the title compound as a colorless oil (3.0 g, 28% yield).

Step 6: 3-(aminomethyl)-4-chloro-6-methylpyridin-2(1H)-one

A solution of tert-butyl((4-chloro-2-methoxy-6-methyl-pyridin-3-yl)methyl)carbamate (3.0 g, 10.46 mmol) in hydrogen chloride (10 mL, 4M in water) was stirred at 100° C. for 2 hours under nitrogen. The mixture was concentrated to afford 3-(aminomethyl)-4-chloro-6-methylpyridin-2(1H)-one as a yellow solid (1.7 g, 94% yield). LCMS (M+H+) m/z: calc'd 173.04; found 173.1. $^1$H NMR (400 MHz, MeOD): δ 6.38 (s, 1H), 4.15 (s, 2H), 2.32 (s, 3H).

Synthesis of 3-(aminomethyl)-6-methyl-4-(methylamino)pyridin-2(1H)-one hydrochloride The title intermediate was synthesized according to the following scheme:

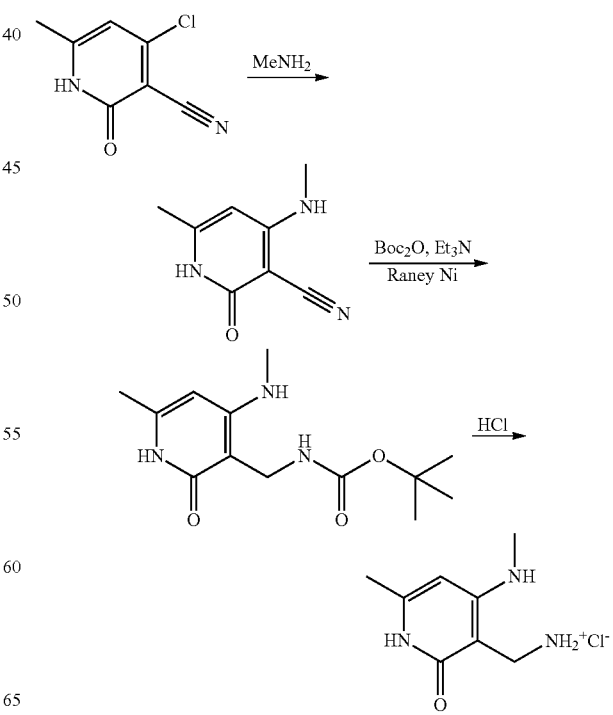

Step 1: 6-methyl-4-(methylamino)-2-oxo-1,2-dihydropyridine-3-carbonitrile

A mixture of 4-chloro-6-methyl-2-oxo-1,2-dihydropyridine-3-carbonitrile (3 g, 17.80 mmol) and 27% methanamine/ethanol solution (50 mL) was stirred under 50 Psi at 40° C. for 12 hours in a 250 mL round-bottom flask. The mixture was then evaporated to give 6-methyl-4-(methylamino)-2-oxo-1,2-dihydropyridine-3-carbonitrile (2.9 g, 100%).

Step 2: tert-butyl ((6-methyl-4-(methylamino)-2-oxo-1,2-dihydropyridin-3-yl)methyl)carbamate To a solution of 6-methyl-4-(methylamino)-2-oxo-1,2-dihydropyridine-3-carbonitrile (2.9 g, 17.77 mmol) in methanol (40 mL) and tetrahydrofuran (10 mL) was added triethylamine (7.19 g, 71.09 mmol) and di-tert-butyl dicarbonate (7.76 g, 35.54 mmol). The mixture was stirred at room temperature for 1 hour, Then di-tert-butyl dicarbonate (5.82 g, 26.66 mmol) and Raney nickel catalyst (3 g) was added to the mixture. The mixture was stirred at room temperature for 12 hours under hydrogen atmosphere. The mixture was then filtered, the filtrate was concentrated to be purified by silica gel chromatography (5% DCM/MeOH) to afford tert-butyl (((6-methyl-4-(methylamino)-2-oxo-1,2-dihydropyridin-3-yl)methyl)carbamate (2 g, 42%).

Step 3: 3-(aminomethyl)-6-methyl-4-(methylamino)pyridin-2(1H)-one hydrochloride A solution of tert-butyl (((6-methyl-4-(methylamino)-2-oxo-1,2-dihydropyridin-3-yl)methyl)carbamate (1.5 g, 5.61 mmol) in 4 M hydrogen chloride/methanol (20 mL) was stirred at 100° C. for 2 hours. The mixture was washed with ethyl acetate (20 mL×2), the aqueous phase was evaporated to afford the title compound (897 mg, yield: 78%). LRMS (M+H$^+$) m/z: calc'd 168.11; found 150.9. $^1$H NMR (400 MHz, METHANOL-d$_4$) δ=6.47 (s, 1H), 4.15 (s, 2H), 3.01 (s, 3H), 2.44 (s, 3H).

The examples in the following table were prepared using the procedures outlined above, or by methods that would be apparent to one of skill in the art based on the methods described herein, using the appropriate starting materials and modifications.

| Methods | Structure/Name | $^1$H NMR | m/z |
| --- | --- | --- | --- |
| A, B, C | (R)-N-((4-methoxy-6-methyl-2-oxo-1,2-dihydropyridin-3-yl)methyl)-2-methyl-1-(1-(1-((1-(trifluoromethyl)cyclopropyl)methyl)piperidin-4-yl)ethyl)-1H-indole-3-carboxamide (Compound 102) | $^1$H NMR (400 MHz, DMSO-d6) δ 11.58 (br.s., 1H), 7.63-7.82 (m, 2H), 7.58 (d, J = 8.03 Hz, 1H), 7.05 (m, 2H), 6.14 (s, 1H), 4.31 (d, J = 4.91 Hz, 2H), 4.03-4.21 (m, 1H), 3.83 (s, 3H), 3.45-3.73 (m, 1H), 2.98 (d, J = 9.14 Hz, 1H), 2.68 (br.s., 1H), 2.59 (s, 3H), 2.33-2.44 (m, 2H), 2.17 (s, 3H), 2.11-2.21 (m, 2H), 1.78-1.96 (m, 2H), 1.56-1.62 (m, 1H), 1.53 (d, J = 6.47 Hz, 3H), 1.28-1.40 (d, J = 8.47 Hz, 1H), 1.06-1.20 (m, 1H), 0.95-1.06 (m, 1H), 0.89 (br.s., 2H), 0.65 (br.s., 2H). | 559 |
| A, B, C | (R)-N-((4-methoxy-6-methyl-2-oxo-1,2-dihydropyridin-3-yl)methyl)-2-methyl-1-(1-(1-(2,2,3,3-tetrafluoropropyl)piperidin-4-yl)ethyl)-1H-indole-3-carboxamide (Compound 103) | $^1$H NMR (400 MHz, Acetone-D6) d 12.06 (br. s, 1H), 7.89 (d, J = 7.87 Hz, 1H), 7.70 (t, J = 4.94 Hz, 1H), 7.62 (d, J = 8.06 Hz, 1H), 6.99-7.12 (m, 2H), 6.15-6.48 (m, 2H), 4.50-4.61 (m, 2H), 4.18-4.30 (m, 1H), 3.93 (s, 3H), 3.04 (d, J = 11.54 Hz, 1H), 2.85-2.96 (m, 2H), 2.73-2.83 (m, 2H), 2.28-2.43 (m, 2H), 2.23 (br.s., 3H), 2.00 (d, J = 12.82 Hz, 1H), 1.62 (d, J = 6.96 Hz, 3H), 1.46 (dq, J = 3.94, 12.18 Hz, 1H), 1.11-1.23 (m, 1H), 0.79 (d, J = 12.82 Hz, 1H) | 551 |

| Methods | Structure/Name | ¹H NMR | m/z |
|---|---|---|---|
| A, B, C | 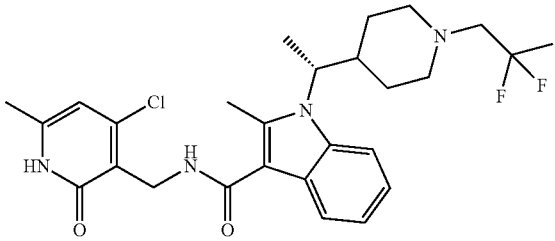<br>(R)-N-((4-chloro-6-methyl-2-oxo-1,2-dihydropyridin-3-yl)methyl)-1-(1-(1-(2,2-difluoropropyl)piperidin-4-yl)ethyl)-2-methyl-1H-indole-3-carboxamide (Compound 105) | ¹H NMR (400 MHz, DMSO-d6) δ = 12.02 (s, 1 H), 7.73 (d, J = 7.1 Hz, 1 H), 7.66 (t, J = 4.8 Hz, 1 H), 7.60 (d, J = 7.6 Hz, 1 H), 7.11-7.00 (m, 2 H), 6.20 (s, 1 H), 4.48-4.37 (m, 2 H), 4.19 (dd, J = 6.9, 10.5 Hz, 1 H), 3.68 (d, J = 12.0 Hz, 1 H), 3.41 (d, J = 12.0 Hz, 1 H), 3.31 (s, 2 H), 2.97 | 520 |
| A, B, C | 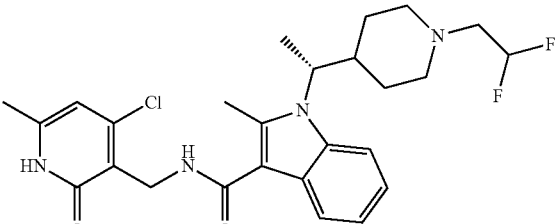<br>(R)-N-((4-chloro-6-methyl-2-oxo-1,2-dihydropyridin-3-yl)methyl)-1-(1-(1-(2,2-difluoroethyl)piperidin-4-yl)ethyl)-2-methyl-1H-indole-3-carboxamide (Compound 106) | 1H NMR (400 MHz, DMSO-d6) δ = 12.05 (br.s., 1 H), 11.35-11.19 (m, 1 H), 7.79-7.65 (m, 2 H), 7.62 (d, J = 7.6 Hz, 1 H), 7.16-7.04 (m, 2 H), 6.21 (d, J = 0.5 Hz, 1 H), 4.45 (d, J = 4.0 Hz, 2 H), 4.11 (br.s., 4 H), 3.70-3.54 (m, 2 H), 3.32 (d, J = 12.1 Hz, 1 H), 3.10 (d, J = 13.6 Hz, 1 H), 2.93-2.81 (m, 1 H), 2.73-2.63 (m, 1 H), 2.58 (s, 2 H), 2.21-2.09 (m, 4 H), 1.80 (d, J = 11.9 Hz, 1 H), 1.57 (d, J = 6.6 Hz, 4 H), 0.88 (d, J = 13.4 Hz, 1 H) | 506 |
| A, B, C | 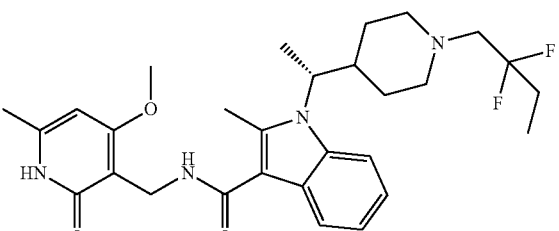<br>(R)-1-(1-(1-(2,2-difluorobutyl)piperidin-4-yl)ethyl)-N-((4-methoxy-6-methyl-2-oxo-1,2-dihydropyridin-3-yl)methyl)-2-methyl-1H-indole-3-carboxamide (Compound 108) | ¹H NMR (500 MHz, DMSO-d6) δ 11.59 (br.s., 1H), 7.74 (d, J = 7.42 Hz, 1H), 7.68 (t, J = 7.42 Hz, 1H), 7.60 (d, J = 7.97 Hz, 1H), 6.98-7.17 (m, 2H), 6.15 (s, 1H), 4.32 (d, J = 4.94 Hz, 2H), 4.05-4.23 (m, 1H), 3.84 (s, 3H), 3.29-3.33 (m, 2H), 2.96 (d, J = 9.89 Hz, 1H), 2.62-2.68 (m, 1H), 2.60 (s, 3H), 2.18 (s, 3H), 2.16-2.22 (m, 2H), 1.76-1.97 (m, 4H), 1.44-1.59 (d, J = 7.42 Hz, 3H), 1.28-1.44 (m, 1H), 0.98-1.11 (m, 1H), 0.90 (t, J = 7.55 Hz, 3H), 0.66 (d, J = 10.99 Hz, 1H). | 529 |

| Methods | Structure/Name | ¹H NMR | m/z |
|---|---|---|---|
| A, B, C | (R)-1-(1-(1-(2,2-difluoroethyl)piperidin-4-yl)ethyl)-N-((4-(difluoromethoxy)-6-methyl-2-oxo-1,2-dihydropyridin-3-yl)methyl)-2-methyl-1H-indole-3-carboxamide (Compound 110) | ¹H NMR (400 MHz, DMSO-d6) δ = 12.13-11.93 (m, 1 H), 11.29-11.10 (m, 1 H), 7.77 (d, J = 7.3 Hz, 1 H), 7.68 (br.s., 1 H), 7.62 J = 7.8 Hz, 1 H), 7.14-7.03 (m, 2 H), 6.11 (s, 2 H), 4.86 (br. s., 4 H), 4.34 (br.s., 2 H), 4.18 (br.s., 1 H), 3.69-3.53 (m, 2 H), 3.32 (d, J = 12.6 Hz, 1 H), 3.10 (d, J = 13.1 Hz, 1 H), 2.90 (br.s., 1 H), 2.68 (d, J = 20.0 Hz, 1 H), 2.58 (s, 2 H), 2.22 (s, 3 H), 2.15 (d, J = 13.9 Hz, 1 H), 1.79 (d, J = 12.6 Hz, 1 H), 1.57 (d, J = 6.6 Hz, 3 H), 0.88 (d, J = 11.6 Hz, 1 H) | 537 |
| A, B, C | (R)-N-((4-(difluoromethoxy)-6-methyl-2-oxo-1,2-dihydropyridin-3-yl)methyl)-1-(1-(1-(2,2-difluoropropyl)piperidin-4-yl)ethyl)-2-methyl-1H-indole-3-carboxamide (Compound 111) | ¹H NMR (500 MHz, DMSO-d6) δ = 10.55-10.42 (m, 1 H), 7.75 (d, J = 7.4 Hz, 1 H), 7.69-7.56 (m, 2 H), 7.13-7.00 (m, 2 H), 6.09 (s, 1 H), 4.57 (br.s., 4 H), 4.32 (br.s., 2 H), 4.16 (br.s., 1 H), 3.71 (br. s., 2 H), 3.63-3.52 (m, 1 H), 3.31 (d, J = 10.4 Hz, 1 H), 3.20-3.09 (m, 1 H), 2.95-2.81 (m, 1 H), 2.75-2.61 (m, 2 H), 2.58 (s, 2 H), 2.25-2.16 (m, 3 H), 2.11 (br.s., 1 H), 1.89-1.67 (m, 3 H), 1.61-1.47 (m, 3 H), 0.84 (d, J = 13.2 Hz, 1 H) | 551 |
| A, B, C | (R)-N-((4-methoxy-6-methyl-2-oxo-1,2-dihydropyridin-3-yl)methyl)-2-methyl-1-(1-(1-(2,2,3,3,3-pentafluoropropyl)piperidin-4-yl)ethyl)-1H-indole-3-carboxamide (Compound 113) | 1H NMR (400 MHz, DMSO-d6) δ = 11.60 (s, 1 H), 7.74 (d, J = 7.4 Hz, 1 H), 7.69 (br.s., 1 H), 7.60 (d, J = 8.0 Hz, 1 H), 7.06 (quin, J = 7.2 Hz, 2H), 6.15 (s, 1 H), 4.32 (d, J = 4.9 Hz, 2 H), 4.23-4.11 (m, 1 H), 3.84 (s, 3 H), 3.10 (dt, J = 6.8, 16.2 Hz, 2 H), 2.97 (d, J = 11.1 Hz, 1 H), 2.69 (d, J = 9.8 Hz, 2 H), 2.60 (s, 3 H), 2.35 (t, J = 11.0 Hz, 1 H), 2.20 (s, 4 H), 2.08-1.99 (m, 1 H), 1.89 (d, J = 12.0 Hz, 1 H), 1.53 (d, J = 6.7 Hz, 3 H), 1.37 (d, J = 12.0 Hz, 1 H), 1.05 (d, J = 9.8 Hz, 1 H), 0.67 (d, J = 12.3 Hz, 1 H) | 569 |

| Methods | Structure/Name | ¹H NMR | m/z |
|---|---|---|---|
| A, B, C | (R)-1-(1-(1-(2-fluoro-2-methylpropyl)piperidin-4-yl)ethyl)-N-((4-methoxy-6-methyl-2-oxo-1,2-dihydropyridin-3-yl)methyl)-2-methyl-1H-indole-3-carboxamide (Compound 116) | 1H NMR (400 MHz, DMSO-d6) δ = 11.61 (s, 1 H), 7.77-7.66 (m, 2 H), 7.64-7.56 (m, 1 H), 7.12-7.01 (m, 3 H), 7.00-6.93 (m, 2 H), 6.15 (s, 1 H), 4.38-4.26 (m, 2 H), 4.17 (br.s., 1 H), 3.84 (s, 3 H), 3.43 (s, 2 H), 2.91-2.81 (m, 1 H), 2.72-2.56 (m, 4 H), 2.19 (s, 3 H), 2.03-1.86 (m, 2 H), 1.67 (br.s., 1 H), 1.56-1.46 (m, 4 H), 1.43-1.33 (m, 1 H), 1.14-1.05 (m, 1 H), 0.70 (br.s., 1 H) | 511 |
| A, B, C | (R)-1-(1-(1-((1-fluorocyclobutyl)methyl)piperidin-4-yl)ethyl)-N-((4-methoxy-6-methyl-2-oxo-1,2-dihydropyridin-3-yl)methyl)-2-methyl-1H-indole-3-carboxamide (Compound 118) | 1H NMR (500 MHz, DMSO-d6) δ = 11.58 (s, 1H), 7.73 (d, J = 7.69 Hz, 1H), 7.63-7.70 (m, 1H), 7.59 (d, J = 7.97 Hz, 1H), 6.98-7.13 (m, 2H), 6.14 (s, 1H), 4.31 (d, J = 4.94 Hz, 2H), 4.04-4.21 (m, 1H), 3.83 (s, 3H), 2.96 (d, J = 10.16 Hz, 1H), 2.68 (br. s, 1H), 2.59 (s, 3H), 2.52-2.55 (m, 1H), 2.45-2.49 (m, 1H), 2.19 (s, 3H), 2.06-2.13 (m, 6H), 1.86 (d, J = 12.63 Hz, 1H), 1.58-1.81 (m, 2H), 1.52 (d, J = 7.14 Hz, 3H), 1.39-1.46 (m, 1H), 1.29-1.39 (m, 1H), 0.91-1.14 (m, 1H), 0.60-0.71 (m, 1H) | 523 |
| A, B, C | (R)-1-(1-(1-((1-fluorocyclopropyl)methyl)piperidin-4-yl)ethyl)-N-((4-methoxy-6-methyl-2-oxo-1,2-dihydropyridin-3-yl)methyl)-2-methyl-1H-indole-3-carboxamide (Compound 119) | 1H NMR (400 MHz, DMSO-d6) δ = 11.59 (s, 1H), 7.74 (d, J = 7.33 Hz, 1H), 7.69 (t, J = 4.93 Hz, 1H), 7.60 (d, J = 7.83 Hz, 1H), 7.01-7.17 (m, 2H), 6.15 (s, 1H), 4.33 (d, J = 5.05 Hz, 2H), 4.10-4.26 (m, 1H), 3.84 (s, 3H), 3.06 (d, J = 9.85 Hz, 1H), 2.75 (br.s., 1H), 2.60-2.72 (m, 2H), 2.61 (s, 3H), 2.20 (s, 3H), 2.14-2.22 (m, 1H), 2.02-2.13 (m, 1H), 1.91 (d, J = 9.85 Hz, 1H), 1.62-1.86 (m, 1H), 1.55 (d, J = 6.82 Hz, 3H), 1.29-1.46 (m, 1H), 1.06 (d, J = 10.36 Hz, 1H), 0.93 (d, J = 18.95 Hz, 2H), 0.68 (d, J = 11.12 Hz, 1H), 0.59 (d, J = 8.59 Hz, 2H) | 509 |

| Methods | Structure/Name | ¹H NMR | m/z |
|---|---|---|---|
| A, B, C | (R)-N-((4-methoxy-6-methyl-2-oxo-1,2-dihydropyridin-3-yl)methyl)-2-methyl-1-(1-(1-(3,3,3-trifluoro-2,2-dimethylpropyl)piperidin-4-yl)ethyl)-1H-indole-3-carboxamide (Compound 136) | | 561 |
| A, B, C | (R)-N-((4-methoxy-6-methyl-2-oxo-1,2-dihydropyridin-3-yl)methyl)-2-methyl-1-(1-(1-((1-(trifluoromethyl)cyclobutyl)methyl)piperidin-4-yl)ethyl)-1H-indole-3-carboxamide (Compound 135) | | 573 |
| H, B, C | (R)-N-((4-chloro-6-methyl-2-oxo-1,2-dihydropyridin-3-yl)methyl)-1-(1-(1-(2-fluoroethyl)piperidin-4-yl)ethyl)-2-methyl-1H-indole-3-carboxamide (Compound 126) | | 488 |

-continued

| Methods | Structure/Name | ¹H NMR | m/z |
|---|---|---|---|
| H, B, C | (R)-N-((4-(difluoromethoxy)-6-methyl-2-oxo-1,2-dihydropyridin-3-yl)methyl)-2-methyl-1-(1-(1-(3,3,3-trifluoropropyl)piperidin-4-yl)ethyl)-1H-indole-3-carboxamide (Compound 143) | | 569 |
| H, B, C | (R)-N-((4-ethyl-6-methyl-2-oxo-1,2-dihydropyridin-3-yl)methyl)-2-methyl-1-(1-(1-(3,3,3-trifluoromethylpropyl)piperidin-4-yl)ethyl)-1H-indole-3-carboxamide (Compound 151) | | 531 |
| H, B, C | (R)-N-((4-methoxy-6-methyl-2-oxo-1,2-dihydropyridin-3-yl)methyl)-2-methyl-1-(1-(1-(4,4,4-trifluorobutyl)piperidin-4-yl)ethyl)-1H-indole-3-carboxamide (Compound 152) | 1H NMR (400 MHz, DMSO-d6) δ 11.63-11.55 (m, 1 H), 7.79-7.72 (m, 1 H), 7.71-7.66 (m, 1 H), 7.63-7.57 (m, 1 H), 7.13-7.00 (m, 2 H), 6.19-6.12 (m, 1 H), 4.59-4.47 (m, 1 H), 4.38-4.26 (m, 2 H), 4.23-4.10 (m, 1 H), 3.84 (s, 3 H), 3.30-3.24 (m, 1 H), 2.98-2.86 (m, 1 H), 2.60 (s, 3 H), 2.20 (s, 6 H), 1.98-1.82 (m, 2 H), 1.64-1.48 (m, 5 H), 1.43-1.27 (m, 2 H), 1.12-0.93 (m, 2 H), 0.75-0.63 (m, 1 H) | 547 |

| Methods | Structure/Name | ¹H NMR | m/z |
|---|---|---|---|
| H, B, C | (R)-N-((4-methoxy-6-methyl-2-oxo-1,2-dihydropyridin-3-yl)methyl)-2-methyl-1-(1-(1-(4,4,4-trifluorobutyl)piperidin-4-yl)ethyl)-1H-indole-3-carboxamide (Compound 152) | | 547 |
| E | (R)-1-(1-(1-(1,3-difluoropropan-2-yl)piperidin-4-yl)ethyl)-N-((4-methoxy-6-methyl-2-oxo-1,2-dihydropyridin-3-yl)methyl)-2-methyl-1H-indole-3-carboxamide (Compound 166) | | 515 |
| A, B, C | (R)-N-((4-methoxy-6-methyl-2-oxo-1,2-dihydropyridin-3-yl)methyl)-2-methyl-1-(1-(1-(2,2,3,3,3-pentafluoropropyl)piperidin-4-yl)ethyl)-1H-indole-3-carboxamide (Compound 170) | | 569 |

| Methods | Structure/Name | ¹H NMR | m/z |
|---|---|---|---|
| G, B, C | (R)-N-((4-methoxy-6-methyl-2-oxo-1,2-dihydropyridin-3-yl)methyl)-2-methyl-1-(1-(1-((S)-3,3,3-trifluoro-2-methoxypropyl)piperidin-4-yl)ethyl)-1H-indole-3-carboxamide (Compound 121) | | 563 |
| G, B, C | (R)-N-((4-methoxy-6-methyl-2-oxo-1,2-dihydropyridin-3-yl)methyl)-2-methyl-1-(1-(1-((S)-3,3,3-trifluoro-2-hydroxypropyl)piperidin-4-yl)ethyl)-1H-indole-3-carboxamide (Compound 156) | | 549 |
| E | (R)-1-(1-(1-(cyclopropylmethyl)piperidin-4-yl)ethyl)-N-((4-methoxy-6-methyl-2-oxo-1,2-dihydropyridin-3-yl)methyl)-2-methyl-1H-indole-3-carboxamide (Compound 145) | | 491 |

| Methods | Structure/Name | ¹H NMR | m/z |
|---|---|---|---|
| E | (R)-1-(1-(1-(4-fluorobenzyl)piperidin-4-yl)ethyl)-N-((4-methoxy-6-methyl-2-oxo-1,2-dihydropyridin-3-yl)methyl)-2-methyl-1H-indole-3-carboxamide (Compound 122) | | 545 |
| E | (R)-N-((4-methoxy-6-methyl-2-oxo-1,2-dihydropyridin-3-yl)methyl)-2-methyl-1-(1-(1-(pyridin-2-ylmethyl)piperidin-4-yl)ethyl)-1H-indole-3-carboxamide (Compound 148) | | 528 |
| E | (R)-1-(1-(1-(2,6-difluorobenzyl)piperidin-4-yl)ethyl)-N-((4-methoxy-6-methyl-2-oxo-1,2-dihydropyridin-3-yl)methyl)-2-methyl-1H-indole-3-carboxamide (Compound 150) | | 563 |

| Methods | Structure/Name | ¹H NMR | m/z |
|---|---|---|---|
| A, B, C | 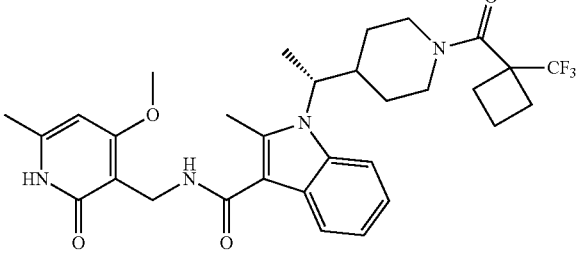<br>(R)-N-((4-methoxy-6-methyl-2-oxo-1,2-dihydropyridin-3-yl)methyl)-2-methyl-1-(1-(1-(1-(trifluoromethyl)cyclobutanecarbonyl)piperidin-4-yl)ethyl)-1H-indole-3-carboxamide (Compound 104) | ¹H NMR (400 MHz, DMSO-d6) δ = 11.59 (br. s, 1H), 7.73 (d, J = 7.69 Hz, 1H), 7.63-7.70 (m, 1H), 7.59 (d, J = 7.97 Hz, 1H), 6.98-7.13 (m, 2H), 6.14 (s, 1H), 4.47-5.55 (m, 1H), 4.32 (d, J = 4.94 Hz, 2H), 4.10-4.31 (m, 2H), 3.83 (s, 3H), 3.56-3.60 (m, 1H), 3.00-3.05 (m, 1H), 2.81-2.87 (m, 1H), 2.62-2.73 (m, 2H), 2.58 (s, 3H), 2.28-2.39 (m, 2H), 2.19 (s, 3H), 2.06-2.14 (m, 1H), 1.85-2.05 (m, 1H), 1.65-1.80 (m, 2H), 1.54 (d, 3H), 0.60-0.95 (m, 2H). | 587 |
| A, B, C | 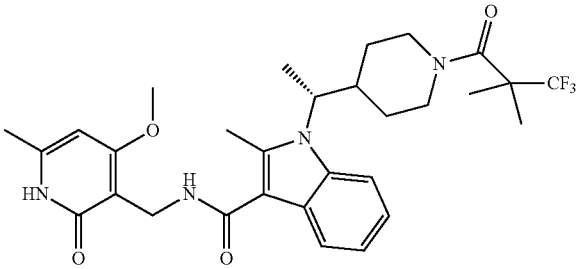<br>(R)-N-((4-methoxy-6-methyl-2-oxo-1,2-dihydropyridin-3-yl)methyl)-2-methyl-1-(1-(1-(3,3,3-trifluoro-2,2-dimethylpropanoyl)piperidin-4-yl)ethyl)-1H-indole-3-carboxamide (Compound 114) | | 575 |
| A, B, C | 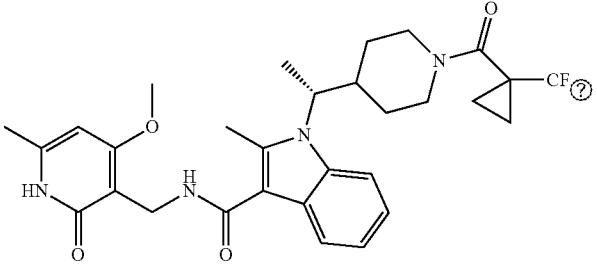<br>(R)-N-((4-methoxy-6-methyl-2-oxo-1,2-dihydropyridin-3-yl)methyl)-2-methyl-1-(1-(1-(1-(trifluoromethyl)cyclopropanecarbonyl)piperidin-4-yl)ethyl)-1H-indole-3-carboxamide (Compound 115) | | 573 |

| Methods | Structure/Name | ¹H NMR | m/z |
|---|---|---|---|
| B | 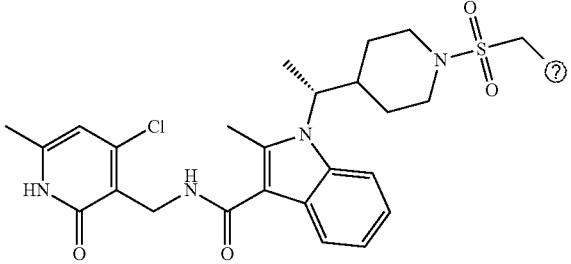<br>(R)-N-((4-chloro-6-methyl-2-oxo-1,2-dihydropyridin-3-yl)methyl)-1-(1-(1-(ethylsulfonyl)piperidin-4-yl)ethyl)-2-methyl-1H-indole-3-carboxamide (Compound 107) | ¹H NMR (400 MHz, DMSO-d6) δ = 12.02 (s, 1 H), 7.73 (d, J = 7.1 Hz, 1 H), 7.66 (t, J = 4.8 Hz, 1 H), 7.60 (d, J = 7.6 Hz, 1 H), 7.11-7.00 (m, 2 H), 6.20 (s, 1 H), 4.48-4.37 (m, 2 H), 4.19 (dd, J = 6.9, 10.5 Hz, 1 H), 3.68 (d, J = 12.0 Hz, 1 H), 3.41 (d, J = 12.0 Hz, 1 H), 3.31 (s, 2 H), 2.97 | 534 |
| B | 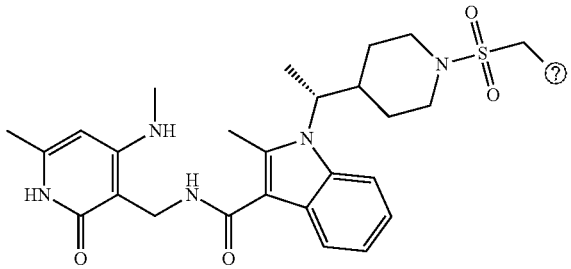<br>(R)-1-(1-(1-(ethylsulfonyl)piperidin-4-yl)ethyl)-2-methyl-N-((6-methyl-4-(methylamino)-2-oxo-1,2-dihydropyridin-3-yl)methyl)-1H-indole-3-carboxamide (Compound 123) | | 528 |
| B | 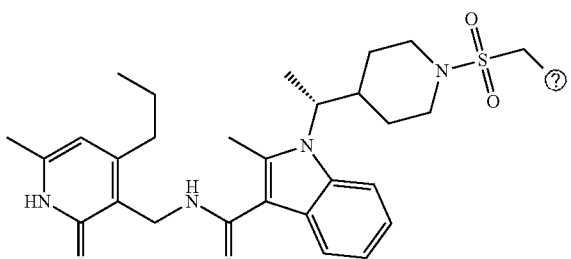<br>(R)-1-(1-(1-(ethylsulfonyl)piperidin-4-yl)ethyl)-2-methyl-N-((6-methyl-2-oxo-4-propyl-1,2-dihydropyridin-3-yl)methyl)-1H-indole-3-carboxamide (Compound 132) | | 541 |

| Methods | Structure/Name | ¹H NMR | m/z |
|---|---|---|---|
| B | 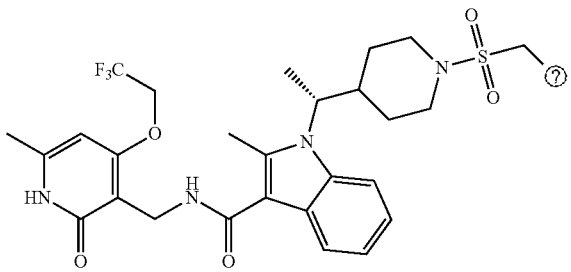<br>(R)-1-(1-(1-(ethylsulfonyl)piperidin-4-yl)ethyl)-2-methyl-N-((6-methyl-4-2-oxo-4-(2,2,2-trifluoroethoxy)-1,2-dihydropyridin-3-yl)methyl)-1H-indole-3-carboxamide (Compound 163) | | 597 |
| B | 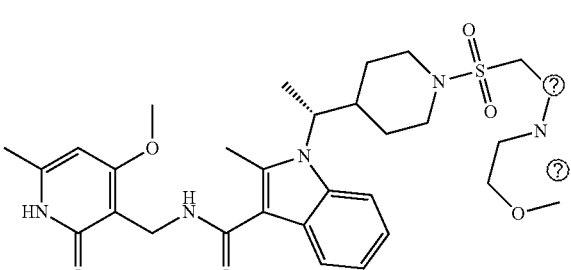<br>(R)-N-((4,6-dimethyl-2-oxo-1,2-dihydropyridin-3-yl)methyl)-2-methyl-1-(1-(1-((2-morpholinoethyl)sulfonyl)piperidin-4-yl)ethyl)-1H-indole-3-carboxamide (Compound 134) | | 598 |
| B | 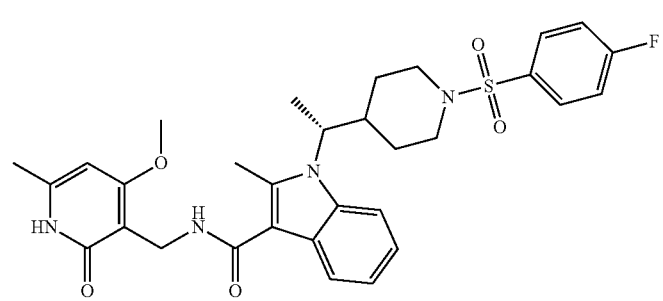<br>(R)-1-(1-(1-((4-fluorophenyl)sulfonyl)piperidin-4-yl)ethyl)-N-((4-methoxy-6-methyl-2-oxo-1,2-dihydropyridin-3-yl)methyl)-2-methyl-1H-indole-3-carboxamide (Compound 137) | | 595 |

| Methods | Structure/Name | ¹H NMR | m/z |
|---|---|---|---|
| B | 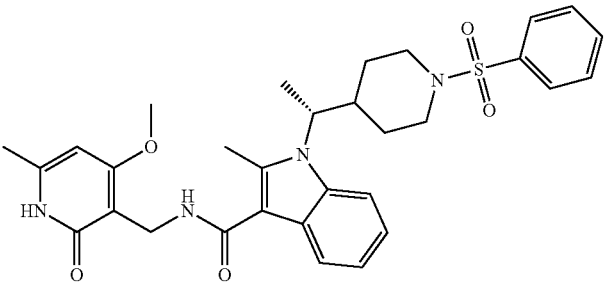<br>(R)-N-((4-methoxy-6-methyl-2-oxo-1,2-dihydropyridin-3-yl)methyl)-2-methyl-1-(1-(1-(phenylsulfonyl)piperidin-4-yl)ethyl)-1H-indole-3-carboxamide (Compound 138) | | 577 |
| D | 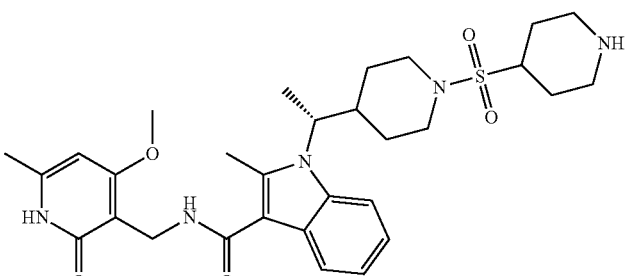<br>(R)-N-((4,6-dimethyl-2-oxo-1,2-dihydropyridin-3-yl)methyl)-2-methyl-1-(1-(1-(piperidin-4-ylsulfonyl)piperidin-4-yl)ethyl)-1H-indole-3-carboxamide (Compound 172) | | 568 |
| D | 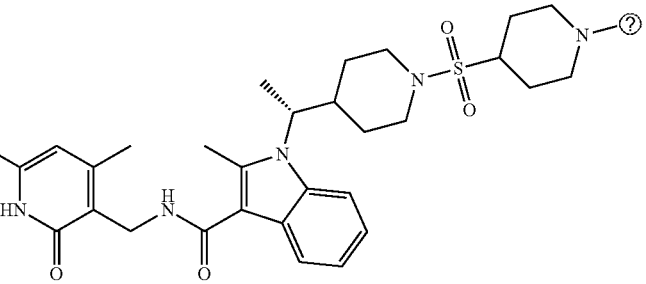<br>(R)-N-((4,6-dimethyl-2-oxo-1,2-dihydropyridin-3-yl)methyl)-2-methyl-1-(1-(1-((1-methylpiperidin-4-yl)sulfonyl)piperidin-4-yl)ethyl)-1H-indole-3-carboxamide (Compound 139) | | 582 |

| Methods | Structure/Name | ¹H NMR | m/z |
|---|---|---|---|
| D | 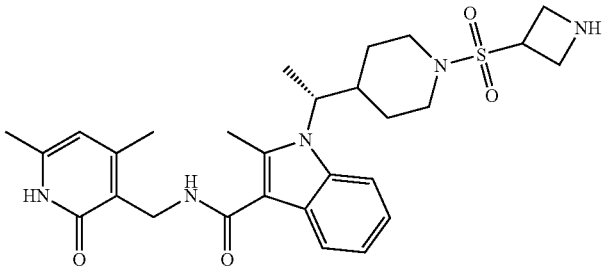<br>(R)-1-(1-(1-(azetidin-3-ylsulfonyl)piperidin-4-yl)ethyl)-N-((4,6-dimethyl-2-oxo-1,2-dihydropyridin-3-yl)methyl)-2-methyl-1H-indole-3-carboxamide (Compound 171) | | 540 |
| D | 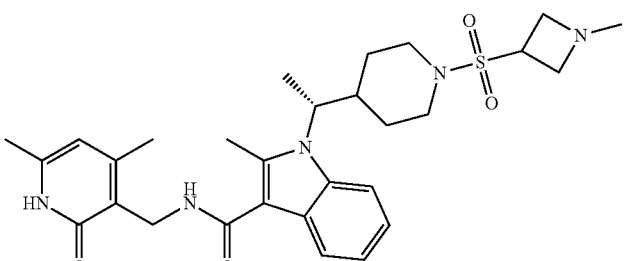<br>(R)-N-((4,6-dimethyl-2-oxo-1,2-dihydropyridin-3-yl)methyl)-2-methyl-1-(1-(1-((1-methylazetidin-3-yl)sulfonyl)piperidin-4-yl)ethyl)-1H-indole-3-carboxamide (Compound 147) | | 553 |
| D | 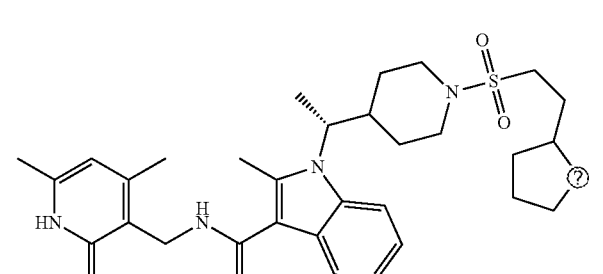<br>(R)-N-((4,6-dimethyl-2-oxo-1,2-dihydropyridin-3-yl)methyl)-2-methyl-1-(1-(1-((2-(pyrrolidin-1-yl)ethyl)sulfonyl)piperidin-4-yl)ethyl)-1H-indole-3-carboxamide (Compound 161) | | 582 |

| Methods | Structure/Name | ¹H NMR | m/z |
|---|---|---|---|
| D | (R)-N-((4-methoxy-6-methyl-2-oxo-1,2-dihydropyridin-3-yl)methyl)-2-methyl-1-(1-(1-pivaloylpiperidin-4-yl)ethyl)-1H-indole-3-carboxamide (Compound 129) | | 521 |
| D | (R)-2-(2-methoxyethoxy)ethyl 4-(1-(3-(((4-methoxy-6-methyl-2-oxo-1,2-dihydropyridin-3-yl)methyl)carbamoyl)-2-methyl-1H-indol-1-yl)ethyl)piperidine-1-carboxylate (Compound 140) | | 583 |
| D | (R)-2,5,8,11,14,17-hexaoxanonadecan-19-yl 4-(1-(3-(((4-methoxy-6-methyl-2-oxo-1,2-dihydropyridin-3-yl)methyl)carbamoyl)-2-methyl-1H-indole-1-yl)ethyl)piperidine-1-carboxylate (Compound 165) | | 759 |

| Methods | Structure/Name | ¹H NMR | m/z |
|---|---|---|---|
| D | 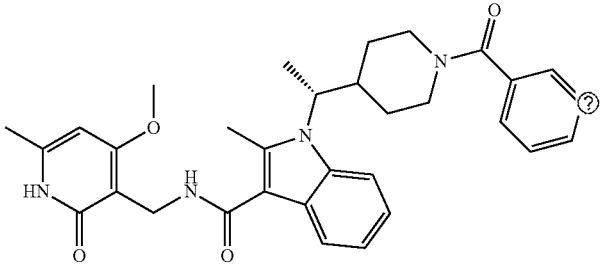<br>(R)-1-(1-(1-benzoylpiperidin-4-yl)ethyl)-N-((4-methoxy-6-methyl-2-oxo-1,2-dihydropyridin-3-yl)methyl)-2-methyl-1H-indole-3-carboxamide (Compound 153) | | 541 |
| D | 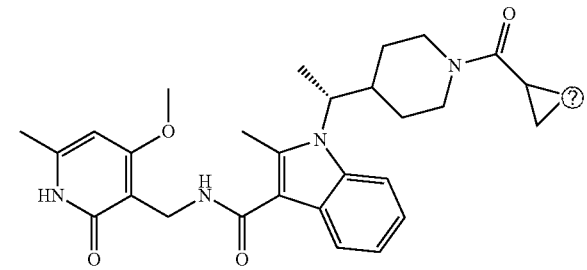<br>(R)-1-(1-(1-(cyclopropanecarbonyl)piperidin-4-yl)ethyl)-N-((4-methoxy-6-methyl-2-oxo-1,2-dihydropyridin-3-yl)methyl)-2-methyl-1H-indole-3-carboxamide (Compound 157) | | 504 |
| J, B, C | 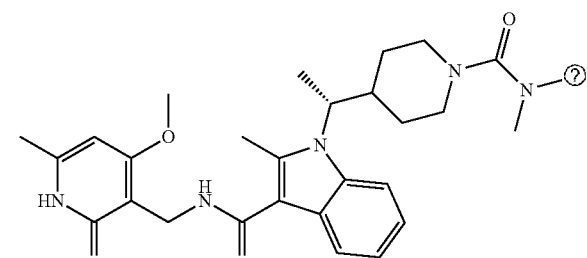<br>(R)-1-(1-(1-(dimethylcarbamoyl)piperidin-4-yl)ethyl)-N-((4-methoxy-6-methyl-2-oxo-1,2-dihydropyridin-3-yl)methyl)-2-methyl-1H-indole-3-carboxamide (Compound 158) | | 508 |

| Methods | Structure/Name | ¹H NMR | m/z |
|---|---|---|---|
| J, B, C | (R)-N-((4-methoxy-6-methyl-2-oxo-1,2-dihydropyridin-3-yl)methyl)-2-methyl-1-(1-(1-(morpholine-4-carbonyl)piperidin-4-yl)ethyl)-1H-indole-3-carboxamide (Compound 167) | | 550 |
| J, B, C | (R)-N-((4,6-dimethyl-2-oxo-1,2-dihydropyridin-3-yl)methyl)-2-methyl-1-(1-(1-(4-methylpiperazine-1-carbonyl)piperidin-4-yl)ethyl)-1H-indole-3-carboxamide (Compound 162) | | 546 |
| E, B, C | (R)-1-(1-(1-(2-(diethylamino)-2-oxoethyl)piperidin-4-yl)ethyl)-N-((4-methoxy-6-methyl-2-oxo-1,2-dihydropyridin-3-yl)methyl)-2-methyl-1H-indole-3-carboxamide (Compound 168) | | 550 |

| Methods | Structure/Name | ¹H NMR | m/z |
|---|---|---|---|
| H | (R)-N-((4-methoxy-6-methyl-2-oxo-1,2-dihydropyridin-3-yl)methyl)-2-methyl-1-(1-(1-(2-oxopropyl)piperidin-4-yl)ethyl)-1H-indole-3-carboxamide (Compound 169) | | 493 |
| E | (R)-N-((4-chloro-6-methyl-2-oxo-1,2-dihydropyridin-3-yl)methyl)-2-methyl-1-(1-(1-(oxetan-3-yl)piperidin-4-yl)ethyl)-1H-indole-3-carboxamide (Compound 112) | | 498 |
| G, B, C | (R)-N-((4,6-dimethyl-2-oxo-1,2-dihydropyridin-3-yl)methyl)-1-(1-(1-(2-methoxy-2-methylpropyl)piperidin-4-yl)ethyl)-2-methyl-1H-indole-3-carboxamide (Compound 127) | | 507 |

| Methods | Structure/Name | ¹H NMR | m/z |
|---|---|---|---|
| G, B, C | 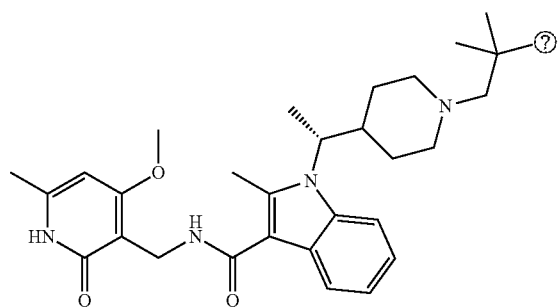<br>(R)-1-(1-(1-(2-methoxy-2-methylpropyl)piperidin-4-yl)ethyl)-N-((4-methoxy-6-methyl-2-oxo-1,2-dihydropyridin-3-yl)methyl)-2-methyl-1H-indole-3-carboxamide (Compound 128) | | 523 |
| G, B, C | 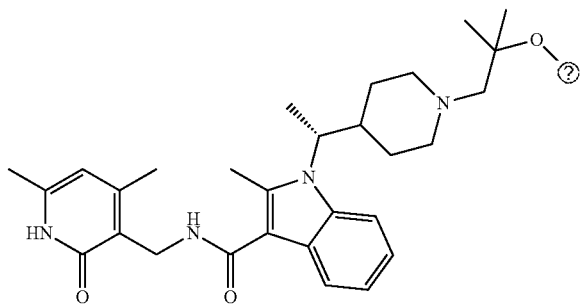<br>(R)-N-((4,6-dimethyl-2-oxo-1,2-dihydropyridin-3-yl)methyl)-1-(1-(1-(2-methoxy-2-methylpropyl)piperidin-4-yl)ethyl)-2-methyl-1H-indole-3-carboxamide (Compound 127) | | 507 |
| F | 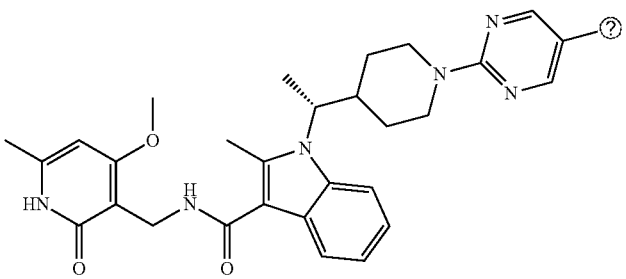<br>(R)-1-(1-(1-(5-fluoropyrimidin-2-yl)piperidin-4-yl)ethyl)-N-((4-methoxy-6-methyl-2-oxo-1,2-dihydropyridin-3-yl)methyl)-2-methyl-1H-indole-3-carboxamide (Compound 120) | | 533 |

| Methods | Structure/Name | ¹H NMR | m/z |
|---|---|---|---|
| F | (R)-1-(1-(1-(5-chloropyrimidin-2-yl)piperidin-4-yl)ethyl)-N-((4-methoxy-6-methyl-2-oxo-1,2-dihydropyridin-3-yl)methyl)-2-methyl-1H-indole-3-carboxamide (Compound 130) | | 549 |
| F | (R)-1-(1-(1-(5-fluoropyridin-2-yl)piperidin-4-yl)ethyl)-N-((4-methoxy-6-methyl-2-oxo-1,2-dihydropyridin-3-yl)methyl)-2-methyl-1H-indole-3-carboxamide (Compound 131) | | 532 |
| F | (R)-N-((4-methoxy-6-methyl-2-oxo-1,2-dihydropyridin-3-yl)methyl)-2-methyl-1-(1-(1-(pyrazin-2-yl)piperidin-4-yl)ethyl)-1H-indole-3-carboxamide (Compound 149) | | 515 |

| Methods | Structure/Name | ¹H NMR | m/z |
|---|---|---|---|
| F | 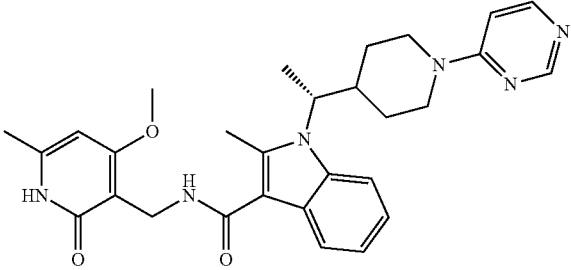<br>(R)-N-((4-methoxy-6-methyl-2-oxo-1,2-dihydropyridin-3-yl)methyl)-2-methyl-1-(1-(1-pyrimidin-4-yl)piperidin-4-yl)ethyl)-1H-indole-3-carboxamide (Compound 164) | | 515 |
| I, B, C | 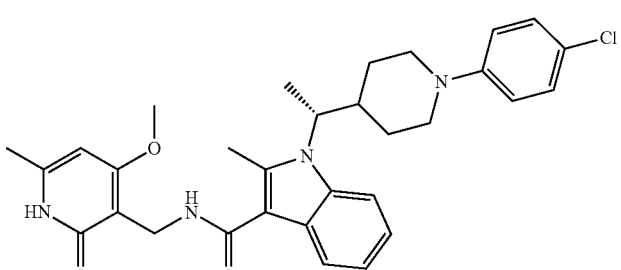<br>(R)-1-(1-(1-(4-chlorophenyl)piperidin-4-yl)ethyl)-N-((4-methoxy-6-methyl-2-oxo-1,2-dihydropyridin-3-yl)methyl)-2-methyl-1H-indole-3-carboxamide (Compound 154) | | 547 |
| I, B, C | 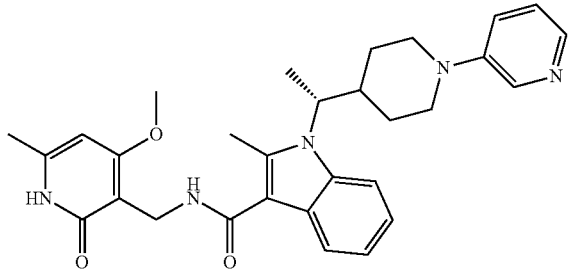<br>(R)-N-((4-methoxy-6-methyl-2-oxo-1,2-dihydropyridin-3-yl)methyl)-2-methyl-1-(1-(1-(pyridin-3-yl)piperidin-4-yl)ethyl)-1H-indole-3-carboxamide (Compound 125) | | 514 |

| Methods | Structure/Name | ¹H NMR | m/z |
|---|---|---|---|
| I, B, C | 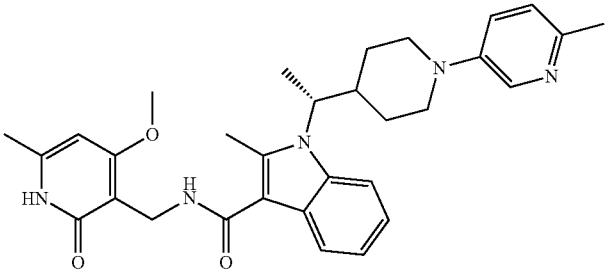<br>(R)-N-((4-methoxy-6-methyl-2-oxo-1,2-dihydropyridin-3-yl)methyl)-2-methyl-1-(1-(1-(6-methylpyridin-3-yl)piperidin-4-yl)ethyl)-1H-indole-3-carboxamide (Compound 133) | | 528 |
| I, B, C | 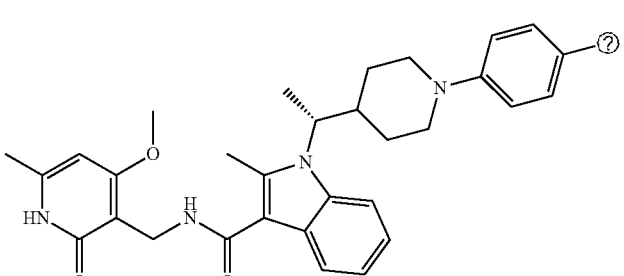<br>(R)-1-(1-(1-(4-fluorophenyl)piperidin-4-yl)ethyl)-N-((4-methoxy-6-methyl-2-oxo-1,2-dihydropyridin-3-yl)methyl)-2-methyl-1H-indole-3-carboxamide (Compound 141) | | 531 |
| I, B, C | 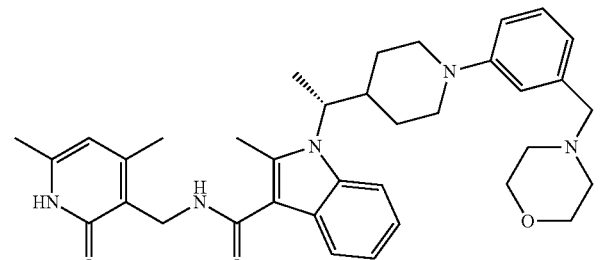<br>(R)-N-((4,6-dimethyl-2-oxo-1,2-dihydropyridin-3-yl)methyl)-2-methyl-1-(1-(1-(3-(morpholinomethyl)phenyl)piperidin-4-yl)ethyl)-1H-indole-3-carboxamide (Compound 144) | | 596 |

| Methods | Structure/Name | ¹H NMR | m/z |
|---------|----------------|--------|-----|
| I, B, C | (R)-N-((4,6-dimethyl-2-oxo-1,2-dihydropyridin-3-yl)methyl)-2-methyl-1-(1-(1-(4-(morpholinomethyl)phenyl)piperidin-4-yl)ethyl)-1H-indole-3-carboxamide (Compound 160) | | 596 |
| I, B, C | (R)-N-((4,6-dimethyl-2-oxo-1,2-dihydropyridin-3-yl)methyl)-2-methyl-1-(1-(1-(5-(morpholinomethyl)pyridin-2-yl)piperidin-4-yl)ethyl)-1H-indole-3-carboxamide (Compound 159) | | 597 |

-continued

| Methods | Structure/Name | $^1$H NMR | m/z |
|---|---|---|---|
| | 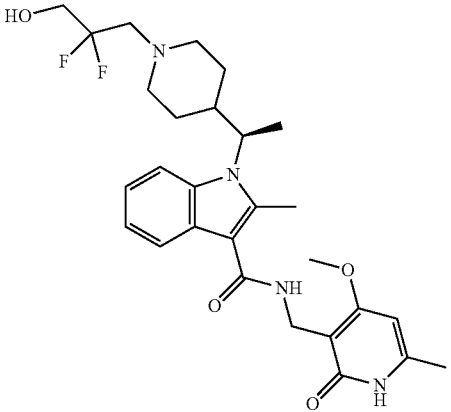

(R)-1-(1-(1-(2,2-difluoro-3-hydroxypropyl)piperidin-4-yl)ethyl)-N-((4-methoxy-6-methyl-2-oxo-1,2-dihydropyridin-3-yl)methyl)-2-methyl-1H-indole-3-carboxamide (Compound 175) | 1H NMR (400 MHz, CD3OD) δ 7.65-7.76 (m, 1H), 7.55-7.62 (m, 1H), 7.08-7.32 (m, 2H), 6.42 (s, 1H), 4.56 (s, 2H), 4.16-4.22 (m, 1H), 3.95 (s, 3H), 3.62-3.75 (m, 2H), 3.46-3.52 (m, 1H), 2.95-3.18 (m, 2H), 2.32-3.75 (m, 4H), 2.46 (s, 3H), 2.18-2.25 (m, 1H), 1.58-1.62 (m, 3H), 1.45-1.52 (m, 1H), 1.12-1.18 (m, 1H). | 531 |
| E | 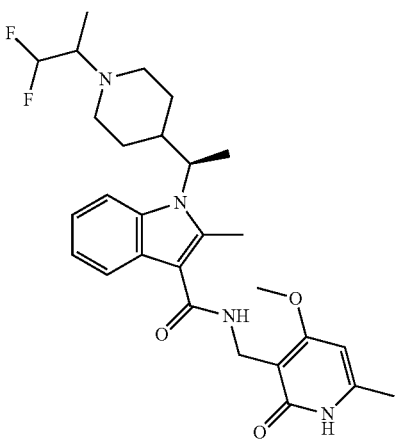

1-((1R)-1-(1-(1,1-difluoropropan-2-yl)piperidin-4-yl)ethyl)-N-((4-methoxy-6-methyl-2-oxo-1,2-dihydropyridin-3-yl)methyl)-2-methyl-1H-indole-3-carboxamide (Compound 177) | 1HNMR (400 MHz, CD3OD) δ 7.70 (m, 1 H), 7.55 (m, 1H), 7.06 (m, 2H), 6.27 (s, 1H), 5.62 (s, 1H), 4.52 (s, 2H), 4.18 (m, 2H), 3.93 (s, 2H), 2.80 (m , 2H), 2.47 (m, 2H), 2.31 (m, 3H), 2.16 (m, 5H), 2.00 (m, 2H), 1.38 (m, 2H), 1.60 (m, 2H), 1.39 (m, 3H), 0.86 (m, 2H). | 515 |

| Methods | Structure/Name | $^1$H NMR | m/z |
|---|---|---|---|
| H, B, C | 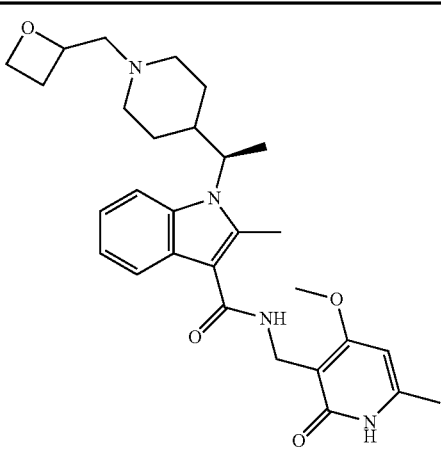<br>N-((4-methoxy-6-methyl-2-oxo-1,2-dihydropyridin-3-yl)methyl)-2-methyl-1-((1R)-1-(1-(oxetan-2-ylmethyl)piperidin-4-yl)ethyl)-1H-indole-3-carboxamide (Compound 179) | 1H NMR (400 MHz, CD3OD) δ 7.70-7.68 (d, J = 7.2 Hz, 1H), 7.56-7.54 (d, J = 7.2 Hz 1H), 7.11-7.04 (m, 2H), 6.26 (s, 1H), 4.62-4.58 (m, 3H), 4.51 (s, 2H), 4.46-4.44 (m, 1H), 4.19-4.17 (m, 1H), 3.93 (s, 3H), 3.03-2.98 (m, 1H), 2.76-2.71 (m, 3H), 2.65 (s, 3H), 2.59-2.54 (m, 1H), 2.31 (s, 3H), 2.23-2.20 (m, 1H), 2.02-1.98 (m, 1H), 1.82-1.80 (m, 1H), 1.60-1.58 (d, J = 6.8 Hz, 3H), 1.41-1.27 (m, 3H), 0.88-0.81 (m, 1H). | 507 |
| H, B, C | 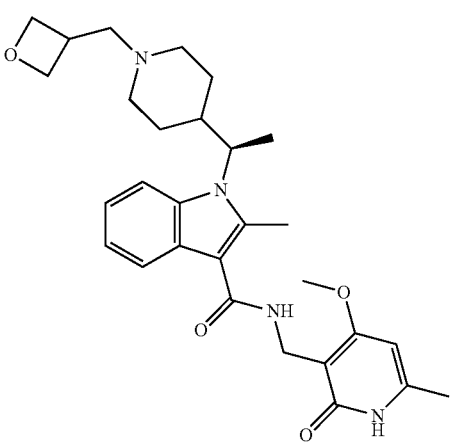<br>(R)-N-((4-methoxy-6-methyl-2-oxo-1,2-dihydropyridin-3-yl)methyl)-2-methyl-1-(1-(1-(oxetan-3-ylmethyl)piperidin-4-yl)ethyl)-1H-indole-3-carboxamide (Compound 180) | 1H NMR (400 MHz, CD3OD) δ 7.62-7.57 (m, 1H), 7.50-7.48 (d, J = 7.2 Hz, 1H), 7.05-6.98 (m, 2H), 6.19 (s, 1H), 4.50 (s, 3H), 4.43 (s, 2H), 4.17-4.02 (m, 4H), 3.85 (s, 3H), 3.84-3.82 (m, 1H), 3.53-3.50 (m, 3H), 3.24-3.20 (m, 1H), 3.10-3.01 (m, 2H), 2.53 (s, 3H), 2.52-2.49 (m, 1H), 2.23 (s, 3H), 2.09-2.05 (m, 1H), 1.56-1.54 (d, J = 5.6 Hz, 3H), 1.52-1.51 (m, 1H), 1.28-1.22 (m, 1H), 0.89-0.85 (m, 1H). | 507 |

| Methods | Structure/Name | ¹H NMR | m/z |
|---|---|---|---|
| | 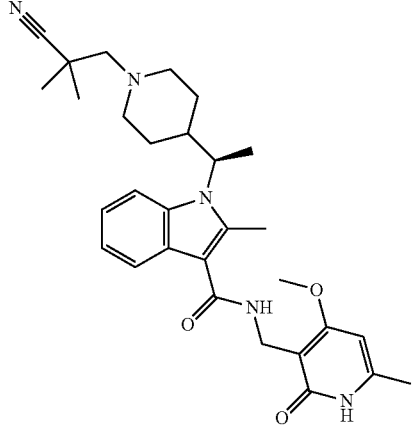<br>(R)-1-(1-(1-(2-cyano-2-methylpropyl)piperidin-4-yl)ethyl)-N-((4-methoxy-6-methyl-2-oxo-1,2-dihydropyridin-3-yl)methyl)-2-methyl-1H-indole-3-carboxamide (Compound 185) | 1H NMR (400 MHz, CD3OD) δ 7.73 (s, 1H), 7.62 (d, J = 6.1 Hz, 1H), 7.16 (s, 2H), 6.77 (s, 1H), 4.56 (s, 2H), 4.28 (s, 1H), 4.08 (s, 3H), 3.75 (d, J = 10.5 Hz, 1H), 3.43 (d, J = 10.8 Hz, 1H), 3.33 (s, 1H), 3.13 (s, 3H), 2.85 (t, J = 12.1 Hz, 1H), 2.64 (s, 3H), 2.49 (s, 3H), 2.33 (d, J = 12.5 Hz, 1H), 1.93 (s, 1H), 1.65 (d, J = 6.6 Hz, 3H), 1.56 (s, 6H), 1.26 (s, 1H), 1.11 (d, J = 13.2 Hz, 1H). | 518 |
| D | 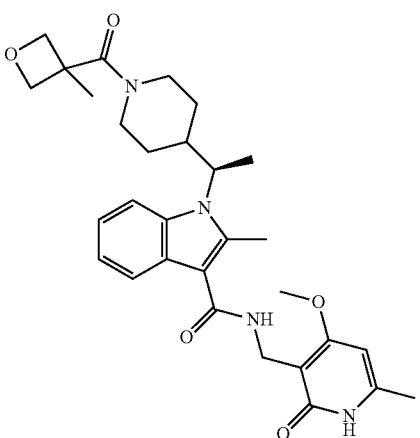<br>(R)-N-((4-methoxy-6-methyl-2-oxo-1,2-dihydropyridin-3-yl)methyl)-2-methyl-1-(1-(1-(3-methyloxetane-3-carbonyl)piperidin-4-yl)ethyl)-1H-indole-3-carboxamide (Compound 189) | 1H NMR (400 MHz, CDCl3) δ 13.21 (s, 1H), 7.85-7.83 (d, J = 8 Hz, 1H), 7.44 (m, 2H), 7.06 (m, 2H), 5.92 (s, 1H), 4.96-4.94 (d, J = 8 Hz, 2H), 4.70 (m, 3H), 4.23 (m, 4H), 3.90 (s, 3H), 2.73 (m, 1H), 2.68 (s, 4H), 2.44 (m, 2H), 2.19 (s, 3H), 1.62 (m, 6H), 1.25-1.23 (d, J = 8 Hz, 1H), 0.93 (m, 2H). | 535 |

| Methods | Structure/Name | ¹H NMR | m/z |
|---|---|---|---|
| D | (R)-N-((4-methoxy-6-methyl-2-oxo-1,2-dihydropyridin-3-yl)methyl)-2-methyl-1-(1-(1-(1-methylcyclopropane-carbonyl)piperidin-4-yl)ethyl)-1H-indole-3-carboxamide (Compound 190) | 1H NMR (400 MHz, CDCl3) δ 12.57 (s, 1H), 7.81-7.79 (d, J = 8 Hz, 1H), 7.40 (m, 2H), 7.01 (m, 2H), 5.86 (s, 1H), 4.59 (m, 3H), 4.02 (m, 3H), 3.84 (s, 3H), 3.62 (m, 1H), 2.36 (s, 3H), 2.17 (m, 2H), 2.13 (s, 3H), 1.98-1.95 (d, J = 12 Hz, 1H), 1.56-1.54 (d, J = 8 Hz, 3H), 1.17 (s, 3H), 0.92 (m, 4H), 0.46 (s, 2H). | 519 |
| D | (R)-N-((4-methoxy-6-methyl-2-oxo-1,2-dihydropyridin-3-yl)methyl)-2-methyl-1-(1-(1-(1-methylcyclopentane-carbonyl)piperidin-4-yl)ethyl)-1H-indole-3-carboxamide (Compound 191) | 1H NMR (400 MHz, CDCl3) δ 12.7 (s, 1H), 7.84 (m, 1H), 7.49 (m, 2H), 7.09 (m, 2H), 5.98 (s, 1H), 4.68 (br s, 2H), 4.12 (m, 1H), 3.93 (s, 3H), 3.40 (m, 3H), 2.70 (s, 3H), 2.27 (br s, 1H), 2.12 (s, 3H), 2.01 (m, 10H), 1.52 (s, 1H), 1.25 (m, 6H), 0.88 (m, 2H). | 547 |

| Methods | Structure/Name | ¹H NMR | m/z |
|---|---|---|---|
|  | 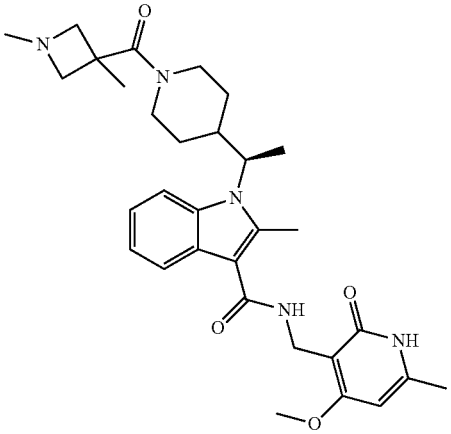<br>(R)-1-(1-(1-(1,3-dimethylazetidine-3-carbonyl)piperidin-4-yl)ethyl)-N-((4-methoxy-6-methyl-2-oxo-1,2-dihydropyridin-3-yl)methyl)-2-methyl-1H-indole-3-carboxamide (Compound 192) | 1H NMR (400 MHz, CDCl3) δ 12.83 (s, 1H), 7.83 (m, 1H), 7.43 (m, 2H), 7.06 (m, 2H), 5.91 (s, 1H), 4.67 (m, 2H), 4.49 (m, 1H), 3.89 (s, 3H), 3.36 (s, 1H), 3.21 (m, 3H), 3.18 (m, 1H), 2.68 (s, 3H), 2.25 (m, 2H), 2.03 (m, 6H), 1.62 (m, 2H), 1.60 (m, 4H), 1.46 (s, 2H), 1.22 (m, 1H), 0.88 (m, 2H). | 548 |
| H | 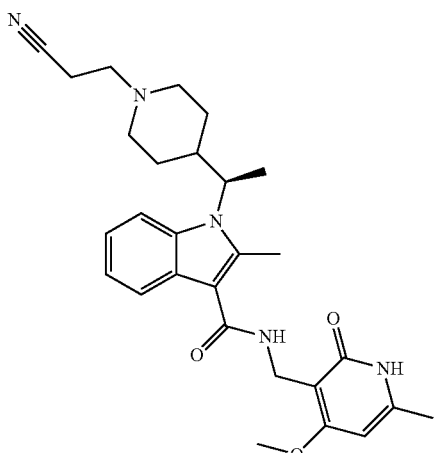<br>(R)-1-(1-(1-(2-cyanoethyl)piperidin-4-yl)ethyl)-N-((4-methoxy-6-methyl-2-oxo-1,2-dihydropyridin-3-yl)methyl)-2-methyl-1H-indole-3-carboxamide (Compound 206) | 1H NMR (400 MHz, DMSO-d6) d 11.60 (br.s., 1 H), 7.74 (d, J = 7.4 Hz, 1 H), 7.69 (t, J = 4.8 Hz, 1 H), 7.60 (d, J = 7.4 Hz, 1 H), 7.13-7.00 (m, 2 H), 6.15 (s, 1 H), 4.40-4.28 (m, 2 H), 4.25-4.10 (m, 1 H), 3.84 (s, 3 H), 2.96 (d, J = 7.0 Hz, 2 H), 2.66 (d, J = 12.0 Hz, 2 H), 2.64-2.56 (m, 4H), 2.47 (br. s., 1 H), 2.25-2.11 (m, 4 H), 2.06-1.82 (m, 2 H), 1.66 (t, J = 10.8 Hz, 1 H), 1.54 (d, J = 7.0 Hz, 3 H), 1.34 (d, J = 8.8 Hz, 1 H), 1.11-0.96 (m, 1 H), 0.68 (d, J = 12.5 Hz, 1 H). | 490 |

| Methods | Structure/Name | ¹H NMR | m/z |
|---|---|---|---|
| H | 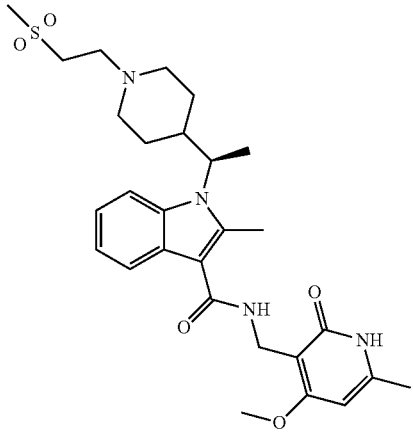<br>(R)-N-((4-methoxy-6-methyl-2-oxo-1,2-dihydropyridin-3-yl)methyl)-2-methyl-1-(1-(1-(2-(methylsulfonyl)ethyl)piperidin-4-yl)ethyl)-1H-indole-3-carboxamide (Compound 207) | 1H NMR (400 MHz, DMSO-d6) d 11.59 (br.s., 1 H), 7.74 (d, J = 7.4 Hz, 1 H), 7.70 (t, J = 4.8 Hz, 1 H), 7.60 (d, J = 7.7 Hz, 1 H), 7.14-6.99 (m, 2 H), 6.15 (s, 1 H), 4.38-4.28 (m, 2 H), 4.24-4.09 (m, 1 H), 3.84 (s, 3 H), 3.22 (t, J = 6.8 Hz, 2 H), 3.06-2.92 (m, 4 H), 2.68 (d, J = 9.0 Hz, 2 H), 2.65-2.55 (m, 4 H), 2.27-2.11 (m, 4 H), 2.04-1.84 (m, 2 H), 1.64 (t, J = 10.7 Hz, 1 H), 1.58-1.45 (m, 3 H), 1.41-1.24 (m, 1 H), 1.02-0.92 (m, 1 H), 0.67 (d, J = 12.7 Hz, 1 H). | 543 |
| D | 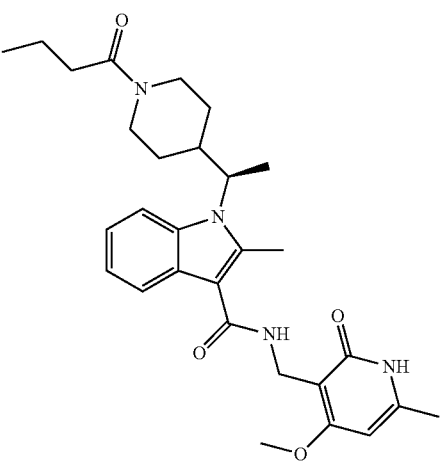<br>(R)-1-(1-(1-butyrylpiperidin-4-yl)ethyl)-N-((4-methoxy-6-methyl-2-oxo-1,2-dihydropyridin-3-yl)methyl)-2-methyl-1H-indole-3-carboxamide (Compound 209) | 1H NMR (400 MHz, CDCl3) δ 12.78 (s, 1H), 7.87-7.85 (m, 1H), 7.53-7.45 (m, 2H), 7.09-7.03 (m, 2H), 5.92 (s, 1H), 4.78-4.75 (m, 0.5H), 4.69-4.65 (m, 2H), 4.45 (m, 0.5H), 4.08 (s, 1H), 3.90 (s, 3H), 3.65-3.62 (d, J = 12 Hz, 1H), 2.73 (s, 3H), 2.73-2.69 (t, 1H), 2.32-2.30 (m, 1H), 1.61-1.60 (d, J = 4 Hz, 1H), 1.56 (s, 6H), 0.98-0.96 (m, 1H), 0.94-0.89 (m, 5H). | 507 |

| Methods | Structure/Name | ¹H NMR | m/z |
|---|---|---|---|
| D | N-((4-methoxy-6-methyl-2-oxo-1,2-dihydropyridin-3-yl)methyl)-2-methyl-1-((1R)-1-(1-(2-methylbutanoyl)piperidin-4-yl)ethyl)-1H-indole-3-carboxamide (Compound 210) | 1H NMR (400 MHz, CDCl3) δ 12.64 (s, 1H), 7.86-7.85 (d, J = 12 Hz, 1H), 7.47 (m, 2H), 7.04 (m, 2H), 5.91 (s, 1H), 4.65 (m, 4H), 4.07 (s, 1H), 3.90 (s, 3H), 3.74-3.70 (d, J = 16 Hz, 1H), 2.73 (m, 1H), 2.48 (s, 3H), 2.46 (m, 3H), 2.18 (s, 3H), 2.03 (s, 1H), 1.61 (s, 3H), 1.07-1.05 (d, J = 8 Hz, 2H), 1.01 (m, 8H). | 521 |
| D | (R)-N-((4-methoxy-6-methyl-2-oxo-1,2-dihydropyridin-3-yl)methyl)-2-methyl-1-(1-(1-(2-oxopropanoyl)piperidin-4-yl)ethyl)-1H-indole-3-carboxamide (Compound 211) | 1H NMR (400 MHz, CDCl3) δ 12.81 (s, 1H), 7.87 (d, J = 7.09 Hz, 1H), 7.50 (d, J = 4.40 Hz, 1H), 7.43 (d, J = 8.07 Hz, 1 H), 7.12-7.00 (m, 2H), 5.92 (s, 1H), 4.70-4.58 (m, 2 H), 4.32 (d, J = 13.69 Hz, 1H), 4.15-4.04 (m, 1H), 3.90 (s, 3H), 3.57 (d, J = 13.45 Hz, 1H), 3.06 (t, J = 12.35 Hz, 1H), 2.84 (s, 1H), 2.73-2.64 (m, 3H), 2.47 (s, 1H), 2.42 (s, 2H), 2.36 (s, 2H), 2.19 (s, 3H), 2.12-1.99 (m, 1H), 1.62 (t, J = 6.85 Hz, 3H), 1.35 (s, 2H), 1.04-0.97 (m, 1H). | 507 |

| Methods | Structure/Name | ¹H NMR | m/z |
|---|---|---|---|
| D | (R)-N-((4-methoxy-6-methyl-2-oxo-1,2-dihydropyridin-3-yl)methyl)-2-methyl-1-(1-(1-(2-phenylacetyl)piperidin-4-yl)ethyl)-1H-indole-3-carboxamide (Compound 212) | ¹H NMR (400 MHz, CDCl3) δ 12.64(s, 1H), 7.84 (m, 1H), 7.83 (s, 1H), 7.39 (m, 1H), 7.25-7.23 (m, 1H), 7.17 (m, 2H), 7.16 (m, 2H), 7.06-7.02 (m, 2H), 5.92 (s, 1H), 4.79-4.68 (m, 0.5H), 4.66 (m, 2H), 4.65 (m, 0.5H), 3.99-3.95 (m, 1H), 3.90 (s, 3H), 3.73 (s, 1H), 3.65 (s, 2H), 2.66-2.62 (s, 1H), 2.59-2.55 (s, 2H), 2.38 (m, 1H), 2.19 (s, 3H), 2.00 (m, 1H), 1.59-1.50 (m, 4H), 1.26-1.20 (m, 1H), 0.98-0.92 (m, 2H), 0.76-0.59 (m, 1H). | 555 |
| D | (R)-N-((4-methoxy-6-methyl-2-oxo-1,2-dihydropyridin-3-yl)methyl)-2-methyl-1-(1-(1-(3-methylbutanoyl)piperidin-4-yl)ethyl)-1H-indole-3-carboxamide (Compound 213) | ¹H NMR (400 MHz, CDCl3) δ 13.09 (s, 1 H), 7.85 (d, J = 7.58 Hz, 1H), 7.53 (s, 1 H), 7.45 (d, J = 7.58 Hz, 1H), 7.12-6.99 (m, 2H), 5.92 (s, 1H), 4.78 (d, J = 12.47 Hz, 1H), 4.71-4.61 (m, 2H), 4.48 (d, J = 12.47 Hz, 1H), 4.12-4.04 (m, 1H), 3.89 (s, 3H), 3.65 (d, J = 13.45 Hz, 1H), 2.75-2.65 (m, 3H), 2.46-2.38 (m, 1H), 2.24-2.15 (m, 4H), 2.14-2.06 (m, 2 H), 2.06-1.97 (m, 2H), 1.90 (s, 2H), 1.62 (d, J = 6.6 Hz, 3H), 1.27-1.18 (m, 1H), 0.96 (dd, J = 5.99, 3.55 Hz, 3H), 0.91 (dd, J = 5.9, 3.2 Hz, 4H). | 521 |

| Methods | Structure/Name | ¹H NMR | m/z |
|---|---|---|---|
| D | (R)-1-(1-(1-(4-cyanobenzyl)piperidin-4-yl)ethyl)-N-((4-methoxy-6-methyl-2-oxo-1,2-dihydropyridin-3-yl)methyl)-2-methyl-1H-indole-3-carboxamide (Compound 214) | H NMR (400 MHz, CDCl3) δ 12.68 (br s, 1H), 7.90-7.78 (m, 1H), 7.77-7.59 (m, 2H), 7.54-7.38 (m, 3H), 7.18-6.98 (m, 2H), 5.95 (s, 1H), 4.94-4.75 (m, 1H), 4.75-4.54 (m, 2H), 4.41-4.06 (m, 1H), 3.98-3.67 (m, 3H), 3.50-3.30 (m, 1H), 3.15-2.76 (m, 2H), 2.70 (s, 2H), 2.57-2.42 (m, 1H), 2.22 (s, 3H), 2.05-1.91 (m, 1H), 1.69-1.58 (m, 3H), 1.46-1.32 (m, 1H), 1.31-1.21 (m, 1H), 1.17-1.04 (m, 1H), 0.94-0.82 (m, 1H). | 566 |
| D | (R)-1-(1-(1-(cyclobutanecarbonyl)piperidin-4-yl)ethyl)-N-((4-methoxy-6-methyl-2-oxo-1,2-dihydropyridin-3-yl)methyl)-2-methyl-1H-indole-3-carboxamide (Compound 216) | ¹H NMR (400 MHz, DMSO-d6) δ 11.60 (s, 1H), 7.75-7.01 (m, 2H), 7.64-7.62 (m, 1H), 7.11-7.03 (m, 2H), 6.15 (s, 1H), 4.48-4.45 (m, 0.5H), 4.32 (d, J = 4.4 Hz, 2H), 4.17-4.13 (m, 1H), 3.84 (s, 3H), 3.74 (m, 0.5H), 3.48 (m, 0.5H), 3.29 (m, 0.5H), 3.18 (m, 0.5H) 2.94 (m, 0.5H), 2.67 (m, 1H), 2.58 (s, 3H), 2.26 (m, 2H), 2.20 (s, 3H), 2.15-1.68 (m, 7H), 1.54 (d, J = 2.8, 3H), 1.17 (m, 1H), 0.86-0.69 (m, 2H). | 519 |

| Methods | Structure/Name | ¹H NMR | m/z |
|---|---|---|---|
| | 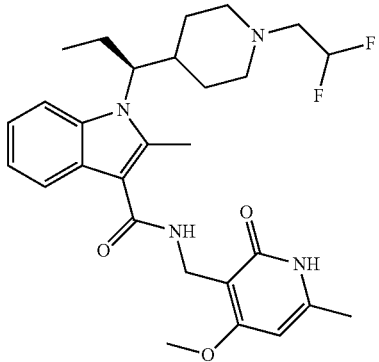<br>(R)-1-(1-(1-(2,2-difluoroethyl)piperidin-4-yl)propyl)-N-((4-methoxy-6-methyl-2-oxo-1,2-dihydropyridin-3-yl)methyl)-2-methyl-1H-indole-3-carboxamide (Compound 219) | 1H NMR (400 MHz, DMSO-d6) d 11.60 (br.s., 1 H), 7.79-7.74 (m, 1 H), 7.71 (t, J = 4.3 Hz, 1 H), 7.65 (s, 1 H), 7.60-7.55 (m, 1 H), 7.04-7.01 (m, 1 H), 6.15 (s, 1 H), 4.32 (d, J = 4.8 Hz, 2 H), 3.95 (dt, J = 4.2, 11.0 Hz, 1 H), 3.85 (s, 3 H), 2.97 (d, J = 11.2 Hz, 1 H), 2.72-2.66 (m, 2 H), 2.63 (t, J = 4.6 Hz, 1 H), 2.61-2.57 (m, 3 H), 2.20 (s, 3 H), 2.17-2.08 (m, 2 H), 2.02-1.80 (m, 4 H), 1.43-1.32 (m, 1 H), 1.24 (d, J = 1.4 Hz, 1 H), 1.13-1.00 (m, 1 H), 0.67 (d, J = 12.8 Hz, 1 H), 0.50 (t, J = 7.3 Hz, 3 H) | |
| H, B, C | 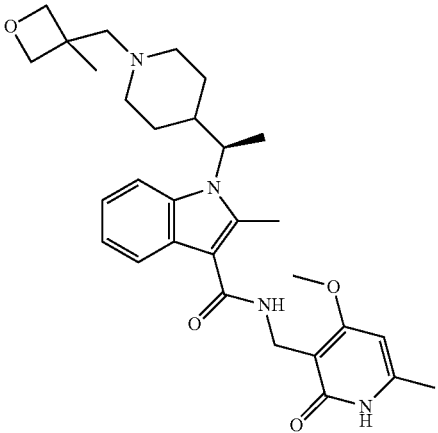<br>(R)-N-((4-methoxy-6-methyl-2-oxo-1,2-dihydropyridin-3-yl)methyl)-2-methyl-1-(1-(1-((3-methyloxetan-3-yl)methyl)piperidin-4-yl)ethyl)-1H-indole-3-carboxamide (Compound 220) | ¹H NMR (400 MHz, CD3OD) δ 7.70-7.68 (d, J = 8.0 Hz, 1H), 7.55-7.53 (d, J = 8.0 Hz, 1H), 7.11-7.04 (m, 2H), 6.25 (s, 1H), 4.52 (s, 2H), 4.46-4.40 (dd, J = 5.6, 20.0 Hz, 2H), 4.27-4.21 (dd, J = 7.0, 17.2 Hz, 2H), 4.16-4.10 (m, 1H), 3.92 (s, 3H), 2.75-2.72 (br s, 2H), 2.59 (s, 3H), 2.52-2.44 (m, 3H), 2.30 (s, 3H), 2.28-2.20 (m, 1H), 2.05-1.98 (m, 2H), 1.75-1.70 (m, 1H), 1.60-1.58 (d, J = 6.8 Hz, 3H), 1.38-1.35 (m, 1H), 1.34 (s, 3H), 1.08-1.07 (m, 1H), 0.81-0.71 (br s, 2H). | 521 |

-continued

| Methods | Structure/Name | ¹H NMR | m/z |
|---|---|---|---|
| | 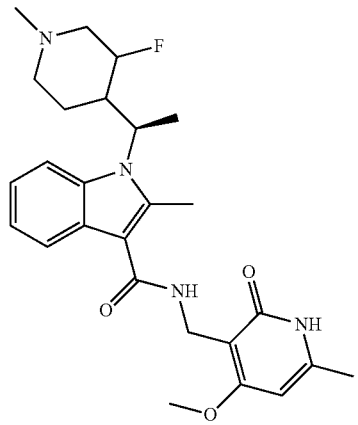

1-((1R)-1-(3-fluoro-1-methylpiperidin-4-yl)ethyl)-N-((4-methoxy-6-methyl-2-oxo-1,2-dihydropyridin-3-yl)methyl)-2-methyl-1H-indole-3-carboxamide (Compound 221) | ¹H NMR (400 MHz, CD3OD) δ 7.77 (d, J = 8.0 Hz, 1H), 7.66 (d, J = 7.5 Hz, 1H), 7.24-7.18 (m, 2H), 6.99 (s, 1H), 4.61 (s, 3H), 4.14 (s, 3H), 3.98-3.88 (m, 1H), 3.67-3.58 (m, 1H), 3.38-3.34 (m, 1H), 2.96-2.89 (m, 1H), 2.87 (s, 3H), 2.66 (s, 3H), 2.56 (s, 3H), 2.32-2.20 (m, 1H), 2.09-1.98 (m, 1H), 1.78 (d, J = 7.0 Hz, 2H), 1.69 (d, J = 7.0 Hz, 1H), 1.36-1.26 (m, 1H), 1.02-0.93 (m, 1H). | 469 |
| H | 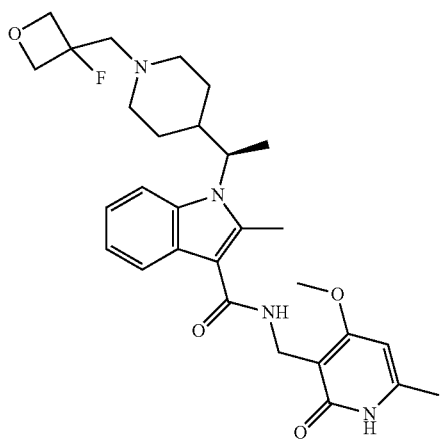

(R)-1-(1-(1-((3-fluorooxetan-3-yl)methyl)piperidin-4-yl)ethyl)-N-((4-methoxy-6-methyl-2-oxo-1,2-dihydropyridin-3-yl)methyl)-2-methyl-1H-indole-3-carboxamide (Compound 222) | ¹H NMR (400 MHz, CD3OD) δ 7.72 (d, J = 7.6 Hz, 1H), 7.58 (d, J = 7.6 Hz, 1H), 7.15-7.08 (m, 2H), 6.30 (s, 1H), 4.71-4.58 (m, 4H), 4.20-4.18 (m, 1H), 3.97 (s, 3H), 3.06 (d, J = 11.6 Hz, 1H), 2.89-2.83 (m, 2H), 2.73 (s, 2H), 2.63 (s, 3H), 2.35 (s, 3H), 2.31-2.22 (m, 2H), 2.05-2.00 (m, 3H), 1.63 (d, J = 6.8 Hz, 3H), 1.47-1.44 (m, 1H), 1.17-1.15 (m, 1H), 0.86-0.83 (m, 1H). | 525 |

| Methods | Structure/Name | ¹H NMR | m/z |
|---|---|---|---|
| D | (R)-1-(1-(1-(3,3-difluorocyclobutanecarbonyl)piperidin-4-yl)ethyl)-N-((4-methoxy-6-methyl-2-oxo-1,2-dihydropyridin-3-yl)methyl)-2-methyl-1H-indole-3-carboxamide (Compound 228) | ¹H NMR (400 MHz, CDCl3) δ 12.94 (s, 1H), 7.88-7.86 (d, J = 8 Hz, 1H), 7.47 (m, 2H), 7.06 (m, 2H), 5.93 (s, 1H), 4.72 (m, 2H), 4.65 (m, 1H), 4.09-4.07 (d, J = 8 Hz, 1H), 3.90 (s, 3H), 3.56 (s, 1H), 2.85 (m, 4H), 2.68 (m, 5H), 2.61 (m, 1H), 2.20 (s, 3H), 2.04 (s, 1H), 1.62 (m, 3H), 1.25 (m, 2H), 0.87 (m, 2H). | 555 |
| D | (R)-1-(1-(1-(2,2-difluoro-3-methoxypropanoyl)piperidin-4-yl)ethyl)-N-((4-methoxy-6-methyl-2-oxo-1,2-dihydropyridin-3-yl)methyl)-2-methyl-1H-indole-3-carboxamide (Compound 230) | 1H NMR (400 MHz, DMSO-d6) d 11.08-11.28 (m, 1H), 7.78 (d, J = 7.2 Hz, 1H), 7.58 (d, J = 8.1 Hz, 1H), 7.46 (br.s., 1H), 7.01-7.15 (m, 2H), 6.07 (s, 1H), 4.37 (d, J = 5.26 Hz, 2H), 4.30 (br.s., 2H), 3.98-4.12 (m, 1H), 3.73-3.90 (m, 5H), 3.29-3.45 (m, 3H), 2.69-2.86 (m, 2H), 2.64 (s, 3H), 2.14-2.27 (m, 3H), 2.00-2.10 (m, 1H), 1.56 (d, J = 7.0 Hz, 3H), 1.24-1.43 (m, 2H), 0.91-1.06 (m, 2H) | 559 |

| Methods | Structure/Name | ¹H NMR | m/z |
|---|---|---|---|
| | 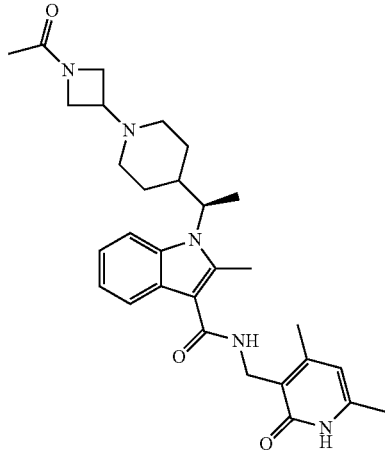<br>(R)-1-(1-(1-(1-acetylazetidin-3-yl)piperidin-4-yl)ethyl)-N-((4,6-dimethyl-2-oxo-1,2-dihydropyridin-3-yl)methyl)-2-methyl-1H-indole-3-carboxamide<br>(Compound 231) | 1H NMR (400 MHz, DMSO-d6) d 11.58 (br.s., 1H), 7.69-7.81 (m, 1H), 7.61 (br.s., 2H), 7.06 (d, J = 7.2 Hz, 2H), 5.89 (s, 1H), 4.32 (t, J = 5.3 Hz, 2H), 4.11-4.24 (m, 1H), 3.79-4.00 (m, 2H), 3.61 (d, J = 3.9 Hz, 1H), 3.13 (dd, J = 4.3, 7.34 Hz, 1H), 2.78-3.07 (m, 2H), 2.65-2.74 (m, 1H), 2.58 (s, 3H), 2.26 (s, 3H), 2.12 (s, 3H), 1.69-1.82 (m, 3H), 1.47-1.64 (m, 3H), 1.20-1.33 (m, 7H) | 518 |
| E | 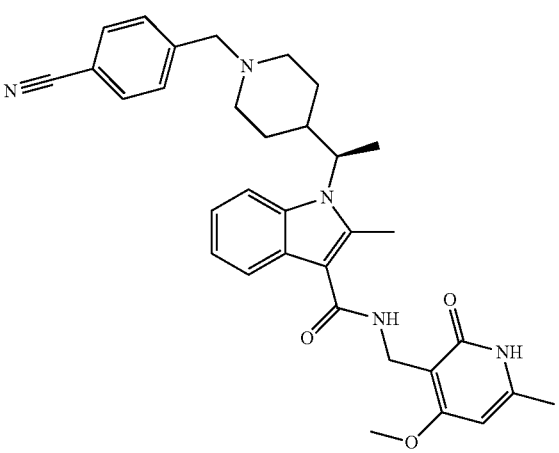<br>(R)-1-(1-(1-(4-cyanobenzyl)piperidin-4-yl)ethyl)-N-((4-methoxy-6-methyl-2-oxo-1,2-dihydropyridin-3-yl)methyl)-2-methyl-1H-indole-3-carboxamide<br>(Compound 232) | 1H NMR (400 MHz, DMSO-d6) d = 11.59 (br.s., 1 H), 7.78-7.63 (m, 4 H), 7.59 (d, J = 7.4 Hz, 1 H), 7.45 (d, J = 8.1 Hz, 2 H), 7.13-7.00 (m, 2 H), 6.13 (s, 1 H), 4.36-4.25 (m, 2 H), 4.21-4.10 (m, 1 H), 3.83 (s, 3 H), 3.48 (s, 2 H), 2.88-2.78 (m, 1 H), 2.63-2.53 (m, 3 H), 2.25-2.12 (m, 4 H), 2.03-1.93 (m, 1 H), 1.89 (s, 2 H), 1.72-1.62 (m, 1 H), 1.56-1.45 (m, 3 H), 1.41-1.31 (m, 1 H), 1.06 (d, J = 13.6 Hz, 1 H), 0.73-0.63 (m, 1 H) | 552 |

| Methods | Structure/Name | 1H NMR | m/z |
|---|---|---|---|
| D | 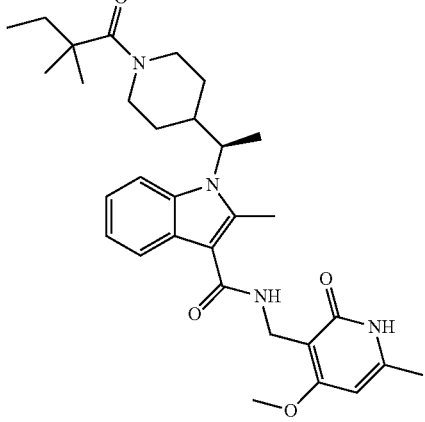<br>(R)-1-(1-(1-(2,2-dimethylbutanoyl)piperidin-4-yl)ethyl)-N-((4-methoxy-6-methyl-2-oxo-1,2-dihydropyridin-3-yl)methyl)-2-methyl-1H-indole-3-carboxamide (Compound 233) | 1H NMR (400 MHz, CDCl3) δ 12.50 (s, 1H), 7.86-7.84 (d, J = 8 Hz, 1H), 7.48 (m, 2H), 7.06 (m, 2H), 5.91 (s, 1H), 4.64 (m, 3H), 4.09 (m, 3H), 3.89 (s, 3H), 2.84 (s, 1H), 2.68 (s, 3H), 2.49 (s, 2H), 2.19 (s, 3H), 2.02-1.99 (d, J = 12 Hz, 1H), 1.54 (m, 3H), 1.18 (s, 7H), 0.96 (s, 2H), 0.83 (m, 3H). | 535 |
| D | 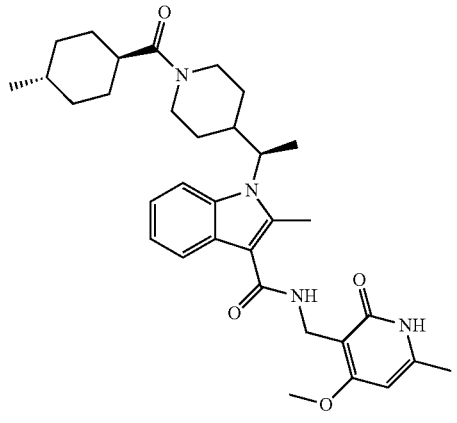<br>N-((4-methoxy-6-methyl-2-oxo-1,2-dihydropyridin-3-yl)methyl)-2-methyl-1-((R)-1-(1-((1r,4R)-4-methylcyclohexanecarbonyl)piperidin-4-yl)ethyl)-1H-indole-3-carboxamide (Compound 234) | 1H NMR (400 MHz, CDCl3) δ 12.78 (s, 1H), 7.86-7.84 (d J = 8 Hz, 1H), 7.49 (m, 2H), 7.05 (m, 2H), 5.91 (s, 1H), 4.70 (m, 4H), 4.07 (m, 1H), 3.90 (s, 3H), 2.68 (s, 1H), 2.50 (s, 3H), 2.26 (m, 2H), 2.18 (s, 4H), 2.01-2.98 (d, J = 12 Hz, 1H), 1.53 (m, 8H), 0.89 (m, 9H). | 561 |

| Methods | Structure/Name | ¹H NMR | m/z |
|---|---|---|---|
| D | (R)-1-(1-(1-(cyclopentanecarbonyl)piperidin-4-yl)ethyl)-N-((4-methoxy-6-methyl-2-oxo-1,2-dihydropyridin-3-yl)methyl)-2-methyl-1H-indole-3-carboxamide (Compound 235) | ¹H NMR (400 MHz, CDCl3) δ 7.87-7.85 (d, J = 8 Hz, 1H), 7.49 (m, 2H), 7.06 (m, 2H), 5.91 (s, 1H), 4.70 (m, 4H), 4.08-4.07 (d, J = 4 Hz, 1H), 3.90 (s, 3H), 3.76-3.73 (d, J = 12 Hz, 1H), 2.75 (m, 5H), 2.68 (m, 2H), 2.18 (s, 3H), 2.02 (s, 1H), 1.75 (m, 5H), 1.53 (m, 3H), 0.95 (m, 4H). | 533 |
| D | (R)-1-(1-(1-(2-methoxy-2-methylpropanoyl)piperidin-4-yl)ethyl)-N-((4-methoxy-6-methyl-2-oxo-1,2-dihydropyridin-3-yl)methyl)-2-methyl-1H-indole-3-carboxamide (Compound 236) | ¹H NMR (400 MHz, DMSO-d6) δ 11.59 (br s, 1H), 7.82-7.60 (m, 3H), 7.17-6.98 (m, 2H), 6.15 (s, 1H), 4.78 (br s, 1H), 4.53 (br s, 1H), 4.33-4.32 (d, J = 4.40 Hz, 2H), 4.24-4.12 (m, 1H), 3.84 (s, 2H), 3.38 (br s, 1H), 3.11 (br s, 3H), 2.73 (br s, H), 2.67 (br s, 1H), 2.59 (s, 3H), 2.20 (s, 3H), 2.10-1.85 (m, 2H), 1.56-1.54 (d, J = 6.85 Hz, 3H), 1.39-1.20 (m, 7H), 0.99-0.74 (m, 2H). | 537 |

| Methods | Structure/Name | ¹H NMR | m/z |
|---|---|---|---|
| D | (R)-N-((4-methoxy-6-methyl-2-oxo-1,2-dihydropyridin-3-yl)methyl)-2-methyl-1-(1-(1-(2-(2-methyl-1H-imidazol-1-yl)acetyl)piperidin-4-yl)ethyl)-1H-indole-3-carboxamide (Compound 237) | ¹H NMR (400 MHz, DMSO-d6) δ 11.57 (br s, 1H), 7.78-7.56 (m, 3H), 7.13-7.00 (m, 2H), 6.91-6.88 (d, J = 12.23 Hz, 1H), 6.69-6.68 (d, J = 3.91 Hz, 1H), 6.13 (br s, 1H), 4.94-4.81 (m, 2H), 4.42-4.39 (d, J = 12.23 Hz, 1H), 4.30 (br s, 2H), 4.19-4.10 (m, 1H), 4.01-3.88 (m, 1H), 3.82 (s, 3H), 3.67-3.64 (d, J = 15.16 Hz, 1H), 2.71 (br s, 1H), 2.65-2.55 (m, 3H), 2.17 (s, 3H), 2.12-2.10 (d, J = 8.56 Hz, 2H), 2.00-1.92 (m, 1H), 1.55-1.53 (d, J = 6.60 Hz, 3H), 1.36-1.32 (m, 1H), 1.25-1.11 (m, 1H), 1.05-1.03 (d, J = 9.54 Hz, 1H), 0.90-0.88 (m, 1H), 0.76-0.67 (m, 1H). | 558 |
| E | (R)-N-((4-methoxy-6-methyl-2-oxo-1,2-dihydropyridin-3-yl)methyl)-2-methyl-1-(1-(1-((1-methyl-1H-pyrazol-4-yl)methyl)piperidin-4-yl)ethyl)-1H-indole-3-carboxamide (Compound 238) | 1H NMR (400 MHz, DMSO-d6) d 11.59 (br.s., 1H), 7.65-7.78 (m, 2H), 7.59 (br.s., 1H), 7.48 (s, 1H), 7.21 (s, 1H), 6.95-7.14 (m, 2H), 6.15 (s, 1H), 4.32 (d, J = 5.0 Hz, 2H), 4.07-4.21 (m, 1H), 3.84 (s, 3H), 3.75 (s, 2H), 3.18-3.30 (m, 2H), 2.87 (d, J = 12.0 Hz, 1H), 2.54-2.73 (m, 4H), 2.20 (s, 3H), 2.06-2.17 (m, 1H), 1.80-1.94 (m, 2H), 1.45-1.63 (m, 4H), 1.22-1.41 (m, 1H), 0.89-1.10 (m, 2H), 0.66 (d, J = 11.2 Hz, 1H) | 531 |

| Methods | Structure/Name | ¹H NMR | m/z |
|---|---|---|---|
| E | (R)-N-((4-methoxy-6-methyl-2-oxo-1,2-dihydropyridin-3-yl)methyl)-2-methyl-1-(1-(1-((1-methyl-1H-imidazol-2-yl)methyl)piperidin-4-yl)ethyl)-1H-indole-3-carboxamide (Compound 239) | 1H NMR (400 MHz, DMSO-d6) d = 11.59 (br.s., 1 H), 7.78-7.65 (m, 2 H), 7.60 (d, J = 7.9 Hz, 1 H), 7.13-6.98 (m, 3 H), 6.70 (d, J = 1.3 Hz, 1 H), 6.14 (s, 1 H), 4.32 (d, J = 5.0 Hz, 2 H), 4.21-4.09 (m, 1 H), 3.84 (s, 3 H), 3.60 (s, 3 H), 3.48-3.37 (m, 2 H), 2.81 (br. s., 1 H), 2.59 (s, 3 H), 2.25-2.11 (m, 4 H), 1.97 (br.s., 1 H), 1.93-1.84 (m, 1 H), 1.67 (br.s., 1 H), 1.53 (d, J = 7.0 Hz, 3 H), 1.24 (br. s., 2 H), 1.08-0.97 (m, 1 H), 0.75-0.65 (m, 1 H) | 531 |
| E | (R)-N-((4-methoxy-6-methyl-2-oxo-1,2-dihydropyridin-3-yl)methyl)-2-methyl-1-(1-(1-(pyrimidin-5-ylmethyl)piperidin-4-yl)ethyl)-1H-indole-3-carboxamide (Compound 240) | 1H NMR (400 MHz, DMSO-d6) d = 11.59 (s, 1 H), 9.06 (s, 1 H), 8.67 (s, 2 H), 7.78-7.65 (m, 2 H), 7.60 (d, J = 7.9 Hz, 1 H), 7.15-6.98 (m, 2 H), 6.14 (s, 1 H), 4.38-4.25 (m, 2 H), 4.22-4.10 (m, 1 H), 3.84 (s, 3 H), 3.46 (s, 2 H), 2.93-2.81 (m, 1 H), 2.65-2.54 (m, 4 H), 2.27-2.12 (m, 4 H), 2.06-1.95 (m, 1 H), 1.94-1.84 (m, 1 H), 1.75-1.63 (m, 1 H), 1.53 (d, J = 6.8 Hz, 3 H), 1.41-1.28 (m, 1 H), 1.14-0.97 (m, 1 H), 0.73-0.63 (m, 1 H) | 529 |

-continued

| Methods | Structure/Name | ¹H NMR | m/z |
|---|---|---|---|
| E | (R)-N-((4-methoxy-6-methyl-2-oxo-1,2-dihydropyridin-3-yl)methyl)-2-methyl-1-(1-(1-(pyrimidin-2-ylmethyl)piperidin-4-yl)ethyl)-1H-indole-3-carboxamide (Compound 241) | 1H NMR (400 MHz, DMSO-d6) Shift = 11.60 (br.s., 1 H), 8.73 (d, J = 5.0 Hz, 2 H), 7.76-7.65 (m, 2 H), 7.59 (d, J = 7.7 Hz, 1 H), 7.36 (t, J = 4.9 Hz, 1 H), 7.13-6.99 (m, 2 H), 6.14 (s, 1 H), 4.36-4.27 (m, 2 H), 4.20-4.09 (m, 1 H), 3.84 (s, 3 H), 3.63 (s, 2 H), 3.00-2.91 (m, 1 H), 2.74-2.64 (m, 1 H), 2.59 (s, 3 H), 2.22-2.07 (m, 4 H), 1.92-1.76 (m, 2 H), 1.53 (d, J = 6.8 Hz, 3 H), 1.40-1.30 (m, 1 H), 1.24 (br.s., 1 H), 1.11-0.99 (m, 1 H), 0.71-0.62 (m, 1 H) | 529 |
| | (R)-1-(1-(1-(4-fluoro-1-methylpiperidine-4-carbonyl)piperidin-4-yl)ethyl)-N-((4-methoxy-6-methyl-2-oxo-1,2-dihydropyridin-3-yl)methyl)-2-methyl-1H-indole-3-carboxamide (Compound 242) | ¹H NMR (400 MHz, CD3OD) δ 7.77-7.76 (d, J = 7.6 Hz, 1H), 7.70-7.69 (d, J = 7.6 Hz, 1H), 7.19 (m, 2H), 6.90 (s, 1H), 4.61 (s, 3H), 4.29-4.25 (m, 2H), 4.13 (s, 3H), 3.60-3.53 (m, 2H), 3.30-3.20 (m, 2H), 2.95-2.93 (m, 3H), 2.81-2.75 (m, 1H), 2.75-2.66 (m, 1H), 2.65 (s, 3H), 2.55 (s, 3H), 2.54-2.37 (m, 5H), 2.17-2.14 (d, J = 11.6 Hz, 1H), 1.68-1.66 (d, J = 6.4 Hz, 3H), 1.40-1.30 (m, 1H), 1.08-0.92 (m, 2H). | 580 |

| Methods | Structure/Name | ¹H NMR | m/z |
|---|---|---|---|
| D | (R)-N-((4-methoxy-6-methyl-2-oxo-1,2-dihydropyridin-3-yl)methyl)-2-methyl-1-(1-(1-(1-methylpiperidine-4-carbonyl)piperidin-4-yl)ethyl)-1H-indole-3-carboxamide (Compound 243) | ¹H NMR (400 MHz, CD3OD) δ 7.74 (d, J = 7.8 Hz, 1H), 7.67 (d, J = 7.3 Hz, 1H), 7.21-7.12 (m, 2H), 6.92 (s, 1H), 4.64 (s, 1H), 4.58 (s, 2H), 4.39-4.29 (m, 1H), 4.27-4.20 (m, 1H), 4.12 (s, 3H), 3.90 (d, J = 13.7 Hz, 1H), 3.59-3.42 (m, 2H), 3.23-3.02 (m, 3H), 2.90-2.84 (m, 2H), 2.82 (s, 1H), 2.72-2.65 (m, 1H), 2.61 (s, 3H), 2.53 (s, 3H), 2.40-2.29 (m, 1H), 2.19-2.05 (m, 1H), 1.98-1.90 (m, 3H), 1.64 (d, J = 6.4 Hz, 3H), 1.38-1.24 (m, 2H), 1.06-0.88 (m, 2H). | 562 |
| E | (R)-N-((4-methoxy-6-methyl-2-oxo-1,2-dihydropyridin-3-yl)methyl)-2-methyl-1-(1-(1-(pyridin-3-ylmethyl)piperidin-4-yl)ethyl)-1H-indole-3-carboxamide (Compound 244) | ¹H NMR (400 MHz, D2O) δ 8.83 (s, 1H), 8.78 (d, J = 5.5 Hz, 1H), 8.50 (d, J = 8.0 Hz, 1H), 8.00-7.93 (m, 1H), 7.63 (d, J = 7.6 Hz, 1H), 7.57 (d, J = 7.6 Hz, 1H), 7.20-7.09 (m, 3H), 6.33 (s, 1H), 4.47-4.38 (m, 4H), 4.24-4.17 (m, 1H), 3.95-3.89 (m, 1H), 3.86 (s, 3H), 3.60 (d, J = 15.6 Hz, 1H), 3.47-3.39 (m, 1H), 3.31 (br s, 1H), 3.14-3.02 (m, 2H), 2.64 (s, 3H), 2.59 (br s, 1H), 2.28 (s, 3H), 1.55 (d, J = 7.0 Hz, 3H), 1.30-1.25 (m, 1H), 1.03 (d, J = 15.2 Hz, 1H). | 528 |

| Methods | Structure/Name | ¹H NMR | m/z |
|---|---|---|---|
| E | (R)-N-((4-methoxy-6-methyl-2-oxo-1,2-dihydropyridin-3-yl)methyl)-2-methyl-1-(1-(1-(pyridin-4-ylmethyl)piperidin-4-yl)ethyl)-1H-indole-3-carboxamide (Compound 245) | ¹H NMR (400 MHz, D2O) δ 8.80-8.72 (m, 2H), 8.00 (d, J = 6.0 Hz, 2H), 7.62 (d, J = 7.5 Hz, 1H), 7.56 (d, J = 7.5 Hz, 1H), 7.20-7.09 (m, 2H), 6.32 (s, 1H), 4.48 (br s, 2H), 4.40 (br s, 2H), 4.24-4.18 (m, 1H), 3.85 (s, 3H), 3.59 (dd, J = 5.8, 12.3 Hz, 2H), 3.30-3.27 (m, 1H), 3.15-3.08 (m, 1H), 2.82 (d, J = 10.5 Hz, 1H), 2.68-2.59 (m, 3H), 2.59-2.52 (m, 1H), 2.27 (s, 3H), 2.25-2.17 (m, 1H), 1.55 (d, J = 7.0 Hz, 3H), 1.36-1.27 (m, 1H), 1.02 (d, J = 14.1 Hz, 1H). | 528 |
| E | (R)-N-((4-methoxy-6-methyl-2-oxo-1,2-dihydropyridin-3-yl)methyl)-2-methyl-1-(1-(1-((2-methylpyridin-4-yl)methyl)piperidin-4-yl)ethyl)-1H-indole-3-carboxamide (Compound 246) | ¹H NMR (400 MHz, CD3OD) δ 8.80-8.79 (d, J = 6.0 Hz, 1H), 8.24 (s, 1H), 8.19-8.17 (d, J = 5.6 Hz, 1H), 7.78-7.76 (d, J = 7.6 Hz, 1H), 7.70-7.68 (d, J = 7.6 Hz, 1H), 7.23-7.17 (m, 2H), 6.95 (s, 1H), 4.61 (s, 4H), 4.35 (s, 1H), 4.18 (s, 3H), 3.68-3.66 (d, J = 10.4 Hz, 1H), 3.36 (s, 1H), 3.28 (s, 1H), 3.01-2.97 (d, J = 12.8 Hz, 1H), 2.85 (s, 3H), 2.82-2.76 (m, 1H), 2.68 (s, 3H), 2.56 (s, 3H), 2.34-2.31 (d, J = 13.2 Hz, 1H), 1.95-1.92 (d, J = 12.0 Hz, 1H), 1.70-1.68 (d, J = 6.8 Hz, 3H), 1.09-1.06 (d, J = 13.2 Hz, 1H). | 542 |

| Methods | Structure/Name | ¹H NMR | m/z |
|---|---|---|---|
| D | (R)-N-((4-methoxy-6-methyl-2-oxo-1,2-dihydropyridin-3-yl)methyl)-2-methyl-1-(1-(1-(2-(3-methylisoxazol-5-yl)acetyl)piperidin-4-yl)ethyl)-1H-indole-3-carboxamide (Compound 247) | ¹H NMR (400 MHz, DMSO-d6) δ 11.60 (br s, 1H), 7.82-7.68 (m, 2H), 7.65-7.63 (d, J = 7.94 Hz, 1H), 7.16-7.00 (m, 2H), 6.15 (br s, 1H), 5.38-5.28 (m, 1H), 4.32 (br s, 1H), 4.18 (br s, 1H), 3.88-3.79 (m, 2H), 3.39 (br s, 1H), 3.29 (s, 1H), 3.21-3.13 (m, 1H), 2.73 (br s, 1H), 2.67 (br s, 1H), 2.59-2.58 (d, J = 5.07 Hz, 2H), 2.45 (br s, 1H), 2.33 (br s, 1H), 2.23-2.12 (m, 3H), 2.04-1.92 (m, 2H), 1.56-1.54 (d, J = 6.62 Hz, 2H), 1.32-1.21 (m, 5H), 0.95-0.91 (t, J = 7.39 Hz, 1H), 0.87-0.83 (t, J = 6.84 Hz, 1H). | 560 |
| | (R)-1-(1-(1-(3,3-difluoropyrrolidine-1-carbonyl)piperidin-4-yl)ethyl)-N-((4-methoxy-6-methyl-2-oxo-1,2-dihydropyridin-3-yl)methyl)-2-methyl-1H-indole-3-carboxamide (Compound 248) | ¹H NMR (400 MHz, CD3OD) δ 7.75-7.73 (m, 1H), 7.65 (t, J = 3.2 Hz, 1H), 7.21-7.15 (m, 2H), 6.93 (s, 1H), 4.58(s, 2H), 4.24-4.17(m, 1H), 4.12 (s, 3H), 3.84-3.70 (m, 1H), 3.67-3.54 (m, 5H), 2.86-2.63 (m, 1H), 2.56 (s, 3H), 2.54-2.49 (m, 4H), 2.33-2.28 (m, 2H), 2.05 (d, J = 13.2 Hz, 2H), 1.64 (d, J = 6.8 Hz, 3H), 1.32-0.80 (m, 4H). | 569 |

| Methods | Structure/Name | ¹H NMR | m/z |
|---|---|---|---|
| | 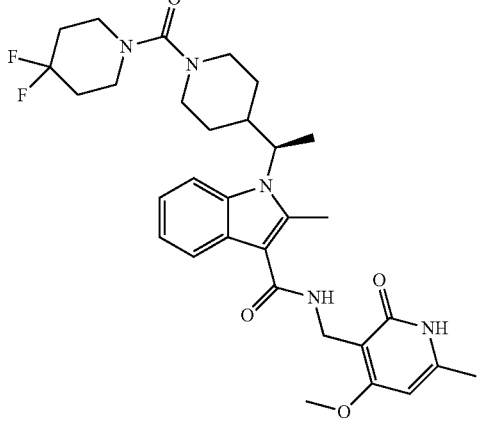<br>(R)-1-(1-(1-(4,4-difluoropiperidine-1-carbonyl)piperidin-4-yl)ethyl)-N-((4-methoxy-6-methyl-2-oxo-1,2-dihydropyridin-3-yl)methyl)-2-methyl-1H-indole-3-carboxamide<br>(Compound 249) | ¹H NMR (400 MHz, CD3OD) δ 7.72 (d, J = 7.2 Hz, 1H), 7.61 (d, J = 7.6 Hz, 1H), 7.06-7.15 (m, 2H), 6.28 (s, 1H), 4.47-4.63 (m, 3H), 4.15-4.26 (m, 1H) , 3.95 (s, 2H), 3.83 (d, J = 13.6 Hz, 1H), 3.52 (d, J = 13.6 Hz, 1H), 3.21-3.27 (m, 1H), 2.83-2.94 (m, 1H), 2.75 (s, 1H), 2.60 (s, 2H), 2.49 (s, 1H), 2.33 (s, 2H), 1.87-2.10 (m, 5H), 1.64 (d, J = 7.2 Hz, 3H), 1.35-1.48 (m, 2H), 1.30 (s, 4H), 0.98-1.11 (m, 2H), 0.82-0.94 (m, 2H). | 583 |
| E | 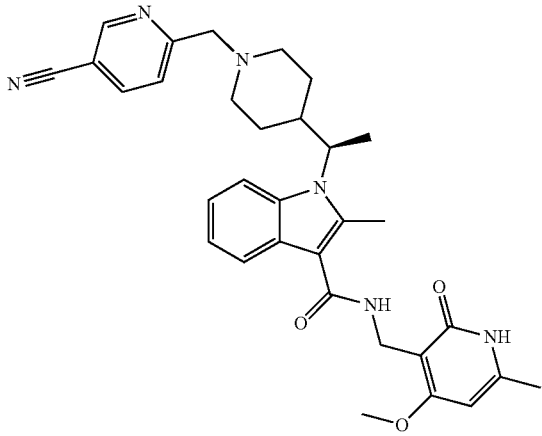<br>(R)-1-(1-(1-((5-cyanopyridin-2-yl)methyl)piperidin-4-yl)ethyl)-N-((4-methoxy-6-methyl-2-oxo-1,2-dihydropyridin-3-yl)methyl)-2-methyl-1H-indole-3-carboxamide<br>(Compound 250) | ¹H NMR (400 MHz, CD3OD) δ 8.81 (s, 1H), 8.12-8.10 (dd, J = 2.0, 8.0 Hz, 1H), 7.70-7.54 (m, 4H), 7.10-7.04 (m, 2H), 6.26 (s, 1H), 4.51 (s, 2H), 4.21-4.17 (m, 1H), 3.92 (s, 3H), 3.72-3.71 (d, J = 4.0 Hz, 2H), 3.03-3.00 (d, J = 11.6 Hz, 1H), 2.74-2.71 (m, 2H), 2.60 (s, 3H), 2.30 (s, 3H), 2.24-2.15 (m, 2H), 2.03-1.92 (m, 3H), 1.70-1.63 (m, 1H), 1.61-1.59 (d, J = 6.8 Hz, 3H). | 553 |

| Methods | Structure/Name | ¹H NMR | m/z |
|---|---|---|---|
| H | 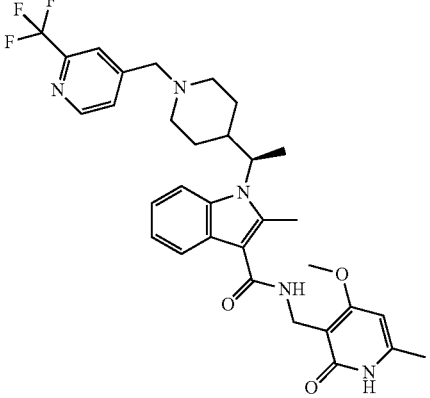<br>(R)-N-((4-methoxy-6-methyl-2-oxo-1,2-dihydropyridin-3-yl)methyl)-2-methyl-1-(1-(1-((2-(trifluoromethyl)pyridin-4-yl)methyl)piperidin-4-yl)ethyl)-1H-indole-3-carboxamide (Compound 251) | ¹H NMR (400 MHz, CDCl3) δ 12.70 (s, 1H), 8.63-8.62 (d, J = 4.0 Hz, 1H), 7.86-7.84 (d, J = 8.0 Hz, 1H), 7.64 (s, 1H), 7.51 (s, 1H), 7.45-7.42 (m, 2H), 7.10-7.02 (m, 2H), 5.91 (s, 1H), 4.71-4.64 (m, 2H), 4.16-4.11 (dd, J = 6.8, 3.2 Hz, 1H), 3.87 (s, 3H), 3.55-3.46 (m, 2H), 2.91-2.89 (d, J = 11.2 Hz, 1H), 2.73 (s, 3H), 2.64-2.61 (d, J = 11.04 Hz, 1H), 2.18 (s, 3H), 2.08-1.94 (m, 2H), 1.82 (t, J = 10.79 Hz, 2H), 1.60 (d, J = 7.03 Hz, 3H), 1.52-1.38 (m, 1H), 1.26 (s, 1H), 1.18-1.08 (m, 1H), 0.97-0.94 (d, J = 12.0, 1H). | 596 |
| H | 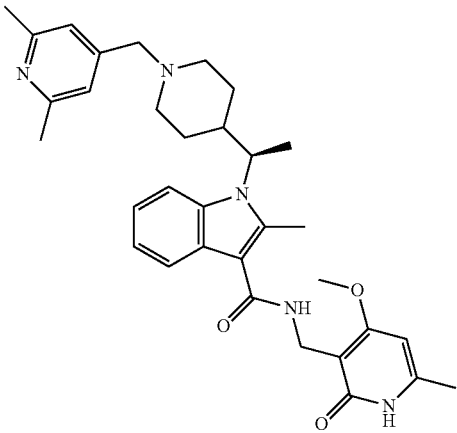<br>(R)-1-(1-(1-((2,6-dimethylpyridin-4-yl)methyl)piperidin-4-yl)ethyl)-N-((4-methoxy-6-methyl-2-oxo-1,2-dihydropyridin-3-yl)methyl)-2-methyl-1H-indole-3-carboxamide (Compound 252) | ¹HNMR (400 MHz, CDCl3) δ 7.85-7.83 (d, J = 7.6 Hz, 1H), 7.49 (s, 1H), 7.45-7.43 (d, J = 8.0 Hz, 1H), 7.12-6.97 (m, 2H), 6.87 (s, 2H), 5.91 (s, 1H), 7.10-7.02 (m, 2H), 5.91 (s, 1H), 4.68-4.64 (dd, J = 9.3, 5.6 Hz, 2H), 4.14-4.10 (m, 1H), 3.89 (s, 3H), 3.40-3.35 (m, 2H), 2.95-2.92 (d, J = 11.2 Hz, 1H), 2.71 (s, 3H), 2.48 (s, 6H), 2.18 (s, 3H), 2.02-1.93 (m, 2H), 1.59-1.58 (d, J = 6.8 Hz, 3H), 1.46 (s, 2H), 1.29-1.21 (m, 2H), 1.13 (d, J = 9.6 Hz, 1H), 0.94-0.91 (d, J = 12.0 Hz, 1H). | 556 |

| Methods | Structure/Name | ¹H NMR | m/z |
|---|---|---|---|
| H | 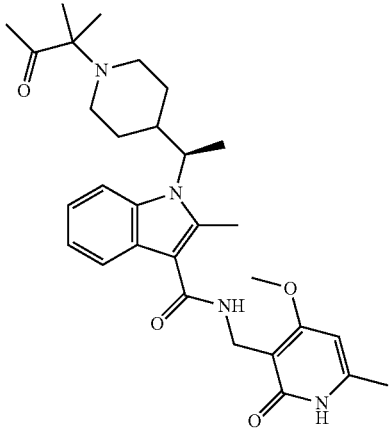<br>(R)-N-((4-methoxy-6-methyl-2-oxo-1,2-dihydropyridin-3-yl)methyl)-2-methyl-1-(1-(1-(2-methyl-3-oxobutan-2-yl)piperidin-4-yl)ethyl)-1H-indole-3-carboxamide (Compound 253) | ¹HNMR (400 MHz, CD3OD) δ 7.72 (d, J = 7.2 Hz, 1H), 7.58 (d, J = 8.0 Hz, 1H), 7.15-7.08 (m, 2H), 6.30 (s, 1H), 4.25-4.20 (m, 1H), 3.97 (s, 3H), 2.80-2.74 (m, 2H), 2.64 (s, 3H), 2.52-2.50 (m, 1H), 2.35 (s, 3H), 2.27-2.25 (m, 2H), 2.22 (s, 3H), 2.07-1.93 (m, 2H), 1.63 (d, J = 8.8 Hz, 3H), 1.45-1.42 (m, 1H), 1.14-1.06 (m, 8H), 0.92-0.89 (m, 1H). | 521 |
| E | 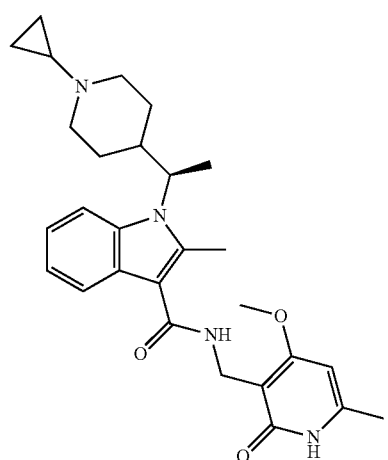<br>(R)-1-(1-(1-cyclopropylpiperidin-4-yl)ethyl)-N-((4-methoxy-6-methyl-2-oxo-1,2-dihydropyridin-3-yl)methyl)-2-methyl-1H-indole-3-carboxamide (Compound 254) | ¹HNMR (400 MHz, CD3OD) δ 7.72 (d, J = 7.6 Hz, 1H), 7.58 (d, J = 8.0 Hz, 1H), 7.12-7.05 (m, 2H), 6.27 (s, 1H), 4.52 (s, 2H), 4.19-4.14 (m, 1H), 3.94 (s, 3H), 3.14-3.12 (m, 1H), 2.86-2.83 (m, 1H), 2.59 (s, 3H), 2.31-2.24 (m, 4H), 2.03-1.93 (m, 2H), 1.61 (d, J = 6.8 Hz, 4H), 1.36-1.33 (m, 2H), 1.03-0.86 (m, 3H), 0.48-0.38 (m, 3H). | 477 |

| Methods | Structure/Name | ¹H NMR | m/z |
|---|---|---|---|
| E | (R)-N-((4-methoxy-6-methyl-2-oxo-1,2-dihydropyridin-3-yl)methyl)-2-methyl-1-(1-(1-((1-methyl-1H-pyrazol-3-yl)methyl)piperidin-4-yl)ethyl)-1H-indole-3-carboxamide (Compound 255) | ¹H NMR (400 MHz, CDCl3) δ 7.84-7.82 (d, J = 7.6 Hz, 1H), 7.52-7.51 (d, J = 4.4 Hz, 1H), 7.44-7.42 (d, J = 8.0 Hz, 1H), 7.24 (s, 1H), 7.05-6.98 (m, 2H), 6.11 (s, 1H), 5.89 (s, 1H), 4.71-4.61 (m, 2H), 4.11-4.06 (m, 1H), 3.88 (s, 3H), 3.83 (s, 3H), 3.48 (s, 2H), 3.05-3.03 (d, J = 10.8 Hz, 1H), 2.74-2.71 (m, 1H), 2.67 (s, 3H), 2.19-2.13 (m, 1H), 2.04 (s, 3H), 2.01-1.98 (m, 1H), 1.94-1.92 (m, 1H), 1.73 (m, 1H), 1.57-1.55 (m, 3H), 1.17-1.11(m, 1H), 0.92 (m, 1H), 0.89 (m, 1H). | 531 |
| D | 1-((1R)-1-(1-(tert-butylsulfinyl)piperidin-4-yl)ethyl)-N-((4-methoxy-6-methyl-2-oxo-1,2-dihydropyridin-3-yl)methyl)-2-methyl-1H-indole-3-carboxamide (Compound 256) | 1H NMR (400 MHz, DMSO-d6) d = 11.59 (br.s., 1 H), 7.77-7.66 (m, 2 H), 7.62 (d, J = 7.8 Hz, 1 H), 7.15-7.00 (m, 2 H), 6.15 (s, 1 H), 4.37-4.27 (m, 2 H), 4.24-4.13 (m, 1 H), 3.84 (s, 3 H), 3.47-3.35 (m, 1 H), 3.17-3.07 (m, 1 H), 2.91-2.82 (m, 1 H), 2.74-2.63 (m, 2 H), 2.63-2.56 (m, 3 H), 2.41-2.28 (m, 1 H), 2.20 (s, 3 H), 2.01-1.91 (m, 1 H), 1.57-1.46 (m, 3 H), 1.08-1.00 (m, 9 H), 0.99-0.93 (m, 1 H), 0.78-0.69 (m, 1 H) | 541 |

| Methods | Structure/Name | ¹H NMR | m/z |
|---|---|---|---|
| E | 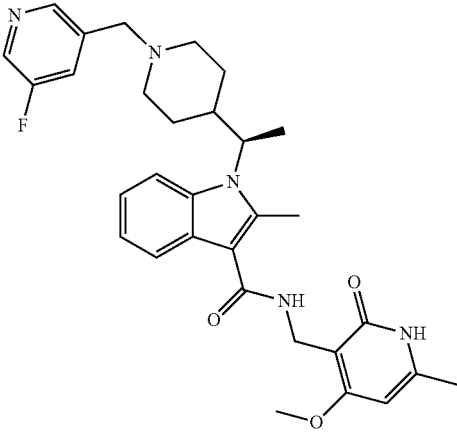<br>(R)-1-(1-(1-((5-fluoropyridin-3-yl)methyl)piperidin-4-yl)ethyl)-N-((4-methoxy-6-methyl-2-oxo-1,2-dihydropyridin-3-yl)methyl)-2-methyl-1H-indole-3-carboxamide (Compound 257) | 1H NMR (400 MHz, DMSO-d6) d = 11.59 (br.s., 1 H), 8.44 (d, J = 2.9 Hz, 1 H), 8.34 (s, 1 H), 7.78-7.65 (m, 2 H), 7.63-7.53 (m, 2 H), 7.14-6.99 (m, 2 H), 6.14 (s, 1 H), 4.38-4.27 (m, 2 H), 4.23-4.10 (m, 1 H), 3.84 (s, 3 H), 3.49 (s, 2 H), 2.94-2.81 (m, 1 H), 2.60 (s, 3 H), 2.19 (s, 4 H), 2.05-1.96 (m, 1 H), 1.95-1.86 (m, 2 H), 1.76-1.64 (m, 1 H), 1.53 (d, J = 6.7 Hz, 3 H), 1.44-1.30 (m, 1 H), 1.14-1.00 (m, 1 H), 0.75-0.63 (m, 1 H) | 546 |
| D | 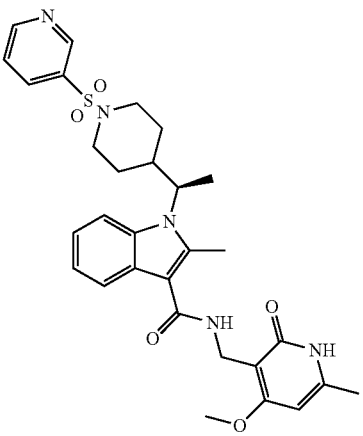<br>(R)-N-((4-methoxy-6-methyl-2-oxo-1,2-dihydropyridin-3-yl)methyl)-2-methyl-1-(1-(1-(pyridin-3-yl)sulfonyl)piperidin-4-yl)ethyl)-1H-indole-3-carboxamide (Compound 258) | 1H NMR (400 MHz, DMSO-d6) d = 11.59 (br.s., 1 H), 8.91-8.82 (m, 2 H), 8.10 (td, J = 1.8, 8.2 Hz, 1 H), 7.75-7.62 (m, 3 H), 7.58-7.48 (m, 1 H), 7.07-6.95 (m, 2 H), 6.15 (s, 1 H), 4.39-4.23 (m, 2 H), 4.20-4.07 (m, 1 H), 3.89-3.73 (m, 4 H), 3.59-3.46 (m, 1 H), 2.64-2.54 (m, 3 H), 2.39-2.22 (m, 2 H), 2.20 (s, 3 H), 2.07-1.93 (m, 2 H), 1.52-1.33 (m, 4 H), 1.16-1.02 (m, 1 H), 0.81-0.70 (m, 1 H) | 578 |

| Methods | Structure/Name | ¹H NMR | m/z |
|---|---|---|---|
| H | (R)-N-((4-methoxy-6-methyl-2-oxo-1,2-dihydropyridin-3-yl)methyl)-2-methyl-1-(1-(1-(pyrimidin-4-yl)methyl)piperidin-4-yl)ethyl)-1H-indole-3-carboxamide (Compound 259) | ¹H NMR (400 MHz, CD3OD) δ 9.38 (s, 1H), 8.98-8.97 (d, J = 5.2 Hz, 1H), 7.81-7.71 (m, 3H), 7.24-7.18 (m, 2H), 7.02 (s, 1H), 4.67-4.66 (d, J = 5.2 Hz, 1H), 4.62 (s, 3H), 4.40-4.36 (m, 1H), 4.16 (s, 3H), 3.85-3.82 (d, J = 10.8 Hz, 1H), 3.55-3.52 (d, J = 11.6 Hz, 1H), 3.30-3.29 (m, 1H), 3.05-2.99 (t, J = 12.0 Hz, 1H), 2.83-2.78 (m, 1H), 2.71 (s, 3H), 2.59 (s, 3H), 2.36-2.35 (m, 1H), 1.91-1.87 (m, 1H), 1.72-1.70 (d, J = 6.8 Hz, 3H), 1.62-1.59 (m, 1H), 1.13-1.09 (d, J = 14.0 Hz, 1H). | 529 |
| E | (R)-1-(1-(1-((3-fluoropyridin-4-yl)methyl)piperidin-4-yl)ethyl)-N-((4-methoxy-6-methyl-2-oxo-1,2-dihydropyridin-3-yl)methyl)-2-methyl-1H-indole-3-carboxamide (Compound 260) | 1H NMR (400 MHz, DMSO-d6) d 11.59 (s, 1 H), 8.47 (d, J = 1.6 Hz, 1 H), 8.37 (d, J = 4.7 Hz, 1 H), 7.74 (d, J = 7.3 Hz, 1 H), 7.68 (t, J = 4.9 Hz, 1 H), 7.60 (d, J = 7.5 Hz, 1 H), 7.42 (t, J = 5.6 Hz, 1 H), 7.12-7.00 (m, 2 H), 6.14 (s, 1 H), 4.39-4.27 (m, 2 H), 4.17 (dd, J = 7.1, 10.0 Hz, 1 H), 3.84 (s, 3 H), 3.53 (s, 2 H), 2.89 (d, J = 10.9 Hz, 1 H), 2.74-2.63 (m, 1 H), 2.60 (s, 3 H), 2.20 (s, 4 H), 2.05 (t, J = 11.0 Hz, 1 H), 1.97-1.84 (m, 1H), 1.73 (br.s., 1 H), 1.53 (d, J = 7.0 Hz, 3 H), 1.38 (d, J = 11.9 Hz, 1 H), 1.08 (d, J = 8.8 Hz, 1 H), 0.69 (d, J = 13.0 Hz, 1 H) | 546 |

-continued

| Methods | Structure/Name | ¹H NMR | m/z |
|---|---|---|---|
| H | 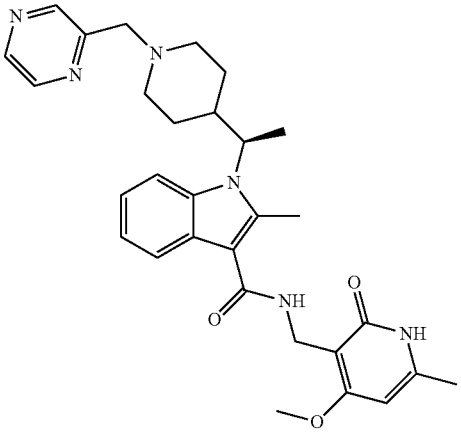<br>(R)-N-((4-methoxy-6-methyl-2-oxo-1,2-dihydropyridin-3-yl)methyl)-2-methyl-1-(1-(1-(pyrazin-2-ylmethyl)piperidin-4-yl)ethyl)-1H-indole-3-carboxamide (Compound 261) | ¹H NMR (400 MHz, CD3OD) δ 8.76-8.74 (m, 2H), 8.70-8.69 (s, 1H), 7.79-7.77 (d, J = 6.8 Hz, 1H), 7.71-7.70 (s, J = 6.8 Hz, 1H), 7.24-7.18 (m, 2H), 7.01 (s, 1H), 4.62 (s, 3H), 4.58-4.55 (m, 1H), 4.38-4.33 (m, 1H), 4.16 (s, 3H), 3.78-3.75 (d, J = 13.2 Hz, 1H), 3.48-3.45 (d, J = 12.4 Hz, 1H), 3.27-3.24 (m, 1H), 3.01-2.98 (t, J = 10.8 Hz, 1H), 2.83-2.73(m, 1H), 2.69 (s, 3H), 2.58 (s, 3H), 2.37-2.34 (d, J = 14.4 Hz, 1H), 1.83-1.79 (m, 1H), 1.71-1.69 (d, J = 12.4 Hz, 1H), 1.54-1.52 (m, 1H), 1.13-1.10 (d, J = 14.0 Hz, 1H). | 529 |
| G, B, C | 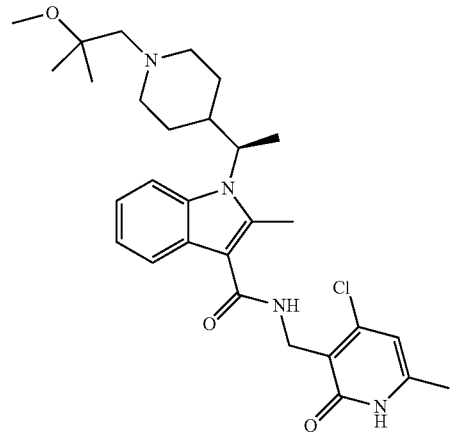<br>(R)-N-(4-chloro-6-methyl-2-oxo-1,2-dihydropyridin-3-yl)methyl)-1-(1-(1-(2-methoxy-2-methylpropyl)piperidin-4-yl)ethyl)-2-methyl-1H-indole-3-carboxamide (Compound 262) | 1H NMR (400 MHz, DMSO-d6) Shift = 12.03 (s, 1 H), 7.76-7.69 (m, 1 H), 7.66 (t, J = 4.8 Hz, 1 H), 7.59 (d, J = 7.7 Hz, 1 H), 7.12-7.00 (m, 2 H), 6.21 (s, 1 H), 4.43 (t, J = 4.7 Hz, 2 H), 4.20-4.10 (m, 1 H), 3.32 (s, 3 H), 3.06 (s, 3 H), 2.84-2.77 (m, 1 H), 2.67 (br. s., 1 H), 2.58 (s, 3 H), 2.17 (s, 4 H), 1.89 (d, J = 11.6 Hz, 2 H), 1.57-1.46 (m, 4 H), 1.07 (d, J = 4.6 Hz, 7 H), 0.66 (d, J = 10.7 Hz, 1 H) | 527 |

| Methods | Structure/Name | ¹H NMR | m/z |
|---|---|---|---|
| E | (R)-1-(1-(1-(3-fluorobenzyl)piperidin-4-yl)ethyl)-N-((4-methoxy-6-methyl-2-oxo-1,2-dihydropyridin-3-yl)methyl)-2-methyl-1H-indole-3-carboxamide (Compound 263) | 1H NMR (500 MHz, DMSO-d6) Shift = 11.59 (br.s., 1 H), 7.79-7.65 (m, 2 H), 7.60 (d, J = 7.8 Hz, 1 H), 7.15-6.97 (m, 2 H), 6.15 (s, 1 H), 4.38-4.27 (m, 2 H), 4.22-4.13 (m, 1 H) 4.11-4.05 (m, 2 H), 3.84 (s, 3 H), 3.00-2.92 (m, 1 H), 2.72-2.63 (m, 2 H), 2.63-2.58 (m, 3 H), 2.54 (q, J = 5.1 Hz, 2 H), 2.23-2.13 (m, 3 H), 2.06-1.97 (m, 1 H), 1.94-1.87 (m, 1 H), 1.74-1.65 (m, 1 H), 1.58-1.47 (m, 3 H), 1.40-1.29 (m, 1 H), 1.09-0.98 (m, 1 H), 0.70-0.63 (m, 1 H) | 549 |
| H | (R)-1-(1-(1-((2-cyanopyridin-4-yl)methyl)piperidin-4-yl)ethyl)-N-((4-methoxy-6-methyl-2-oxo-1,2-dihydropyridin-3-yl)methyl)-2-methyl-1H-indole-3-carboxamide (Compound 264) | ¹H NMR (400 MHz, CD3OD) δ 8.59 (d, J = 4.8 Hz, 1H), 7.83 (s, 1H), 7.20 (d, J = 7.2 Hz, 1H), 7.61-7.55 (m, 2H), 7.12-7.06 (m, 2H), 6.27 (s, 1H), 4.53 (s, 2H), 4.23-4.19 (m, 1H), 3.94 (s, 3H), 3.59-3.51 (m, 2H), 2.93 (d, J = 11.2 Hz, 1H), 2.65 (s, 1H), 2.62 (s, 3H), 2.15 (s, 4H), 2.12-2.09 (m, 1H), 2.04-2.02 (m, 1H), 1.83-1.78 (m, 1H), 1.62 (d, J = 7.2 Hz, 3H), 1.48-1.44 (m, 1H), 1.18-1.15 (m, 1H), 0.88-0.84 (m, 1H). | 553 |

| Methods | Structure/Name | ¹H NMR | m/z |
|---|---|---|---|
| D | 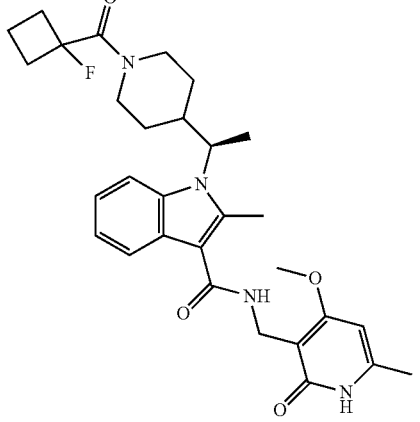<br>(R)-1-(1-(1-(1-fluorocyclobutanecarbonyl)piperidin-4-yl)ethyl)-N-((4-methoxy-6-methyl-2-oxo-1,2-dihydropyridin-3-yl)methyl)-2-methyl-1H-indole-3-carboxamide (Compound 265) | ¹H NMR (400 MHz, CD3OD) δ 7.71-7.69 (d, J = 8 Hz, 1H), 7.61-7.59 (d, J = 8 Hz, 1H), 7.13-7.06 (m, 2H), 6.27 (s, 1H), 4.60-4.38 (m, 3H), 4.28-4.19 (m, 1H), 3.93 (s, 3H), 3.75-3.72 (d, J = 12 Hz, 1H), 2.74 (m, 1H), 2.59-2.56 (d, J = 12 Hz, 2H), 2.43 (d, J = 8 Hz, 4H), 2.39-2.31 (m, 5H), 2.24 (s, 1H), 2.08 (br s, 1H), 1.63-1.58 (m, 4H), 1.32-1.28 (m, 2H), 1.01-0.91 (m, 2H). | 537 |
| | 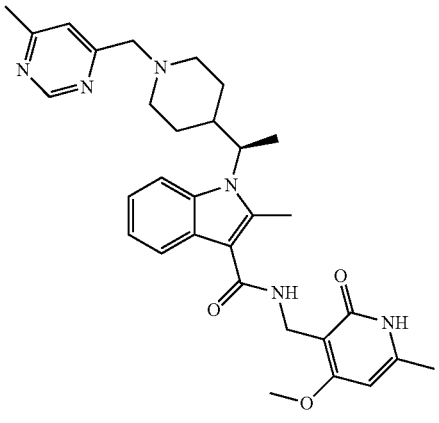<br>(R)-N-((4-methoxy-6-methyl-2-oxo-1,2-dihydropyridin-3-yl)methyl)-2-methyl-1-(1-(1-((6-methylpyrimidin-4-yl)methyl)piperidin-4-yl)ethyl)-1H-indole-3-carboxamide (Compound 266) | ¹H NMR (400 MHz, CD3OD) δ 8.89 (s, 1H), 7.72 (d, J = 7.2 Hz, 1H), 7.57 (d, J = 8.0 Hz, 1H), 7.48 (s, 2H), 7.11-7.06 (m, 2H), 6.28 (s, 1H), 4.53 (s, 2H), 4.23-4.19 (m, 1H), 3.94 (s, 3H), 3.59-3.51 (m, 2H), 2.93 (d, J = 11.2 Hz, 1H), 2.65 (s, 1H), 2.62 (s, 3H), 2.52 (s, 3H), 2.15 (s, 4H), 2.12-2.09 (m, 1H), 2.04-2.02 (m, 1H), 1.83-1.78 (m, 1H), 1.62 (d, J = 6.4 Hz, 3H), 1.48-1.44 (m, 1H), 1.18-1.15 (m, 1H), 0.88-0.84 (m, 1H). | 543 |

| Methods | Structure/Name | ¹H NMR | m/z |
|---|---|---|---|
| H | (R)-N-((4-methoxy-6-methyl-2-oxo-1,2-dihydropyridin-3-yl)methyl)-2-methyl-1-(1-(1-((6-methylpyridin-2-yl)methyl)piperidin-4-yl)ethyl)-1H-indole-3-carboxamide (Compound 267) | ¹H NMR (400 MHz, CD3OD) δ 7.68-7.63 (m, 2H), 7.55 (d, J = 7.6 Hz, 1H), 7.25 (d, J = 7.6 Hz, 1H), 7.16-7.06 (m, 3H), 6.27 (s, 1H), 4.51 (s, 2H), 4.21-4.15 (m, 1H), 3.92 (s, 3H), 3.66 (s, 1H), 3.29 (s, 3H), 3.09 (s, 1H), 2.78 (s, 1H), 2.59 (s, 3H), 2.30 (s, 4H), 2.05-2.02 (m, 2H), 1.62 (d, J = 6.8 Hz, 3H), 1.49-1.46 (m, 1H), 1.42-1.28 (m, 1H), 1.19-1.13 (m, 1H), 0.88-0.84 (m, 1H). | 542 |
| H | (R)-1-(1-(1-((4-cyanopyridin-3-yl)methyl)piperidin-4-yl)ethyl)-N-((4-methoxy-6-methyl-2-oxo-1,2-dihydropyridin-3-yl)methyl)-2-methyl-1H-indole-3-carboxamide (Compound 268) | ¹H NMR (400 MHz, CD3OD) δ 8.79-8.72 (m, 2H), 8.14 (s, 1H), 7.72-7.65 (m, 1H), 7.56 (d, J = 8.4 Hz, 1H), 7.12-7.06 (m, 2H), 6.27 (s, 1H), 4.53 (s, 2H), 4.22-4.18 (m, 1H), 3.94 (s, 3H), 3.56 (s, 2H), 2.95 (d, J = 10.8 Hz, 1H), 2.72-2.60 (m, 4H), 2.32 (s, 3H), 2.16-2.10 (m, 1H), 2.05-2.02 (m, 1H), 1.82-1.80 (m, 1H), 1.62 (d, J = 7.2 Hz, 3H), 1.45-1.42 (m, 1H), 1.29-1.12 (m, 2H), 0.88-0.84 (m, 1H). | 552 |

| Methods | Structure/Name | ¹H NMR | m/z |
|---|---|---|---|
| D | (R)-N-((4-methoxy-6-methyl-2-oxo-1,2-dihydropyridin-3-yl)methyl)-2-methyl-1-(1-(1-(tetrahydro-2H-pyran-4-carbonyl)piperidin-4-yl)ethyl)-1H-indole-3-carboxamide (Compound 269) | ¹H NMR (400 MHz, DMSO-d6) δ 11.60 (br s, 1H), 7.79-7.67 (m, 2H), 7.65-7.63 (d, J = 7.72 Hz, 1H), 7.13-7.02 (m, 2H), 6.15 (s, 1H), 4.52-4.49 (d, J = 11.47 Hz, 1H), 4.40-4.29 (m, 2H), 4.23-4.02 (m, 2H), 3.90-3.74 (m, 5H), 3.31-3.27 (d, J = 13.23 Hz, 2H), 3.05-2.99 (t, J = 12.46 Hz, 1H), 2.87 (br s, 1H), 2.80-2.64 (m, 2H), 2.63-2.53 (m, 3H), 2.20 (s, 3H), 1.96-1.93 (d, J = 13.01 Hz, 1H), 1.64-1.46 (m, 6H), 1.42 (br s, 1H), 1.37-1.19 (m, 1H), 1.16-1.13 (d, J = 11.47 Hz, 1H), 0.99-0.82 (m, 1H), 0.72 (br s, 1H). | 549 |
| D | N-((4-methoxy-6-methyl-2-oxo-1,2-dihydropyridin-3-yl)methyl)-2-methyl-1-((1R)-1-(1-(tetrahydrofuran-3-carbonyl)piperidin-4-yl)ethyl)-1H-indole-3-carboxamide (Compound 270) | ¹H NMR (400 MHz, DMSO-d6) δ 11.60 (br s, 1H), 7.81-7.68 (m, 2H), 7.65-7.63 (d, J = 7.72 Hz, 1H), 7.16-6.98 (m, 2H), 6.15 (s, 1H), 4.52-4.49 (d, J = 11.91 Hz, 1H), 4.40-4.29 (m, 2H), 4.28-4.09 (m, 2H), 4.06-4.03 (d, J = 14.55 Hz, 1H), 3.91-3.81 (m, 3H), 3.80-3.73 (m, 1H), 3.73-3.57 (m, 3H), 3.27-3.14 (m, 1H), 3.03 (br s, 1H), 2.76-2.65 (m, 1H), 2.64-2.54 (m, 3H), 2.20 (s, 3H), 2.05-1.87 (m, 3H), 1.55-1.54 (d, J = 6.62 Hz, 2H), 1.37-1.09 (m, 2H), 0.94-0.81 (m, 1H), 0.71 (br s, 1H). | 535 |

| Methods | Structure/Name | ¹H NMR | m/z |
|---|---|---|---|
| A, B, C | 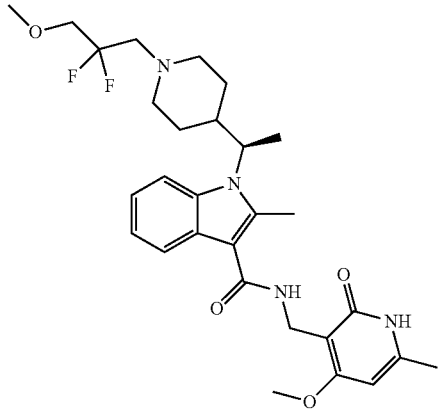<br>(R)-1-(1-(1-(2,2-difluoro-3-methoxypropyl)piperidin-4-yl)ethyl)-N-((4-methoxy-6-methyl-2-oxo-1,2-dihydropyridin-3-yl)methyl)-2-methyl-1H-indole-3-carboxamide(Compound 181) | 1H NMR (400 MHz, DMSO-d6) d 11.60 (br.s., 1H), 7.66-7.82 (m, 2H), 7.60 (d, J = 7.4 Hz, 1H), 7.05 (q, J = 7.1 Hz, 2H), 6.15 (s, 1H), 4.32 (br.s., 2H), 4.15 (br.s., 1H), 3.84 (d, J = 2.9 Hz, 3H), 3.60 (t, J = 12.9 Hz, 2H), 3.32 (s, 3H), 2.94 (d, J = 10.3 Hz, 1H), 2.55-2.77 (m, 6H), 2.08-2.31 (m, 5H), 1.80-1.97 (m, 2H), 1.53 (d, J = 5.5 Hz, 3H), 1.35 (d, J = 11.6 Hz, 1H), 1.05 (d, J = 12.0 Hz, 1H), 0.65 (d, J = 10.5 Hz, 1H) | 545 |
| D | 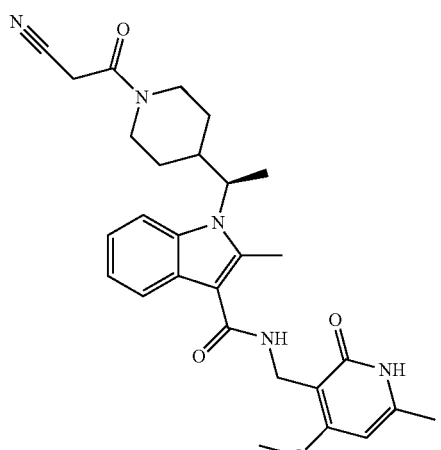<br>(R)-1-(1-(1-(2-cyanoacetyl)piperidin-4-yl)ethyl)-N-((4-methoxy-6-methyl-2-oxo-1,2-dihydropyridin-3-yl)methyl)-2-methyl-1H-indole-3-carboxamide (Compound 186) | | 504 |

| Methods | Structure/Name | $^1$H NMR | m/z |
|---|---|---|---|
| D | 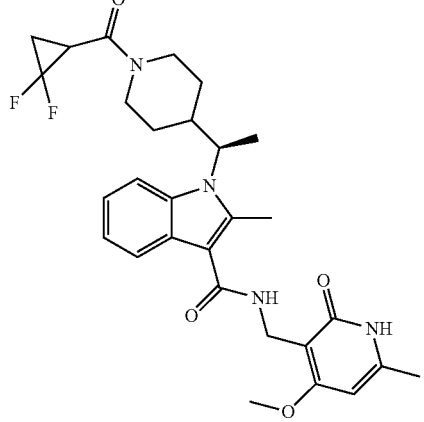<br>1-1-((1R)-1-(1-(2,2-difluorocyclopropane-1-carbonyl)piperidin-4-yl)ethyl)-N-((4-methoxy-6-methyl-2-oxo-1,2-dihydropyridin-3-yl)methyl)-2-methyl-1H-indole-3-carboxamide<br>(Compound 229) | 1H NMR (400 MHz, DMSO-d6) d 11.05-11.34 (m, 1H), 7.79 (d, J = 7.2 Hz, 1H), 7.58 (d, J = 7.9 Hz, 1H), 7.44 (br.s., 1H), 7.04-7.15 (m, 2H), 6.07 (s, 1H), 4.39 (d, J = 5.04 Hz, 2H), 4.30 (br.s., 2H), 3.91-4.09 (m, 1H), 3.87 (s, 3H), 2.93 (br.s., 4H), 2.65 (s, 3H), 2.23 (s, 3H), 2.04 (br.s., 1H), 1.89 (dd, J = 5.7, 13.1 Hz, 1H), 1.67-1.81 (m, 1H), 1.58 (d, J = 7.0 Hz, 3H), 1.23-1.39 (m, 1H), 0.96 (d, J = 3.9 Hz, 2H) | 541 |

$IC_{50}$ measurements for Inhibitors using EZH2

EZH2 Assay: Assays were carried out by mixing rPRC2 together with biotinylated oligonucleosome substrates in the presence of the radio-labeled enzyme co-factor, S-adenosyl-L-methionine ($^3$H SAM) (Perkin Elmer) and monitoring the enzymatically mediated transfer of tritiated methyl groups from $^3$H SAM to histone lysine residues. The amount of resulting tritiated methyl histone product was measured by first capturing the biotinylated oligonucleosomes in streptavidin (SAV) coated FlashPlates (Perkin Elmer), followed by a wash step to remove un-reacted $^3$H SAM, and then counting on a TopCount NXT 384 well plate scintillation counter (Perkin Elmer). The final assay conditions for EZH2 were as follows: 50 mM Tris Buffer pH 8.5, 1 mM DTT, 69 µM Brij-35 detergent, 5.0 mM MgCl$_2$, 0.1 mg/mL BSA, 0.2 µM $^3$H SAM, 0.2 µM biotinylated oligonucleosomes, 3.6 µM H3K27me3 peptide and 2 nM EZH2.

Compound $IC_{50}$ measurements were obtained as follows: Compounds were first dissolved in 100% DMSO as 10 mM stock solutions. Ten point dose response curves were generated by dispensing varying amounts of the 10 mM compound solution in 10 wells of the 384 well plate (Echo; Labcyte), pure DMSO was then used to backfill the wells to insure all wells have the same amount of DMSO. A 12.5 µL volume of the HMT enzyme, H3K27me3 peptide and oligonucleosome substrate in assay buffer was added to each well of the assay plate using a Multidrop Combi (Thermo-Fisher). Compounds were pre-incubated with the enzyme for 20 min, followed by initiation of the methyltransferase reaction by addition of 12.5 µL of $^3$H SAM in assay buffer (final volume=25 µL). The final concentrations of compounds ranged from a top default concentration of 80 µM down to 0.16 µM in ten 2-fold dilution steps. Reactions were carried out for 60 minutes and quenched with 20 µL per well of 1.96 mM SAH, 50 mM Tris pH 8.5, 200 mM EDTA. Stopped reactions were transferred to SAV coated FlashPlates (Perkin Elmer), incubated for 120 min, washed with a plate washer, and then read on the TopCount NXT (1.0 min/well) to measure the amount of methyl histone product formed during the reaction. The amount of methyl histone product was compared with the amount of product formed in the 0% and 100% inhibition control wells allowing the calculation of % Inhibition in the presence of the individual compounds at various concentrations. $IC_{50}$'s were computed using a 4 parameter fit non-linear curve fitting software package (XLFIT, part of the database package, ActivityBase (IDBS)) where the four parameters were $IC_{50}$, Hill slope, pre-transitional baseline (0% INH), and post-transitional baseline (100% INH); with the latter two parameters being fixed to zero and 100%, respectively, by default.

Assay for Y641N EZH2 was performed as above using reconstituted H3K27Me2 oligonucleosomes as substrate.

Table 3 shows the activity of selected compounds of this invention in the EZH2 and Y641N EZH2 activity inhibition assay. $IC_{50}$ values are reported as follows: "A" indicates an $IC_{50}$ value of less than 100 nM; "B" indicates an $IC_{50}$ value of 100 nM to 1 µM; "C" indicates an $IC_{50}$ value of greater than 1 µM and less than 10 µM for each enzyme; "D" indicates an $IC_{50}$ value of greater than 10 µM for each enzyme; and "*(X µM)" indicates that no inhibition was observed at the highest concentration (i.e., X µM) of compound tested.

$EC_{50}$ Measurements for Inhibitors in HeLa Cell Assays
H3K27me3 MSD Hela Assay.

Trypsinized HeLa cells were counted and diluted in 10% DMEM (Life Technologies, Cat. #10569) to 5000 cells/75 µL. Seventy-five µL of cells were place in each well of a 96-well flat-bottomed plate and incubated at 37° C. for 4 hours. Twenty-five µL of test compound (at various concentrations) was added to the cells and incubation continued at 37° C. for 96 hours. Media was then removed and the cells rinsed once with ice cold PBS. Forty µL of ice-cold MSD Buffer AT (10 mM HEPES, pH 7.9, 5 mM $MgCl_2$, 0.25M sucrose, Benzonase (1:10000), 1% Triton X-100 supplemented with fresh 1× Protease Inhibitor cocktail and 1 mM 4-(2-Aminoethyl)benzenesulfonyl fluoride hydrochloride (AEBSF)) was added to each well and the plates placed on ice for 30 minutes. Ten µL of 5M NaCl was then added to each well and incubation on ice continued for another 15 minutes. The material in each well was suspended pipetting up and down and then transferred to a new 96 well plate. The emptied wells were rinsed with 150 uL ice-cold 20 mM Tris pH 7.5, 1 mM EDTA, 1 mM EGTA, supplemented with fresh 1× Protease Inhibitor cocktail and 1 mM AEBSF ("NO salt NO detergent buffer) and transferred to the respective wells in the new plate. Three hundred µL of NO Salt NO detergent buffer was then added to each well of lysates and the plates frozen at −80° C.

On the same day, an appropriate number of MSD standard bind 96-well plates were coated with 30 µL/well of total H3 capture antibody (Millipore, Cat # MAB3422) at 1 µg/mL concentration in PBS. The antibody solution was evenly distributed first by tapping gently on the sides of the plates and then by shaking the plates for a few minutes at 1000 rpm. Antibody coated plates were stored at 4° C. overnight.

The next day the lysates are thawed to RT. The antibody coated MSD plates are washed 3× with TBS-T (Tris-buffered saline (Fisher Scientific, Cat #BP2471-1)+0.2% Tween-20). One-hundred fifty µL of 5% Blocker A in TBS-T is added to each well. The wells are covered and shaken on a shaker at RT for one hour. The Blocker A step is repeated a second time. After removing the blocker, 25 µL of cell lysate is transferred into each antibody coated well. The plates are shaken for 2 hours at RT, the lysate removed and the plates again washed with Blocker A in TBS-T. Twenty-five µL of appropriate freshly prepared antibody mix (including both primary and secondary antibodies) is added to each well and the plates shaken for 1 hour at RT. The antibody mix used was one (or both) of those indicated in the table below:

| Ab | Concentration (µg/mL) | Primary Ab (µL) | Anti-rabbit detection Ab (µL) | 1% blocker A (µL) |
|---|---|---|---|---|
| H3K27me3 | 33 | 37.88 | 5.00 | 5000 |
| H3 | 12 | 52.08 | 5.00 | 5000 |

Both H3 antibodies were obtained from Cell Signalling (Cat #s 4499 and 9733). The goat anti-rabbit antibody was obtained from Meso-Scale Discovery (Cat #R32AB-1).

The antibody mix was then removed and the wells washed with Blocker A. One hundred-fifty µL of freshly prepared 1×MSD Read Buffer (Meso-Scale Discovery; Cat #R927C-2) was then added to each well and the plates read on a MSD Sector 2400 Plate Reader.

Data was analyzed using Assay Assistant (Constellation Pharmaceuticals In-house product) and Activity Base (IDBS Ltd, Surrey, UK) template. Data files were imported to Assay Assistant and assay conditions were specified. A unique Analysis ID was created and the data files exported to Activity Base. An analysis template was created on Activity Base to measure dose-dependent inhibition of H3K27me3 mark and cell viability respectively. Readout of DMSO wells were used to normalize the data. Resulting curves were fitted using Activity base software Model 205 (IDBS Ltd, Surrey, UK). The data was checked for quality, validated and integrated in excel format using SARview (IDBS Ltd, Surrey, UK).

H3K27me3 Alpha Hela Assay (AlphaLISA).

Ten different doses of each test compound (in a series of 3-fold dilutions) were plated in duplicate 384-well tissue culture treated plates (Catalog #781080; Greiner Bio One; Monroe, N.C.). Hela cells grown in culture were trypsinized and counted using a Countess® cell counter (Catalog # C10281; Life Technologies, Grand Island, N.Y.). Cell were diluted to 67,000 cells per mL in 10% DMEM (Catalog #10569-010 Life Technologies, Grand Island, N.Y.) and 15 µL (1,000 cells) were plated into each well using the Biotek MicroFlo™ Select Dispenser (BioTek Instruments, Inc. Vermont, USA),) of the 384-well plate. Plates were incubated at 37° C./5% $CO_2$ for 72 hrs. One of the duplicate plates was processed for HeLa assay and the other for viability.

To the plate processed for AlphaLISA was added 5 µL per well Cell-Histone Lysis buffer (1λ) (Catalog # AL009F1 Perkin Elmer; Waltham, Mass.) and the plate was incubated at RT for 30 minutes on a plate shaker with low speed (Model#4625-Q Thermo Scientific; Waltham, Mass.). Then, 10 µL per well Histone Extraction buffer (catalog # AL009F2; Perkin Elmer; Waltham, Mass.) was added and the plate further incubated at RT for 20 min on plate shaker with low speed. To each well was then added 10 µL per well of a 5× mix of anti-K27me3 acceptor beads plus Biotinylated anti-Histone H3 (C-ter) Antibody (diluted to 3 nM final) (Catalog #AL118 Perkin Elmer; Waltham, Mass.). Dilution of the acceptor beads and then anti-Histone H3 was with 1× Histone Detection buffer (Catalog # AL009F3 Perkin Elmer; Waltham, Mass.) which was produced diluted from the 10× stock provided. The plate was sealed with an aluminum plate sealer and incubated at 23° C. for 60 min. We then added 10 µL 5× solution of Streptavidin Donor beads (Catalog #6760002 Perkin Elmer; Waltham, Mass.) (20 µg/mL final in 1× Histone Detection Buffer), sealed the plate with Aluminum plate sealer and incubated at 23° C. for 30 min. The plates were then read using an EnVision-Alpha Reader (model #2104 Perkin Elmer; Waltham, Mass.).

Cell viability was assayed by adding 15 µL of Cell Titer Glo ((Catalog #G7571 Promega Madison, Wis.) to each well with cells with media. The plates were incubated foat RT for 15-20 minutes on a plate shaker at low speed. The plates were then read using an EnVision-Alpha Reader (model #2104 Perkin Elmer; Waltham, Mass.).

Data from both assays was analyzed using Assay Assistant (Constellation Pharmaceuticals In-house product) and Activity Base (IDBS Ltd, Surrey, UK) template. Data files were imported to Assay Assistant and assay conditions were specified. A unique Analysis ID was created and the data files exported to Activity Base. An analysis template was created on Activity Base to measure dose-dependent inhibition of H3K27me3 mark and cell viability respectively. Readout of DMSO wells were used to normalize the data. Resulting curves were fitted using Activity base software Model 205 (IDBS Ltd, Surrey, UK). The data was checked for quality, validated and integrated in excel format using SARview (IDBS Ltd, Surrey, UK).

Table 3 shows the activity of selected compounds of this invention in the HeLa cell assays described above. $EC_{50}$ values are reported as follows: "A" indicates an $EC_{50}$ value of less than 400 nM; "B" indicates an $EC_{50}$ value of 400 nM to 2 µM; "C" indicates an $EC_{50}$ value of greater than 2 µM.

TABLE 3

IC$_{50}$ and EC$_{50}$ values for selected compounds.

| Compound | EZH2_nuc_BSA_Brij_1.5 (IC50) | EZH2_Y641N_nuc_BSA_Brij_6.0 (IC50) | EZH2_Cell_H3K27me3_Alpha_HeLa (EC50_K27me3) |
|---|---|---|---|
| 101 | A | A | A |
| 102 | A | A | A |
| 103 | A | A | A |
| 104 | A | A | A |
| 105 | A | A | A |
| 106 | A | A | A |
| 107 | A | A | A |
| 108 | A | — | A |
| 109 | A | A | A |
| 110 | A | A | A |
| 111 | A | A | A |
| 112 | A | A | A |
| 113 | A | A | A |
| 114 | A | — | A |
| 115 | A | A | A |
| 116 | A | A | A |
| 117 | A | A | A |
| 118 | A | A | A |
| 119 | A | A | A |
| 120 | A | A | A |
| 121 | A | A | A |
| 122 | A | A | A |
| 123 | A | A | A |
| 124 | A | A | A |
| 125 | A | A | A |
| 126 | A | A | A |
| 127 | A | — | A |
| 128 | — | — | A |
| 129 | A | A | A |
| 130 | A | A | A |
| 131 | A | A | A |
| 132 | A | A | A |
| 133 | A | A | A |
| 134 | A | A | A |
| 135 | — | — | A |
| 136 | B | B | A |
| 137 | A | A | A |
| 138 | A | A | A |
| 139 | A | A | A |
| 140 | A | A | A |
| 141 | A | A | A |
| 142 | A | A | A |
| 143 | A | A | A |
| 144 | A | A | B |
| 145 | A | A | B |
| 146 | A | A | B |
| 147 | A | A | B |
| 148 | A | A | B |
| 149 | A | A | B |
| 150 | A | A | B |
| 151 | A | A | B |
| 152 | A | A | B |
| 153 | A | A | B |
| 154 | A | A | B |
| 155 | A | A | B |
| 156 | A | A | B |
| 157 | A | A | B |
| 158 | A | A | B |
| 159 | A | A | B |
| 160 | A | A | B |
| 161 | A | A | B |
| 162 | A | A | B |
| 163 | A | B | B |
| 164 | A | A | C |
| 165 | A | B | C |
| 166 | A | A | C |
| 167 | A | A | C |
| 168 | A | A | C |
| 169 | A | — | — |
| 171 | A | A | — |
| 172 | A | A | — |
| 175 | A | — | B |
| 177 | A | — | A |
| 179 | A | — | B |
| 180 | A | — | C |

TABLE 3-continued

IC$_{50}$ and EC$_{50}$ values for selected compounds.

| Compound | EZH2_nuc_BSA_Brij_1.5 (IC50) | EZH2_Y641N_nuc_BSA_Brij_6.0 (IC50) | EZH2_Cell_H3K27me3_Alpha_HeLa (EC50_K27me3) |
|---|---|---|---|
| 181 | A | — | A |
| 185 | A | — | B |
| 186 | A | — | B |
| 189 | A | — | B |
| 190 | A | — | B |
| 191 | A | — | B |
| 192 | A | — | C |
| 206 | A | — | A |
| 207 | A | — | C |
| 209 | A | — | B |
| 210 | A | — | B |
| 211 | A | — | B |
| 212 | A | — | A |
| 213 | A | — | A |
| 214 | A | — | B |
| 216 | A | — | A |
| 219 | A | — | A |
| 220 | A | — | A |
| 221 | A | — | A |
| 222 | A | — | A |
| 228 | A | — | B |
| 229 | A | — | B |
| 230 | A | — | A |
| 231 | A | — | B |
| 232 | A | — | A |
| 233 | A | — | A |
| 234 | A | — | A |
| 235 | A | — | B |
| 236 | A | — | A |
| 237 | A | — | C |
| 238 | A | — | C |
| 239 | A | — | B |
| 240 | A | — | B |
| 241 | A | — | B |
| 242 | A | — | B |
| 243 | A | — | C |
| 244 | A | — | B |
| 245 | A | — | A |
| 246 | A | — | A |
| 247 | A | — | B |
| 248 | A | — | B |
| 249 | A | — | B |
| 250 | A | — | A |
| 251 | A | — | A |
| 252 | A | — | A |
| 253 | A | — | A |
| 254 | A | — | A |
| 255 | A | — | C |
| 256 | A | — | A |
| 257 | A | — | A |
| 258 | A | — | B |
| 259 | A | — | A |
| 260 | A | — | A |
| 261 | A | — | A |
| 262 | A | — | A |
| 263 | A | — | A |
| 264 | A | — | A |
| 265 | A | — | A |
| 266 | A | — | A |
| 267 | A | — | A |
| 268 | A | — | A |
| 269 | A | — | B |
| 270 | A | — | C |

The invention claimed is:

1. A compound having structural formula I:

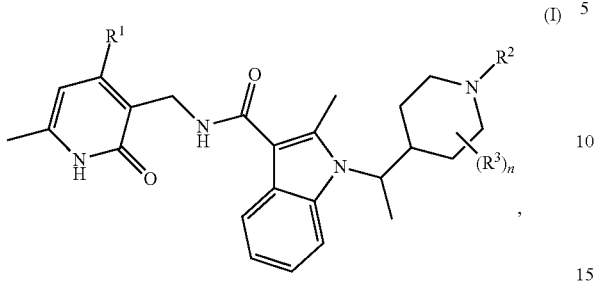

or a substantially pure enantiomer thereof, or a pharmaceutically acceptable salt of either of the foregoing, wherein:

$R^1$ is selected from —Cl, —CH$_3$, —CH$_2$CH$_3$, —CH$_2$CH$_2$CH$_3$, —NH(CH$_3$), —OCH$_3$, —OCHF$_2$, —OCF$_3$, and —OCH$_2$CF$_3$;

$R^2$ is selected from -aryl, -cycloalkyl, —CH$_2$-aryl, —CH$_2$-heteroaryl, —CH$_2$-cycloalkyl, —CH$_2$CH$_2$-heterocyclyl, —S(O)$_2$-aryl, —S(O)$_2$-heteroaryl, —S(O)$_2$-cycloalkyl, —S(O)$_2$-heterocyclyl, —S(O)$_2$—CH$_2$CH$_2$-heterocyclyl, —C(O)-cycloalkyl, —C(O)-aryl, —C(O)-heterocyclyl, —C(O)—CH$_2$-aryl, —C(O)—CH$_2$-heteroaryl, —C(O)—N(CH$_3$)$_2$, —C(O)—[OCH$_2$CH$_2$]$_{2-6}$-OCH$_3$, —C(O)CH$_2$CN, —C(O)CH$_2$CH$_2$CH$_3$, —C(O)CH$_2$CH(CH$_3$)$_2$, —CH$_2$CH$_2$CN, —CH$_2$CH$_2$S(O)$_2$CH$_3$, —CH$_2$S(O)$_2$CH$_3$, —CH$_2$CH$_2$NHC(O)CH$_3$, —CH$_2$CH(OCH$_3$)CF$_3$, —CH$_2$CH$_2$CH$_2$CF$_3$, —CH$_2$CH(OH)CF$_3$, —CH(CH$_2$F)CH$_2$F, and —R$^4$—C(R$^5$)(R$^6$)—R$^7$, wherein:

$R^4$ is selected from —CH$_2$—, —CH(CH$_3$)—, —C(CH$_3$)$_2$—, —C(O)— and —S(O)$_2$—;

each of $R^5$ and $R^6$ is independently selected from fluoro, —CH$_3$, and —CH$_2$CH$_3$, or $R^5$ and $R^6$ are taken together to form =O;

$R^7$ is selected from hydrogen, fluoro, —CN, —CH$_3$, —CH$_2$OH, —CH$_2$OCH$_3$, —CF$_2$H, —CFH$_2$, —CF$_3$, —CF$_2$CH$_3$, —CH$_2$CH$_3$, —OCH$_3$, and —N(C$_1$-C$_3$ alkyl)$_2$, and any aryl, heteroaryl, heterocyclyl or cycloalkyl portion of $R^2$ is optionally substituted with up to two substituents independently selected from bromo, chloro, fluoro, —CN, —CH$_3$, —CF$_3$, —C(O)CH$_3$, and morpholin-4-ylmethyl;

each $R^3$, when present, is independently selected from =O and fluoro;

n is 0, 1, 2, 3, or 4, wherein:

when n is 0, $R^1$ is —CH$_3$, —CH$_2$CH$_3$, —OCH$_3$, or —OCHF$_2$, $R^5$ is fluoro, and $R^6$ is fluoro, then $R^7$ is other than fluoro;

when n is 0, $R^1$ is —CH$_3$, —CH$_2$CH$_3$, —OCH$_3$, or —OCHF$_2$, $R^5$ is —CH$_3$, and $R^6$ is —CH$_3$, then $R^7$ is other than hydrogen; and the compound is other than:

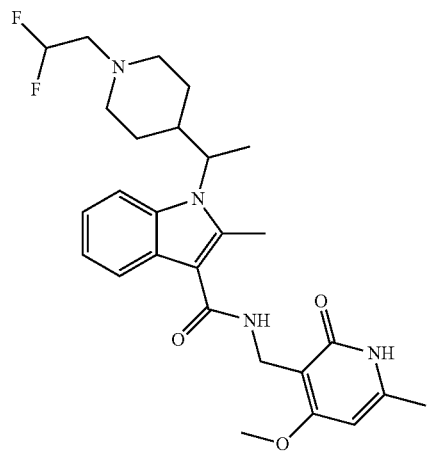 [SMILES: COc1cc(C)[nH]c(=O)c1CNC(=O)c1c(C)n(C(C)C2CCN(CC(F)F)CC2)c2ccccc12]

or a substantially pure enantiomer thereof or a pharmaceutically acceptable salt thereof.

2. The compound of claim 1 having structural formula Ia:

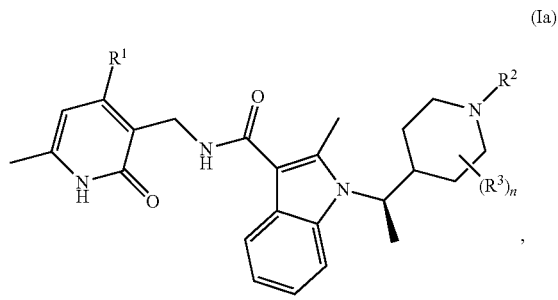

or a pharmaceutically acceptable salt thereof, wherein $R^1$, $R^2$, $R^3$ and n are as defined as in claim 1.

3. The compound of claim 1 having structural formula Ib:

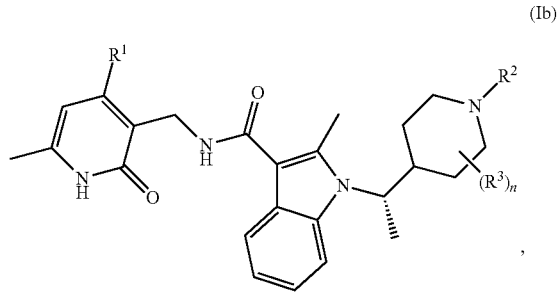

or a pharmaceutically acceptable salt thereof, wherein $R^1$, $R^2$, $R^3$ and n are as defined as in claim 1.

4. The compound of claim 3, wherein $R^1$ is selected from —OCH$_3$, chloro, methyl, —OCHF$_2$, —NH(CH$_3$), —CH$_2$CH$_3$, —CH$_2$CH$_2$CH$_3$, and —OCH$_2$CF$_3$.

5. The compound of claim 4, wherein $R^1$ is selected from chloro, —OCH$_3$ and —OCHF$_2$.

6. The compound of claim 5, wherein $R^2$ is selected from —(CH$_2$)$_3$CF$_3$, —CH$_2$CH(OH)CF$_3$, —CH$_2$CH(OCH$_3$)CF$_3$, —CH$_2$CF$_2$H, —CH$_2$CF$_2$CH$_3$, —CH$_2$CF$_2$CH$_2$CH$_3$, —CH₂CF₂CF₃, —CH₂CF₂CF₂H, —CH₂C(O)N(CH₂CH₃)₂, —CH₂C(O)CH₃, —CH₂C(CH₃)₂OCH₃, —CH₂C(CH₃)₂F, —CH₂C(CH₃)₂CF₃, —CH(CFH₂)₂, —C(O)N(CH₃)₂, —C(O)C(CH₃)₃, —C(O)C(CH₃)₂CF₃, —C(O)—[OCH₂CH₂]₆CH₃, —C(O)—[OCH₂CH₂]₂CH₃, —C(CH₃)₂C(O)CH₃, —C(O)C(CH₃)₂CH₂CH₃, —C(O)C(CH₃)₂OCH₃, —C(O)C(O)CH₃, —C(O)CF₂CH₂OCH₃, —C(O)CH(CH₃)CH₂CH₃, —CH(CH₃)CF₂H, —CH₂C(CH₃)₂CN, —CH₂CF₂CH₂OCH₃, —CH₂CF₂CH₂OH, —S(O)₂C(CH₃)₃, —CH₂-cyclopropyl, —S(O)₂-phenyl, —S(O)₂-cyclopropyl, —C(O)-phenyl, —C(O)-cyclopropyl, 4-cyanophenylcarbonyl, benzylcarbonyl, 2-methyl-1H-imidazol-1-ylacetyl, 3-methylisoxazol-5 acetyl, 1-fluorocyclobutylcarbonyl, 1-methylcyclopentylcarbonyl, 1-methylcyclopropylcarbonyl, 2,2-difluorocyclopropylcarbonyl, 3,3-difluorocyclopentylcarbonyl, 4-methylcyclohexylcarbonyl, cyclobutylcarbonyl, cyclopentylcarbonyl, 1,3-dimehtylazetidin-3-ylcarbonyl, 1-methyl-4-fluoropiperidin-4-ylcarbonyl, 1-methylpiperidin-4-ylcarbonyl, 2,2-difluoropyrrolidin-1-ylcarbonyl, 3-methyloxetan-3-ylcarbonyl, 4,4-difluoropiperidine-1-ylcarbonyl, tetrahydrofuran-3-ylcarbonyl, tetrahydropyran-4-ylcarbonyl, 3-fluorobenzyl, 4-cyanobenzyl, 1-methyl-1H-pyrazol-2-ylmethyl, 1-methyl-1H-pyrazol-3-ylmethyl, 1-methyl-1H-pyrazol-4-ylmethyl, 2,6-dimethylpyridin-4-ylmethyl, 2-cyanopyridin-4-ylmethyl, 2-methylpyridin-4-ylmethyl, 2-trifluoromethylpyridin-4-ylmethyl, 3-fluoropyridin-4-ylmethyl, 4-cyanopyridin-3-ylmethyl, 5-cyanopyridin-2-ylmethyl, 5-fluoropyridin-3-ylmethyl, 6-methylpyridin-2-ylmethyl, 6-methylpyrimidin-4-ylmethyl, pyrazin-2-ylmethyl, pyridin-3-ylmethyl, pyridin-4-ylmethyl, pyridin-3-ylsulfonyl, pyrimidin-2-ylmethyl, pyrimidin-4-ylmethyl, pyrimidin-5-ylmethyl, cyclopropyl, azetidin-3-ylsulfonyl, morpholin-4-ylethylsulfonyl, morpholin-4-ylcarbonyl, pyrrolidin-1-ylethylsulfonyl, pyridin-2-ylmethyl, piperidin-4-ylsulfonyl, 4-methylpiperazin-1-ylcarbonyl, 4-fluorophenylsulfonyl, 4-fluorophenylmethyl, 4-fluorophenyl, 4-chlorophenyl, 4-(morpholin-1-ylmethyl)phenyl, 3,5-difluorophenylmethyl, 3-(morpholin-4-ylmethyl)phenyl, 2,6-difluorophenylmethyl, 1-trifluoromethylcycloprop-1-ylmethyl, 1-trifluoromethylcycloprop-1-ylcarbonyl, 1-trifluoromethylcyclobut-1-ylmethyl, 1-trifluoromethylcyclobut-1-ylcarbonyl, 1-methylpiperidin-4-ylsulfonyl, 1-methylazetidin-3-ylsulfonyl, 1-fluorocycloprop-1-ylmethyl, and 1-fluorocyclobut-1-ylmethyl.

7. The compound of claim 5, wherein $R^2$ is selected from —(CH₂)₃CF₃, —CH₂CH(OH)CF₃, —CH₂CH(OCH₃)CF₃, —CH₂CF₂H, —CH₂CF₂CH₃, —CH₂CF₂CH₂CH₃, —CH₂CF₂CF₃, —CH₂CF₂CF₂H, —CH₂C(O)N(CH₂CH₃)₂, —CH₂C(O)CH₃, —CH₂C(CH₃)₂OCH₃, —CH₂C(CH₃)₂F, —CH₂C(CH₃)₂CF₃, —CH(CFH₂)₂, —C(O)N(CH₃)₂, —C(O)C(CH₃)₃, —C(O)C(CH₃)₂CF₃, —C(O)—[OCH₂CH₂]₆CH₃, —C(O)—[OCH₂CH₂]₂CH₃, —CH₂-cyclopropyl, —S(O)₂-phenyl, —S(O)₂-cyclopropyl, —C(O)-phenyl, —C(O)-cyclopropyl, azetidin-3-ylsulfonyl, morpholin-4-ylethylsulfonyl, morpholin-4-ylcarbonyl, pyrrolidin-1-ylethylsulfonyl, pyridin-2-ylmethyl, piperidin-4-ylsulfonyl, 4-methylpiperazin-1-ylcarbonyl, 4-fluorophenylsulfonyl, 4-fluorophenylmethyl, 4-fluorophenyl, 4-chlorophenyl, 4-(morpholin-1-ylmethyl)phenyl, 3,5-difluorophenylmethyl, 3-(morpholin-4-ylmethyl)phenyl, 2,6-difluorophenylmethyl, 1-trifluoromethylcycloprop-1-ylmethyl, 1-trifluoromethylcycloprop-1-ylcarbonyl, 1-trifluoromethylcyclobut-1-ylmethyl, 1-trifluoromethylcyclobut-1-ylcarbonyl, 1-methylpiperidin-4-ylsulfonyl, 1-methylazetidin-3-ylsulfonyl, 1-fluorocycloprop-1-ylmethyl, and 1-fluorocyclobut-1-ylmethyl.

8. The compound of claim 5, wherein
$R^2$ is selected from —CH₂-aryl, —CH₂-cycloalkyl, —C(O)-cycloalkyl, and —R⁴—C(R⁵)(R⁶)—R⁷, wherein:
$R^4$ is —CH₂—;
each of $R^5$ and $R^6$ is independently selected from fluoro and —CH₃;
$R^7$ is selected from hydrogen, fluoro, —CH₃, —CF₂H, —CF₃, and —CF₂CH₃, any aryl or cycloalkyl portion of $R^2$ is optionally substituted with up to two substituents independently selected from fluoro and —CF₃; and
n is 0.

9. The compound of claim 5, wherein $R^2$ is selected from —CH₂CF₂CF₃, —CH₂CF₂CH₃, —CH₂CF₂CHF₂, —CH₂CHF₂, —CH₂CF₂CH₂CH₃, —CH₂CF(CH₃)₂, —C(CH₃)₂C(O)CH₃, —C(O)C(CH₃)₂CH₂CH₃, —C(O)C(CH₃)₂OCH₃, —C(O)CF₂CH₂OCH₃, —C(O)CH₂CH(CH₃)₂, —CH(CH₃)CF₂H, —CH₂C(CH₃)₂OCH₃, —CH₂CF₂CH₂OCH₃, —CH₂CH₂CN, —S(O)₂C(CH₃)₃, 2,6-dimethylpyridin-4-ylmethyl, 1-fluorocyclobutylcarbonyl, 2-cyanopyridin-4-ylmethyl, 2-methylpyridin-4-ylmethyl, 2-trifluoromethylpyridin-4-ylmethyl, 3-fluorobenzyl, 3-fluoropyridin-4-ylmethyl, 4-cyanobenzyl, 4-cyanopyridin-3-ylmethyl, 4-methylcyclohexylcarbonyl, 5-cyanopyridin-2-ylmethyl, 5-fluoropyridin-3-ylmethyl, 6-methylpyridin-2-ylmethyl, 6-methylpyrimidin-4-ylmethyl, benzylcarbonyl, cyclobutylcarbonyl, cyclopropyl, pyrazin-2-ylmethyl, pyrimidin-4-ylmethyl 1-trifluoromethylcyclopropylmethyl, 1-trifluoromethylcyclobutylcarbonyl, 3,5-difluorophenylmethyl, 1-fluorocyclobutylmethyl, and 1-fluorocyclopropylmethyl.

10. The compound of claim 5, wherein $R^2$ is selected from —CH₂CF₂CF₃, —CH₂CF₂CH₃, —CH₂CF₂CHF₂, —CH₂CHF₂, —CH₂CF₂CH₂CH₃, —CH₂CF(CH₃)₂, 1-trifluoromethylcyclopropylmethyl, 1-trifluoromethylcyclobutylcarbonyl, 3,5-difluorophenylmethyl, 1-fluorocyclobutylmethyl, and 1-fluorocyclopropylmethyl.

11. A compound having structural formula II:

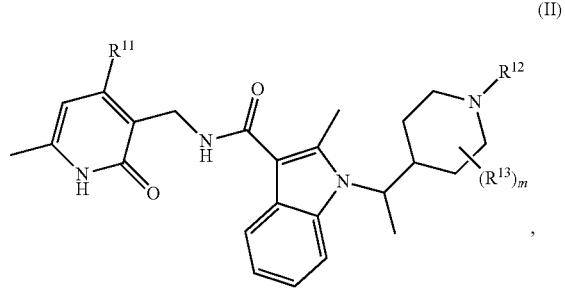

(II)

or a substantially pure enantiomer thereof, or a pharmaceutically acceptable salt of either of the foregoing, wherein:
$R^{11}$ is selected from Cl, —CH₃, —CH₂CH₃, —CH₂CH₂CH₃, —NH(CH₃), —OCH₃, —OCHF₂, —OCF₃, and —OCH₂CF₃;
$R^{12}$ is selected from optionally substituted pyridin-3-yl; optionally substituted pyrimidin-4-yl; optionally substituted pyrazin-2-yl; pyridin-2-yl substituted with one or more substituents independently selected from halo, methyl and morpholin-4-ylmethyl; pyrimidin-2-yl substituted with one or more substituents independently selected from halo, methyl and morpholin-4-ylmethyl;

oxetan-3-yl substituted with one or more fluoro; and
azetidin-3-yl substituted with acetyl;
each $R^{13}$, when present, is independently selected from
=O and fluoro; and
m is 0, 1, 2, 3, or 4.

12. The compound of claim 11 having structural formula IIa:

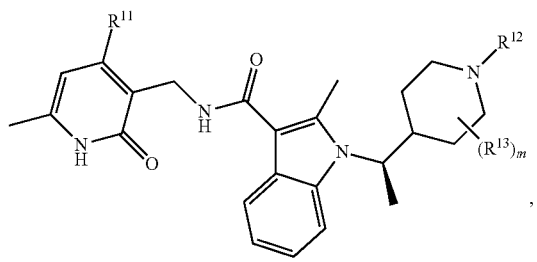
(IIa)

or a pharmaceutically acceptable salt thereof, wherein $R^{11}$, $R^{12}$, $R^{13}$ and m are as defined as in claim 1.

13. The compound of claim 11 having structural formula IIb:

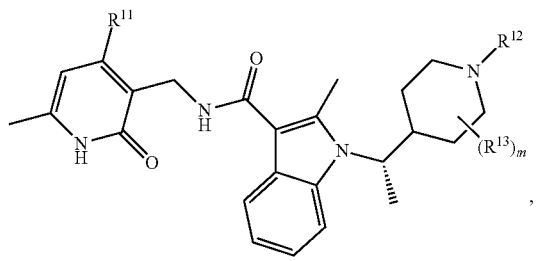
(IIb)

or a pharmaceutically acceptable salt thereof, wherein $R^{11}$, $R^{12}$, $R^{13}$ and m are as defined as in claim 1.

14. The compound of claim 13, wherein $R^{11}$ is selected from chloro, —OCH₃, —NH(CH₃), and —CH₃.

15. The compound of claim 14, wherein $R^{12}$ is selected from 5-chloropyrimindin-2-yl, 5-fluoropyrimidin-2-yl, pyridin-3-yl, pyrazin-2-yl, 6-methylpyridin-3-yl, 5-fluoropyridin-2-yl, 5-(morpholin-4-ylmethyl)pyridin-2-yl, pyrimidin-4-yl, 5-bromopyrimidin-2-yl, and 1-acetylazetidin-3-yl.

16. The compound of claim 14, wherein $R^{12}$ is selected from 5-chloropyrimindin-2-yl, 5-fluoropyrimidin-2-yl, pyridin-3-yl, pyrazin-2-yl, 6-methylpyridin-3-yl, 5-fluoropyridin-2-yl, 5-(morpholin-4-ylmethyl)pyridin-2-yl, pyrimidin-4-yl, and 5-bromopyrimidin-2-yl.

17. A compound selected from any one of:

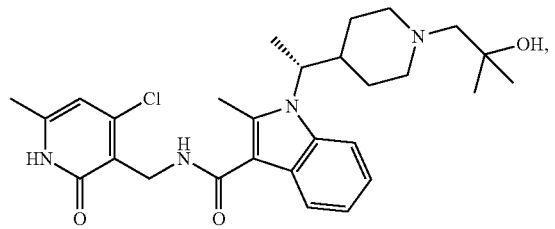

-continued

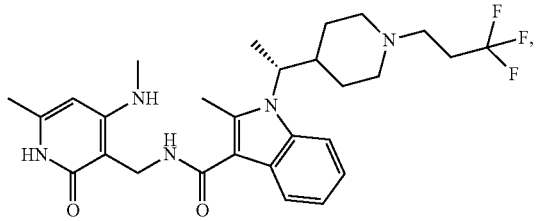

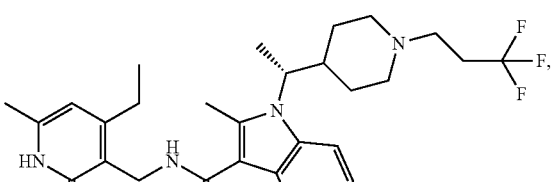

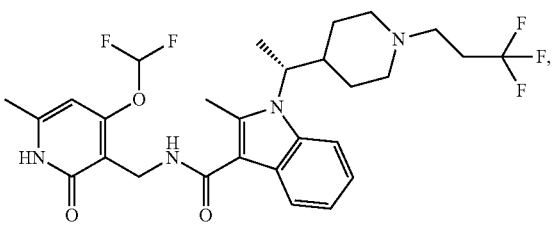

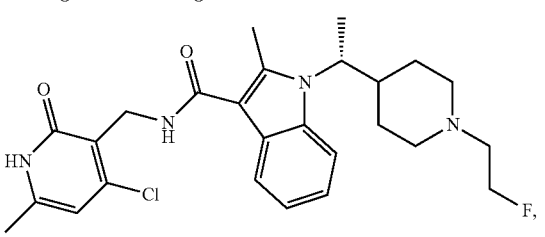

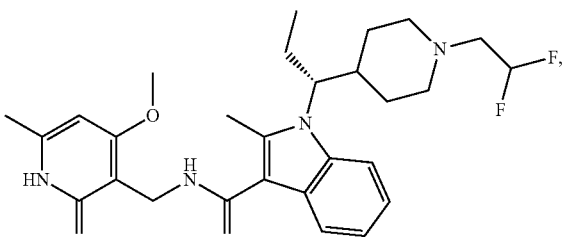

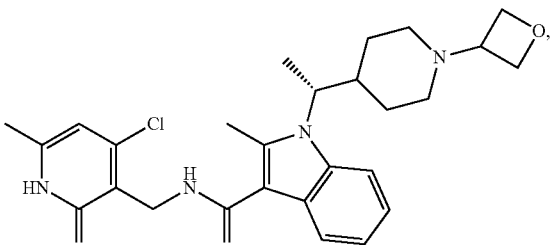

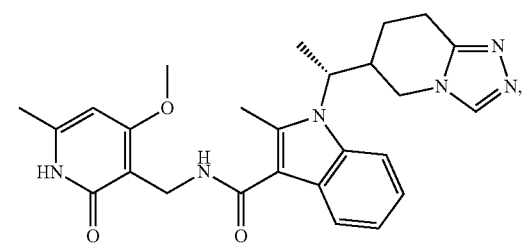

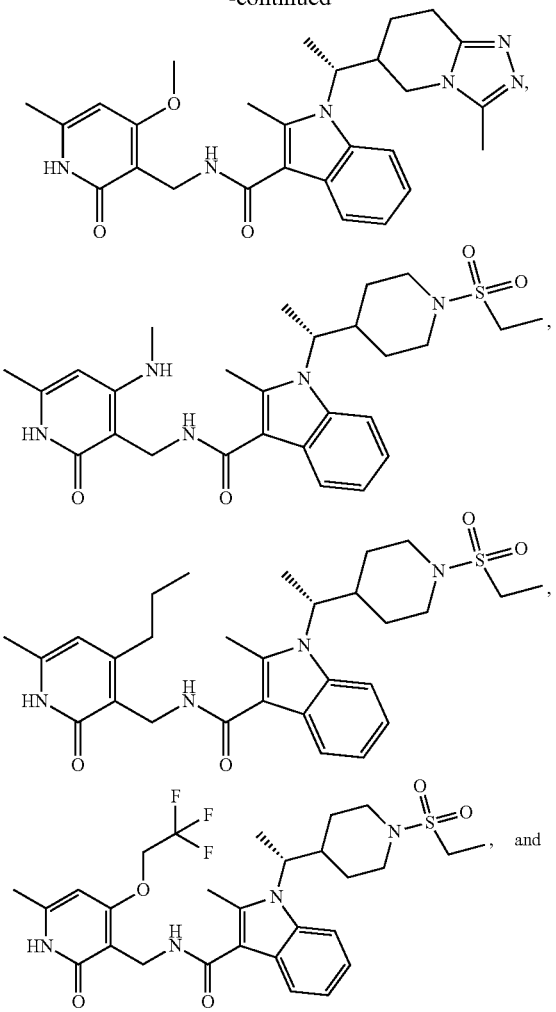

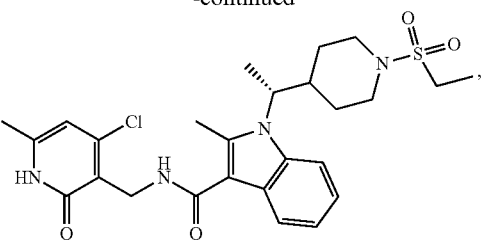

or a pharmaceutically acceptable salt thereof.

18. A composition comprising a compound of claim 1; and a pharmaceutically acceptable carrier.

19. A method of treating cancer in a patient comprising the step of administering to the patient in need thereof a compound according to claim 1.

20. The compound of claim 1, wherein $R^4$ is selected from —C(CH$_3$)$_2$—, —C(O)— and —S(O)$_2$—.

21. The compound of claim 1, wherein $R^2$ is selected from -aryl, -cycloalkyl, —CH$_2$-aryl, —CH$_2$-heteroaryl, —CH$_2$-cycloalkyl, —CH$_2$CH$_2$-heterocyclyl, —S(O)$_2$-aryl, —S(O)$_2$-heteroaryl, —S(O)$_2$-cycloalkyl —S(O)$_2$-heterocyclyl, —S(O)$_2$—CH$_2$CH$_2$-heterocyclyl, —C(O)-cycloalkyl, —C(O)-aryl, —C(O)-heterocyclyl, —C(O)—CH$_2$-aryl, —C(O)—CH$_2$-heteroaryl, —C(O)—N(CH$_3$)$_2$, —C(O)—[OCH$_2$CH$_2$]$_{2-6}$-OCH$_3$, —C(O)CH$_2$CN, —C(O)CH$_2$CH$_2$CH$_3$, —C(O)CH$_2$CH(CH$_3$)$_2$, —CH$_2$CH$_2$CN, —CH$_2$CH$_2$S(O)$_2$CH$_3$, —CH$_2$S(O)$_2$CH$_3$, —CH$_2$CH$_2$NHC(O)CH$_3$, —CH$_2$CH(OCH$_3$)CF$_3$, —CH$_2$CH$_2$CH$_2$CF$_3$, —CH$_2$CH(OH)CF$_3$, and —CH(CH$_2$F)CH$_2$F.

* * * * *

UNITED STATES PATENT AND TRADEMARK OFFICE
CERTIFICATE OF CORRECTION

PATENT NO. : 9,969,716 B2  
APPLICATION NO. : 14/911343  
DATED : May 15, 2018  
INVENTOR(S) : Brian K. Albrecht et al.

Page 1 of 1

It is certified that error appears in the above-identified patent and that said Letters Patent is hereby corrected as shown below:

In the Claims

Column 251, Claim 6, Line 13, replace "3-methylisoxazol-5 acetyl," with --3-methylisoxazol-5-ylacetyl--.

Column 253, Claim 12, Line 24, replace "claim 1" with --claim 11--.
      Claim 13, Line 43, replace "claim 1" with --claim 11--.

Signed and Sealed this  
Thirty-first Day of July, 2018

Andrei Iancu  
*Director of the United States Patent and Trademark Office*